(12) United States Patent
Hagihara et al.

(10) Patent No.: US 7,855,222 B2
(45) Date of Patent: Dec. 21, 2010

(54) METHODS FOR TREATING A DISEASE IN WHICH RHO KINASE IS INVOLVED

(75) Inventors: Masahiko Hagihara, Ube (JP); Ken-ichi Komori, Ube (JP); Hidetoshi Sunamoto, Ube (JP); Hiroshi Nishida, Ube (JP); Takeshi Matsugi, Ikoma (JP); Tadashi Nakajima, Ikoma (JP); Masakazu Hatano, Ikoma (JP); Kazutaka Kido, Ikoma (JP); Hideaki Hara, Ikoma (JP)

(73) Assignees: UBE Industries, Ltd., Yamaguchi (JP); Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 12/456,652

(22) Filed: Jun. 19, 2009

(65) Prior Publication Data

US 2009/0264468 A1 Oct. 22, 2009

Related U.S. Application Data

(62) Division of application No. 10/575,645, filed as application No. PCT/JP2004/015663 on Oct. 15, 2004, now Pat. No. 7,563,906.

(30) Foreign Application Priority Data

| Oct. 15, 2003 | (JP) | ............................. 2003-354917 |
| Aug. 20, 2004 | (JP) | ............................. 2004-270561 |

(51) Int. Cl.
*A01N 43/56* (2006.01)
*A61K 31/40* (2006.01)
*C07D 231/00* (2006.01)
*C07D 233/56* (2006.01)

(52) U.S. Cl. .................. 514/403; 548/346.1; 548/356.1
(58) Field of Classification Search ................. 514/403; 548/346.1, 356.1
See application file for complete search history.

(56) References Cited

U.S. PATENT DOCUMENTS

| 5,798,380 | A | 8/1998 | Kaufman et al. |
| 6,110,912 | A | 8/2000 | Kaufman et al. |
| 6,555,539 | B2 | 4/2003 | Reich et al. |
| 6,586,425 | B2 | 7/2003 | Kaufman et al. |
| 7,563,906 | B2 * | 7/2009 | Hagihara et al. ......... 548/346.1 |
| 2004/0102437 | A1 | 5/2004 | Takami et al. |

FOREIGN PATENT DOCUMENTS

| EP | 0956865 | A1 | 11/1999 |
| EP | 1034793 | A1 | 9/2000 |
| EP | 1256574 | A1 | 11/2002 |
| EP | 14035255 | A1 | 3/2004 |
| WO | WO 97/23222 | A1 | 7/1997 |
| WO | WO 98/06433 | A1 | 2/1998 |
| WO | WO 99/64011 | A1 | 12/1999 |
| WO | WO 00/57914 | A1 | 5/2000 |
| WO | WO 01/56598 | A1 | 8/2001 |
| WO | WO 01/56988 | A1 | 8/2001 |
| WO | WO 00/09162 | A1 | 2/2002 |
| WO | WO 02/076976 | A2 | 10/2002 |
| WO | WO 02/076977 | A2 | 10/2002 |
| WO | WO 02/100833 | A1 | 12/2002 |

OTHER PUBLICATIONS

Masayoshi Vehata et al., "Calcium Sensitization of Smooth Muscle Mediated by a Rho-associated Protein Kinase in Hypertension," *Nature*, vol. 389, Oct. 30, 1997, pp. 990-994.

George A. Patani et al., "Bioisosterism: A Rational Approach in Drug Design,"*Chem. Rev.*, (1996), vol. 96, No. 8, pp. 3147-3176.

* cited by examiner

*Primary Examiner*—Susannah Chung
(74) *Attorney, Agent, or Firm*—Holtz, Holtz, Goodman & Chick, P.C.

(57) ABSTRACT

A method for treating a disease in which Rho kinase is involved. The method is carried out by administering to a patient in need thereof a pharmaceutically effective amount of a compound of the following formula or a pharmaceutically acceptable salt thereof:

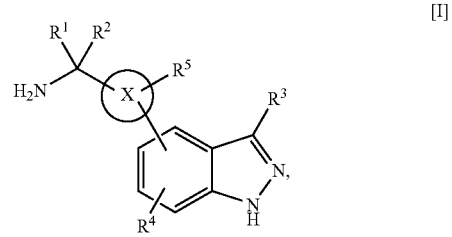

wherein the ring X is a benzene ring or a pyridine ring; $R^1$ and $R^2$ are hydrogen or alkyl or together form a cycloalkene ring; $R^3$ is hydrogen, substituted alkyl, unsubstituted alkenyl, carboxyl or an ester or an amide thereof, amino or a cyano; $R^4$ is hydrogen, hydroxyl, substituted or unsubstituted alkoxy, unsubstituted alkenyloxy, unsubstituted cycloalkyloxy, substituted or unsubstituted alkyl, unsubstituted alkenyl, unsubstituted cycloalkyl, amino, substituted or unsubstituted alkylamino, nitro, cyano or a monocyclic heterocycle; and $R^5$ is a halogen atom or a hydrogen atom.

12 Claims, 2 Drawing Sheets

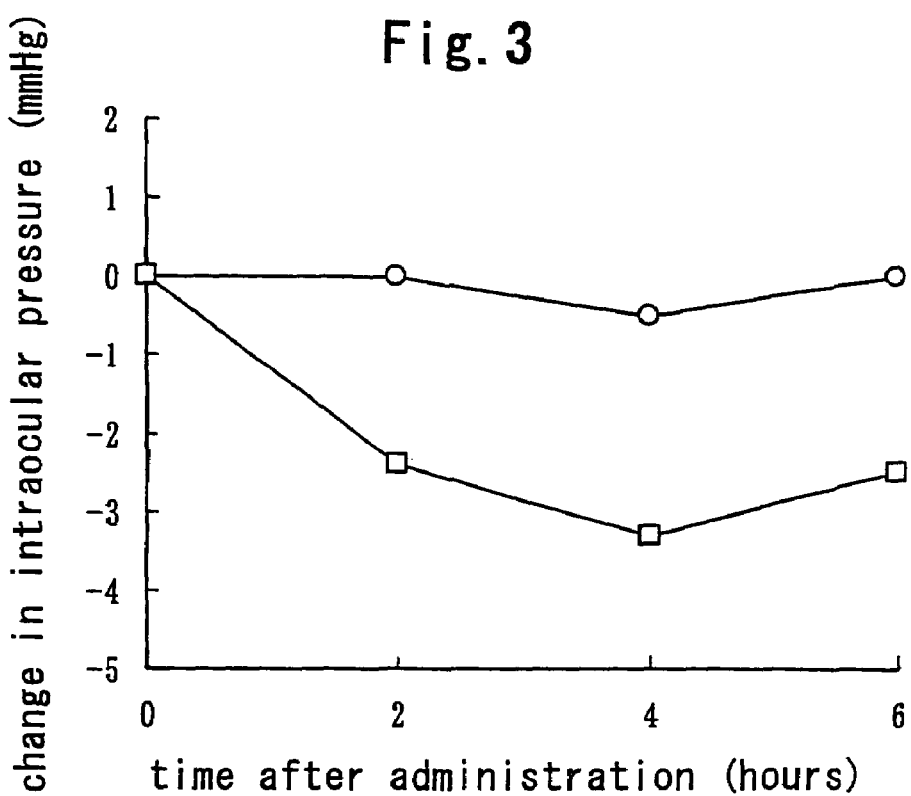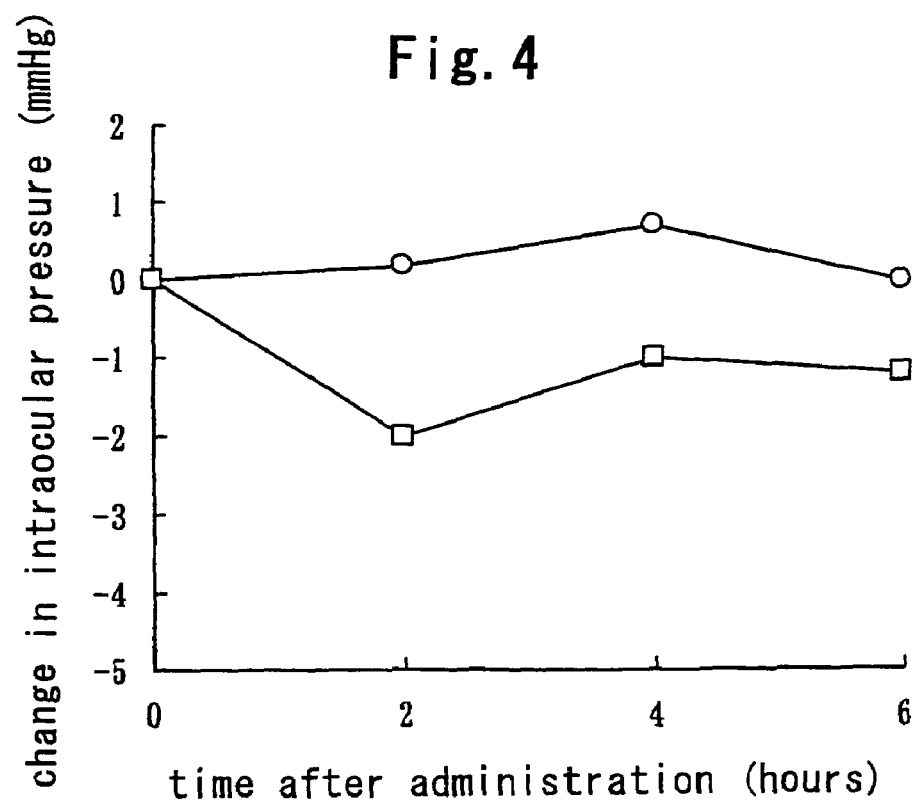

METHODS FOR TREATING A DISEASE IN WHICH RHO KINASE IS INVOLVED

CROSS-REFERENCE TO RELATED APPLICATIONS

This application is a divisional application of application Ser. No. 10/575,645 filed Apr. 13, 2006 (U.S. Pat. No. 7,563,906), which is a United States national phase application under 35 USC 371 of International application PCT/JP2004/015663 filed Oct. 15, 2004. The entire contents of each of U.S. application Ser. No. 10/575,645 and International application PCT/JP2004/015663 are hereby incorporated by reference herein.

TECHNICAL FIELD

The present invention relates to a novel indazole derivative or a salt thereof useful as a pharmaceutical. The indazole derivative according to the present invention has a Rho kinase inhibiting action and is useful as a treating agent for diseases in which Rho kinase is involved such as eye diseases including glaucoma.

BACKGROUND ART

Rho, a low-molecule GTP-binding protein, is activated by signals from various cell membrane receptors.

The activated Rho functions, via Rho kinase signal transduction and actomyosin signal transduction, as a molecular switch for various cellular phenomena such as contraction of smooth muscles, morphological changes in cells, cell movement, cell division, intercellular adhesion, platelet aggregation, leukocyte aggregation, infiltration and increase of cancer cells.

It has been also known that such cellular phenomena deeply participate in diseases such as hypertension, angina pectoris, asthma, peripheral circulatory disorder, premature delivery, arteriosclerosis, cancer, inflammatory diseases, autoimmune diseases, AIDS, fertilization and implantation of a fertilized egg, osteoporosis, cerebral function disturbance, gastrointestinal dysfunction by bacteria, glaucoma and retinopathy.

Accordingly, it is believed that, when Rho is inhibited, prevention and/or treatment of the aforementioned diseases in which Rho is participated are/is possible.

On the other hand, it has been also known that, when Rho kinase, which exists in the downstream of signal transduction mediated by Rho, is inhibited, various cellular phenomena caused by Rho are able to be suppressed.

Thus, compounds which inhibit the Rho kinase are believed to be effective preventive and/or treating agents for the aforementioned diseases in which Rho is participated such as hypertension, angina pectoris, asthma, peripheral circular disorder, premature delivery, arteriosclerosis, cancer, inflammatory diseases, autoimmune diseases, AIDS, fertilization and implantation of fertilized egg, osteoporosis, cerebral function disturbance, gastrointestinal dyfunction by bacteria, glaucoma and retinopathy (WO 98/06433).

A Rho kinase inhibitor is usually defined as an inhibitor for serine/threonine kinase activated as a result of activation of Rho. The Rho kinase inhibitor includes compounds which inhibit protein having serine/threonine kinase activity such as ROKα (ROCK-II), ROKβ (ROCK-I, p160ROCK) and others.

Examples of the known Rho kinase inhibitor are amide derivatives disclosed in WO 98/06433; isoquinoline sulfonyl derivatives disclosed in WO 97/23222, Nature 389, 990-994 (1997) and WO 99/64011; heterocyclic amino derivatives disclosed in WO 01/56988; indazole derivatives disclosed in WO 02/100833; and quinazoline derivatives disclosed in WO 02/076976 and WO 02/076977.

It has been also disclosed in WO 00/09162 and WO 00/57914 that a Rho kinase inhibitor is useful as a treating agent for glaucoma.

However, in any of the aforementioned documents, there is no specific disclosure for the indazole derivative according to the present invention.

DISCLOSURE OF THE INVENTION

It is a very interesting matter to create novel indazole derivatives which are useful as pharmaceuticals and to find new pharmacological actions of such derivatives.

In order to solve the above matter, the present inventors have made synthetic studies for novel indazole derivatives and have succeeded in creating many novel compounds.

Further, when usefulness of the indazole derivatives of the present invention as pharmaceuticals has been variously investigated, it has been found that the present indazole derivatives have a Rho kinase inhibiting action and are useful as treating agents for diseases in which Rho kinase is involved.

Further, in order to check the application of the present indazole derivatives to specific diseases in which Rho is involved, an intraocular pressure-reducing action of the present indazole derivatives was also studied. As a result, it was found that the present indazole derivatives exhibited an excellent intraocular pressure-reducing action and are useful as treating agents for eye diseases such as glaucoma, and whereupon the present invention has been achieved.

Thus, the present invention relates to a compound represented by the following formula [I] or a salt thereof (hereinafter, that will be referred to as "the present invention compound" unless otherwise stated) and also to a pharmaceutical composition containing the present invention compound. In particular, the present invention relates to a Rho kinase inhibitor comprising the present invention compound as an active ingredient and further to a treating agent for eye diseases such as glaucoma.

The present invention compound has the chemical structural characteristics as shown in the following 1) to 4).

1) An indazole ring is a main skeleton.

2) A ring X is directly bonded to an indazole ring.

3) A ring X has an amino-substituted alkyl group or cycloalkyl group.

4) In the above 3), the amino group is located at 1-position of the alkyl group or the cycloalkyl group.

Each of the chemical structural characteristics of 1) to 4) as such and/or a combination thereof are/is important in achievement of the Rho kinase inhibiting action of the present invention compound.

Further, in addition to the aforementioned 1) to 4), the present invention compound where 5) the carbon atom in which the amino group of the above 3) is introduced is not an asymmetric carbon atom exhibits a particularly good Rho kinase inhibiting action.

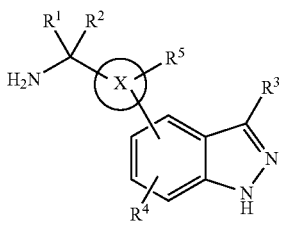

[In the formula, a ring X is a benzene ring or a pyridine ring;

$R^1$ and $R^2$ are, the same or different, hydrogen atom or a substituted or unsubstituted alkyl group;

$R^1$ and $R^2$ can be bonded to form a substituted or unsubstituted cycloalkane ring;

$R^3$ and $R^4$ are, the same or different, one or more group(s) selected from the group consisting of halogen atom, hydrogen atom, hydroxyl group, a substituted or unsubstituted alkoxy group, a substituted or unsubstituted alkenyloxy group, a substituted or unsubstituted alkynyloxy group, a substituted or unsubstituted cycloalkyloxy group, a substituted or unsubstituted cycloalkenyloxy group, a substituted or unsubstituted aryloxy group, a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted aryl group, carboxyl group or an ester or an amide thereof, hydrocarbonyl group, a substituted or unsubstituted alkylcarbonyl group, a substituted or unsubstituted arylcarbonyl group, amino group, a substituted or unsubstituted alkylamino group, a substituted or unsubstituted arylamino group, mercapto group, a substituted or unsubstituted alkylthio group, a substituted or unsubstituted arylthio group, sulfinic acid group or an ester or an amide thereof, hydrosulfinyl group, a substituted or unsubstituted alkylsulfinyl group, a substituted or unsubstituted arylsulfinyl group, sulfonic acid group or an ester or an amide thereof, hydrosulfonyl group, a substituted or unsubstituted alkylsulfonyl group, a substituted or unsubstituted arylsulfonyl group, nitro group, cyano group and a substituted or unsubstituted monocyclic heterocylic group;

$R^5$ is one or more group(s) selected from the group consisting of halogen atom, hydrogen atom, hydroxyl group, a substituted or unsubstituted alkoxy group, a substituted or unsubstituted aryloxy group, a substituted or unsubstituted alkyl group and a substituted or unsubstituted aryl group;

and, hereinafter, they have the same meanings.]

The present invention provides a novel indazole derivative or a salt thereof which is useful as a pharmaceutical. In particular, the present invention compound exhibits an excellent Rho kinase inhibiting action and is useful as a treating agent for diseases in which Rho kinase is involved such as eye diseases including glaucoma.

BRIEF DESCRIPTION OF THE DRAWINGS

FIG. 3 is a graph which shows the changes in intraocular pressure in each administration group with lapse of time. The intraocular pressure is shown by the pressure change from the initial intraocular pressure. □ shows the group to which the test compound 3 was administered and ○ shows a control group.

FIG. 4 is a graph which shows the changes in intraocular pressure in each administration group with lapse of time. The intraocular pressure is shown by the pressure change from the initial intraocular pressure. □ shows the group to which the test compound 4 was administered and ○ shows a control group.

BEST MODE FOR CARRYING OUT THE INVENTION

Figure 1:
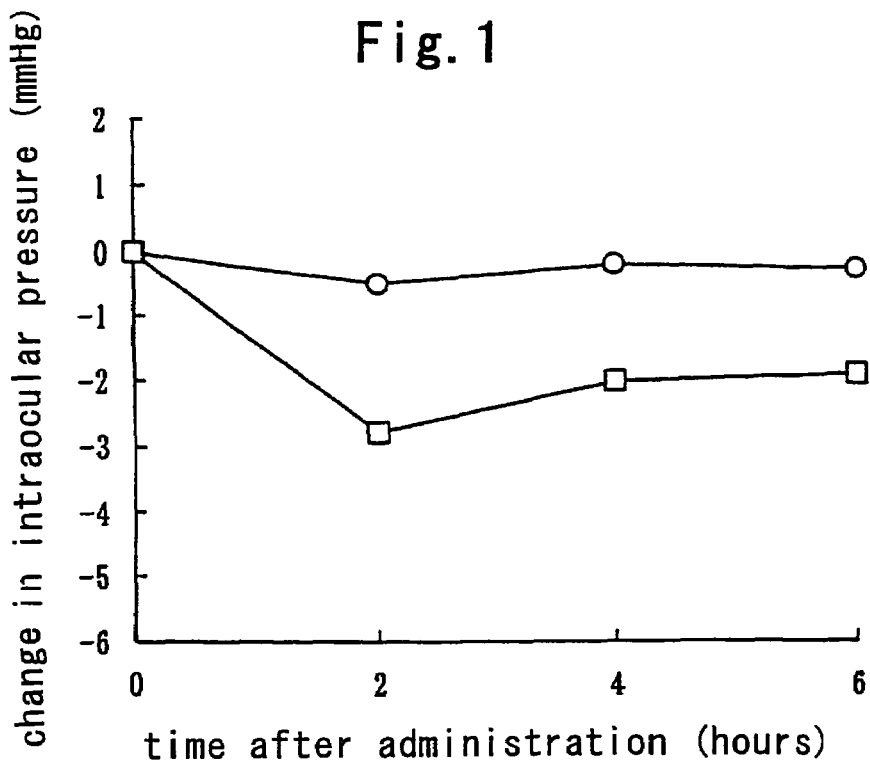
FIG. 1 is a graph which shows the changes in intraocular pressure in each administration group with lapse of time. The intraocular pressure is shown by the pressure change from the initial intraocular pressure. □ shows the group to which the test compound 1 was administered and ○ shows a control group.

Each of the rings, atoms or groups which are described in the present specification will now be illustrated in detail as hereunder.

"A cycloalkane group" is a cycloalkane group having 3 to 8 carbon atoms. Specific examples thereof are cyclopropane, cyclobutane, cyclopentane, cyclohexane, cycloheptane and cyclooctane.

"A monocyclic heterocycle" is a saturated or unsaturated monocyclic heterocycle having one or more hetero atom(s) selected from nitrogen atom, oxygen atom and sulfur atom in a ring.

Specific examples of the saturated monocyclic heterocycle are that having nitrogen atom in a ring such as pyrrolidine, pyrazolidine, imidazolidine, triazolidine, piperidine, hexahydropyridazine, hexahydropyrimidine, piperazine, homopiperidine and homopiperazine; that having oxygen atom in a ring such as tetrahydrofuran and tetrahydropyran; that having sulfur atom in a ring such as tetrahydrothiophene and tetrahydrothiopyran; that having nitrogen atom and oxygen atom in a ring such as oxazolidine, isoxazolidine and morpholine; and that having nitrogen atom and sulfur atom in a ring such as thiazolidine, isothiazolidine and thiomorpholine.

Specific examples of the unsaturated monocyclic heterocycle are that having nitrogen atom in a ring such as dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine and pyrazine; that having oxygen atom in a ring such as dihydrofuran, furan, dihydropyran and pyran; that having sulfur atom in a ring such as dihydrothiophene, thiophene, dihydrothiopyran and thiopyran; that having nitrogen atom and oxygen atom in a ring such as dihydrooxazole, oxazole, dihydroisoxazole, isoxazole, dihydrooxazine and oxazine; and that having nitrogen atom and sulfur atom in a ring such as dihydrothiazole, thiazole, dihydroisothiazole, isothiazole, dihydrothiazine and thiazine.

"Halogen atom" is fluorine, chlorine, bromine or iodine.

"Alkyl" is a straight or branched alkyl having 1 to 6 carbon atom(s). Specific examples thereof are methyl, ethyl, n-propyl, n-butyl, n-pentyl, n-hexyl, isopropyl, isobutyl, sec-butyl, tert-butyl and isopentyl.

"Alkoxyl" is a straight or branched alkoxyl having 1 to 6 carbon atom(s). Specific examples thereof are methoxy, ethoxy, n-propoxy, n-butoxy, n-pentoxy, n-hexyloxy, isopropoxy, isobutoxy, sec-butoxy, tert-butoxy and isopentoxy.

"Alkenyloxy" is a straight or branched alkenyloxy having 2 to 8 carbon atoms. Specific examples thereof are vinyloxy, allyloxy, 1-propenyloxy, 3-butenyloxy, 3-pentenyoxy, 4-hexenyloxy, 5-heptenyloxy, 7-octenyloxy and 1-methylvinyloxy.

"Alkynyloxy" is a straight or branched alkynyloxy having 2 to 8 carbon atoms. Specific examples thereof are ethynyloxy, 2-propynyloxy, 2-butynyloxy, 3-pentynyloxy, 4-hexynyloxy, 5-heptynyloxy, 7-octynyloxy and 2-methylbutynyloxy.

"Cycloalkyloxy" is a cycloalkyloxy having 3 to 8 carbon atoms. Specific examples thereof are cyclopropyloxy, cyclobutyloxy, cyclopentyloxy, cyclohexyloxy, cycloheptyloxy and cyclooctyloxy.

"Cycloalkenyloxy" is a cycloalkenyloxy having 3 to 8 carbon atoms. Specific examples thereof are cyclopropenyloxy, cyclobutenyloxy, cyclopentenyloxy, cyclohexenyloxy, cycloheptenyloxy and cyclooctenyloxy.

"Aryloxy" is a monocyclic or a di-cyclic or tri-cyclic fused polycyclic aromatic hydrocarbonoxy having 6 to 14 carbon atoms. Specific examples thereof are phenoxy, naphthyloxy, anthryloxy and phenanthryloxy.

"Alkenyl" is a straight or branched alkenyl having 2 to 8 carbon atoms. Specific examples thereof are vinyl, allyl, 1-propenyl, 3-butenyl, 3-pentenyl, 4-hexenyl, 5-heptenyl, 7-octenyl and 1-methylvinyl.

"Alkynyl" is a straight or branched alkynyl having 2 to 8 carbon atoms. Specific examples thereof are ethynyl, 2-propynyl, 2-butynyl, 3-pentynyl, 4-hexynyl, 5-heptynyl, 7-octynyl and 2-methylbutynyl.

"Cycloalkyl" is a cycloalkyl having 3 to 8 carbon atoms. Specific examples thereof are cyclopropyl, cyclobutyl, cyclopentyl, cyclohexyl, cycloheptyl and cyclooctyl.

"Cycloalkenyl" is a cycloalkenyl having 3 to 8 carbon atoms. Specific examples thereof are cyclopropenyl, cyclobutenyl, cyclopentenyl, cyclohexenyl, cycloheptenyl and cyclooctenyl.

"Aryl" is a monocyclic or di-cyclic or tri-cyclic fused polycyclic aromatic hydrocarbon having 6 to 14 carbon atoms. Specific examples thereof are phenyl, naphthyl, anthryl and phenanthryl.

"Ester of carboxyl group" is an ester comprising carboxyl group residue with an alkyl alcohol, aryl alcohol, etc. Specific examples of the alkyl alcohol are methanol, ethanol, propanol and butanol and specific examples of the aryl alcohol are phenol and naphthol.

"Amide of carboxyl group" is an amide comprising carboxyl group residue with ammonia, primary or secondary amine, etc. The amine can be either an alkylamine or an arylamine and specific examples of the alkylamine are methylamine, ethylamine, ethylmethylamine, dimethylamine, diethylamine and dihexylamine while specific examples of the arylamine are aniline, naphthylamine, methylphenylamine, ethylphenylamine and diphenylamine.

"Alkylcarbonyl" is a straight or branched alkylcarbonyl having 2 to 7 carbon atoms. Specific examples thereof are methylcarbonyl, ethylcarbonyl, n-propylcarbonyl, n-butylcarbonyl, n-pentylcarbonyl, n-hexylcarbonyl, isopropylcarbonyl, isobutylcarbonyl, sec-butylcarbonyl, tert-butylcarbonyl and isopentylcarbonyl.

"Arylcarbonyl" is a monocyclic or di-cyclic or tri-cyclic fused polycyclic aromatic hydrocarbon carbonyl having 7 to 15 carbon atoms. Specific examples thereof are phenylcarbonyl, naphthylcarbonyl, anthrylcarbonyl and phenanthrylcarbonyl.

"Alkylamino" is a mono- or dialkylamino. Specific examples thereof are methylamino, ethylamino, ethyl methylamino, dimethylamino, diethylamino and dihexylamino.

"Arylamino" is a mono- or diarylamino. Specific examples thereof are phenylamino, naphthylamino, methyl phenylamino, ethyl phenylamino and diphenylamino.

"Alkylthio" is a straight or branched alkylthio having 1 to 6 carbon atom(s). Specific examples thereof are methylthio, ethylthio, n-propylthio, n-butylthio, n-pentylthio, n-hexylthio, isopropylthio, isobutylthio, sec-butylthio, tert-butylthio and isopentylthio.

"Arylthio" is a monocyclic or a di-cyclic or tri-cyclic fused polycyclic aromatic hydrocarbon thio having 6 to 14 carbon atoms. Specific examples thereof are phenylthio, naphthylthio, anthrylthio and phenanthrylthio.

"Ester of sulfinic acid group" is an ester formed from sulfinic acid group and alkyl alcohol, aryl alcohol, etc. Specific examples of the alkyl alcohol are methanol, ethanol, propanol and butanol while specific examples of the aryl alcohol are phenol and naphthol.

"Amide of sulfinic amide group" is an amide formed from sulfinic acid and ammonia, a primary or second amine, etc. The amine can be either alkylamine or arylamine and specific examples of the alkylamine are methylamine, ethylamine, ethyl methylamine, dimethylamine, diethylamine and dihexylamine while specific examples of the arylamine are aniline, naphthylamine, methyl phenylamine, ethyl phenylamine and diphenylamine.

"Alkylsulfinyl" is a straight or branched alkylsulfinyl having 1 to 6 carbon atom(s). Specific examples thereof are methylsulfinyl, ethylsulfinyl, n-propylsulfinyl, n-butylsulfinyl, n-pentylsulfinyl, n-hexylsulfinyl, isopropylsulfinyl, isobutylsulfinyl, sec-butylsulfinyl, tert-butylsulfinyl and isopentylsulfinyl.

"Arylsulfinyl" is a monocyclic or a di-cyclic or tri-cyclic fused polycyclic aromatic hydrocarbon sulfinyl having 6 to 14 carbon atoms. Specific examples thereof are phenylsulfinyl, naphthylsulfinyl, anthrylsulfinyl and phenanthrylsulfinyl.

"Ester of sulfonic acid group" is an ester formed from sulfonic acid group and alkyl alcohol, aryl alcohol, etc. Specific examples of the alkyl alcohol are methanol, ethanol, propanol and butanol while specific examples of the aryl alcohol are phenol and naphthol.

"Amide of sulfonic acid group" is an amide formed from sulfonic acid group and ammonia, a primary or secondary amine, etc. The amine may be either alkylamine or arylamine and specific examples of the alkylamine are methylamine, ethylamine, ethyl methylamine, dimethylamine, diethylamine and dihexylamine while specific examples of the arylamine are aniline, naphthylamine, methyl phenylamine, ethyl phenylamine and diphenylamine.

"Alkylsulfonyl" is a straight or branched alkylsulfonyl having 1 to 6 carbon atom(s). Specific examples thereof are methylsulfonyl, ethylsulfonyl, n-propylsulfonyl, n-butylsulfonyl, n-pentylsulfonyl, n-hexylsulfonyl, isopropylsulfonyl, isobutylsulfonyl, sec-butylsulfoyl, tert-butylsulfonyl and isopentylsulfonyl.

"Arylsulfonyl" is a monocyclic or a di-cyclic or tri-cyclic fused polycyclic aromatic hydrocarbon sulfonyl having 6 to 14 carbon atoms. Specific examples thereof are phenylsulfonyl, naphthylsulfonyl, anthrylsulfonyl and phenanthrylsulfonyl.

"Alkoxyimino" is a straight or branched alkoxyimino having 1 to 6 carbon atom(s). Specific examples thereof are methoxyimino, ethoxyimino, n-propoxyimino, n-butoxyimino, n-pentoxyimino, n-hexyloxyimino, isopropoxyimino, isobutoxyimino, sec-butoxyimino, tert-butoxyimino and isopentoxyimino.

"Aryloxyimino" is a monocyclic or di- or tricyclic fused polycyclic aromatic hydrocarbon oxyimino having 6 to 14 carbon atom(s). Specific examples thereof are phenoxyimino, naphthyloxyimino, anthryloxyimino and phenanthryloxyimino.

"Substituted cycloalkane ring" is a cycloalkane ring having one or more group(s) selected from halogen atom, hydroxyl group, alkoxy group, aryloxy group, alkyl group, cycloalkyl group, aryl group, carboxyl group or ester or amide thereof, amino group, alkylamino group, arylamino group, nitro group and cyano group as substituent(s).

"Substituted monocyclic heterocycle" is a monocyclic heterocylic group having one or more group(s) selected from halogen atom, hydroxyl group, alkoxy group, aryloxy group, alkyl group, cycloalkyl group, aryl group, carboxy group or an ester or an amide thereof, amino group, alkylamino group, arylamino group, mercapto group, alkylthio group, arylthio group, formyl group, alkylcarbonyl group, arylcarbonyl group, nitro group and cyano group as substituent(s).

"Substituted alkyl group" is an alkyl group having one or more group(s) selected from halogen atom, hydroxyl group, alkoxy group, aryloxy group, cycloalkyl group, aryl group, aryl group substituted with halogen atom, aryl group substituted with alkoxy group, carboxy group or an ester or an amide thereof, amino group, alkylamino group, arylamino group, nitro group, cyano group, hydroxyimino group, alkoxyimino group and aryloxyimino group as substituent(s).

"Substituted alkoxy group" is an alkoxy group having one or more group(s) selected from halogen atom, hydroxyl group, alkoxy group, aryloxy group, cycloalkyl group, aryl group, aryl group substituted with halogen atom, aryl group substituted with alkoxy group, carboxy group or an ester or an amide thereof, amino group, alkylamino group, arylamino group, nitro group, cyano group, hydroxyimino group, alkoxyimino group and aryloxyimino group as substituent(s).

"Substituted alkenyloxy group" is an alkenyloxy group having one or more group(s) selected from halogen atom, hydroxyl group, alkoxy group, aryloxy group, cycloalkyl group, aryl group, aryl group substituted with halogen atom, aryl group substituted with alkoxy group, carboxy group or an ester or an amide thereof, amino group, alkylamino group, arylamino group, nitro group and cyano group as substituent(s).

"Substituted alkynyloxy group" is an alkynyloxy group having one or more group(s) selected from halogen atom, hydroxyl group, alkoxy group, aryloxy group, cycloalkyl group, aryl group, aryl group substituted with halogen atom, aryl group substituted with alkoxy group, carboxy group or an ester or an amide thereof, amino group, alkylamino group, arylamino group, nitro group and cyano group as substituent(s).

"Substituted cycloalkyloxy group" is a cycloalkyloxy group having one or more group(s) selected from halogen atom, hydroxyl group, alkoxy group, aryloxy group, alkyl group, cycloalkyl group, aryl group, carboxy group or an ester or an amide thereof, amino group, alkylamino group, arylamino group, nitro group and cyano group as substituent(s).

"Substituted cycloalkenyloxy group" is a cycloalkenyloxy group having one or more group(s) selected from halogen atom, hydroxyl group, alkoxy group, aryloxy group, alkyl group, cycloalkyl group, aryl group, carboxy group or an ester or an amide thereof, amino group, alkylamino group, arylamino group, nitro group and cyano group as substituent(s).

"Substituted aryloxy group" is an aryloxy group having one or more group(s) selected from halogen atom, hydroxyl group, alkoxy group, aryloxy group, alkyl group, cycloalkyl group, aryl group, carboxy group or an ester or an amide thereof, amino group, alkylamino group, arylamino group, nitro group and cyano group as substituent(s).

"Substituted alkenyl group" is an alkenyl group having one or more group(s) selected from halogen atom, hydroxyl group, alkoxy group, aryloxy group, cycloalkyl group, aryl group, aryl group substituted with halogen atom, aryl group substituted with alkoxy group, carboxy group or an ester or an amide thereof, amino group, alkylamino group, arylamino group, nitro group, cyano group, hydroxyimino group, alkoxyimino group and aryloxyimino group as substituent(s).

"Substituted alkynyl group" is an alkynyl group having one or more group(s) selected from halogen atom, hydroxyl group, alkoxy group, aryloxy group, cycloalkyl group, aryl group, aryl group substituted with halogen atom, aryl group substituted with alkoxy group, carboxy group or an ester or an amide thereof, amino group, alkylamino group, arylamino group, nitro group and cyano group as substituent(s).

"Substituted cycloalkyl group" is a cycloalkyl group having one or more group(s) selected from halogen atom, hydroxyl group, alkoxy group, aryloxy group, alkyl group, cycloalkyl group, aryl group, carboxy group or an ester or an amide thereof, amino group, alkylamino group, arylamino group, nitro group and cyano group as substituent(s).

"Substituted cycloalkenyl group" is a cycloalkenyl group having one or more group(s) selected from halogen atom, hydroxyl group, alkoxy group, aryloxy group, alkyl group, cycloalkyl group, aryl group, carboxy group or an ester or an amide thereof, amino group, alkylamino group, arylamino group, nitro group and cyano group as substituent(s).

"Substituted aryl group" is an aryl group having one or more group(s) selected from halogen atom, hydroxyl group, alkoxy group, aryloxy group, alkyl group, cycloalkyl group, aryl group, carboxy group or an ester or an amide thereof, amino group, alkylamino group, arylamino group, nitro group, cyano group, hydroxyimino group, alkoxyimino group and aryloxyimino group as substituent(s).

"Substituted alkylcarbonyl group" is an alkylcarbonyl group having one or more group(s) selected from halogen atom, hydroxyl group, alkoxy group, aryloxy group, cycloalkyl group, aryl group, aryl group substituted with halogen atom, aryl group substituted with alkoxy group, carboxy group or an ester or an amide thereof, amino group, alkylamino group, arylamino group, nitro group and cyano group as substituent(s).

"Substituted arylcarbonyl group" is an arylcarbonyl group having one or more group(s) selected from halogen atom, hydroxyl group, alkoxy group, aryloxy group, alkyl group, cycloalkyl group, aryl group, carboxy group or an ester or an amide thereof, amino group, alkylamino group, arylamino group, nitro group and cyano group as substituent(s).

"Substituted alkylamino group" is an alkylamino group in which an alkyl moiety thereof has one or more group(s) selected from halogen atom, hydroxyl group, alkoxy group, aryloxy group, cycloalkyl group, aryl group, aryl group substituted with halogen atom, aryl group substituted with alkoxy group, carboxy group or an ester or an amide thereof, amino group, alkylamino group, arylamino group, nitro group and cyano group as substituent(s).

"Substituted arylamino group" is an arylamino group in which an aryl moiety thereof has one or more group(s)

selected from halogen atom, hydroxyl group, alkoxy group, aryloxy group, alkyl group, cycloalkyl group, aryl group, carboxy group or an ester or an amide thereof, amino group, alkylamino group, arylamino group, nitro group and cyano group as substituent(s).

"Substituted alkylthio group" is an alkylthio group having one or more group(s) selected from halogen atom, hydroxyl group, alkoxy group, aryloxy group, cycloalkyl group, aryl group, aryl group substituted with halogen, aryl group substituted with alkoxy group, carboxy group or an ester or an amide thereof, amino group, alkylamino group, arylamino group, nitro group and cyano group as substituent(s).

"Substituted arylthio group" is an arylthio group in which an aryl moiety thereof has one or more group(s) selected from halogen atom, hydroxyl group, alkoxy group, aryloxy group, alkyl group, cycloalkyl group, aryl group, carboxy group or an ester or an amide thereof, amino group, alkylamino group, arylamino group, nitro group and cyano group as substituent(s).

"Substituted alkylsulfinyl group" is an alkylsulfinyl group having one or more group(s) selected from halogen atom, hydroxyl group, alkoxy group, aryloxy group, cycloalkyl group, aryl group, aryl group substituted with halogen, aryl group substituted with alkoxy group, carboxy group or an ester or an amide thereof, amino group, alkylamino group, arylamino group, nitro group and cyano group as substituent(s).

"Substituted arylsulfinyl group" is an arylsulfinyl group in which an aryl moiety thereof has one or more group(s) selected from halogen atom, hydroxyl group, alkoxy group, aryloxy group, alkyl group, cycloalkyl group, aryl group, carboxy group or an ester or an amide thereof, amino group, alkylamino group, arylamino group, nitro group and cyano group as substituent(s).

"Substituted alkylsulfonyl group" is an alkylsulfonyl group having one or more group(s) selected from halogen atom, hydroxyl group, alkoxy group, aryloxy group, cycloalkyl group, aryl group, aryl group substituted with halogen, aryl group substituted with alkoxy group, carboxy group or an ester or an amide thereof, amino group, alkylamino group, arylamino group, nitro group and cyano group as substituent(s).

"Substituted arylsulfonyl group" is an arylsulfonyl group in which an aryl moiety thereof has one or more group(s) selected from halogen atom, hydroxyl group, alkoxy group, aryloxy group, alkyl group, cycloalkyl group, aryl group, carboxy group or an ester or an amide thereof, amino group, alkylamino group, arylamino group, nitro group and cyano group as substituent(s).

When the present invention compound has free hydroxyl group, amino group, alkylamino group or arylamino group as a substituent, such a group may be protected by a protective group.

Examples of the protective group for a free hydroxyl group are those which have been commonly used as protective groups for free hydroxyl group including a substituted or unsubstituted alkyl group or an unsubstituted alkenyl group such as methoxymethyl group, benzyl group, trityl group, 4-methoxyphenylmethyl group, benzyloxymethyl group, methyl group and allyl group; a substituted or unsubstituted heterocyclic group such as 3-bromotetrahydropyranyl group, tetrahydropyranyl group and tetrahydrofuranyl group; a substituted or unsubstituted alkylcarbonyl group or a substituted or unsubstituted arylcarbonyl group such as trifluoroacetyl group, acetyl group, 4-chlorobenzoyl group and benzoyl group; a substituted or unsubstituted alkyloxycarbonyl group, an unsubstituted alkenyloxycarbonyl group or a substituted or unsubstituted aryloxycarbonyl group such as benzyloxycarbonyl group, 4-methoxybenzyloxycarbonyl group, 9-fluorenylmethoxycarbonyl group, methoxycarbonyl group, ethoxycarbonyl group, isobutoxycarbonyl group, tert-butoxycarbonyl group, vinyloxycarbonyl group, allyloxycarbonyl group, 4-nitrophenyloxycarbonyl group and phenyloxycarbonyl group; and a substituted silyl group such as trimethylsilyl group, triethylsilyl group, triisopropylsilyl group, tert-butyldimethylsilyl group and tert-butyldiphenylsilyl group.

Examples of the protective group for free amino group, alkylamino group or arylamino group are those which have been commonly used as protective groups for free amino group, alkylamino group or arylamino group including a substituted alkyl group or an unsubstituted alkenyl group such as benzyl group, trityl group, diphenylmethyl group, (4-methoxyphenyl)diphenylmethyl group and allyl group; hydrocarbonyl group is formyl group; a substituted or unsubstituted alkylcarbonyl group, a substituted or unsubstituted arylcarbonyl group or an unsubstituted heterocyclic carbonyl group such as trichloroacetyl group, trifluoroacetyl group, acetyl group, 4-chlorobenzoyl group, benzoyl group and picolinoyl group; a substituted or unsubstituted alkyloxycarbonyl group or a substituted or unsubstituted aryloxycarbonyl group such as 2,2,2-trichloroethoxycarbonyl group, benzyloxycarbonyl group, diphenylmethoxy carbonyl group, methoxycarbonyl group, isobutoxycarbonyl group, tert-butoxycarbonyl group, 3-nitrophenoxycarbonyl group and phenoxycarbonyl group; and a substituted or unsubstituted alkylsulfonyl group or a substituted or unsubstituted arylsulfonyl group such as benzylsulfonyl group, tolylsulfonyl group, methylsulfonyl group, 4-chlorophenylsulfonyl group, 2,4,6-trimethylphenylsulfonyl group and phenylsulfonyl group.

The nitrogen atom of the indazole ring of the present invention compound can be protected with a protective group.

Examples of the protective group for a nitrogen atom of the indazole ring are those which have been commonly used as the protective groups for a nitrogen atom of the indazole ring including a substituted alkyl group or an unsubstituted alkenyl group such as benzyl group, trityl group, diphenylmethyl group, (4-methoxyphenyl)diphenylmethyl group and allyl group; hydrocarbonyl group is formyl group; a substituted or unsubstituted alkylcarbonyl group, a substituted or unsubstituted arylcarbonyl group or an unsubstituted heterocyclic carbonyl group such as trichloroacetyl group, trifluoroacetyl group, acetyl group, 4-chlorobenzoyl group, benzoyl group and picolinoyl group; a substituted or unsubstituted alkyloxycarbonyl group or a substituted or unsubstituted aryloxycarbonyl group such as 2,2,2-trichloroethoxycarbonyl group, benzyloxycarbonyl group, diphenylmethoxycarbonyl group, methoxycarbonyl group, isobutoxycarbonyl group, tert-butoxycarbonyl group, phenoxycarbonyl group and 3-nitrophenoxycarbonyl group; and a substituted or unsubstituted alkylsulfonyl group or a substituted or unsubstituted arylsulfonyl group such as benzylsulfonyl group, tolylsulfonyl group, methylsulfonyl group, 4-chlorophenylsulfonyl group, 2,4,6-trimethylphenylsulfonyl group and phenylsulfonyl group.

With regard to a "salt" in the present invention compound, there is no particular limitation so far as it is a pharmaceutically acceptable salt and its examples are a salt with inorganic acid such as hydrochloric acid, hydrobromic acid, hydroiodic acid, nitric acid, sulfuric acid and phosphoric acid; a salt with organic acid such as acetic acid, fumaric acid, maleic acid, succinic acid, citric acid, tartaric acid, adipic acid, lactic acid, methanesulfonic acid, trifluoromethanesulfonic acid, p-toluenesulfonic acid and trifluoroacetic acid; a salt with alkali metal such as lithium, sodium and potassium; a salt with alkali earth metal such as calcium and magnesium; and a quaternary salt with ammonia and methyl iodide.

In the "plural groups" in the present invention, such groups can be the same or different. Incidentally, halogen atom, hydrogen atom and monocyclic heterocycle are also covered within a "group".

When there are geometrical isomers such as a syn-anti isomer and an optical isomer in the present invention compound, such an isomer is also within the scope of the present invention.

The present invention compound can be also in a form of a hydrate or a solvate.

Preferred examples of the present invention compound defined as above in the formula [I] are compounds where the aforementioned substituted alkoxy group, substituted alkyl group, substituted alkenyl group and/or substituted aryl group are (is) those (that) substituted with one or more group(s) selected from the group consisting of halogen atom, hydroxyl group, an unsubstituted alkoxy group, an unsubstituted aryl group, hydroxyimino group and an unsubstituted alkoxyimino group, or a salt thereof.

Other preferred examples of the present invention compound defined as above in the formula [I] are the compounds which are defined by one or more combination(s) of those chosen from the following six choices of i) to vi) or a salt thereof.

i) a ring X is benzene ring or pyridine ring;
ii) $R^1$ and $R^2$ are hydrogen atom or alkyl group;
iii) $R^1$ and $R^2$ are bonded to form an unsubstituted cycloalkane ring;
iv) $R^3$ is hydrogen atom, a substituted alkyl group, an unsubstituted alkenyl group, carboxyl group or an ester or an amide thereof, amino group or cyano group;
v) $R^4$ is hydrogen atom, hydroxyl group, a substituted or unsubstituted alkoxy group, an unsubstituted alkenyloxy group, an unsubstituted cycloalkyloxy group, a substituted or unsubstituted alkyl group, an unsubstituted alkenyl group, an unsubstituted cycloalkyl group, amino group, an unsubstituted alkylamino group, nitro group, cyano group or a monocyclic heterocycle group; and
vi) $R^5$ is halogen atom or hydrogen atom.

Preferred examples of the formula [I] among the above are as follows.

i) a ring X is benzene ring or pyridine ring;
ii) $R^1$ and $R^2$ are hydrogen atom or alkyl group;
iii) $R^1$ and $R^2$ can be bonded to form an unsubstituted cycloalkane ring;
iv) $R^3$ is hydrogen atom, a substituted alkyl group, an unsubstituted alkenyl group, carboxyl group or an ester or an amide thereof, amino group or cyano group;
v) $R^4$ is hydrogen atom, hydroxyl group, a substituted or unsubstituted alkoxy group, an unsubstituted alkenyloxy group, an unsubstituted cycloalkyloxy group, a substituted or unsubstituted alkyl group, an unsubstituted alkenyl group, an unsubstituted cycloalkyl group, amino group, an unsubstituted alkylamino group, nitro group, cyano group or a monocyclic heterocycle group; and
vi) $R^5$ is halogen atom or hydrogen atom.

In the present invention compound defined as above in the formula [I], other preferred examples are compounds where the substituted alkoxy group is that substituted with halogen atom and/or the substituted alkyl group is that substituted with one or more group(s) selected from the group consisting of hydroxyl group and hydroxyimino group, or a salt thereof.

More preferred examples of the present invention compound defined as above in the formula [I] are the compounds which are defined by one or more combination(s) of those chosen from the following six choices of i) to vi) or a salt thereof.

i) a ring X is benzene ring or pyridine ring;
ii) $R^1$ and $R^2$ are hydrogen atom, methyl group or ethyl group;
iii) $R^1$ and $R^2$ are bonded to form a cyclopentane ring;
iv) $R^3$ is hydrogen atom, hydroxymethyl group, hydroxyiminomethyl group, 1-methylvinyl group, carboxyl group, methoxycarbonyl group, aminocarbonyl group, amino group or cyano group;
v) $R^4$ is hydrogen atom, hydroxyl group, methoxy group, ethoxy group, n-propyloxy group, n-butyloxy group, isopropyloxy group, difluoromethoxy group, 2-fluoroethoxy group, 2,2,2-trifluoroethoxy group, allyloxy group, cyclopropyloxy group, cyclopropylmethyloxy group, ethyl group, vinyl group, hydroxymethyl group, 1-hydroxyethyl group, 2-hydroxyethyl group, cyclopropyl group, amino group, methylamino group, dimethylamino group, diethylamino group, nitro group, cyano group, pyrrolidine ring, pyrrole ring, pyrazole ring, oxazole ring, isoxazole ring, piperidine ring, pyridine ring or morpholine ring; and
vi) $R^5$ is chlorine atom or hydrogen atom.

The particularly preferred examples in the formula [I] are the following compounds in the formula [I] or a salt thereof.

i) a ring X is benzene ring or pyridine ring;
ii) $R^1$ and $R^2$ are hydrogen atom, methyl group or ethyl group;
iii) $R^1$ and $R^2$ can be bonded to form a cyclopentane ring;
iv) $R^3$ is hydrogen atom, hydroxymethyl group, hydroxyiminomethyl group, 1-methylvinyl group, carboxyl group, methoxycarbonyl group, aminocarbonyl group, amino group or cyano group;
v) $R^4$ is hydrogen atom, hydroxyl group, methoxy group, ethoxy group, n-propyloxy group, n-butyloxy group, isopropyloxy group, difluoromethoxy group, 2-fluoroethoxy group, 2,2,2-trifluoroethoxy group, allyloxy group, cyclopropyloxy group, cyclopropylmethyloxy group, ethyl group, vinyl group, hydroxymethyl group, 1-hydroxyethyl group, 2-hydroxyethyl group, cyclopropyl group, amino group, methylamino group, dimethylamino group, diethylamino group, nitro group, cyano group, pyrrolidine ring, pyrrole ring, pyrazole ring, oxazole ring, isoxazole ring, piperidine ring, pyridine ring or morpholine ring; and
vi) $R^5$ is chlorine atom or hydrogen atom.

As mentioned hereinabove already, the present invention compound has the chemical structural characteristic as shown in the following 1) to 4) and, in addition, each of such chemical structural characteristics of 1) to 4) and/or a combination thereof are/is very important in exhibiting the inhibiting action of the present invention compound for Rho kinase.

1) An indazole ring is a main skeleton.
2) A ring X is directly bonded to an indazole ring.
3) A ring X has an amino-substituted alkyl group or cycloalkyl group.
4) In the above 3), the amino group is located at 1-position of the alkyl group or the cycloalkyl group.

In particular, in addition to those 1) to 4), the present invention compound in which 5) the carbon atom in which the amino group of the above 3) is introduced is not an asymmetric carbon atom exhibits a particularly good Rho kinase inhibiting action and the present invention compound having those chemical structure is more preferred.

Further, the present invention compound in which a ring X is directly bonded to the 5-position of the indazole ring exhibits much more Rho kinase inhibiting action and the present invention compound where the ring X is located at that position is still more preferred.

Incidentally, the present invention compound in which the alkyl group or the cycloalkyl group which is substituted with an amino group as mentioned in the above 3) is a) bonded to 4-position of a benzene ring when the ring X is benzene and b) bonded to 5-position of a pyridine ring when the ring X is a pyridine ring exhibits far more Rho kinase inhibiting action and the present invention compound where the ring X is located at such that position is particularly preferred.

The particularly preferred examples of the present invention compound are the compounds which will be shown below or a salt thereof. Incidentally, in the chemical structural formulae, Me is methyl group, Et is ethyl group, Bn is benzyl group and Ac is acetyl group unless otherwise mentioned.

5-[4-(1-Amino-1-methylethyl)phenyl]-1H-indazole

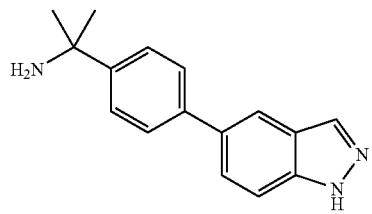

1-Acetyl-5-[4-(1-amino-1-methylethyl)phenyl]-1H-indazole

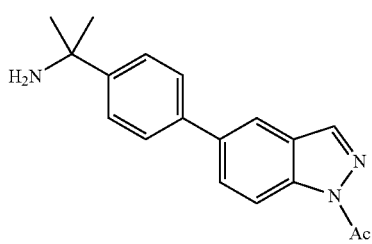

5-[5-(1-Amino-1-methylethyl)pyridin-2-yl]-1H-indazole

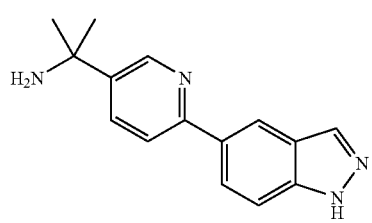

5-[4-(1-Amino-1-methylethyl)phenyl]-4-nitro-1H-indazole

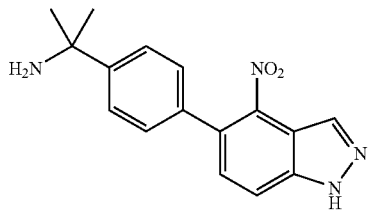

4-Amino-5-[4-(1-amino-1-methylethyl)phenyl]-1H-indazole

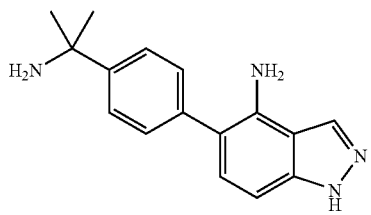

5-[4-(1-Amino-1-methylethyl)phenyl]-4-benzylamino-1H-indazole

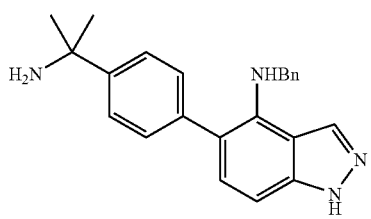

5-[4-(1-Amino-1-methylethyl)phenyl]-4-methylamino-1H-indazole

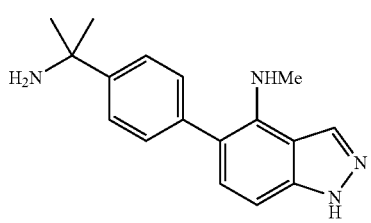

5-[4-(1-Amino-1-methylethyl)phenyl]-3-methoxy-
carbonyl-1H-indazole

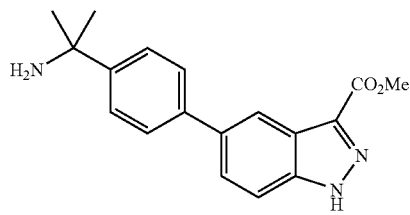

5-[4-(1-Amino-1-methylethyl)phenyl]-3-carboxy-
1H-indazole

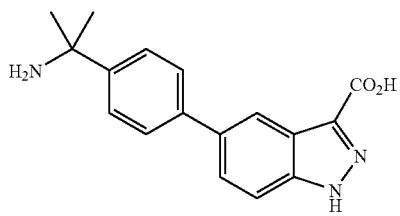

3-Aminocarbonyl-5-[4-(1-amino-1-methylethyl)
phenyl]-1H-indazole

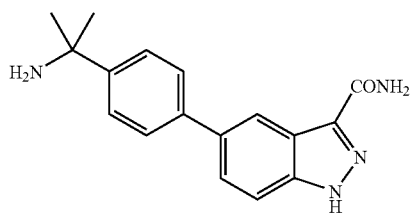

3-Amino-5-[4-(1-amino-1-methylethyl)phenyl]-1H-
indazole

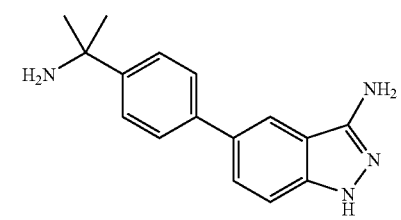

5-[4-(1-Amino-1-methylethyl)phenyl]-3-hydroxy-
iminomethyl-1H-indazole

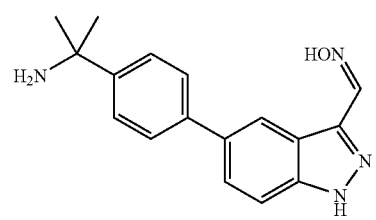

5-[4-(1-Amino-1-methylethyl)phenyl]-3-cyano-1H-
indazole

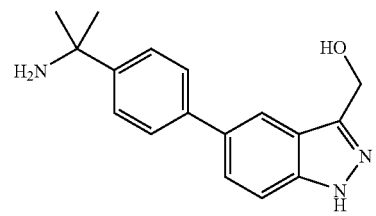

5-[4-(1-Amino-1-methylethyl)phenyl]-3-hydroxym-
ethyl-1H-indazole

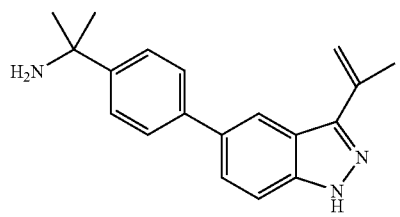

5-[4-(1-Amino-1-methylethyl)phenyl]-3-(1-meth-
ylvinyl)-1H-indazole

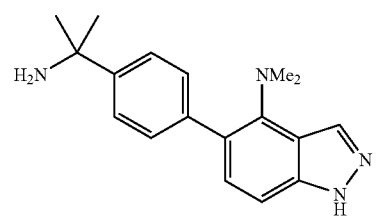

5-[4-(1-Amino-1-methylethyl)phenyl]-4-dimethy-
lamino-1H-indazole

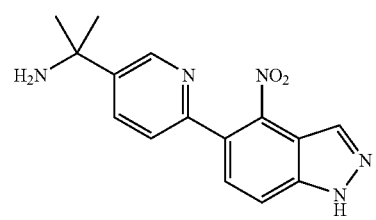

5-[5-(1-Amino-1-methylethyl)pyridin-2-yl]-4-nitro-
1H-indazole 4-(N-Acetylamino)-5-[4-(1-amino-1-methylethyl)phenyl]-1H-indazole

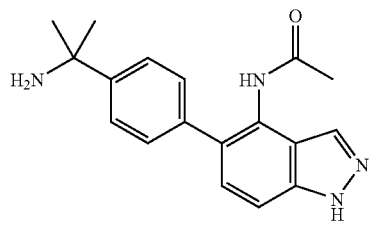

5-[4-(Aminomethyl)phenyl]-4-nitro-1H-indazole

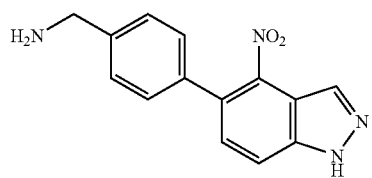

4-Amino-5-[4-(aminomethyl)phenyl]-1H-indazole

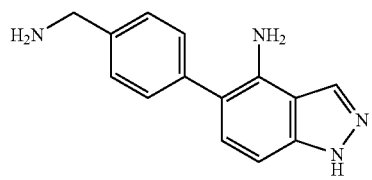

4-Amino-5-[4-(1-aminocyclopentyl)phenyl]-1H-indazole

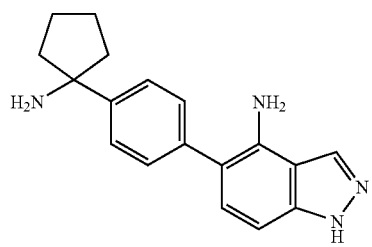

4-Amino-5-[4-(1-amino-1-ethylpropyl)phenyl]-1H-indazole

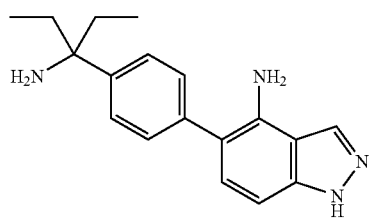

5-[4-(Aminomethyl)phenyl]-4-dimethylamino-1H-indazole

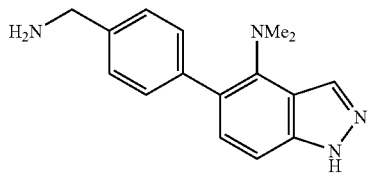

5-[4-(1-Aminocyclopentyl)phenyl]-4-dimethylamino-1H-indazole

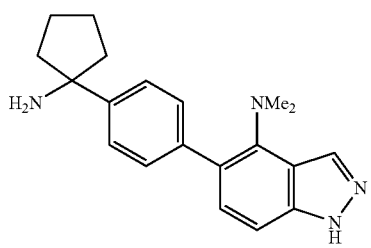

5-[4-(1-Amino-1-ethylpropyl)phenyl]-4-dimethylamino-1H-indazole

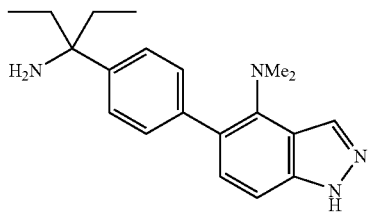

5-[4-(1-Aminoethyl)phenyl]-4-dimethylamino-1H-indazole

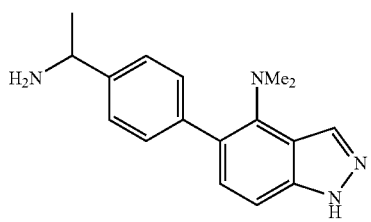

5-[5-(1-Amino-1-methylethyl)-3-chloropyridin-2-yl]-1H-indazole

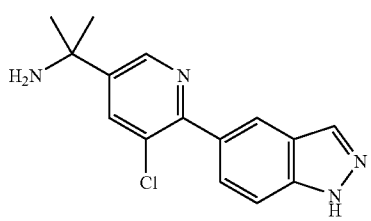

5-[5-(1-Amino-1-methylethyl)pyridin-2-yl]-4-ethyl-1H-indazole

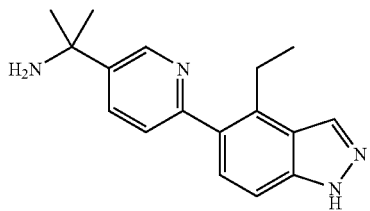

5-[5-(1-Amino-1-methylethyl)pyridin-2-yl]-4-cyclopropyl-1H-indazole

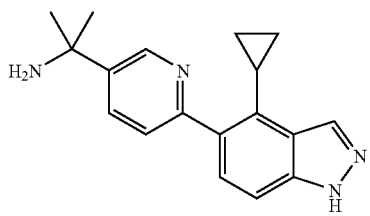

5-[5-(1-Amino-1-methylethyl)pyridin-2-yl]-4-vinyl-1H-indazole

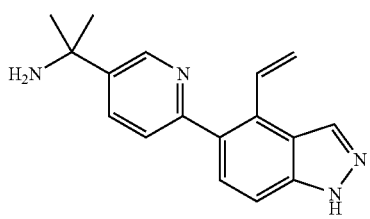

5-[4-(1-Amino-1-methylethyl)phenyl]-4-diethylamino-1H-indazole

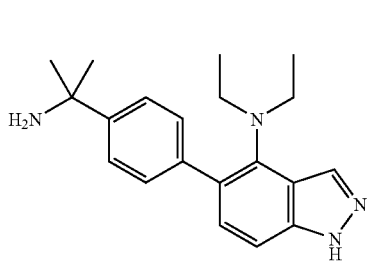

5-[4-(1-Amino-1-methylethyl)phenyl]-4-(2-hydroxyethyl)-1H-indazole

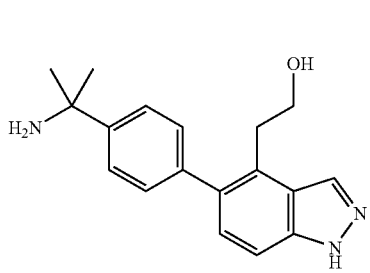

5-[5-(1-Amino-1-methylethyl)pyridin-2-yl]-4-(2-hydroxyethyl)-1H-indazole

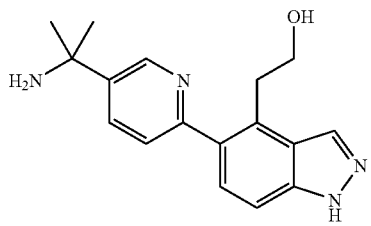

5-[4-(1-Amino-1-methylethyl)phenyl]-4-(1-hydroxyethyl)-1H-indazole

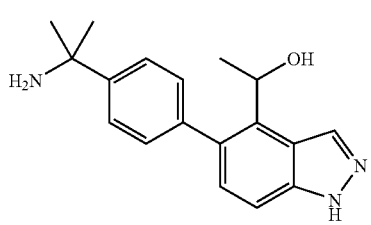

5-[4-(1-Amino-1-methylethyl)phenyl]-4-hydroxymethyl-1H-indazole

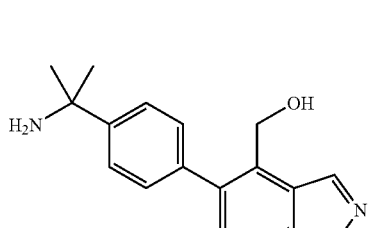

5-[4-(1-Amino-1-methylethyl)phenyl]-4-cyano-1H-indazole

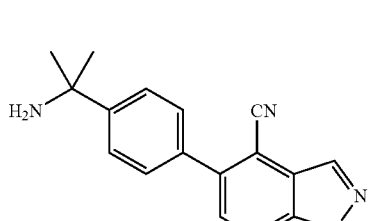

6-[4-(1-Amino-1-methylethyl)phenyl]-1H-indazole

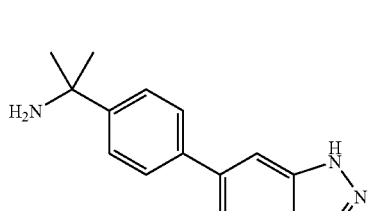

1-Acetyl-6-[4-(1-amino-1-methylethyl)phenyl]-1H-indazole

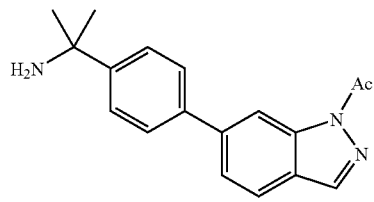

5-[4-(1-Amino-1-methylethyl)phenyl]-4-(pyrrol-1-yl)-1H-indazole

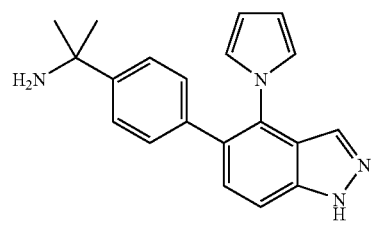

5-[4-(1-Amino-1-methylethyl)phenyl]-4-isopropoxy-1H-indazole

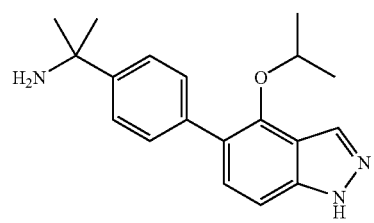

5-[4-(1-Amino-1-methylethyl)phenyl]-4-(piperidin-1-yl)-1H-indazole

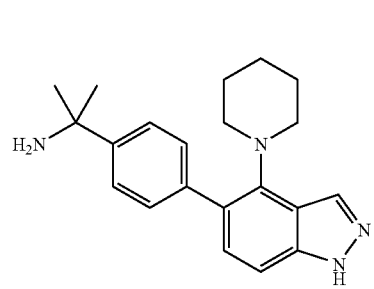

5-[4-(1-Amino-1-methylethyl)phenyl]-4-(pyrrolidin-1-yl)-1H-indazole

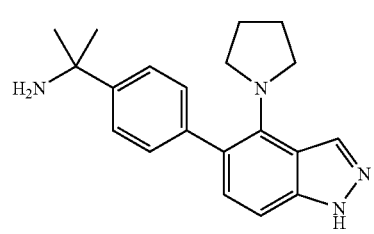

5-[4-(1-Amino-1-methylethyl)phenyl]-4-(morpholin-4-yl)-1H-indazole

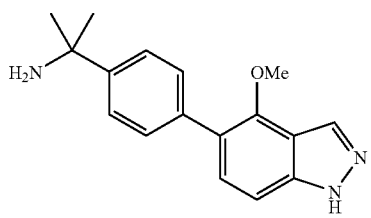

5-[4-(1-Amino-1-methylethyl)phenyl]-4-methoxy-1H-indazole

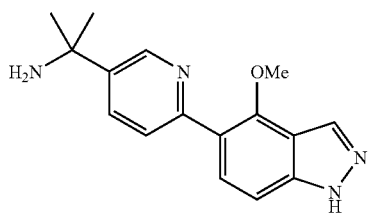

5-[5-(1-Amino-1-methylethyl)pyridin-2-yl]-4-methoxy-1H-indazole

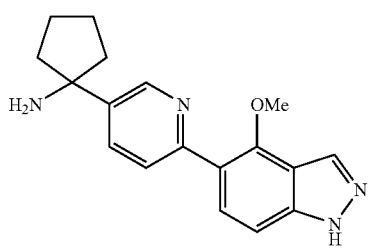

5-[5-(1-Aminocyclopentyl)pyridin-2-yl]-4-methoxy-1H-indazole

23

5-[5-(1-Amino-1-methylethyl)pyridin-2-yl]-4-
ethoxy-1H-indazole

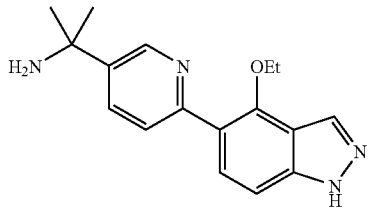

5-[4-(1-Amino-1-methylethyl)phenyl]-4-hydroxy-
1H-indazole

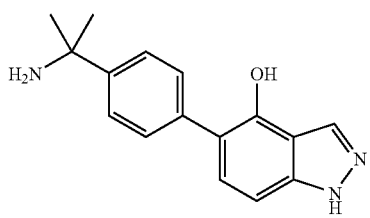

5-[4-(1-Amino-1-methylethyl)phenyl]-4-ethoxy-1H-
indazole

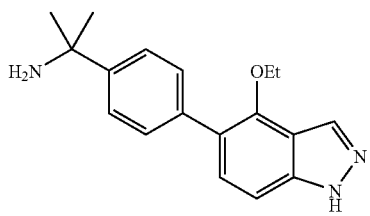

5-[5-(1-Amino-1-methylethyl)pyridin-2-yl]-4-iso-
propoxy-1H-indazole

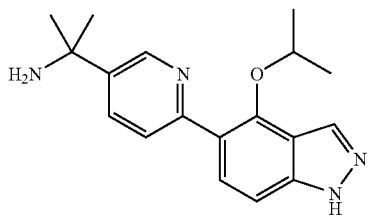

5-[5-(1-Amino-1-ethylpropyl)pyridin-2-yl]-4-meth-
oxy-1H-indazole

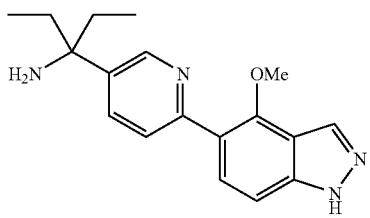

24

5-[4-(1-Amino-1-methylethyl)phenyl]-4-n-propoxy-
1H-indazole

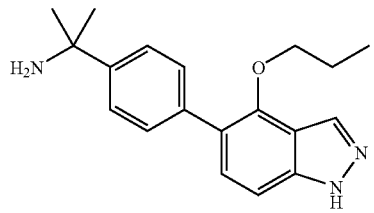

5-[4-(1-Amino-1-methylethyl)phenyl]-4-difluo-
romethoxy-1H-indazole

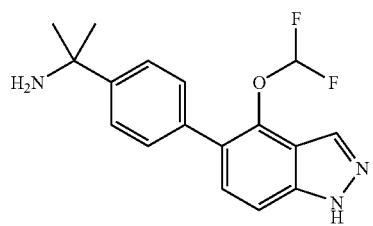

5-[4-(1-Amino-1-methylethyl)phenyl]-4-(2,2,2-trif-
luoroethoxy)-1H-indazole

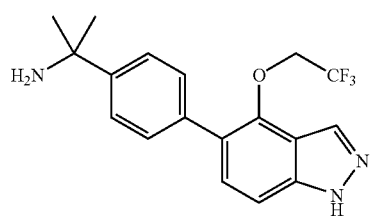

5-[4-(1-Amino-1-methylethyl)phenyl]-4-n-butoxy-
1H-indazole

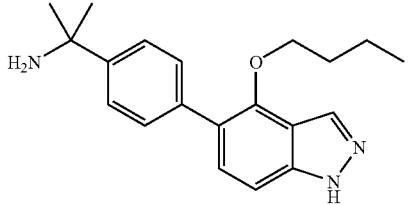

5-[4-(1-Amino-1-methylethyl)phenyl]-4-(2-fluoroet-
hoxy)-1H-indazole

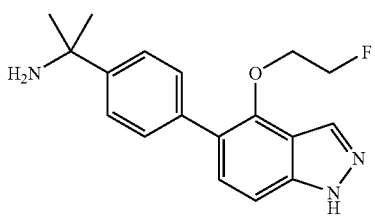

25

4-Allyloxy-5-[4-(1-amino-1-methylethyl)phenyl]-1H-indazole

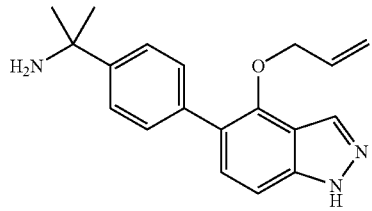

5-[5-(1-Amino-1-methylethyl)pyridin-2-yl]-4-n-propoxy-1H-indazole

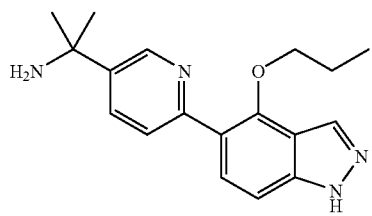

5-[5-(1-Amino-1-methylethyl)pyridin-2-yl]-4-difluoromethoxy-1H-indazole

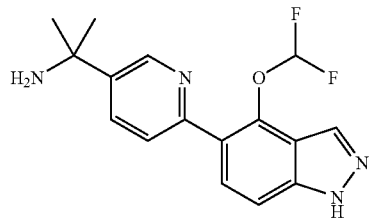

5-[5-(1-Amino-1-ethylpropyl)pyridin-2-yl]-4-ethoxy-1H-indazole

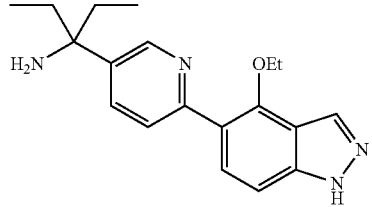

5-[4-(1-Amino-1-methylethyl)phenyl]-4-(pyridin-4-yl)-1H-indazole

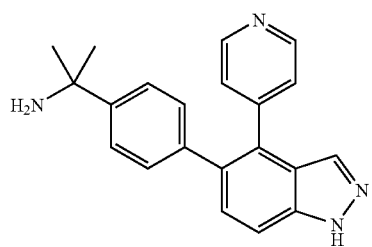

26

5-[4-(1-Amino-1-methylethyl)phenyl]-4-(pyridin-3-yl)-1H-indazole

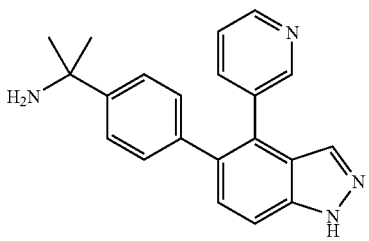

5-[4-(1-Amino-1-methylethyl)phenyl]-4-(pyridin-2-yl)-1H-indazole

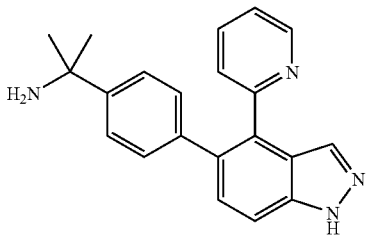

5-[4-(1-Amino-1-methylethyl)phenyl]-4-(pyrazol-4-yl)-1H-indazole

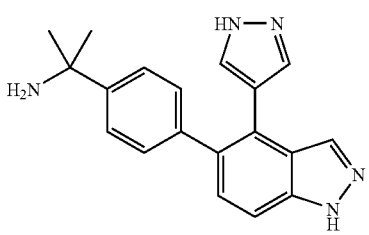

5-[5-(1-Amino-1-methylethyl)pyridin-2-yl]-4-(pyrazol-4-yl)-1H-indazole

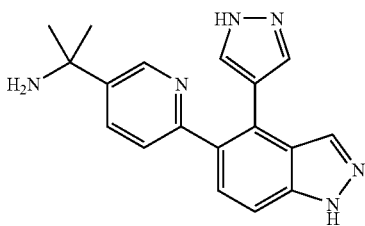

27

5-[4-(1-Amino-1-methylethyl)phenyl]-4-(oxazol-5-yl)-1H-indazole

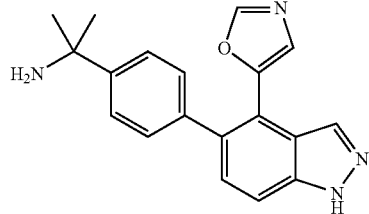

5-[4-(1-Amino-1-methylethyl)phenyl]-4-(pyrazol-3-yl)-1H-indazole

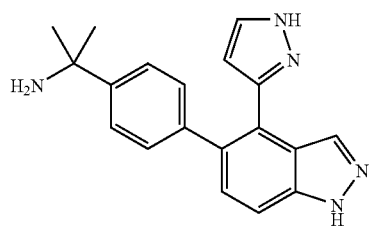

5-[4-(1-Amino-1-methylethyl)phenyl]-4-(isoxazol-5-yl)-1H-indazole

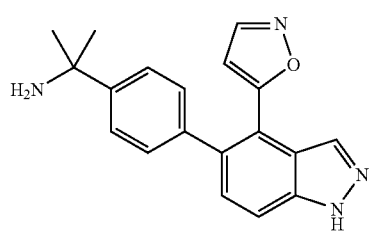

5-[5-(1-Amino-1-methylethyl)pyridin-2-yl]-4-hydroxy-1H-indazole

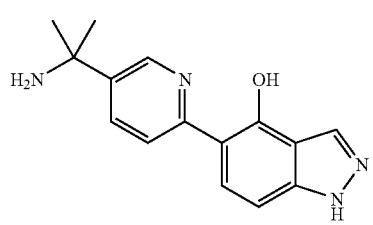

28

5-[5-(1-Amino-1-methylethyl)pyridin-2-yl]-4-cyclopropyloxy-1H-indazole

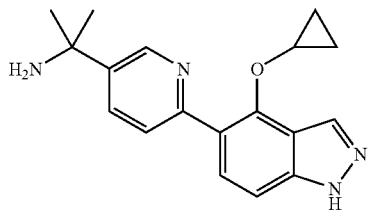

5-[5-(1-Amino-1-ethylpropyl)pyridin-2-yl]-4-cyclopropyloxy-1H-indazole

5-[4-(1-Amino-1-ethylpropyl)phenyl]-4-difluoromethoxy-1H-indazole

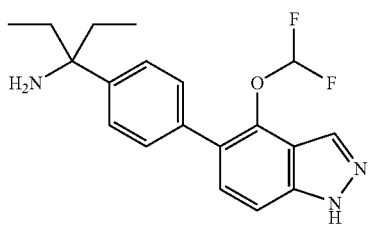

5-[5-(1-Amino-1-methylethyl)pyridin-2-yl]-4-cyclopropylmethyloxy-1H-indazole

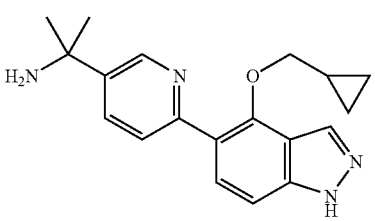

Representative process for the production of the present invention compound will be shown below. Incidentally, specific process for the production of each of the present invention compounds will be illustrated in detail under the item of "Production Examples" in the Examples which will be mentioned later.

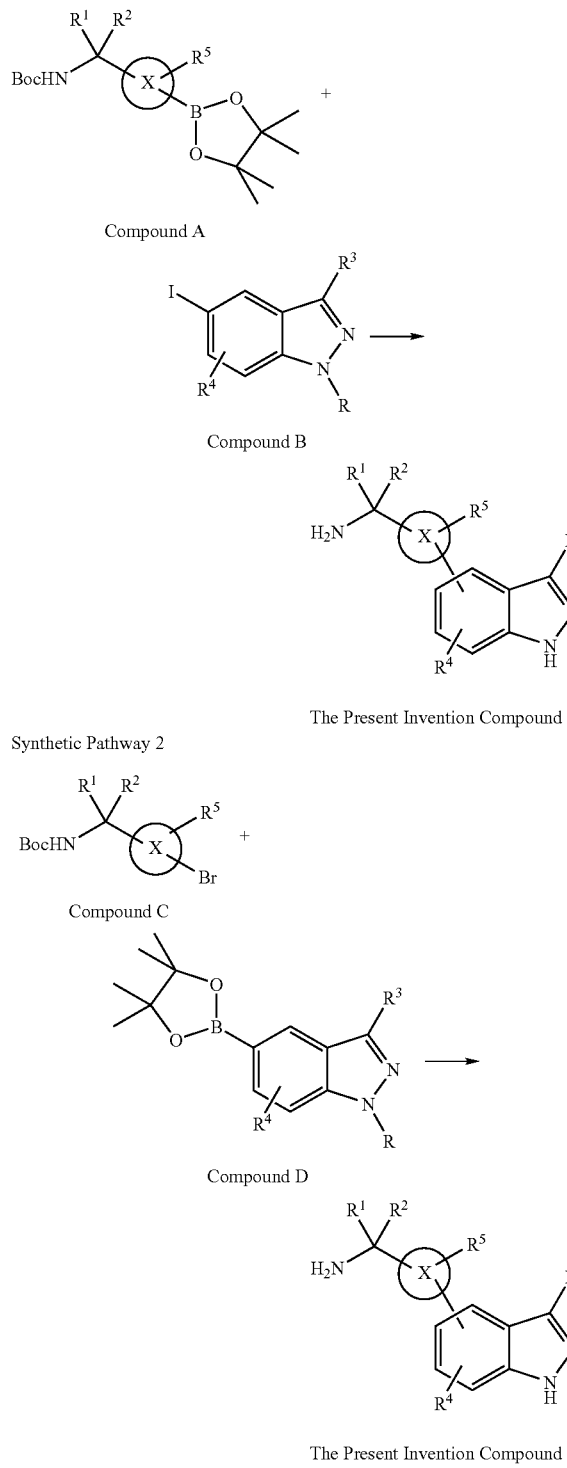

Synthetic pathway 1 or synthetic pathway 2: The compound A is subjected to a coupling reaction with the compound B, or the compound C is subjected to a coupling reaction with the compound D, in an organic solvent in the presence of a metal catalyst and/or a base catalyst whereupon the present invention compound is able to be produced.

When a protective group is used for the convenience of the production in the aforementioned production process, the protective group is able to be eliminated by a commonly used method after the reaction.

With regard to the substituent(s) on the ring X and/or the indazole ring, desired substituent(s) may be introduced in its initial stage or it is also acceptable that, after the fundamental skeleton is manufactured by the aforementioned method, the desired substituent(s) may be introduced into the fundamental skeleton using oxidation, reduction, alkylation, esterification, amidation, oximation, dehydrating reaction, deprotecting reaction, acetylation, hydrolysis, triflating, coupling reaction, cyclization reaction and/or a commonly used synthetic method in which the aforementioned reactions are combined.

With regard to a process for the production of synthetic intermediates for the present invention compound, that will be illustrated in detail under the item of "Production Examples" in the Examples which will be mentioned later.

In order to find the utility of the present invention compound, a Rho kinase inhibiting activity of the present invention compound was evaluated. The details thereof will be illustrated under the item of "Pharmacological Test (Test for Evaluation of Rho Kinase Inhibiting Activity)" in the Examples which will be mentioned later. The evaluation of the Rho kinase inhibiting activity of the present invention compound was carried out in accordance with the methods mentioned in *J. Biol. Chem.*, 274, 32418 (1999) by Kaibuchi, et al. and mentioned in the instruction manual for use attached to the commercially available activated ROCK II [Upstate Biotechnology, Catalog No. 14-338 (5 units/50 µl)]. As a result, the present invention compound was found to have an excellent Rho kinase inhibiting action and to be very useful as a treating agent for diseases in which Rho kinase is involved.

Further, in order to check the application of the present invention compound to specific diseases in which Rho kinase is involved, an intraocular pressure-reducing action of the present invention compound was also studied. The details thereof will be illustrated under the item of "Pharmacological Test (Test for Measurement of Intraocular Pressure Reduction)" in the Examples which will be mentioned later. It was found that, when the present invention compound was topically administered to the eye of cynomolgus monkey (*Macaca fascicularis*) (sex: male; one group comprising 2 to 6 monkeys), the present invention compound exhibited an excellent intraocular pressure-reducing action and is useful as a treating agent for eye diseases such as glaucoma as well.

As mentioned already, Rho kinase has been known to deeply participate in diseases such as hypertension, angina pectoris, asthma, peripheral circular disorder, premature delivery, arteriosclerosis, cancer, inflammatory diseases, autoimmune diseases, AIDS, fertilization and implantation of fertilized egg, osteoporosis, cerebral function disturbance, gastrointestinal dysfunction by bacteria, glaucoma and retinopathy. Accordingly, the present invention compound is very much expected as a treating agent for diseases in which Rho kinase is involved.

A Rho kinase inhibitor in the present invention means a compound which inhibits a serine/threonine kinase which is activated as a result of activation of Rho.

Examples of glaucoma in the present invention are primary open angle glaucoma, normal tension glaucoma, hypersecretion glaucoma, ocular hypertension, acute angle-closure glaucoma, chronic angle-closure glaucoma, combined mechanism glaucoma, steroid glaucoma, amyloid glaucoma, neovascular glaucoma, malignant glaucoma, capsular glaucoma and plateau iris syndrome.

The present invention compound is able to be administered either orally or parenterally. Examples of the dosage form are tablets, capsules, granules, powders, injections and eye drops and they are able to be made into the pharmaceutical preparations by combining the commonly known techniques.

For example, preparations for oral use such as tablets, capsules, granules and powders are able to be prepared by combining the present invention compound together, if necessary, with excipient such as lactose, mannitol, starch, crystalline cellulose, light anhydrous silicic acid, calcium carbonate and calcium hydrogen phosphate; lubricant such as stearic acid, magnesium stearate and talc; binder such as starch, hydroxypropyl cellulose, hydroxypropyl methylcellulose and polyvinylpyrrolidone; disintegrating agent such as carboxymethyl cellulose, lowly substituted hydroxypropyl methylcellulose and calcium citrate; coating agent such as hydroxypropyl methylcellulose, macrogol and silicone resin; stabilizer such as ethyl p-hydroxybenzoate and benzyl alcohol; and corrigent such as sweetener, sour agent and flavor.

Parenteral preparations such as injections and eye drops are able to be prepared by combining the present invention compound together, if necessary, with isotonicity agent such as glycerol, propylene glycol, sodium chloride, potassium chloride, sorbitol and mannitol; buffer such as phosphoric acid, phosphate, citric acid, glacial acetic acid, ε-aminocaproic acid and trometamol; pH adjusting agent such as hydrochloric acid, citric acid, phosphoric acid, glacial acetic acid, sodium hydroxide, potassium hydroxide, sodium carbonate and sodium hydrogen carbonate; solubilizing or dispersing agent such as polysorbate 80, polyoxyethylene hydrogenated castor oil 60, macrogol 4000, purified soybean lecithin and polyoxyethylene (160) polyoxypropylene (30) glycol; polymer of a cellulose type such as hydroxypropyl methylcellulose and hydroxypropyl cellulose; thickener such as polyvinyl alcohol and polyvinylpyrrolidone; stabilizer such as edetic acid and sodium edetate; commonly used preservative or antiseptic such as sorbic acid, potassium sorbate, benzalkonium chloride, benzethonium chloride, methyl p-hydroxybenzoate, propyl p-hydroxybenzoate and chlorobutanol; and soothing agent such as chlorobutanol, benzyl alcohol and lidocaine.

In the case of injections and eye drops, it is desired that pH is adjusted to 4.0 to 8.0 and that osmotic pressure ratio is adjusted to about 1.0.

Dose of the present invention compound is able to be appropriately selected depending upon symptom, age, dosage form, etc. For example, in the case of oral preparations, usually 0.01 to 1,000 mg per day, preferably 1 to 100 mg per day is able to be administered once daily or by dividing into several times a day. In the case of eye drops, usually those having a concentration of 0.0001% to 10% (w/v), preferably 0.01% to 5% (w/v) is able to be administered once daily or by dividing into several times a day.

Production examples of the present invention compounds (Examples 1 to 31) and synthetic intermediates (Referential Examples 1 to 48), pharmaceutical preparation examples and results of pharmacological test are shown as hereunder. Incidentally, those examples are for better understanding of the present invention and are not intended to limit the scope of the present invention. Rf values in the physical property in Examples stand for the data measured by a thin-layer chromatography (using TLC Plate Silica Gel 60 $F_{254}$ (trade name) manufactured by Merck) and, in the chemical structural formulae, Me stands for methyl group, Bn stands for benzyl group, Ac stands for acetyl group, Boc stands for tert-butoxycarbonyl group, Tf stands for trifluoromethanesulfonyl group, TBS stands for tert-butyldimethylsilyl group and THP stands for tetrahydropyranyl group unless otherwise mentioned.

PRODUCTION EXAMPLES

Referential Example 1

Synthesis of 1-bromo-4-(1-cyano-1-methylethyl) benzene (Referential Compound 1-1)

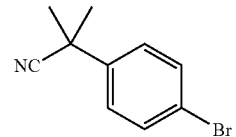

Sodium hydride (a 60% dispersion in mineral oil) (45 g, 1.100 mmol) was dividedly added at 0° C., in an argon stream with stirring, to a solution of 100 g (510 mmol) of 4-bromophenylacetonitrile in 1,500 ml of N,N-dimethylformamide. Then 95 ml (1.500 mmol) of methyl iodide was dropped thereinto at 0° C. with stirring followed by stirring at 10° C. for 1 hour.

After the reaction was finished, the reaction solution was slowly added to 900 g of a saturated aqueous solution of ammonium chloride, then 500 ml of water was added thereto and the mixture was extracted with 2,000 ml of ethyl acetate. The organic layer was washed with a saturated aqueous solution of sodium chloride, dried over anhydrous sodium sulfate and concentrated in vacuo to give 110 g of the title compound as a dark brown oily substance. (Yield: 96%).

Rf value: 0.78 (n-hexane:ethyl acetate=1:1 (v/v))

Mass spectrum (CI, m/z): 224, 226 ($M^+$+1)

$^1$H-NMR spectrum (CDCl$_3$, δ ppm): 1.71 (s, 6H), 7.32-7.38 (m, 2H), 7.49-7.54 (m, 2H)

As hereunder, the referential compounds 1-2 to 1-7 were produced in accordance with the production process for the referential compound 1-1.

1-Bromo-4-(1-cyano-1-ethylpropyl)benzene (Referential Compound 1-2)

Property: light orange oily substance

Rf value: 0.64 (n-hexane:ethyl acetate=4:1 (v/v))

Mass spectrum (CI, m/z): 252, 254 ($M^+$+1)

$^1$H-NMR spectrum (CDCl$_3$, δ ppm): 0.91 (dd, J1=7.2 Hz, J2=7.2 Hz, 6H), 1.87 (dq, J1=14.3 Hz, J2=7.2 Hz, 2H), 2.04 (dq, J1=14.3 Hz, J2=7.2 Hz, 2H), 7.21-7.28 (m, 2H), 7.48-7.55 (m, 2H)

1-Bromo-4-(1-cyanocyclopentyl)benzene (Referential Compound 1-3)

Property: brown oily substance

Rf value: 0.50 (n-hexane:ethyl acetate=4:1 (v/v))

Mass spectrum (EI, m/z): 249, 251 ($M^+$)

$^1$H-NMR spectrum (CDCl$_3$, δ ppm): 1.90-2.10 (m, 6H), 2.40-2.55 (m, 2H), 7.30-7.36 (m, 2H), 7.45-7.55 (m, 2H)

2-Bromo-5-(1-cyano-1-methylethyl)pyridine (Referential Compound 1-4)

Rf value: 0.32 (n-hexane:ethyl acetate=4:1 (v/v))

Mass spectrum (CI, m/z): 225, 227 ($M^+$+1)

IR spectrum (KBr, cm$^{-1}$): 2243

$^1$H-NMR spectrum (CDCl$_3$, δ ppm): 1.76 (s, 6H), 7.52 (d, J=8.3 Hz, 1H), 7.67 (dd, J1=8.3 Hz, J2=2.7 Hz, 1H), 8.50 (d, J=2.7 Hz, 1H)

5-(1-Cyano-1-methylethyl)-2,3-dichloropyridine (Referential Compound 1-5)

IR spectrum (KBr, cm$^{-1}$): 2239
Mass spectrum (CI, m/z): 215 (M$^+$+1)
$^1$H-NMR spectrum (CDCl$_3$, δ ppm): 1.77 (s, 6H), 7.88 (d, J=2.4 Hz, 1H), 8.43 (d, J=2.4 Hz, 1H)

2-Bromo-5-(1-cyanocyclopentyl)pyridine (Referential Compound 1-6)

Property: colorless oily substance
Rf value: 0.60 (n-hexane:ethyl acetate=1:1 (v/v))
Mass spectrum (CI, m/z): 251, 253 (M$^+$+1)
$^1$H-NMR spectrum (CDCl$_3$, δ ppm): 1.90-2.20 (m, 6H), 2.40-2.60 (m, 2H), 7.51 (dd, J1=8.3 Hz, J2=0.7 Hz, 1H), 7.64 (dd, J1=8.3 Hz, J2=2.7 Hz, 1H), 8.47 (dd, J1=2.7 Hz, J2=0.7 Hz, 1H)

2-Bromo-5-(1-cyano-1-ethylpropyl)pyridine (Referential Compound 1-7)

Rf value: 0.85 (n-hexane:ethyl acetate=1:1 (v/v))
Mass spectrum (CI, m/z): 253, 255 (M$^+$+1)
$^1$H-NMR spectrum (CDCl$_3$, δ ppm): 0.95 (dd, J1=7.3 Hz, J2=7.3 Hz, 6H), 1.91 (dq, J1=14.2 Hz, J2=±7.3 Hz, 2H), 2.12 (dq, J1=14.2 Hz, J2=7.3 Hz, 2H), 7.52 (dd, J1=8.4 Hz, J2=0.8 Hz, 1H), 7.59 (dd, J1=8.4 Hz, J2=2.7 Hz, 1H), 8.42 (dd, J1=2.7 Hz, J2=0.8 Hz, 1H)

Referential Example 2

Synthesis of 4-(1-aminocarbonyl-1-methylethyl)-1-bromobenzene (Referential Compound 2-1)

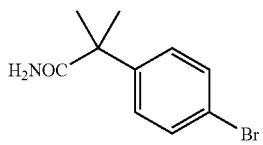

Potassium trimethylsilanolate (purity: 90%) (250 g, 1.800 mmol) was added at room temperature to a solution of 100 g (450 mmol) of 1-bromo-4-(1-cyano-1-methylethyl)benzene (referential compound 1-1) in 1,000 ml of toluene with stirring in an argon stream and the mixture was stirred for 4.5 hours under a condition of heating to reflux.

After the reaction was finished, the reaction solution was cooled down to room temperature and 500 ml of water was dropped thereinto. The mixed solution was stirred for 25 minutes at room temperature and the resulting solid was filtered off and washed with 400 ml of water to give 99 g of the title compound as white powder (yield: 92%).

Melting point: 139 to 141° C.
Rf value: 0.23 (n-hexane:ethyl acetate=1:1 (v/v))
Mass spectrum (CI, m/z): 242, 244 (M$^+$+1)
$^1$H-NMR spectrum (CDCl$_3$, δ ppm): 1.56 (s, 6H), 5.18 (brs, 1H), 5.52 (brs, 1H), 7.25-7.30 (m, 2H), 7.46-7.51 (m, 2H)

Hereinafter, referential compounds 2-2 to 2-3 were produced in accordance with the production process for the referential compound 2-1.

4-(1-Aminocarbonyl-1-ethylpropyl)-1-bromobenzene (Referential Compound 2-2)

Property: white powder
Rf value: 0.42 (n-hexane:ethyl acetate=1:1 (v/v))
Mass spectrum (CI, m/z): 270, 272 (M$^+$+1)
$^1$H-NMR spectrum (CDCl$_3$, δ ppm): 0.76 (dd, J1=7.4 Hz, J2=7.4 Hz, 6H), 1.98 (q, J=7.4 Hz, 2H), 1.99 (q, J=7.4 Hz, 2H), 5.04-5.36 (m, 2H), 7.18-7.24 (m, 2H), 7.45-7.51 (m, 2H)

4-(1-Aminocarbonylcyclopentyl)-1-bromobenzene (Referential Compound 2-3)

Property: orange powder
Melting point: 154 to 155° C.
Rf value: 0.20 (n-hexane:ethyl acetate=1:1 (v/v))
Mass spectrum (CI, m/z): 268, 270 (M$^+$+1)
$^1$H-NMR spectrum (CDCl$_3$, δ ppm): 1.50-2.13 (m, 6H), 2.40-2.55 (m, 2H), 4.95-5.35 (m, 2H), 7.20-7.30 (m, 2H), 7.45-7.55 (m, 2H)

Referential Example 3

Synthesis of 5-(1-aminocarbonyl-1-methylethyl)-2-bromopyridine (Referential Compound 3-1)

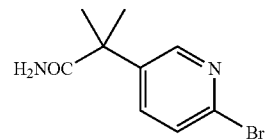

A 35% aqueous solution of hydrogen peroxide (9.60 ml, 93.3 mmol) and 1.86 g (13.5 mmol) of potassium carbonate were added, at 0° C., to a solution of 1.50 g (6.66 mmol) of 2-bromo-5-(1-cyano-1-methylethyl)pyridine (referential compound 1-4) in 15 ml of dimethyl sulfoxide and the mixture was stirred for 15 minutes. After that, a cooling bath was removed and the mixture was stirred on a water bath for 2 hours.

After the reaction was finished, the reaction solution was poured into 200 ml of water and the mixture was extracted with 500 ml of 1,2-dichloroethane. The organic layer was successively washed with water and a saturated aqueous solution of sodium chloride, dried over anhydrous magnesium sulfate and concentrated in vacuo to give 1.63 g of the title compound as white powder (yield: quantitative).

Rf value: 0.17 (n-hexane:ethyl aetate=1:1 (v/v))
Mass spectrum (CI, m/z): 243, 245 (M$^+$+1)
$^1$H-NMR spectrum (CDCl$_3$, δ ppm): 1.61 (s, 6H), 5.36 (brs, 2H), 7.47 (dd, J1=8.3 Hz, J2=0.7 Hz, 1H), 7.59 (dd, J1=8.3 Hz, J2=2.7 Hz, 1H), 8.42 (dd, J1=2.7 Hz, J2=0.7 Hz, 1H)

As hereunder, the referential compound 3-2 was produced in accordance with the production process for the referential compound 3-1.

5-(1-Aminocarbonyl-1-methylethyl)-2,3-dichloropyridine (Referential Compound 3-2)

Rf value: 0.38 (chloroform:methanol=97:3 (v/v))
Mass spectrum (CI, m/z): 233 (M$^+$+1)
$^1$H-NMR spectrum (CDCl$_3$, δ ppm): 1.62 (s, 6H), 5.50 (brs, 2H), 7.81 (d, J=2.2 Hz, 1H), 8.34 (d, J=2.2 Hz, 1H)

Referential Example 4

Synthesis of 1-bromo-4-(1-tert-butoxycarbony-lamino-1-methylethyl)benzene (Referential Compound 4-1)

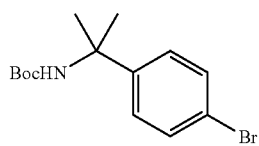

In an argon stream, 260 g (600 mmol) of [bis(trifluoroacetoxy)iodo]benzene was added, at room temperature with stirring, to a solution of 99 g (410 mmol) of 4-(1-aminocarbonyl-1-methylethyl)-1-bromobenzene (Referential Compound 2-1) in 1,000 ml of tert-butanol and the mixture was stirred for 30 minutes under a condition of heating to reflux. After that, 100 ml (1.200 mmol) of pyridine was added thereto and the mixture was stirred for 1 hour under the condition of heating to reflux.

After the reaction was finished, the reaction solution was concentrated in vacuo, 500 g of a 10 weight % aqueous solution of citric acid was added to the resulting residue and the mixture was extracted with 2,000 ml of toluene. The organic layer was successively washed with a saturated aqueous solution of sodium hydrogen carbonate and a saturated aqueous solution of sodium chloride, dried over anhydrous sodium sulfate and concentrated in vacuo. n-Hexane (200 ml) was added to the resulting residue and the resulting solid was filtered off and washed with 400 ml of cold n-hexane to give 77 g of the title compound as light brown powder (yield: 60%).

Melting point: 92 to 93° C.
Rf value: 0.56 (n-hexane:ethyl acetate=4:1 (v/v))
Mass spectrum (EI, m/z): 313, 315 ($M^+$)
$^1$H-NMR spectrum (CDCl$_3$, δ ppm): 1.36 (brs, 9H), 1.59 (s, 6H), 4.90 (brs, 1H), 7.24-7.299 (m, 2H), 7.39-7.45 (m, 2H)

As hereunder, the referential compounds 4-2 to 4-7 were produced in accordance with the production process for the referential compound 4-1.

1-Bromo-4-(1-tert-butoxycarbonylamino-1-ethylpropyl)benzene (Referential Compound 4-2)

Property: white powder
Melting point: 88 to 91° C.
Rf value: 0.61 (n-hexane:ethyl acetate=4:1 (v/v))
Mass spectrum (CI, m/z): 342, 344 ($M^++1$)
$^1$H-NMR spectrum (CDCl$_3$, δ ppm): 0.74 (dd, J1=7.3 Hz, J2=7.3 Hz, 6H), 1.39 (brs, 9H), 1.75-2.10 (m, 4H), 4.73 (brs, 1H), 7.17-7.23 (m, 2H), 7.40-7.46 (m, 2H)

1-Bromo-4-(1-tert-butoxycarbonylaminocyclopentyl)-benzene (Referential Compound 4-3)

Property: dark brown powder
Melting point: 112 to 113° C.
Rf value: 0.50 (n-hexane:ethyl acetate=4:1 (v/v))
Mass spectrum (EI, m/z): 339, 341 ($M^+$)
$^1$H-NMR spectrum (CDCl$_3$, δ ppm): 1.35 (brs, 9H), 1.70-2.35 (m, 8H), 4.86 (brs, 1H), 7.20-7.30 (m, 2H), 7.35-7.45 (m, 2H)

2-Bromo-5-(1-tert-butoxycarbonylamino-1-methylethyl)pyridine (Referential Compound 4-4)

Melting point: 100 to 103° C.
Rf value: 0.53 (n-hexane:ethyl acetate=2:1 (v/v))
Mass spectrum (CI, m/z): 315, 317 ($M^++1$)
$^1$H-NMR spectrum (CDCl$_3$, δ ppm): 1.37 (brs, 9H), 1.61 (s, 6H), 4.95 (brs, 1H), 7.41 (dd, J1=8.3 Hz, J20.7 Hz, 1H), 7.56 (dd, J1=8.3 Hz, J2=2.7 Hz, 1H), 8.40 (dd, J1=2.7 Hz, J2=0.7 Hz, 1H)

5-(1-tert-Butoxycarbonylamino-1-methylethyl)-2,3-dichoropyridine (Referential Compound 4-5)

Rf value: 0.86 (n-hexane:ethyl acetate=3:2 (v/v))
Mass spectrum (CI, m/z): 305 ($M^++1$)
$^1$H-NMR spectrum (CDCl$_3$, δ ppm): 1.37 (brs, 9H), 1.62 (s, 6H), 4.95 (brs, 1H), 7.76 (d, J=2.4 Hz, 1H), 8.32 (d, J=2.4 Hz, 1H)

2-Bromo-5-(1-tert-butoxycarbonylaminocyclopentyl)-pyridine (Referential Compound 4-6)

Property: white powder
Melting point: 123 to 124° C.
Rf value: 0.30 (n-hexane:ethyl acetate=4:1 (v/v))
Mass spectrum (CI, m/z): 341, 343 ($M^++1$)
$^1$H-NMR spectrum —(CDCl$_3$, δ ppm): 1.35 (brs, 9H), 1.70-2.40 (m, 8H), 4.89 (brs, 1H), 7.41 (dd, J1=8.3 Hz, J2=0.7 Hz, 1H), 7.58 (dd, J1=8.3 Hz, J2=2.7 Hz, 1H), 8.40 (dd, J1=2.7 Hz, J2=0.7 Hz, 1H)

2-Bromo-5-(1-tert-butoxycarbonylamino-1-ethylpropyl)pyridine (Referential Compound 4-7)

Rf value: 0.25 (n-hexane:ethyl acetate=1:4 (v/v))
Mass spectrum (CI, m/z): 343, 345 ($M^++1$)
$^1$H-NMR spectrum (CDCl$_3$, δ ppm): 0.78 (dd, J1=7.4 Hz, J2=7.4 Hz, 6H), 1.38 (brs, 9H), 1.75-1.90 (m, 2H), 1.95-2.15 (m, 2H), 4.74 (brs, 1H), 7.41 (dd, J1=8.3 Hz, J2=0.7 Hz, 1H), 7.50 (dd, J1=8.3 Hz, J2=2.7 Hz, 1H), 8.34 (dd, J1=2.7 Hz, J2=0.7 Hz, 1H)

Referential Example 5

Synthesis of 1-bromo-4-(1-tert-butoxycarbonylamino-ethyl)benzene (Referential Compound 5)

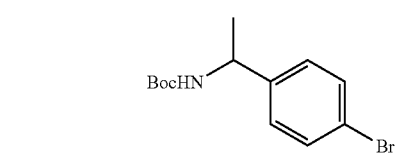

Triethylamine (2.09 ml) was added to a solution of 2.00 g (10.0 mmol) of 4-(1-aminoethyl)-1-bromobenzene in 22.3 ml of dichloromethane, the mixture was cooled on an ice bath and 2.87 ml (12.0 mmol) of di-tert-butyl dicarbonate was added thereto in an argon stream with stirring. After that, temperature of the mixture was raised up to room temperature and stirring was conducted for 1 hour.

After the reaction was finished, the reaction solution was poured into 200 ml of water and the mixture was extracted with 200 ml of chloroform. The organic layer was successively washed with water, a saturated aqueous solution of sodium hydrogen carbonate and a saturated aqueous solution of sodium chloride, dried over anhydrous magnesium sulfate and concentrated in vacuo. The resulting powder was washed twice with each 10 ml of hexane to give 2.71 g of the title compound as white powder (yield: 90%).

Rf value: 0.55 (n-hexane:ethyl acetate=4:1 (v/v))

Mass spectrum (FAB, m/z): 300, 302 (M$^+$+1)

$^1$H-NMR spectrum (DMSO-d$_6$, δ ppm): 1.27 (d, J=6.8 Hz, 3H), 1.36 (brs, 9H), 4.51-4.64 (m, 1H), 7.25 (d, J=8.3 Hz, 2H), 7.35-7.45 (m, 1H), 7.49 (d, J=8.3 Hz, 2H)

Referential Example 6

Synthesis of 4-(1-tert-butoxycarbonylamino-1-methyl-ethyl)-1-(4,4,5,5-tetramethyl[1,3,2]dioxaborolanyl)benzene (Referential Compound 6-1)

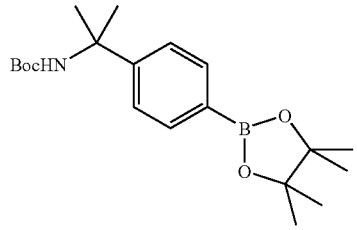

A 0.95M sec-butyl lithium/n-hexane solution (370 ml, 350 mmol) was dropped, in an argon stream with stirring at −78° C., into a solution of 50 g (160 mmol) of 1-bromo-4-(1-tert-butoxycarbonylamino-1-methylethyl)benzene (referential compound 4-1) in 800 ml of diethyl ether and the mixture was stirred for 30 minutes. After that, 97 ml (480 mmol) of 2-isopropoxy-4,4,5,5-tetramethyl[1,3,2]dioxaborolane was dropped thereinto at −78° C. and the mixture was stirred at −50° C. for 2 hours.

After the reaction was finished, 300 g of a saturated aqueous solution of ammonium chloride and then 450 ml of water were successively added thereto and the mixture was separated into layers. An aqueous layer was extracted with 300 ml of ethyl acetate again and the organic layers were combined, washed with a saturated aqueous solution of sodium chloride, dried over anhydrous sodium sulfate and concentrated in vacuo. n-Hexane (100 ml) was added to the resulting residue and the resulting solid was filtered off and successively washed with 100 ml of a mixed solvent (n-hexane:ethyl acetate=4:1 (v/v)) and 100 ml of n-hexane to give 33 g of the title compound as white powder (yield: 58%).

Melting point: 142 to 144° C.

Rf value: 0.38 (n-hexane:ethyl acetate=4:1 (v/v))

Mass spectrum (CI, m/z): 362 (M$^+$+1)

$^1$H-NMR spectrum (CDCl$_3$, δ ppm): 1.10-1.50 (m, 21H), 1.61 (s, 0.6H), 4.93 (brs, 1H), 7.37-7.42 (m, 2H), 7.74-7.79 (m, 2H)

As hereunder, the referential compound 6-2 was produced in accordance with the production process for the referential compound 6-1.

4-(1-tert-Butoxycarbonylamino-1-ethylpropyl)-1-(4,4,5,5-tetramethyl[1,3,2]dioxaborolanyl)benzene (Referential Compound 6-2)

Property: white powder

Melting point: 141 to 144° C.

Rf value: 0.55 (n-hexane:ethyl acetate=4:1 (v/v))

Mass spectrum (CI, m/z): 390 (M$^+$+1)

$^1$H-NMR spectrum (CDCl$_3$, δ ppm): 0.73 (t, J=7.3 Hz, 6H), 1.34 (s, 12H), 1.38 (brs, 9H), 1.87-2.11 (m, 4H), 4.79 (brs, 1H), 7.29-7.36 (m, 2H), 7.73-7.78 (m, 2H)

Referential Example 7

Synthesis of 4-(1-tert-butoxycarbonylaminocyclopentyl)-1-(4,4,5,5-tetramethyl[1,3,2]dioxaborolanyl)benzene (Referential Compound 7-1)

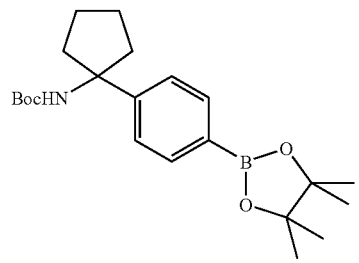

1-Bromo-4-(1-tert-butoxycarbonylaminocyclopentyl)benzene (referential compound 4-3) (340 mg, 1.0 mmol) was added to a solution of 294 mg (3.0 mmol) of potassium acetate, 41 mg (0.050 mmol) of a 1:1 adduct of 1,1'-bis(diphenylphosphino) ferrocene palladium (II) chloride with dichloromethane and 279 mg (1.1 mmol) of bis(pinacolato)diboron in 6.0 ml of 1,4-dioxane and the mixture was stirred with heating at 90° C. for 10 hours.

After the reaction was finished, 50 ml of toluene and 25 ml of water were added thereto, the mixture was filtered through Celite (trade name) and the resulting filtrate was extracted with toluene. The organic layer was dried over anhydrous magnesium sulfate and concentrated in vacuo. The resulting residue was subjected to a silica gel column chromatography (eluting solvent: n-hexane:ethyl acetate=6:1 (v/v)), the fraction containing the aimed substance was concentrated in vacuo, n-hexane was added to the concentrate and the resulting solid was filtered off to give 156 mg of the title compound as white powder (yield: 40%).

Melting point: 154 to 155° C.

Rf value: 0.40 (n-hexane:ethyl acetate=4:1 (v/v))

Mass spectrum (EI, m/z): 387 (M$^+$)

$^1$H-NMR spectrum (CDCl$_3$, δ ppm): 1.00-1.50 (m, 21H), 1.70-2.30 (m, 8H), 4.87 (brs, 1H), 7.39 (d, J=8.2 Hz, 2H), 7.75 (d, J=8.2 Hz, 2H)

As hereunder, the referential compound 7-2 was produced in accordance with the production process for the referential compound 7-1.

4-(1-tert-Butoxycarbonylamino)ethyl-1-(4,4,5,5-tetramethyl[1,3,2]dioxaborolanyl)benzene (Referential Compound 7-2)

Rf value: 0.40 (n-hexane:ethyl acetate=4:1 (v/v))
Mass spectrum (CI, m/z): 348 (M$^+$+1)
$^1$H-NMR spectrum (DMSO-d$_6$, δ ppm): 1.24-1.31 (m, 15H), 1.35 (brs, 9H), 4.51-4.65 (m, 1H), 7.29 (d, J=8.1 Hz, 2H), 7.35-7.44 (m, 1H), 7.61 (d, J=8.1 Hz, 2H)

Referential Example 8

Synthesis of 2-bromo-5-(bromomethyl)pyridine (Referential Compound 8)

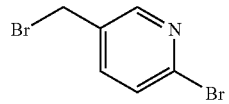

N-Bromosuccinimide (16 g, 91 mmol) and 0.40 g (2.4 mmol) of 2,2'-azobis(isobutyronitrile) were added to a solution of 12 g (70 mmol) of 2-bromo-5-methylpyridine in 100 ml of 1,2-dichloroethane and the mixture was stirred at 85° C. After 15 minutes, 0.40 g (2.4 mmol) of 2,2'-azobis(isobutyronitrile) was added thereto and the mixture was stirred for 15 minutes.

After the reaction was finished, water was added to the reaction solution and the organic layer was separated therefrom. The organic layer was dried over anhydrous magnesium sulfate and concentrated in vacuo. The resulting residue was subjected to a silica gel column chromatography (eluting solvent: n-hexane:ethyl acetate=10:1 to 9:1 (v/v)) and the fraction containing the aimed substance was concentrated in vacuo to give 15 g of the title compound as white powder (yield: 89%).

Rf value: 0.63 (n-hexane:ethyl acetate=9:1 (v/v))
Mass spectrum (CI, m/z): 250, 252, 254 (M$^+$+1)
$^1$H-NMR spectrum (CDCl$_3$, δ ppm): 4.42 (s, 2H), 7.49 (d, J=8.3 Hz, 1H), 7.61 (dd, J1=8.3 Hz, J2=2.7 Hz, 1H), 8.39 (d, J=2.7 Hz, 1H)

Referential Example 9

Synthesis of 5-chloromethyl-2,3-dichloropyridine (Referential Compound 9)

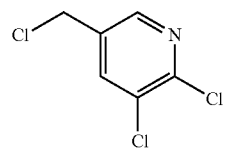

Pyridine (1.0 ml, 12 mmol) and 18 ml (250 mmol) of thionyl chloride were gradually added, at 0° C., to a solution of 30 g (168 mmol) of 5,6-dichloro-3-pyridinemethanol in 250 ml of chloroform and the mixture was stirred for 2 hours at room temperature.

After the reaction was finished, the reaction solution was poured into a mixed solvent of chloroform and water and potassium carbonate was added thereto so that pH of an aqueous layer was made alkaline. The organic layer was separated therefrom and dried over anhydrous sodium sulfate and concentrated in vacuo to give 37 g of the title compound as a light brown oily substance (yield: quantitative)

Rf value: 0.80 (n-hexane:ethyl acetate=9:1 (v/v))
Mass spectrum (CI, m/z): 196 (M$^+$+1)
$^1$H-NMR spectrum (CDCl$_3$, δ ppm): 4.54-4.55 (m, 2H), 7.84-7.85 (m, 1H), 8.30-8.31 (m, 1H)

Referential Example 10

Synthesis of 2-bromo-5-(cyanomethyl)pyridine (Referential Compound 10-1)

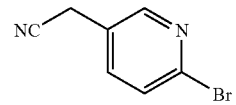

Potassium cyanide (7.80 g, 120 mmol) was added to a solution of 15.0 g (60.0 mmol) of 2-bromo-5-bromomethylpyridine (Referential Compound 8) in 150 ml of N,N-dimethylformamide and the mixture was slowly stirred at 60° C. for 15 minutes. After that, water was added thereto little by little until potassium cyanide was completely dissolved and then the mixture was stirred at 60° C. for 15 minutes.

After the reaction was finished, the reaction solution was poured into ethyl acetate/saturated aqueous solution of ammonium chloride and the organic layer was separated therefrom. The organic layer was dried over anhydrous magnesium sulfate and concentrated in vacuo. The resulting residue was subjected to a silica gel column chromatography (eluting solvent: n-hexane:ethyl acetate=9:1 to 7:3 (v/v)) and the fraction containing the aimed substance was concentrated in vacuo to give 9.24 g of the title compound as pale yellow powder (yield: 61%).

Rf value: 0.15 (n-hexane:ethyl acetate=4:1 (v/v))
Mass spectrum (CI, m/z): 197, 199 (M$^+$+1)
IR spectrum (KBr, cm$^{-1}$): 2253
$^1$H-NMR spectrum (CDCl$_3$, δ ppm): 3.74 (s, 2H), 7.61-7.53 (m, 2H), 8.36-8.35 (m, 1H)

As hereunder, referential compound 10-2 was produced in accordance with the production process for the referential compound 10-1.

5-Cyanomethyl-2,3-dichloropyridine (Referential Compound 10-2)

Mass spectrum (CI, m/z): 187 (M$^+$+1)
$^1$H-NMR spectrum (CDCl$_3$, δ ppm): 3.77-3.78 (m, 2H), 7.82-7.84 (m, 1H), 8.27-8.29 (m, 1H)

Referential Example 11

Synthesis of 5-iodo-1H-indazole (referential compound 11-1)

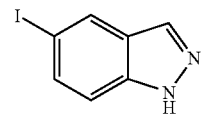

At 0° C., 95 ml (570 mmol) of 6N hydrochloric acid was dropped into a solution of 25.0 g (188 mmol) of 5-amino-1H-indazole in 320 ml of N,N-dimethylformamide and the mixture was stirred for 20 minutes. After that, a solution of 13.6 g (197 mmol) of sodium nitrite in 75 ml of water was dropped thereinto keeping the temperature of the reaction solution at below 10° C. throughout. After stirring for 30 minutes, 32.8 g (198 mmol) of potassium iodide was divisionally added thereto, then a cooling bath was removed to warm up the mixture gradually to room temperature.

After the reaction was finished, the reaction solution was poured into 1,000 ml of water and the mixture was neutralized with an aqueous solution of sodium hydroxide and extracted with 1,500 ml of toluene and then with each 500 ml of the same twice. The organic layer was washed with a saturated aqueous solution of sodium chloride, dried over anhydrous magnesium sulfate and concentrated in vacuo. The resulting residue was subjected to a silica gel column chromatography (eluting solvent: n-hexane:ethyl acetate=2:1 (v/v)), and the fraction containing the aimed substance was concentrated in vacuo. Ethyl acetate (50 ml) was added to the resulting crude crystals, the mixture was heated to dissolve it, 300 ml of n-hexane was added thereto and the resulting solid was filtered off to give 5.80 g of the title compound as white powder (yield: 13%).

Rf value: 0.45 (n-hexane:ethyl acetate=1:1 (v/v))
Mass spectrum (CI, m/z): 245 ($M^+$+1)
$^1$H-NMR spectrum (CDCl$_3$, δ ppm): 7.30 (ddd, J1=8.8 Hz, J2=1.1 Hz, J3=0.7 Hz, 1H), 7.63 (dd, J1=8.8 Hz, J2=1.5 Hz, 1H), 8.01 (d, J=1.1 Hz, 1H), 8.14 (dd, J1=1.5 Hz, J2=0.7 Hz, 1H), 10.17 (brs, 1H)

As hereunder, referential compounds 11-2 to 11-3 were produced in accordance with the production process for the referential compound 11-1.

6-Iodo-1H-indazole (Referential Compound 11-2)

Rf value: 0.43 (n-hexane:ethyl acetate=1:1 (v/v))
Mass spectrum (CI, m/z): 245 ($M^+$+1)
$^1$H-NMR spectrum (DMSO-d$_6$, δ ppm): 7.39 (dd, J1=8.5 Hz, J2=1.3 Hz, 1H), 7.60 (dd, J1=8.5 Hz, J2=0.7 Hz, 1H), 7.94-7.96 (m, 1H), 8.08 (d, J=1.0 Hz, 1H), 13.14 (brs, 1H)

4-(2-Hydroxyethyl)-5-iodo-1H-indazole (referential compound 11-3)

Rf value: 0.65 (ethyl acetate)
Mass spectrum (CI, m/z): 289 ($M^+$+1)
$^1$H-NMR spectrum (DMSO-d$_6$, δ ppm): 3.14-3.20 (m, 2H), 3.58-3.66 (m, 2H), 4.81 (t, J=5.5 Hz, 1H), 7.20 (dd, J1=8.7 Hz, J2=1.0 Hz, 1H), 7.64 (d, J=8.7 Hz, 1H), 8.13 (d, J=1.0 Hz, 1H), 13.15 (brs, 1H)

Referential Example 12

Synthesis of 1-acetyl-5-iodo-1H-indazole (Referential Compound 12-1)

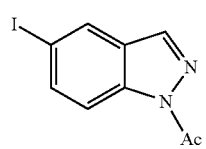

Acetic acid (10 ml) and 20 ml of acetic anhydride were added to 1.02 g (4.18 mmol) of 5-iodo-1H-indazole (referential compound 11-1) and the mixture was stirred at room temperature for 30 minutes.

After the reaction was finished, the reaction solution was poured into 300 ml of water and the resulting solid was filtered off to give 1.08 g of the title compound as white powder (yield: 90%).

Rf value: 0.49 (n-hexane:ethyl acetate=4:1 (v/v))
Mass spectrum (CI, m/z): 287 ($M^+$+1)
$^1$H-NMR spectrum (CDCl$_3$, δ ppm): 2.78 (s, 3H), 7.81 (dd, J1=8.8 Hz, J21.6 Hz, 1H), 8.05 (d, J=0.9 Hz, 1H), 8.10 (dd, J1=1.6 Hz, J2=0.7 Hz, 1H), 8.23 (ddd, J1=8.8 Hz, J2=0.9 Hz, J3=0.7 Hz, 1H)

As hereunder, the referential compounds 12-2 to 12-4 were produced in accordance with the production process for the referential compound 12-1.

1-Acetyl-3-tert-butoxycarbonylamino-5-iodo-1H-indazole (Referential Compound 12-2)

Rf value: 0.31 (n-hexane:ethyl acetate=4:1 (v/v))
Mass spectrum (CI, m/z): 402 ($M^+$+1)
$^1$H-NMR spectrum (CDCl$_3$, δ ppm): 1.57 (s, 9H), 2.66 (s, 3H), 7.03 (brs, 1H), 7.80 (dd, J1=8.8 Hz, J2=1.7 Hz, 1H), 8.19 (dd, J1=8.8 Hz, J2=0.5 Hz, 1H), 8.46-8.47 (m, 1H)

1-Acetyl-5-iodo-3-(1-methylvinyl)-1H-indazole (Referential Compound 12-3)

Rf value: 0.73 (n-hexane:ethyl acetate=4:1 (v/v))
Mass spectrum (CI, m/z): 327 ($M^+$+1)
$^1$H-NMR spectrum (CDCl$_3$, δ ppm): 2.30 (dd, J1=1.3 Hz, J2=0.8 Hz, 3H), 2.75 (s, 3H), 5.59-5.61 (m, 1H), 5.82-5.84 (m, 1H), 7.80 (dd, J1=8.8 Hz, J2=1.7 Hz, 1H), 8.23-8.28 (m, 2H)

1-Acetyl-6-iodo-1H-indazole (Referential Compound 12-4)

Rf value: 0.46 (n-hexane:ethyl acetate=4:1 (v/v))
Mass spectrum (CI, m/z): 287 ($M^+$+1)
$^1$H-NMR spectrum (CDCl$_3$, δ ppm): 2.78 (s, 3H), 7.46 (dd, J1=8.3 Hz, J2=0.7 Hz, 1H), 7.67 (dd, J1=8.3 Hz, J2=1.3 Hz, 1H), 8.07 (d, J=0.7 Hz, 1H), 8.89-8.90 (m, 1H)

Referential Example 13

Synthesis of 5-iodo-4-nitro-1H-indazole (Referential Compound 13)

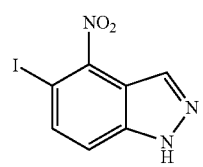

Nitric acid (12.5 ml) was gradually dropped, at 0° C., into a solution of 1.57 g (6.43 mmol) of 5-iodo-1H-indazole (referential compound 11-1) in 25 ml of concentrated sulfuric acid and the mixture was stirred for 1 hour. After that, a cooling bath was removed to warm up the mixture gradually to room temperature.

After the reaction was finished, the reaction solution was gradually poured into 150 ml of ice water, and the mixture was neutralized with an aqueous solution of sodium hydroxide and extracted with each 300 ml of ethyl acetate for three times. The organic layer was washed with a saturated aqueous solution of sodium chloride, dried over anhydrous magnesium sulfate and concentrated in vacuo. The resulting residue was subjected to a silica gel column chromatography (eluting solvent: n-hexane:ethyl acetate=3:1 (v/v)) and the fraction containing the aimed substance was concentrated in vacuo to give 0.90 g of the title compound as yellow powder (yield: 48%).

Rf value: 0.32 (n-hexane:ethyl acetate=1:1 (v/v))

Mass spectrum (CI, m/z): 290 ($M^++1$)

$^1$H-NMR spectrum (CDCl$_3$, δ ppm): 7.69 (dd, J1=8.8 Hz, J2=1.0 Hz, 1H), 7.98 (d, J=8.8 Hz, 1H), 8.23 (d, J=1.0 Hz, 1H), 13.88 (brs, 1H)

Referential Example 14

Synthesis of 1-tert-butoxycarbonyl-5-iodo-4-nitro-1H-indazole (Referential Compound 14-1)

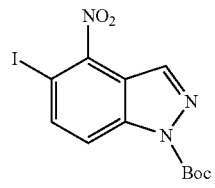

4-Dimethylaminopyridine (38.0 mg, 0.31 mmol) and 18 ml of tetrahydrofuran were added to 898 mg (3.11 mmol) of 5-iodo-4-nitro-1H-indazole (Referential Compound 13). After that, a solution of 1.36 g (6.23 mmol) of di-tert-butyl dicarbonate in 9 ml of tetrahydrofuran was added thereto with stirring in an argon stream and the mixture was stirred at room temperature for 1 hour.

After the reaction was finished, the reaction solution was concentrated in vacuo, the resulting residue was subjected to a silica gel column chromatography (eluting solvent: n-hexane:ethyl acetate=20:1 (v/v)) and the fraction containing the aimed substance was concentrated in vacuo to give 1.17 g of the title compound as yellow powder (yield: 97%).

Rf value: 0.33 (n-hexane:ethyl acetate=4:1 (v/v))

Mass spectrum (CI, m/z): 390 ($M^++1$)

$^1$H-NMR spectrum (CDCl$_3$, δ ppm): 1.73 (s, 9H), 8.11 (d, J=8.8 Hz, 1H), 8.19 (dd, J1=8.8 Hz, J20.7 Hz, 1H), 8.40 (d, J=0.7 Hz, 1H)

As hereunder, the referential compounds 14-2 to 14-3 were produced in accordance with the production process for the referential compound 14-1.

1-tert-Butoxycarbonyl-5-iodo-3-methoxycarbonyl-1H-indazole (Referential Compound 14-2)

Rf value: 0.51 (n-hexane:ethyl acetate=2:1 (v/v))

Mass spectrum (CI, m/z): 403 ($M^++1$)

$^1$H-NMR spectrum (CDCl$_3$, δ ppm): 1.73 (s, 9H), 4.05 (s, 3H), 7.32 (dd, J1=8.9 Hz, J2=1.7 Hz, 1H), 7.99 (dd, J1=8.9 Hz, J2=0.7 Hz, 1H), 8.64 (dd, J1=1.7 Hz, J2=0.7 Hz, 1H)

1-tert-Butoxycarbonyl-3-formyl-5-iodo-1H-indazole (Referential Compound 14-3)

Rf value: 0.54 (n-hexane:ethyl acetate=4:1 (v/v))

Mass spectrum (CI, m/z): 373 ($M^++1$)

$^1$H-NMR spectrum (CDCl$_3$, δ ppm): 1.76 (s, 9H), 7.85 (dd, J1=9.0 Hz, J2=1.7 Hz, 1H), 7.96 (dd, J1=9.0 Hz, J2=0.7 Hz, 1H), 8.71 (dd, J1=1.7 Hz, J2=0.7 Hz, 1H), 10.30 (s, 1H)

Referential Example 15

Synthesis of 5-iodo-3-methoxycarbonyl-1H-indazole (Referential Compound 15)

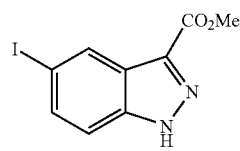

A solution of 2.72 g (68.0 mmol) of sodium hydroxide in 120 ml of water was added to 17.5 g (64.1 mmol) of 5-iodoisatin and the mixture was stirred at room temperature for 15 minutes. After that, a solution of 4.96 g (71.9 mmol) of sodium nitrite in 20 ml of water was added at 0° C. thereto and a solution of 12.2 g (124 mmol) of concentrated sulfuric acid in 120 ml of water was dropped thereinto keeping the temperature of the reaction solution at not higher than 10° C. throughout. After stirring for 30 minutes, a solution of 30.8 g (162 mmol) of anhydrous tin (II) chloride in 60 ml of concentrated hydrochloric acid was dropped thereinto keeping the temperature of the reaction solution at not higher than 10° C. throughout. After finishing the dropping, a cooling bath was removed to warm up the mixture gradually to room temperature and stirred for 2 hours and the mixture was stirred for 2 hours.

After that, the resulting solid was filtered off, 300 ml of methanol and 1 ml of concentrated sulfuric acid were added to 22.9 g of the resulting crude crystals and the mixture was heated to reflux with stirring for 10 hours.

After the reaction was finished, the reaction solution was filtered and the filtrate was concentrated in vacuo and poured into 500 ml of water. The mixed solution was neutralized with an aqueous solution of sodium hydroxide and extracted with 1,000 ml of chloroform. The organic layer was washed with a saturated aqueous solution of sodium chloride, dried over anhydrous magnesium sulfate and concentrated in vacuo. The resulting residue was subjected to a silica gel column chromatography (eluting solvent: n-hexane:ethyl acetate=2:1 (v/v)) and the fraction containing the aimed substance was concentrated in vacuo. Ethyl acetate (50 ml) was added to the resulting crude crystals, the mixture was heated to dissolve it, 300 ml of n-hexane was added thereto and the resulting solid was filtered off to give 4.93 g of the title compound as brown powder (yield: 26%).

Rf value: 0.44 (n-hexane:ethyl acetate=1:1 (v/v))

Mass spectrum (CI, m/z): 303 ($M^++1$)

$^1$H-NMR spectrum (CDCl$_3$, δ ppm): 4.06 (s, 3H), 7.38 (dd, J1=8.8 Hz, J2=0.6 Hz, 1H), 7.72 (dd, J1=8.8 Hz, J2=1.5 Hz, 1H), 8.64 (dd, J1=1.5 Hz, J2=0.6 Hz, 1H), 10.70 (brs, 1H)

Referential Example 16

Synthesis of 3-carboxy-5-iodo-1H-indazole (Referential Compound 16)

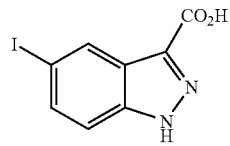

Tetrahydrofuran (10 ml), 2 ml of methanol and 8 ml of 1N aqueous solution of sodium hydroxide were added to 328 mg (1.09 mmol) of 5-iodo-3-methoxycarbonyl-1H-indazole (Referential Compound 15) and the mixture was stirred at 75° C. for 4 hours.

After the reaction was finished, concentrated hydrochloric acid was added to the reaction solution to adjust to pH L and the mixture was concentrated in vacuo. Water (50 ml) was added to the resulting residue and the resulting solid was filtered off to give 189 mg of the title compound as yellow powder (yield: 60%).

Mass spectrum (CI, m/z): 289 ($M^+ +1$)

$^1$H-NMR spectrum (DMSO-$d_6$, δ ppm): 7.52 (d, J=8.8 Hz, 1H), 7.68 (dd, J1=8.8 Hz, J2=1.7 Hz, 1H), 8.44 (d, J=1.7 Hz, 1H), 13.11 (brs, 1H), 13.94 (brs, 1H)

Referential Example 17

Synthesis of 3-tert-butoxycarbonylamino-5-iodo-1H-indazole (Referential Compound 17)

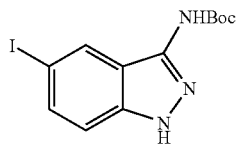

A solution of 140 mg (1.4 mmol) of triethylamine in 1 ml of tert-butanol and a solution of 260 mg (0.95 mmol) of diphenyl phosphoryl azide in 1 ml of tert-butanol were added to a solution of 180 mg (0.62 mmol) of 3-carboxy-5-iodo-1H-indazole (referential compound 16) in 5 ml of tert-butanol with stirring in an argon stream and the mixture was heated to reflux for 7 hours with stirring.

After the reaction was finished, the reaction solution was poured into 50 ml of a saturated aqueous solution of ammonium chloride and the mixture was extracted with 100 ml of ethyl acetate. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=2:1 (v/v)) and the fraction containing the aimed substance was concentrated in vacuo to give 33 mg of the title compound as yellow powder (yield: 15%).

Rf value: 0.32 (n-hexane:ethyl acetate=1:1 (v/v))

Mass spectrum (EI, m/z): 359 ($M^+ +1$)

$^1$H-NMR spectrum (CDCl$_3$, δ ppm): 1.54 (s, 9H), 6.91 (brs, 1H), 7.16 (dd, J1=8.8 Hz, J2=0.5 Hz, 1H), 7.61 (dd, J1=8.8 Hz, J2=1.7 Hz, 1H), 8.36-8.37 (m, 1H), 9.47 (brs, 1H)

Referential Example 18

Synthesis of 3-hydroxymethyl-5-iodo-1H-indazole (Referential Compound 18)

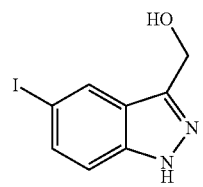

A 1M solution (32 ml, 32.0 mmol) of diisobutyl aluminum hydride in toluene was dropped at −78° C. into a solution of 2.41 g (7.89 mmol) of 5-iodo-3-methoxycarbonyl-1H-indazole (referential compound 15) in 80 ml of tetrahydrofuran with stirring in an argon stream. The mixture was stirred at −78° C. for 30 minutes and then stirred at 0° C. for 2.5 hours.

After the reaction was finished, a saturated aqueous solution of ammonium chloride was gradually added to the reaction solution at 0° C., then 300 ml of ethyl acetate was added thereto and the mixture was filtered through Celite. The filtrate was dried over anhydrous magnesium sulfate and concentrated in vacuo to give 2.31 g of the title compound as yellow powder (yield: quantitative).

Rf value: 0.25 (n-hexane:ethyl acetate=1:1 (v/v))

Mass spectrum (CI, m/z): 275 ($M^+ +1$)

$^1$H-NMR spectrum (DMSO-$d_6$, δ ppm): 4.75 (d, J=5.8 Hz, 2H), 5.26 (t, J=5.8 Hz, 1H), 7.35 (dd, J1=8.8 Hz, J2=0.7 Hz, 1H), 7.56 (dd, J1=8.8 Hz, J2=1.7 Hz, 1H), 8.25 (dd, J1=1.7 Hz, J2=0.7 Hz, 1H), 12.93 (brs, 1H)

Referential Example 19

Synthesis of 3-formyl-5-iodo-1H-indazole (Referential Compound 19)

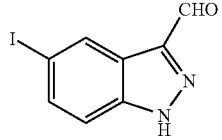

Manganese dioxide (6.94 g, 79.8 mmol) was added to a solution of 2.31 g (8.43 mmol) of 3-hydroxymethyl-5-iodo-1H-indazole (referential compound 18) in 50 ml of tetrahydrofuran and 50 ml of dichloromethane and the mixture was stirred at room temperature for 1 hour.

After the reaction was finished, the reaction solution was filtered and the filtrate was concentrated in vacuo. The resulting residue was subjected to a silica gel column chromatography (eluting solvent: n-hexane ethyl acetate=1:1 (v/v)) and the fraction containing the aimed substance was concentrated in vacuo to give 1.84 g of the title compound as brown powder (yield: 80%).

Rf value: 0.57 (n-hexane:ethyl acetate=1:1 (v/v))

Mass spectrum (CI, m/z): 273 ($M^+ +1$)

$^1$H-NMR spectrum (DMSO-d$_6$, δ ppm): 7.58 (dd, J1=8.8 Hz, J2=0.7 Hz, 1H), 7.76 (dd, J1=8.8 Hz, J2=1.7 Hz, 1H), 8.49 (dd, J1=1.7 Hz, J2=0.7 Hz, 1H), 10.17 (s, 1H), 14.30 (brs, 1H)

Referential Example 20

Synthesis of 3-(1-hydroxy-1-methylethyl)-5-iodo-1H-indazole (Referential Compound 20)

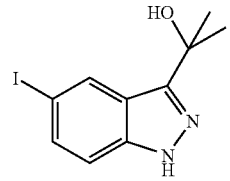

A 0.96M solution (8.1 ml, 7.8 mmol) of methyl magnesium bromide in tetrahydrofuran was added at 0° C. to a solution of 300 mg (0.99 mmol) of 5-iodo-3-methoxycarbonyl-1H-indazole (referential compound 15) in 5 ml of tetrahydrofuran with stirring in an argon stream and the mixture was stirred at room temperature for 5 hours.

After the reaction was finished, 50 ml of a saturated aqueous solution of ammonium chloride was added to the reaction solution at 0° C. and the mixture was extracted with 100 ml of ethyl acetate. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=2:1 (v/v)) and the fraction containing the aimed substance was concentrated in vacuo to give 220 mg of the title compound as yellow powder (yield: 74%).

Rf value: 0.32 (n-hexane:ethyl acetate=1:1 (V/v))
Mass spectrum (CI, m/z): 303 (M$^+$+1)
$^1$H-NMR spectrum (DMSO-d$_6$, δ ppm): 1.56 (s, 6H), 5.27 (s, 1H), 7.33 (d, J=8.8 Hz, 1H), 7.53 (dd, J1=8.8 Hz, J2=1.6 Hz, 1H), 8.39 (d, J=1.6 Hz, 1H), 12.77 (brs, 1H)

Referential Example 21

Synthesis of 5-iodo-3-(1-methylvinyl)-1H-indazole (Referential Compound 21)

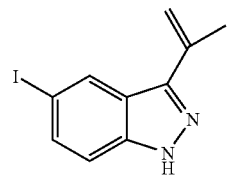

A solution (6 ml) of 4N hydrogen chloride/1,4-dioxane was added to 115 mg (0.381 mmol) of 3-(1-hydroxy-1-methylethyl)-5-iodo-1H-indazole (referential compound 20) and the mixture was heated to reflux for 4 hours with stirring.

After the reaction was finished, the reaction solution was concentrated in vacuo. The resulting residue was subjected to a silica gel column chromatography (eluting solvent: n-hexane:ethyl acetate=6:1 (v/v)) and the fraction containing the aimed substance was concentrated in vacuo to give 37.0 mg of the title compound as yellow powder (yield: 34%).

Rf value: 0.37 (n-hexane:ethyl acetate=4:1 (v/v))
Mass spectrum (CI, m/z): 285 (M$^+$+1)
$^1$H-NMR spectrum (CDCl$_3$, δ ppm): 2.30 (dd, J=1.5 Hz, J2=1.0 Hz, 3H), 5.41-5.44 (m, 1H), 5.72-5.74 (m, 1H), 7.26 (dd, J1=8.8 Hz, J2=0.7 Hz, 1H), 7.63 (dd, J1=8.8 Hz, J2=1.5 Hz, 1H), 8.33 (dd, J1=1.5 Hz, J2=0.7 Hz, 1H), 9.90 (brs, 1H)

Referential Example 22

Synthesis of 2-benzyloxy-6-nitrotoluene (referential compound 22-1)

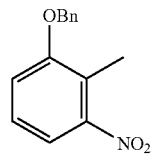

Potassium carbonate (41.5 g, 300 mmol) and 200 ml of N,N-dimethylformamide were added to 30.6 g (200 mmol) of 2-methyl-3-nitrophenol. After that, 23.8 ml (200 mmol) of benzyl bromide was added thereto with stirring in an argon stream and the mixture was stirred at room temperature for 3 hours.

After the reaction was finished, the reaction solution was poured into 1,000 ml of water and the mixture was extracted with 800 ml of toluene and 500 ml of the same for two times. The organic layer was successively washed with water and a saturated aqueous solution of sodium chloride, dried over anhydrous magnesium sulfate and concentrated in vacuo to give 49.3 g of the title compound as yellow powder (yield: quantitative).

Rf value: 0.48 (n-hexane:ethyl acetate=4:1 (v/v))
Mass spectrum (CI, m/z): 244 (M$^+$+1)
$^1$H-NMR spectrum (CDCl$_3$, δ ppm): 2.42 (s, 3H), 5.13 (s, 2H), 7.08-7.11 (m, 1H), 7.21-7.27 (m, 1H), 7.32-7.44 (m, 6H)

As hereunder, the referential compounds 22-2 to 22-3 were produced in accordance with the production process for referential compound 22-1.

2-Ethoxy-6-nitrotoluene (Referential Compound 22-2)

Rf value: 0.55 (n-hexane:ethyl acetate=5:1 (v/v))
Mass spectrum (CI, m/z): 182 (M$^+$+1)
$^1$H-NMR spectrum (CDCl$_3$, δ ppm): 1.46 (t, J=6.9 Hz, 3H), 2.37 (s, 3H), 4.08 (q, J=6.9 Hz, 2H), 7.02 (d, J=8.2 Hz, 1H), 7.16-7.23 (m, 1H), 7.35-7.42 (m, 1H)

6-Nitro-3-n-propoxytoluene (Referential Compound 22-3)

Rf value: 0.62 (n-hexane:ethyl acetate=4:1 (v/v))
Mass spectrum (CI, m/z): 196 (M$^+$+1)
$^1$H-NMR spectrum (CDCl$_3$, δ ppm): 1.07 (t, J=7.4 Hz, 3H), 1.80-1.92 (m, 2H), 2.37 (s, 3H), 3.97 (t, J=6.3 Hz, 2H), 7.02 (d, J+=7.3 Hz, 1H), 7.20-7.26 (m, 1H), 7.36-7.40 (m, 1H)

Referential Example 23

Synthesis of 3-benzyloxy-2-methylaniline (Referential Compound 23)

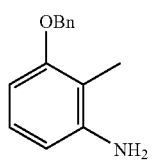

Zinc (52.3 g, 800 mmol) was added, in a divided manner, at 0° C. to a solution of 49.3 g (203 mmol) of 2-benzyloxy-6-nitrotoluene. (referential compound 22-1) in 400 ml of methanol and 200 ml of acetic acid in an argon stream with stirring and the mixture was stirred for 1 hour.

After the reaction was finished, the reaction solution was poured into 1,600 ml of water and the mixture was extracted with 1,500 ml of ethyl acetate. The organic layer was successively washed with water, a saturated aqueous solution of sodium hydrogen carbonate and a saturated aqueous solution of sodium chloride, dried over anhydrous magnesium sulfate and concentrated in vacuo to give 44.0 g of the title compound as a brown oily substance (yield: quantitative).

Rf value: 0.22 (n-hexane:ethyl acetate=4:1 (v/v))
Mass spectrum (EI, m/z): 213 (M$^+$)
$^1$H-NMR spectrum (CDCl$_3$, δ ppm): 2.11 (s, 3H), 3.64 (brs, 2H), 5.05 (s, 2H), 6.36-6.39 (m, 1H), 6.41 (d, J=8.3 Hz, 1H), 6.93-6.99 (m, 1H), 7.29-7.46 (m, 5H)

Referential Example 24

Synthesis of 3-benzyloxy-2-methylacetanilide (Referential Compound 24-1)

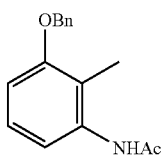

Acetic anhydride (28.3 ml, 299 mmol) was added to a solution of 44.0 g (206 mmol) of 3-benzyloxy-2-methylaniline (referential compound 23) in 400 ml of ethyl acetate and the mixture was heated to reflux with stirring for 30 minutes.

After the reaction was finished, the reaction solution was poured into 2,000 ml of hexane and the resulting solid was filtered off and washed with hexane to give 44.9 g of the title compound as white powder (yield: 85%).

Rf value: 0.24 (n-hexane:ethyl acetate ~1:1 (v/v))
Mass spectrum (CI, m/z): 256 (M$^+$+1)
$^1$H-NMR spectrum (DMSO-d$_6$, δ ppm): 2.04 (s, 3H), 2.06 (s, 3H), 5.11 (s, 2H), 6.87 (d, J=7.9 Hz, 1H), 6.96-7.00 (m, 1H), 7.09 (dd, J1=7.9 Hz, J2=7.9 Hz, 1H), 7.29-7.48 (m, 5H), 9.31 (brs, 1H)

As hereunder, the referential compounds 24-2 to 24-4 were produced in accordance with the production process for the referential compound 24-1.

3-Methoxy-2-methylacetanilide (Referential Compound 24-2)

Rf value: 0.20 (n-hexane:ethyl acetate=1:1 (v/v))
Mass spectrum (CI, m/z): 180 (M$^+$+1)
$^1$H-NMR spectrum (DMSO-d$_6$, δ ppm): 2.00 (s, 3H), 2.03 (s, 3H), 3.78 (s, 3H), 6.78 (d, J=8.0 Hz, 1H), 6.93-6.97 (m, 1H), 7.07-7.13 (m, 1H), 9.29 (brs, 1H)

3-Ethoxy-2-methylacetanilide (Referential Compound 24-3)

Rf value: 0.10 (n-hexane:ethyl acetate=5:1 (v/v))
Mass spectrum (CI, m/z): 194 (M$^+$+1)
$^1$H-NMR spectrum (CDCl$_3$, δ ppm): 1.42 (t, J=6.9 Hz, 3H), 2.13 (s, 3H), 2.20 (s, 3H), 4.02 (q, J=6.9 Hz, 2H), 6.69 (d, J=8.1 Hz, 1H), 6.94 (brs, 1H), 7.13 (dd, J1=8.1 Hz, J2=8.1 Hz, 1H), 7.35 (d, J=8.1 Hz, 1H)

2-Methyl-3-n-propoxyacetanilide (Referential Compound 24-4)

Rf value: 0.33 (n-hexane:ethyl acetate=1:1 (v/v))
Mass spectrum (CI, m/z): 208 (M$^+$+1)
$^1$H-NMR spectrum (DMSO-d$_6$, δ ppm): 1.00 (t, 7.4 Hz, 3H), 1.68-1.80 (m, 2H), 2.01 (s, 3H), 2.03 (s, 3H), 3.91 (t, J=6.3 Hz, 2H), 6.76 (d, J=8.1 Hz, 1H), 6.93 (d, J=7.8 Hz, 1H), 7.04-7.10 (m, 1H), 9.28 (brs, 1H)

Referential Example 25

Synthesis of 1-acetyl-4-benzyloxy-1H-indazole (Referential Compound 25-1)

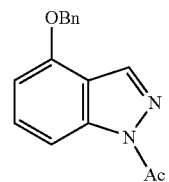

Tetra-n-butylammonium bromide (1.61 g, 4.99 mmol), 19.6 g (200 mmol) of potassium acetate and 450 ml of ethyl acetate were added to 25.5 g (100 mmol) of 3-benzyloxy-2-methylacetanilide (referential compound 24-1). After that, 28.4 ml (300 mmol) of acetic anhydride and 26.8 ml (200 mmol) of isoamyl nitrite were added thereto with stirring under an argon stream and the mixture was heated to reflux with stirring for 9 hours.

After the reaction was finished, the reaction solution was added to 500 ml of water to separate into layers. The organic layer was successively washed with a saturated aqueous solution of sodium hydrogen carbonate and a saturated aqueous solution of sodium chloride, dried over anhydrous magnesium sulfate and concentrated in vacuo.

The resulting residue was subjected to a silica gel column chromatography (eluting solvent: n-hexane:ethyl acetate=50:1 to 20:1 (v/v)) and the fraction containing the aimed substance was concentrated in vacuo to give 17.7 g of the title compound as yellow powder (yield: 66%).

Rf value: 0.41 (n-hexane:ethyl acetate=4:1 (v/v))
Mass spectrum (CI, m/z): 267 (M$^+$+1)

$^1$H-NMR spectrum (CDCl$_3$, δ ppm): 2.78 (s, 3H), 5.24 (s, 2H), 6.78 (d, J=7.9 Hz, 1H), 7.34-7.50 (m, 6H), 8.00-8.03 (m, 1H), 8.24 (d, J=1.0 Hz, 1H)

As hereunder, the referential compounds 25-2 to 25-4 were produced in accordance with the production process for the referential compound 25-1.

1-Acetyl-4-methoxy-1H-indazole (referential compound 25-2)

Rf value: 0.53 (n-hexane:ethyl acetate=2:1 (v/v))
Mass spectrum (CI, m/z): 191 (M$^+$+1)
$^1$H-NMR spectrum (CDCl$_3$, δ ppm): 2.78 (s, 3H), 3.98 (s, 3H), 6.71 (d, J=8.1 Hz, 1H), 7.46 (dd, J1=8.3 Hz, J2=8.1 Hz, 1H), 7.98-8.01 (m, 1H), 8.20 (d, J=0.7 Hz, 1H)

1-Acetyl-4-ethoxy-1H-indazole (Referential Compound 25-3)

Rf value: 0.55 (n-hexane:ethyl acetate=2:1 (v/v))
Mass spectrum (CI, m/z): 205 (M$^+$+1)
$^1$H-NMR spectrum (CDCl$_3$, δ ppm): 1.50 (t, J=7.2 Hz, 3H), 2.78 (s, 3H), 4.21 (q, J=7.2 Hz, 2H), 6.69 (d, J=7.8 Hz, 1H), 7.40-7.48 (m, 1H), 7.99 (dd, J1=8.3 Hz, J2=0.7 Hz, 1H), 8.20 (d, J=0.7 Hz, 1H)

1-Acetyl-4-n-propoxy-1H-indazole (Referential Compound 25-4)

Rf value: 0.54 (n-hexane:ethyl acetate=4:1 (v/v))
Mass spectrum (CI, m/z): 219 (M$^+$+1)
$^1$H-NMR spectrum (CDCl$_3$, δ ppm): 1.10 (t, J=7.3 Hz, 3H), 1.84-1.97 (m, 2H), 2.78 (s, 3H), 4.10 (t, 6.6 Hz, 2H), 6.69 (d, J=8.0 Hz, 1H), 7.44 (dd, J1=8.3 Hz, J2=8.0 Hz, 1H), 7.95-7.99 (m, 1H), 8.20 (d, J=0.7 Hz, 1H)

Referential Example 26

Synthesis of 4-benzyloxy-5-bromo-1H-indazole (Referential Compound 26-1)

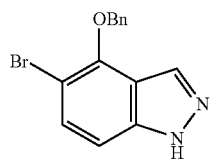

N-Bromosuccinimide (13.0 g, 73.0 mmol) was added, at 0° C., to a solution of 17.7 g (66.5 mmol) of 1-acetyl-4-benzyloxy-1H-indazole (referential compound 25-1) in 330 ml of tetrahydrofuran in an argon stream with stirring and the mixture was stirred for 30 minutes and then stirred at room temperature for 15 hours.

After that, 300 ml of methanol and 130 ml of a 1N aqueous solution of sodium hydroxide were added to the reaction solution and the mixture was stirred at room temperature for 30 minutes.

After the reaction was finished, the reaction solution was neutralized with 1N aqueous hydrochloric acid solution and concentrated in vacuo. The resulting residue was extracted with 500 ml of ethyl acetate and the organic layer was successively washed with a saturated aqueous solution of sodium hydrogen carbonate and a saturated aqueous solution of sodium chloride, dried over anhydrous magnesium sulfate and concentrated in vacuo. The resulting residue was subjected to a silica gel column chromatography (eluting solvent: n-hexane:ethyl acetate=6:1 to 4:1 (v/v)) and the fraction containing the aimed substance was concentrated in vacuo to give 13.6 g of the title compound as light orange powder (yield: 67%).

Rf value: 0.25 (n-hexane:ethyl acetate=2:1 (v/v))
Mass spectrum (EI, m/z): 302, 304 (M$^+$)
$^1$H-NMR spectrum (CDCl$_3$, δ ppm): 5.40 (s, 2H), 7.10 (dd, J1=8.8 Hz, J2=1.0 Hz, 1H), 7.33-7.44 (m, 3H), 7.49-7.55 (m, 3H), 8.06 (d, J=1.0 Hz, 1H), 10.14 (brs, 1H)

As hereunder, the referential compounds 26-2 to 26-5 were produced in accordance with the production process for the referential compound 26-1.

5-Bromo-4-methoxy-1H-indazole (Referential Compound 26-2)

Rf value: 0.17 (n-hexane:ethyl acetate=2:1 (v/v))
Mass spectrum (EI, m/z): 226, 228 (M$^+$)
$^1$H-NMR spectrum (CDCl$_3$, δ ppm): 4.25 (s, 3H), 7.06 (dd, J1=8.7 Hz, J2=1.0 Hz, 1H), 7.49 (d, J=8.7 Hz, 1H), 8.23 (d, J=1.0 Hz, 1H), 10.09 (brs, 1H)

5-Bromo-4-ethoxy-1H-indazole (Referential Compound 26-3)

Rf value: 0.30 (n-hexane:ethyl acetate=2:1 (v/v))
Mass spectrum (CI, m/z): 241, 243 (M$^+$+1)
$^1$H-NMR spectrum (CDCl$_3$, δ ppm): 1.52 (t, J=6.9 Hz, 3H), 4.46 (q, J=6.9 Hz, 2H), 7.06 (dd, J1=8.8 Hz, J2=1.0 Hz, 1H), 7.49 (d, J=8.8 Hz, 1H), 8.14 (d, J=1.0 Hz, 1H), 10.11 (brs, 1H)

5-Bromo-4-n-propoxy-1H-indazole (Referential Compound 26-4)

Rf value: 0.28 (n-hexane:ethyl acetate=2:1 (v/v))
Mass spectrum (CI, m/z): 255, 257 (M$^+$+1)
$^1$H-NMR spectrum (CDCl$_3$, δ ppm): 1.14 (t, J=7.4 Hz, 3H), 1.86-1.99 (m, 2H), 4.37 (t, J=6.5 Hz, 2H), 7.05 (dd, J1=8.8 Hz, J2=1.1 Hz, 1H), 7.49 (d, J=8.8 Hz, 1H) 8.16 (d, J=1.1 Hz, 1H), 10.17 (brs, 1H)

5-Bromo-4-hydroxy-1-(tetrahydropyran-2-yl)-1H-indazole (Referential Compound 26-5)

Rf value: 0.51 (n-hexane:ethyl acetate=2:1 (v/v))
Mass spectrum (EI, m/z): 296, 298 (M$^+$)
$^1$H-NMR spectrum (CDCl$_3$, δ ppm): 1.60-1.84 (m, 3H), 2.05-2.19 (m, 2H), 2.47-2.60 (m, 1H), 3.69-3.77 (m, 1H), 3.98-4.16 (m, 1H), 5.63-5.70 (m, 1H), 5.95 (s, 1H), 7.07 (dd, J1=8.9 Hz, J2=0.8 Hz, 1H), 7.38 (d, J=8.9 Hz, 1H), 8.09 (d, J=0.8 Hz, 1H)

Referential Example 27

Synthesis of 4-benzyloxy-5-bromo-2-(tetrahydropyran-2-yl)-2H-indazole (Referential Compound 27-1)

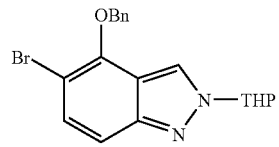

Pyridinium p-toluenesulfonate (3.39 g, 13.5 mmol) and 450 ml of methylene chloride were added to 13.6 g (44.9 mmol) of 4-benzyloxy-5-bromo-1H-indazole (Referential Compound 26-1). After that, 12.3 ml (135 mmol) of 3,4-dihydro-2H-pyran was added thereto at 0° C. with stirring in an argon stream and the mixture was stirred for 30 minutes. After that, it was stirred at room temperature for 3 hours.

After the reaction was finished, the reaction solution was poured into 300 ml of a saturated aqueous solution of sodium hydrogen carbonate to separate into layers. The organic layer was successively washed with a 10% aqueous solution of citric acid, water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=6:1 (v/v)) and a high polar fraction (Rf value: 0.36 (n-hexane:ethyl acetate=2:1 (v/v)) was concentrated in vacuo to give 15.5 g of the title compound as an orange oily substance (yield: 89%).

Rf value: 0.36 (n-hexane:ethyl acetate=2:1 (v/v))

Mass spectrum (EI, m/z): 386, 388 (M$^+$)

$^1$H-NMR spectrum (CDCl$_3$, δ ppm): 1.66-1.80 (m, 3H), 2.02-2.23 (m, 3H), 3.73-3.81 (m, 1H), 4.09-4.14 (m, 1H), 5.27 (s, 2H), 5.60-5.64 (m, 1H), 7.32-7.43 (m, 5H), 7.51-7.54 (m, 2H), 8.07 (s, 1H)

As hereunder, the referential compounds 27-2 to 27-8 were produced in accordance with the production process for the referential compound 27-1.

5-Iodo-4-nitro-2-(tetrahydropyran-2-yl)-2H-indazole (Referential Compound 27-2)

Rf value: 0.37 (n-hexane:ethyl acetate=2:1 (v/v))

Mass spectrum (CI, m/z): 374 (M$^+$+1)

$^1$H-NMR spectrum (CDCl$_3$, δ ppm): 1.67-1.83 (m, 3H), 2.04-2.30 (m, 3H), 3.76-3.84 (m, 1H), 4.12-4.18 (m, 1H), 5.69-5.73 (m, 1H), 7.66 (dd, J1=9.0 Hz, J2=1.0 Hz, 1H), 7.88 (d, J=9.0 Hz, 1H), 8.56 (d, J=1.0 Hz, 1H)

5-Iodo-2-(tetrahydropyran-2-yl)-2H-indazole (Referential Compound 27-3)

Rf value: 0.39 (n-hexane:ethyl acetate=2:1 (v/v))

Mass spectrum (EI, m/z): 328 (M$^+$)

$^1$H-NMR spectrum (CDCl$_3$, δ ppm): 1.64-1.80 (m, 3H), 2.02-2.25 (m, 3H), 3.73-3.82 (m, 1H), 4.09-4.16 (m, 1H), 5.63-5.68 (m, 1H), 7.45-7.53 (m, 2H), 8.06-8.08 (m, 1H), 8.09 (s, 1H)

5-Nitro-2-(tetrahydropyran-2-yl)-2H-indazole (Referential Compound 27-4)

Rf value: 0.34 (n-hexane:ethyl acetate=2:1 (v/v))

Mass spectrum (CI, m/z): 248 (M$^+$+1)

$^1$H-NMR spectrum (CDCl$_3$, δ ppm): 1.64-1.91 (m, 3H), 2.00-2.22 (m, 2H), 2.27-2.39 (m, 1H), 3.77-3.86 (m, 1H), 4.12-4.20 (m, 1H), 5.70-5.74 (m, 1H), 7.77 (ddd, J1=9.5 Hz, J2=0.7 Hz, J3=0.5 Hz, 1H), 8.10 (dd, J1=9.5 Hz, J2=2.2 Hz, 1H), 8.47 (d, J=0.5 Hz, 1H), 8.75 (dd, J1=2.2 Hz, J2=0.7 Hz, 1H)

5-Iodo-2-(tetrahydropyran-2-yl)-4-[2-(tetrahydropyran-2-yloxy)ethyl]-2H-indazole (Referential Compound 27-5)

Mass spectrum (EI, m/z): 456 (M$^+$).

$^1$H-NMR spectrum (DMSO-d$_6$, δ ppm): 1.26-1.82 (m, 9H), 1.88-2.07 (m, 2H), 2.25-2.53 (m, 1H), 3.25-3.40 (m, 2H), 3.48-3.91 (m, 6H), 4.55-4.61 (m, 1H), 5.58-5.84 (m, 1H), 7.41 (d, J=8.8 Hz, 1H), 7.74 (d, J=8.8 Hz, 1H), 8.21 (s, 1H)

5-tert-Butyldimethylsilyloxy-4-formyl-2-(tetrahydropyran-2-yl)-2H-indazole (Referential Compound 27-6)

Rf value: 0.63 (n-hexane:ethyl acetate=1:1 (v/v))

Mass spectrum (CI, m/z): 361 (M$^+$+1)

$^1$H-NMR spectrum (CDCl$_3$, δ ppm): 0.30 (s, 6H), 1.05 (s, 9H), 1.50-2.30 (m, 6H), 3.70-3.85 (m, 1H), 4.05-4.20 (m, 1H), 5.70-5.80 (m, 1H), 6.99 (d, J=9.3 Hz, 1H), 7.93 (d, J=9.3 Hz, 1H), 8.82 (s, 1H), 10.54 (s, 1H)

5-(tert-Butyldimethylsilyloxy)-4-methylcarbonyl-2-(tetrahydropyran-2-yl)-2H-indazole (Referential Compound 27-7)

Property: white powder

Rf value: 0.37 (n-hexane:ethyl acetate=2:1 (v/v))

Mass spectrum (CI, m/z): 375 (M$^+$+1)

$^1$H-NMR spectrum (CDCl$_3$, δ ppm): 0.32 (s, 6H), 1.02 (s, 9H), 1.62-1.82 (m, 3H), 2.00-2.13 (m, 1H), 2.15-2.30 (m, 2H), 2.69 (s, 3H), 3.73-3.82 (m, 1H), 4.06-4.15 (m, 1H), 5.65-5.73 (m, 1H), 6.99 (d, J=9.4 Hz, 1H), 7.82 (d, J=9.4 Hz, 1H), 8.67 ('s, 1H)

5-Bromo-4-methoxy-2-(tetrahydropyran-2-yl)-2H-indazole (referential compound 27-8)

Rf value: 0.27 (n-hexane:ethyl acetate=2:1 (v/v))

Mass spectrum (EI, m/z): 310, 312 (M$^+$)

$^1$H-NMR spectrum (CDCl$_3$, δ ppm): 1.68-1.81 (m, 3H), 2.04-2.29 (m, 3H), 3.75-3.83 (m, 1H), 4.08-4.36 (m, 4H), 5.63-5.68 (m, 1H), 7.31 (dd, J1=9.0 Hz, J2=1.0 Hz, 1H), 7.36 (d, J=9.0 Hz, 1H), 8.28 (d, J=1.0 Hz, 1H)

Referential Example 28

Synthesis of 4-benzyloxy-5-bromo-1-(tetrahydropyran-2-yl)-1H-indazole (Referential Compound 28-1)

In the synthesis for referential compound 27-1, a low polar fraction (Rf value: 0.52 (n-hexane:ethyl acetate=2:1 (v/v)) was concentrated in vacuo to give 1.18 g of the title compound as a yellow oily substance (yield: 7%).

Rf value: 0.52 (n-hexane:ethyl acetate=2:1 (v/v))

Mass spectrum (EI, m/z): 386, 388 (M$^+$)

$^1$H-NMR spectrum (CDCl$_3$, δ ppm): 1.66-1.79 (m, 3H), 2.04-2.15 (m, 2H), 2.49-2.55 (m, 1H), 3.69-3.78 (m, 1H), 3.98-4.04 (m, 1H), 5.36 (s, 2H), 5.64-5.68 (m, 1H), 7.20 (dd, J1=8.9 Hz, J2=0.9 Hz, 1H), 7.31-7.43 (m, 3H), 7.49-7.60 (m, 3H), 7.99 (d, J=0.9 Hz, 1H)

As hereunder, the referential compounds 28-2 to 28-4 were produced in accordance with the production process for the referential compound 28-1.

5-Bromo-4-ethoxy-1-(tetrahydropyran-2-yl)-1H-indazole (Referential Compound 28-2)

Rf value: 0.60 (n-hexane:ethyl acetate=2:1 (v/v))
Mass spectrum (EI, m/z): 324, 326 (M$^+$)
$^1$H-NMR spectrum (CDCl$_3$, δ ppm): 1.50 (t, J=6.9 Hz, 3H), 1.65-1.84 (m, 3H), 2.03-2.16 (m, 2H), 2.47-2.55 (m, 1H), 3.69-3.77 (m, 1H), 3.99-4.04 (m, 1H), 4.42 (q, J=6.9 Hz, 2H), 5.60-5.68 (m, 1H), 7.15 (dd, J=8.8 Hz, J=1.0 Hz, 1H), 7.48 (d, J=8.8 Hz, 1H), 8.07 (d, J=1.0 Hz, 1H)

5-Bromo-4-n-propoxy-1-(tetrahydropyran-2-yl)-1H-indazole (Referential Compound 28-3)

Rf value: 0.50 (n-hexane:ethyl acetate=2:1 (v/v))
Mass spectrum (EI, m/z): 338, 340 (M$^+$)
$^1$H-NMR spectrum (CDCl$_3$, δ ppm): 1.12 (t, J=7.3 Hz, 3H), 1.56-1.81 (m, 3H), 1.84-1.96 (m, 2H), 2.02-2.18 (m, 2H), 2.47-2.60 (m, 1H), 3.68-3.77 (m, 1H), 3.99-4.04 (m, 1H), 4.33 (t, J=6.6 Hz, 2H), 5.63-5.68 (m, 1H), 7.15 (dd, J1=8.8 Hz, J2=0.7 Hz, 1H), 7.48 (d, J=8.8 Hz, 1H), 8.08 (d, J=0.7 Hz, 1H)

4-Benzyloxy-1-(tetrahydropyran-2-yl)-1H-indazole (Referential Compound 28-4)

Rf value: 0.70 (n-hexane:ethyl acetate=2:1 (v/v))
Mass spectrum (EI, m/z): 308 (M$^+$)
$^1$H-NMR spectrum (CDCl$_3$, δ ppm): 1.56-1.83 (m, 3H), 2.05-2.18 (m, 2H), 2.45-2.64 (m, 1H), 3.69-3.78 (m, 1H), 4.01-4.09 (m, 1H), 5.23 (s, 2H), 5.65-5.73 (m, 1H), 6.55 (d, J=7.6 Hz, 1H), 7.16 (dd, J1=7.6 Hz, J2=0.7 Hz, 1H), 7.23-7.50 (m, 6H), 8.13 (d, J=0.7 Hz, 1H)

Referential Example 29

Synthesis of 1-acetyl-5-(4,4,5,5-tetramethyl[1,3,2]-dioxaborolanyl)-1H-indazole (Referential Compound 29-1)

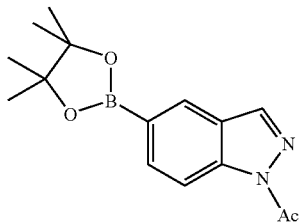

Dichlorobis(triphenylphosphine) palladium (270 mg, 0.38 mmol) and 18 ml of 1,4-dioxane were added to 1.1 g (3.8 mmol) of 1-acetyl-5-iodo-1H-indazole (referential compound 12-1). After that, 1.7 ml (12 mmol) of 4,4,5,5-tetramethyl[1,3,2]dioxaborolane and 1.6 ml (12 mmol) of triethylamine were added thereto with stirring in an argon stream and the mixture was stirred at 80° C. for 1 hour.

After the reaction was finished, the reaction solution was poured into 50 ml of water and the mixture was extracted with 200 ml of ethyl acetate. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=10:1 (v/v)) and the fraction containing the aimed substance was concentrated in vacuo to give 0.70 g of the title compound as yellow powder (yield: 64%).

Rf value: 0.41 (n-hexane:ethyl acetate=4:1 (v/v))
Mass spectrum (CI, m/z): 287 (M$^+$+1)
$^1$H-NMR spectrum (CDCl$_3$, δ ppm): 1.37 (s, 12H), 2.79 (s, 3H), 7.98 (dd, J1=8.3 Hz, J2=1.0 Hz, 1H), 8.12 (d, J=0.7 Hz, 1H), 8.22-8.24 (m, 1H), 8.42 (ddd, J1=8.3 Hz, J2=1.0 Hz, J3=0.7 Hz, 1H)

As hereunder, the referential compounds 29-2 to 29-6 were produced in accordance with the production process for the referential compound 29-1.

2-(Tetrahydropyran-2-yl)-5-(4,4,5,5-tetramethyl-[1,3,2]dioxaborolanyl)-2H-indazole (Referential Compound 29-2)

Rf value: 0.29 (n-hexane:ethyl acetate=2:1 (v/v))
Mass spectrum (EI, m/z): 328 (M$^+$)
$^1$H-NMR spectrum (CDCl$_3$, δ ppm): 1.36 (s, 12H), 1.63-1.84 (m, 3H), 2.03-2.27 (m, 3H), 3.74-3.83 (m, 1H), 4.08-4.16 (m, 1H), 5.65-5.70 (m, 1H), 7.62-7.71 (m, 2H), 8.18 (s, 1H), 8.24-8.25 (m, 1H)

4-Benzyloxy-1-(tetrahydropyran-2-yl)-5-(4,4,5,5-tetramethyl[1,3,2]dioxaborolanyl)-1H-indazole (Referential Compound 29-3)

Rf value: 0.31 (n-hexane:ethyl acetate=4:1 (v/v))
Mass spectrum (CI, m/z): 435 (M$^+$+1)
$^1$H-NMR spectrum (CDCl$_3$, δ ppm): 1.36 (s, 12H), 1.65-1.79 (m, 3H), 2.02-2.18 (m, 2H), 2.49-2.63 (m, 1H), 3.70-3.79 (m, 1H), 4.01-4.07 (m, 1H), 5.37 (s, 2H), 5.66-5.71 (m, 1H), 7.24 (dd, J1=8.4 Hz, J2=0.7 Hz, 1H), 7.29-7.41 (m, 3H), 7.57-7.62 (m, 2H), 7.72 (d, J=8.4 Hz, 1H), 8.09 (d, J=0.7 Hz, 1H)

4-Ethoxy-1-(tetrahydropyran-2-yl)-5-(4,4,5,5-tetramethyl[1,3,2]dioxaborolanyl)-1H-indazole (Referential Compound 29-4)

Rf value: 0.32 (n-hexane:ethyl acetate=4:1 (v/v))
Mass spectrum (CI, m/z): 373 (M$^+$+1)
$^1$H-NMR spectrum (CDCl$_3$, δ ppm): 1.36 (s, 12H), 1.45 (t, J=7.1 Hz, 3H), 1.57-1.79 (m, 3H), 2.02-2.17 (m, 2H), 2.50-2.62 (m, 1H), 3.69-3.78 (m, 1H), 4.00-4.06 (m, 1H), 4.35 (q, J=7.1 Hz, 2H), 5.62-5.70 (m, 1H), 7.21 (dd, J1=8.4 Hz, J2=0.9 Hz, 1H), 7.67 (d, J=8.4 Hz, 1H), 8.10 (d, J=0.9 Hz, 1H)

4-n-Propoxy-1-(tetrahydropyran-2-yl)-5-(4,4,5,5-tetramethyl[1,3,2]dioxaborolanyl)-1H-indazole (referential compound 29-5)

Rf value: 0.31 (n-hexane:ethyl acetate=4:1 (v/v))
Mass spectrum (CI, m/z): 387 (M$^+$+1)
$^1$H-NMR spectrum (CDCl$_3$, δ ppm): 1.10 (t, J=7.4 Hz, 3H), 1.36 (s, 12H), 1.64-1.79 (m, 3H), 1.81-1.93 (m, 2H), 2.01-2.16 (m, 2H), 2.49-2.62 (m, 1H), 3.69-3.78 (m, 1H), 4.00-4.05 (m, 1H), 4.29 (t, J=6.4 Hz, 2H), 5.64-5.69 (m, 1H), 7.18 (dd, J1=8.5 Hz, J2=0.9 Hz, 1H), 7.67 (d, J=8.5 Hz, 1H), 8.11 (d, J=0.9 Hz, 1H) 4-Cyclopropyloxy-1-(tetrahydropyran-2-yl)-5-(4,4,5,5-tetramethyl[1,3,2]dioxaborolanyl)-1H-indazole (Referential Compound 29-6)

Rf value: 0.44 (n-hexane:ethyl acetate=2:1 (v/v))
Mass spectrum (CI, m/z): 385 (M$^+$+1)
$^1$H-NMR spectrum (CDCl$_3$, δ ppm): 0.68-0.73 (m, 2H), 0.90-0.95 (m, 2H), 1.35 (s, 12H), 1.65-1.83 (m, 3H), 2.03-2.18 (m, 2H), 2.51-2.64 (m, 1H), 3.70-3.78 (m, 1H), 4.01-

4.05 (m, 1H), 4.35-4.41 (m, 1H), 5.65-5.73 (m, 1H), 7.17 (dd, J1=8.4 Hz, J2=0.7 Hz, 1H), 7.64 (d, J=8.4 Hz, 1H), 8.28 (d, J=0.7 Hz, 1H)

Referential Example 30

Synthesis of 4-nitro-2-(tetrahydropyran-2-yl)-5-(4,4,5,5-tetramethyl[1,3,2]dioxaborolanyl)-2H-indazole (Referential Compound 30-1)

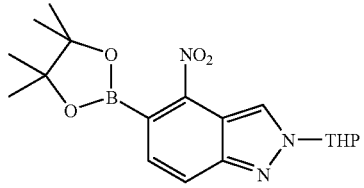

A 1:1 adduct of 1,1'-bis(diphenyl-phosphino)ferrocene palladium (II) chloride with dichloromethane (1.43 g, 1.75 mmol), 2.13 g (21.7 mmol) of potassium acetate, 2.75 g (10.8 mmol) of bis(pinacolato)diboron and 100 ml of N,N-dimethylformamide were added to 2.68 g (7.18 mmol) of 5-iodo-4-nitro-2-(tetrahydropyran-2-yl)-2H-indazole (referential compound 27-2) and the mixture was stirred at 80° C. for 2.5 hours in an argon stream.

After the reaction was finished, the reaction solution was poured into 400 ml of water and the mixture was extracted with 500 ml of toluene. The organic layer was washed with a saturated aqueous solution of sodium chloride, dried over anhydrous magnesium sulfate and concentrated in vacuo. The resulting residue was subjected to a silica gel column chromatography (eluting solvent: n-hexane:ethyl acetate=4:1 (v/v)) and the fraction containing the aimed substance was concentrated in vacuo to give 717 mg of the title compound as yellow powder (yield: 27%).

Rf value: 0.29 (n-hexane:ethyl acetate=2:1 (v/v))

Mass spectrum (CI, m/z): 374 ($M^+$+1)

$^1$H-NMR spectrum (CDCl$_3$, δ ppm): 1.46 (s, 12H), 1.67-1.83 (m, 3H), 2.04-2.10 (m, 1H), 2.21-2.30 (m, 2H), 3.77-3.85 (m, 1H), 4.15-4.20 (m, 1H), 5.72-5.76 (m, 1H), 7.37 (d, J=8.5 Hz, 1H), 8.07 (dd, J1=8.5 Hz, J2=0.7 Hz, 1H), (d, J=0.7 Hz, 1H)

As hereunder, the referential compounds 30-2 to 30-4 were produced in accordance with the production process for the referential compound 30-1.

2-(Tetrahydropyran-2-yl)-4-[2-(tetrahydropyran-2-yl-oxy)ethyl]-5-(4,4,5,5-tetramethyl[1,3,2]dioxaborolanyl)-2H-indazole (Referential Compound 30-2)

Rf value: 0.29 (n-hexane:ethyl acetate=2:1 (v/v))

Mass spectrum (EI, m/z): 456 ($M^+$)

$^1$H-NMR spectrum (CDCl$_3$, δ ppm): 1.36 (s, 12H), 1.39-1.80 (m, 9H), 2.00-2.22 (m, 2H), 2.50-2.59 (m, 1H), 3.35-3.47 (m, 1H), 3.52-3.78 (m, 5H), 3.92-4.08 (m, 2H), 4.55-4.59 (m, 1H), 5.66-5.71 (m, 1H), 7.39 (d, J=8.5 Hz, 1H), 7.80 (d, J=8.5 Hz, 1H), 8.18 (s, 1H)

4-Benzyloxy-2-(tetrahydropyran-2-yl)-5-(4,4,5,5-tetramethyl[1,3,2]dioxaborolanyl)-2H-indazole (Referential Compound 30-3)

Rf value: 0.37 (toluene:ethyl acetate=19:1 (v/v))

Mass spectrum (EI, m/z): 434 ($M^+$)

$^1$H-NMR spectrum (DMSO$_4$-d$_6$, δ ppm): 1.31 (s, 12H), 1.53-1.80 (m, 3H), 1.90-2.10 (m, 2H), 2.19-2.33 (m, 1H), 3.65-3.80 (m, 1H), 3.95-4.07 (m, 1H), 5.38 (s, 2H), 5.71-5.76 (m, 1H), 7.25 (dd, J1=8.8 Hz, J2=1.0 Hz, 1H), 7.30-7.44 (m, 4H), 7.66-7.71 (m, 2H), 8.79-8.80 (m, 1H)

4-Methoxy-2-(tetrahydropyran-2-yl)-5-(4,4,5,5-tetramethyl[1,3,2]dioxaborolanyl)-2H-indazole (Referential Compound 30-4)

Rf value: 0.20 (n-hexane:ethyl acetate=2:1 (v/v))

Mass spectrum (EI, m/z): 358 ($M^+$)

$^1$H-NMR spectrum (CDCl$_3$, δ ppm): 1.36 (s, 12H), 1.66-1.77 (m, 3H), 2.03-2.28 (m, 3H), 3.74-3.85 (m, 1H), 4.08-4.16 (m, 4H), 5.63-5.67 (m, 1H), 7.36 (dd, J1=8.8 Hz, J2=1.0 Hz, 1H), 7.54 (d, J=8.8 Hz, 1H), 8.28 (d, J=1.0 Hz, 1H)

Referential Example 31

Synthesis of 4-methoxycarbonylmethyl-5-nitro-2-(tetrahydropyran-2-yl)-2H-indazole (Referential Compound 31)

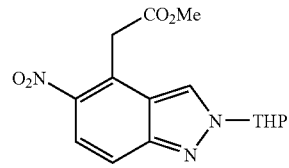

A solution of 24.6 g (100 mmol) of 5-nitro-2-(tetrahydropyran-2-yl)-2H-indazole (referential compound 27-4) and 10.5 ml (120 mmol) of methyl chloroacetate in 400 ml of N,N-dimethylformamide was dropped into a solution of 33.7 g (300 mmol) of potassium tert-butoxide in 100 ml of N,N-dimethylformamide at −40° C. during 50 minutes and the mixture was stirred at −40° C. for 30 minutes.

After the reaction was finished, temperature of the reaction solution was returned to room temperature, the solution was neutralized with 1N hydrochloric acid and 4,000 ml of water was added thereto. The resulting solid was filtered off and successively washed with 500 ml of water, 400 ml of methanol and 300 ml of diethyl ether to give 50.4 g of the title compound as pale yellow powder (yield: 79%).

Rf value: 0.21 (n-hexane:ethyl acetate=2:1 (v/v))

Mass spectrum (CI, m/z): 320 ($M^+$+1)

$^1$H-NMR spectrum (CDCl$_3$, δ ppm): 1.68-1.81 (m, 3H), 2.03-2.16 (m, 2H), 2.28-2.35 (m, 1H), 3.72 (s, 3H), 3.75-3.85 (m, 1H), 4.14-4.20 (m, 1H), 4.29 (s, 2H), 5.67-5.72 (m, 1H), 7.71 (dd, J1=9.3 Hz, J2=0.5 Hz, 1H), 8.02 (d, J=9.3 Hz, 1H), 8.47 (d, J=0.5 Hz, 1H)

Referential Example 32

Synthesis of 5-amino-4-methoxycarbonylmethyl-2-(tetrahydropyran-2-yl)-2H-indazole (Referential Compound 32)

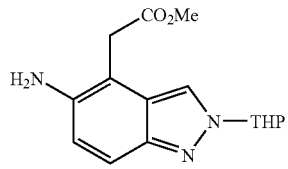

Tetrahydrofuran (50 ml) and 20 ml of methanol were added to 2.88 g (9.02 mmol) of 4-methoxycarbonylmethyl-5-nitro-2-(tetrahydropyran-2-yl)-2H-indazole (referential compound 31), then a suspension of 4.40 g of 5% palladium-carbon (wet) in 20 ml of ethyl acetate was added thereto and the mixture was stirred in a hydrogen atmosphere at room temperature for 1.5 hours.

After the reaction was finished, the reaction solution was filtered through Celite and the filtrate was concentrated in vacuo to give 2.52 g of the title compound as a brown oily substance (yield: 97%).

Rf value: 0.19 (n-hexane:ethyl acetate=1:1 (v/v))
Mass spectrum (EI, m/z): 289 (M$^+$)
$^1$H-NMR spectrum (DMSO-d$_6$, δ ppm): 1.54-1.78 (m, 3H), 1.92-2.01 (m, 2H), 2.08-2.22 (m, 1H), 3.58 (s, 3H), 3.61-3.73 (m, 3H), 3.90-4.00 (m, 1H), 4.79 (brs, 2H), 5.56-5.61 (m, 1H), 6.84 (d, J=9.0 Hz, 1H), 7.30 (dd, J1=9.0 Hz, J2=1.0 Hz, 1H), 8.05 (d, J=1.0 Hz, 1H)

Referential Example 33

Synthesis of 5-tert-butoxycarbonylamino-4-methoxycarbonylmethyl-2-(tetrahydropyran-2-yl)-2H-indazole (Referential Compound 33)

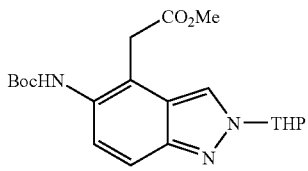

Di-tert-butyl dicarbonate (15 g, 69 mmol) was added to a solution of 17 g (60 mmol) of 5-amino-4-methoxycarbonylmethyl-2-(tetrahydropyran-2-yl)-2H-indazole (Referential Compound 32) in 75 ml of tetrahydrofuran with stirring in an argon stream and the mixture was heated to reflux with stirring for 1.5 hours.

After the reaction was finished, the reaction solution was concentrated in vacuo, 75 ml of a saturated aqueous solution of ammonium chloride was added to the resulting residue and the mixture was extracted with 250 ml of ethyl acetate. The organic layer was successively washed with water and a saturated aqueous solution of sodium chloride, dried over anhydrous magnesium sulfate and concentrated in vacuo. n-Hexane was added to the resulting residue and the resulting solid was filtered off to give 16 g of the title compound as slightly brown powder (yield: 69%).

Rf value: 0.41 (n-hexane:ethyl acetate=1:1 (v/v))
Mass spectrum (EI, m/z): 389 (M$^+$)
$^1$H-NMR spectrum (DMSO-d$_6$, δ ppm): 1.44 (s, 9H), 1.53-1.83 (m, 3H), 1.92-2.29 (m, 3H), 3.57 (s, 3H), 3.67-3.76 (m, 1H), 3.88 (s, 2H), 3.94-4.04 (m, 1H), 5.68-5.73 (m, 1H), 7.14 (dd, J1=9.0 Hz, J2=1.0 Hz, 1H), 7.47 (d, J=9.0 Hz, 1H), 8.48 (d, J=1.0 Hz, 1H), 8.63 (brs, 1H)

Referential Example 34

Synthesis of 5-tert-butoxycarbonylamino-4-(2-hydroxyethyl)-2-(tetrahydropyran-2-yl)-2H-indazole (Referential Compound 34)

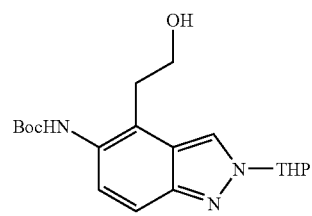

Sodium borohydride (3.4 g, 90 mmol) was dividedly added to a solution of 12 g (30 mmol) of 5-tert-butoxycarbonylamino-4-methoxycarbonylmethyl-2-(tetrahydropyran-2-yl)-2H-indazole (referential compound 33) in 100 ml of methanol with stirring on a water bath and the mixture was stirred on the water bath for 2 hours. Further, 1.1 g (30 mmol) of sodium borohydride was dividedly added thereto and the mixture was stirred on the water bath for 2 hours.

After the reaction was finished, the reaction solution was gradually poured into 300 ml of a saturated aqueous solution of ammonium chloride and the mixture was extracted with 500 ml of ethyl acetate. The organic layer was successively washed with water and a saturated aqueous solution of sodium chloride, dried over anhydrous magnesium sulfate and concentrated in vacuo. The resulting residue was recrystallized from diethyl ether/n-hexane to give 10 g of the title compound as white powder, (yield: 95%).

Rf value: 0.17 (n-hexane:ethyl acetate=1:1 (v/v))
Mass spectrum (EI, m/z): 361 (M$^+$)
$^1$H-NMR spectrum (DMSO-d$_6$, δ ppm): 1.45 (s, 9H), 1.54-1.82 (m, 3H), 1.91-2.30 (m, 3H), 2.95 (t, J=6.7 Hz, 2H), 3.57-3.76 (m, 2H), 3.97-4.02 (m, 1H), 4.91-4.94 (m, 1H), 5.67-5.72 (m, 1H), 7.21 (d, J=9.3 Hz, 1H), 7.40 (d, J=9.3 Hz, 1H), 8.49 (s, 1H), 8.55 (brs, 1H)

Referential Example 35

Synthesis of 5-amino-4-(2-hydroxyethyl)-1H-indazole dihydrochloride (Referential Compound 35)

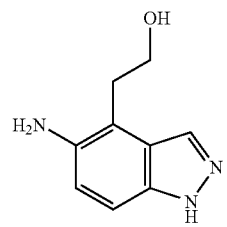

A solution of about 4.2N hydrogen chloride/ethanol (200 ml) was added at room temperature to a solution of 16 g (43 mmol) of 5-tert-butoxycarbonylamino-4-(2-hydroxyethyl)-2-(tetrahydropyran-2-yl)-2H-indazole (referential compound 34) in 100 ml of ethanol and the mixture was stirred at room temperature for 2 hours.

After the reaction was finished, 200 ml of diethyl ether was added to the reaction solution and the resulting solid was filtered off to give 9.6 g of the title compound as white powder (yield: 89%).

Mass spectrum (CI, m/z): 178 (M$^+$+1)

$^1$H-NMR spectrum (DMSO-d$_6$, δ ppm): 3.22 (t, J=6.6 Hz, 2H), 3.75 (t, J=6.6 Hz, 2H), 7.43 (d, J=8.8 Hz, 1H) (dd, J1=8.8 Hz, J2=1.0 Hz, 1H), 8.24 (d, J=1.0 Hz, 1H), 10.25 (brs, 3H)

Referential Example 36

Synthesis of
5-hydroxy-4-methylcarbonyl-1H-indazole
(Referential Compound 36)

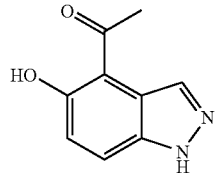

Aluminum chloride (30 g, 220 mmol) was added to a solution of 10 g (67 mmol) of 5-methoxy-1H-indazole (cf. R. A. Bartsche, et al., *J. Heterocyclic Chem.*, 21, 1063 (1984)) in 200 ml of 1,2-dichloroethane at room temperature in an argon stream and the mixture was stirred for 30 minutes. After that, 12 ml (170 mmol) of acetyl chloride was added thereto at room temperature and the mixture was stirred at 60° C. for 2.5 hours.

After the reaction was finished, the reaction solution was allowed to cool, water was added thereto and the mixture was extracted with chloroform. The organic layer was successively washed with a saturated aqueous solution of sodium hydrogen carbonate and a saturated aqueous solution of sodium chloride, dried over anhydrous magnesium sulfate and concentrated in vacuo. The resulting residue was washed with chloroform to give 3.6 g of the title compound as yellow powder (yield: 30%).

Melting point: 188 to 191° C.

Rf value: 0.14 (n-hexane:ethyl acetate=2:1 (v/v))

Mass spectrum (CI, m/z): 177 (M$^+$+1)

$^1$H-NMR spectrum (DMSO-d$_6$, δ ppm): 2.79 (s, 3H), 7.05 (d, J=8.9 Hz, 1H), 7.81 (dd, J1=8.9 Hz, J2=0.9 Hz, 1H), 8.25 (d, J=0.9 Hz, 1H), 12.61 (brs, 1H), 13.38 (brs, 1H)

Referential Example 37

Synthesis of 4-formyl-5-methoxy-1H-indazole
(Referential Compound 37)

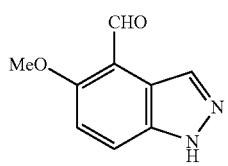

Aluminum chloride (45.0 g, 337 mmol) was added to a solution of 25.0 g (169 mmol) of 5-methoxy-1H-indazole in 500 ml of methylane chloride in an argon stream and the mixture was stirred at room temperature for 30 minutes. This was cooled down to −10° C., 17.5 ml (193 mmol) of dichloromethyl methyl ether was dropped thereinto during 20 minutes and the mixture was stirred at 0° C. for 2 hours.

After the reaction was finished, 300 ml of a mixed solution of methanol:water 1:1 (v/v) was gradually added to the reaction solution at 0° C. and the resulting solid was filtered off, washed with chloroform. Then 300 ml of chloroform, 150 ml of methanol and 150 ml of a saturated aqueous solution of sodium bicarbonate were added to the resulting solid and the mixture was stirred at room temperature for 1 hour. The resulting mixed solution was extracted with 150 ml of a mixed solvent of chloroform:methanol=2:1 (v/v) and the organic layer was dried over anhydrous magnesium sulfate and concentrated in vacuo. Chloroform was added to the resulting solid, the mixture was subjected to an ultrasonic treatment. The solid was filtered off and washed with chloroform to give 7.20 g of the title compound as green powder (yield: 24%).

Rf value: 0.50 (ethyl acetate)

Mass spectrum (CI, m/z): 177 (M$^+$+1)

$^1$H-NMR spectrum (DMSO-d$_6$, δ ppm): 4.00 (s, 3H), 7.40 (d, J=9.0 Hz, 1H), 7.93 (dd, J1=9.0 Hz, J2=1.0 Hz, 1H), 8.43 (d, J=1.0 Hz, 1H), 10.57 (s, 1H), 13.32 (brs, 1H)

Referential Example 38

Synthesis of 4-formyl-5-hydroxy-1H-indazole
monohydrobromide (Referential Compound 38)

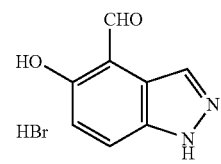

A solution of 25.0 g (100 mmol) of boron tribromide in 50 ml of methylene chloride was added to a solution of 10.1 g (57.3 mmol) of 4-formyl-5-methoxy-1H-indazole (Referential Compound 37) in 50 ml of methylene chloride and the mixture was stirred at room temperature for 2 hours. After that, 50.0 ml of a 1.0M boron tribromide/methylene chloride solution was added thereto and the mixture was stirred for 7 hours.

After the reaction was finished, the reaction solution was cooled down to 0° C. and methanol was gradually added thereto. The mixture was concentrated in vacuo, a mixed solvent of diethyl ether:methanol=9:1 (v/v) was added thereto and the resulting solid was filtered off to give 11.2 g of the title compound as light gray powder (yield: 81%).

Rf value: 0.35 (chloroform:methanol: 28% aqueous ammonia=10:1:0.1 (v/v/v))

Mass spectrum (CI, m/z): 163 (M$^+$+1)

$^1$H-NMR spectrum (DMSO-d$_6$, δ ppm): 7.09 (d, J=9.0 Hz, 1H), 7.78 (dd, J1=9.0 Hz, J2=1.0 Hz, 1H), 8.36 (d, J=1.0 Hz, 1H), 10.53 (s, 1H), 10.66 (brs, 2H)

Referential Example 39

Synthesis of 5-tert-butyldimethylsilyloxy-4-formyl-1H-indazole (Referential Compound 39-1)

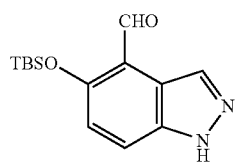

N,N-Diisopropylethylamine (1.50 ml, 8.61 mmol) and 700 mg (4.64 mmol) of tert-butyldimethylsilyl chloride were added at 0° C. to a solution of 955 mg (3.93 mmol) of 4-formyl-5-hydroxy-1H-indazole monohydrobromide (Referential Compound 38) in 15 ml of tetrahydrofuran and the mixture was stirred at room temperature for 15 hours.

After the reaction was finished, water was added to the reaction solution and the mixture was extracted with ethyl acetate. The organic layer was washed with a saturated aqueous solution of sodium chloride, dried over anhydrous magnesium sulfate and concentrated in vacuo. The resulting residue was subjected to a silical gel column chromatography (eluting solvent: n-hexane:ethyl acetate=2:1 to 1:1 (v/v)) and the fraction containing the aimed substance was concentrated in vacuo to give 964 mg of the title compound as white solid (yield: 88%).

Rf value: 0.45 (n-hexane:ethyl acetate=1:1 (v/v))
Mass spectrum (CI, m/z): 277 (M$^+$+1)
$^1$H-NMR spectrum (CDCl$_3$, δ ppm): 0.31 (s, 6H), 1.06 (s, 9H), 7.11 (d, J=9.1 Hz, 1H), 7.82 (d, J=9.1 Hz, 1H), 8.59 (s, 1H), 10.63 (s, 1H)

As hereunder, the referential compound 39-2 was produced in accordance with the production process for the referential compound 39-1.

5-(tert-Butyldimethylsilyloxy)-4-methylcarbonyl-1H-indazole (Referential Compound 39-2)

Rf value: 0.28 (n-hexane:ethyl acetate=2:1 (v/v))
Mass spectrum (CI, m/z): 291 (M$^+$+1)
$^1$H-NMR spectrum (CDCl$_3$, δ ppm): 0.35 (s, 6H), 1.04 (s, 9H), 2.73 (s, 3H), 7.28 (d, J=9.4 Hz, 1H), 7.89 (dd, J1=9.4 Hz, J2=0.8 Hz, 1H), 8.83 (d, J=0.8 Hz, 1H)

Referential Example 40

Synthesis of 4-formyl-5-hydroxy-2-(tetrahydropyran-2-yl)-2H-indazole (referential compound 40-1)

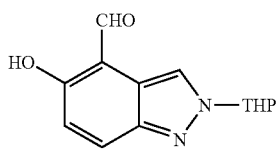

A 1.0M solution (34.0 ml, 34.0 mmol) of tetrabutylammonium fluoride/tetrahydrofuran was added, at 0° C., to a solution of 10.1 g (28.0 mmol) of 5-tert-butyldimethylsilyloxy-4-formyl-2-(tetrahydropyran-2-yl)-2H-indazole (referential compound 27-6) in 150 ml of tetrahydrofuran and the mixture was stirred at 0° C. for 1.5 hours.

After the reaction was finished, water was added to the reaction solution and the mixture was extracted with chloroform. The organic layer was washed with a saturated aqueous solution of sodium chloride, dried over anhydrous magnesium sulfate and concentrated in vacuo. The resulting residue was subjected to a silica gel column chromatography (eluting solvent: n-hexane:ethyl acetate=6:1 to 3:2 (v/v)) and the fraction containing the aimed substance was concentrated in vacuo to give 4.5 g of the title compound as a yellow foamy substance (yield: 65%)

Rf value: 0.10 (n-hexane:ethyl acetate=4:1 (v/v))
Mass spectrum (CI, m/z): 247 (M$^+$+1)
$^1$H-NMR spectrum (CDCl$_3$, δ ppm): 1.60-1.90 (m, 3H), 1.97-2.30 (m, 3H), 3.70-3.85 (m, 1H), 4.05-4.20 (m, 1H), 5.60-5.75 (m, 1H), 7.00 (d, J=9.3 Hz, 1H), 7.92 (dd, J1=9.3 Hz, J2=1.0 Hz, 1H), 8.31 (d, J=1.0 Hz, 1H), 10.25 (s, 1H), 12.10 (brs, 1H)

As hereunder, the referential compound 40-2 was produced in accordance with the production process for the referential compound 40-1.

5-Hydroxy-4-methylcarbonyl-2-(tetrahydropyran-2-yl)-1-2H-indazole (Referential Compound 40-2)

Property: yellow powder
Rf value: 0.28 (n-hexane:ethyl acetate=2:1 (v/v))
Mass spectrum (CI, m/z): 261 (M$^+$+1)
$^1$H-NMR spectrum (CDCl$_3$, δ ppm): 1.62-1.84 (m, 3H), 2.01-2.12 (m, 1H), 2.13-2.25 (m, 2H), 2.74 (s, 3H), 3.71-3.82 (m, 1H), 4.08-4.16 (m, 1H), 5.62-5.67 (m, 1H), 7.01 (d, J=9.4 Hz, 1H), 7.89 (dd, J1=9.4 Hz, J2=0.9 Hz, 1H), 8.07 (d, J=0.9 Hz, 1H), 14.09 (s, 1H)

Referential Example 41

Synthesis of 4-formyl-2-(tetrahydropyran-2-yl)-5-trifluoromethanesulfonyloxy-2H-indazole (referential compound 41-1)

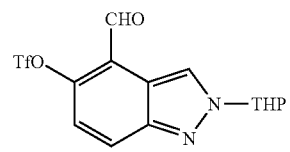

N-Phenylbis(trifluoromethanesulfonimide) (9.80 g, 27.4 mmol) and 15.0 ml (108 mmol) of triethylamine were added to a solution of 4.50 g (18.3 mmol) of 4-formyl-5-hydroxy-2-(tetrahydropyran-2-yl)-2H-indazole (referential compound 40-1) in 100 ml of methylene chloride in an argon stream and the mixture was stirred at room temperature for 1 hour.

After the reaction was finished, water was added to the reaction solution and the mixture was extracted with chloroform. The organic layer was dried over anhydrous magnesium sulfate and concentrated in vacuo. The resulting residue was subjected to a silica gel column chromatography (eluting solvent: n-hexane:ethyl acetate=6:1 to 4:1 (v/v)) and the fraction containing the aimed substance was concentrated in vacuo to give 6.00 g of the title compound as white powder (yield: 87%).

Rf value: 0.30 (n-hexane:ethyl acetate=4:1 (v/v))
Mass spectrum (CI, m/z): 379 (M$^+$+1)
$^1$H-NMR spectrum (CDCl$_3$, δ ppm): 1.60-1.90 (m, 3H), 2.00-2.14 (m, 1H), 2.15-2.30 (m, 2H), 3.74-3.87 (m, 1H), 4.10-4.22 (m, 1H), 5.70-5.80 (m, 1H), 7.30 (d, J=9.3 Hz, 1H), 8.12 (dd, J1=9.3 Hz, J2=1.0 Hz, 1H), 8.96 (d, J=1.0 Hz, 1H), 10.49 (s, 1H)

As hereunder, the referential compound 41-2 was produced in accordance with the production process for the referential compound 41-1.

4-Methylcarbonyl-2-(tetrahydropyran-2-yl)-5-(trifluoromethanesulfonyloxy)-2H-indazole (Referential Compound 41-2)

Property: pale yellow oily substance
Rf value: 0.74 (n-hexane:ethyl acetate=1:1 (v/v))
Mass spectrum (CI, m/z): 393 (M$^+$+1)
$^1$H-NMR spectrum (CDCl$_3$, δ ppm): 1.65-1.87 (m, 3H), 1.97-2.29 (m, 3H), 2.76 (s, 3H), 3.74-3.85 (m, 1H), 4.10-4.18 (m, 1H), 5.67-5.73 (m, 1H), 7.26 (d, J=9.3 Hz, 1H), 7.96 (dd, J1=9.3 Hz, J2=1.00 Hz, 1H), 8.65 (d, J=1.0 Hz, 1H)

Referential Example 42

Synthesis of 3-amino-2-methylanisole (Referential Compound 42-1)

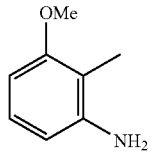

A suspension of 9.98 g of 5% palladium-carbon (wet) in 100 ml of ethanol was added to a solution of 30.7 g (184 mmol) of 2-methyl-3-nitroanisole in 300 ml of ethanol and the mixture was stirred for 3 hours at room temperature in a hydrogen atmosphere.

After the reaction was finished, the reaction solution was filtered through Celite and the filtrate was concentrated in vacuo to give 25.5 g of the title compound as a slightly purple oily substance (yield: quantitative).
Rf value: 0.38 (n-hexane:ethyl acetate=2:1 (v/v))
Mass spectrum (EI, m/z): 137 (M$^+$)
$^1$H-NMR spectrum (CDCl$_3$, δ ppm): 2.04-2.05 (m, 3H), 3.60 (brs, 2H), 3.80 (s, 3H), 6.33-6.37 (m, 2H), 6.94-7.01 (m, 1H)

As hereunder, the referential compounds 42-2 to 42-3 were produced in accordance with the production process for the referential compound 42-1.

3-Ethoxy-2-methylaniline (Referential Compound 42-2)

Rf value: 0.45 (n-hexane:ethyl acetate=5:1 (v/v))
Mass spectrum (EI, m/z): 151 (M$^+$+1)
$^1$H-NMR spectrum (CDCl$_3$, δ ppm): 1.40 (t, J=7.1 Hz, 3H), 2.05 (s, 3H), 3.60 (brs, 2H), 4.00 (q, J=7.1 Hz, 2H), 6.28-6.36 (m, 2H), 6.90-6.98 (m, 1H)

2-Methyl-3-n-propoxyaniline (Referential Compound 42-3)

Rf value: 0.41 (n-hexane:ethyl acetate=4:1 (v/v))
Mass spectrum (EI, m/z): 165 (M$^+$)
$^1$H-NMR spectrum (CDCl$_3$, δ ppm): 1.04 (t, J=7.3 Hz, 3H), 1.74-1.87 (m, 2H), 2.06 (s, 3H), 3.59 (brs, 2H), 3.89 (t, J=6.3 Hz, 2H), 6.31-6.35 (m, 2H), 6.90-6.98 (m, 1H)

Referential Example 43

Synthesis of 4-benzyloxy-1H-indazole (Referential Compound 43)

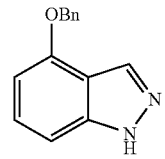

A 1N aqueous solution of sodium hydroxide (6.1 ml) was added to a solution of 500 mg (1.88 mmol) of 1-acetyl-4-benzyloxy-1H-indazole (referential compound 25-1) in 6.1 ml of methanol in an argon stream with stirring and the mixture was stirred at room temperature for 30 minutes.

After the reaction was finished, a 1N aqueous solution of hydrochloric acid was added to the reaction solution to neutralize it and the mixture was concentrated in vacuo. The resulting residue was extracted with 50 ml of ethyl acetate and the organic layer was successively washed with a saturated aqueous solution of sodium hydrogen carbonate and a saturated aqueous solution of sodium chloride, dried over anhydrous magnesium sulfate and concentrated in vacuo to give 397 mg of the title compound as yellow solid (yield: 94%).
Rf value: 0.39 (n-hexane:ethyl acetate=2:1 (v/v))
Mass spectrum (CI, m/z): 225 (M$^+$+1)
$^1$H-NMR spectrum (CDCl$_3$, δ ppm): 5.24 (s, 2H), 6.56 (d, J=7.6 Hz, 1H), 7.05-7.13 (m, 1H), 7.25-7.55 (m, 6H), 8.19 (d, J=1.0 Hz, 1H), 10.10 (brs, 1H)

Referential Example 44

Synthesis of 4-hydroxy-1-(tetrahydropyran-2-yl)-1H-indazole (Referential Compound 44)

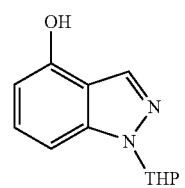

Ethanol (27 ml) was added to 3.80 g (12.3 mmol) of 4-benzyloxy-1-(tetrahydropyran-2-yl)-1H-indazole (Referential Compound 28-4), then 1.9 g of 5% palladium-carbon (wet) was added thereto and the mixture was stirred at room temperature for 2.5 hours in a hydrogen atmosphere.

After the reaction was finished, the reaction solution was filtered through Celite and the filtrate was concentrated in vacuo to give 2.99 g of the title compound as a colorless oily substance (yield: quantitative).
Rf value: 0.34 (n-hexane:ethyl acetate=2:1 (v/v))
Mass spectrum (EI, m/z): 218 (M$^+$)
$^1$H-NMR spectrum (CDCl$_3$, δ ppm): 1.54-1.79 (m, 3H), 2.04-2.19 (m, 2H), 2.45-2.60 (m, 1H), 3.70-3.78 (m, 1H), 4.01-4.07 (m, 1H), 5.65-5.70 (m, 1H), 5.72 (brs, 1H), 6.47 (dd, J1=7.3 Hz, J2=0.7 Hz, 1H), 7.12-7.16 (m, 1H), 7.22 (dd, J1=7.3 Hz, J2=7.2 Hz, 1H), 8.09 (d, J=0.7 Hz, 1H)

Referential Example 45

Synthesis of 5-bromo-4-(2-chloroethyloxy)-1-(tetrahydropyran-2-yl)-1H-indazole (Referential Compound 45)

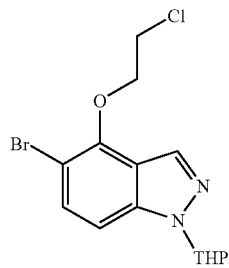

Potassium carbonate (1.04 g, 7.50 mmol) and 30 l of N,N-dimethylformamide were added to 2.03 g (6.82 mmol) of 5-bromo-4-hydroxy-1-(tetrahydropyran-2-yl)-1H-indazole (Referential Compound 26-5). After that, 1.70 ml (20.5 mmol) of 1-bromo-2-chloroethane was added thereto in an argon stream with stirring and the mixture was stirred at 70° C. for 1.0 hour.

After the reaction was finished, the reaction solution was poured into 200 ml of water and the mixture was extracted with 200 ml of toluene. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=5:1 (v/v)) and the fraction containing the aimed product was concentrated in vacuo to give 2.08 g of the title compound as brown solid (yield: 85%).

Rf value: 0.67 (n-hexane:ethyl acetate=2:1 (v/v))
Mass spectrum (CI, m/z): 358, 360 (M$^+$+1)
$^1$H-NMR spectrum (CDCl$_3$, δ ppm): 1.65-1.81 (m, 3H), 2.05-2.25 (m, 2H), 2.47-2.58 (m, 1H), 3.70-3.78 (m, 1H), 3.88 (t, J=5.8 Hz, 2H), 3.99-4.13 (m, 1H), 4.53 (t, J=5.8 Hz, 2H), 5.65-5.73 (m, 1H), 7.23 (dd, J1=8.8 Hz, J2=0.9 Hz, 1H), 7.48 (d, J=8.8 Hz, 1H), 8.13 (d, J=0.9 Hz, 1H)

Referential Example 46

Synthesis of 5-bromo-1-(tetrahydropyran-2-yl)-4-vinyloxy-1H-indazole (Referential Compound 46)

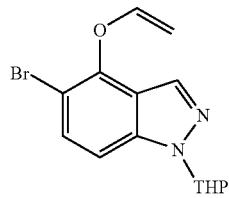

A 50% aqueous solution (5.64 ml) of sodium hydroxide and 1.88 g (5.53 mmol) of tetra-n-butylammonium hydrogen sulfate were added to a solution of 1.99 g (5.53 mmol) of 5-bromo-4-(2-chloroethyloxy)-1-(tetrahydropyran-2-yl)-1H-indazole (referential compound 45) in 47 ml of toluene in an argon stream with stirring and the mixture was stirred at room temperature for 2 hours.

After the reaction was finished, the reaction solution was poured into 200 ml of water and the mixture was extracted with 200 ml of ethyl acetate. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=5:1 (v/v)) and the fraction containing the aimed product was concentrated in vacuo to give 1.41 g of the title compound as white powder (yield: 79%).

Rf value: 0.72 (n-hexane:ethyl acetate=2:1 (v/v))
Mass spectrum (EI, m/z): 322, 324 (M$^+$)
$^1$H-NMR spectrum (CDCl$_3$, δ ppm): 1.63-1.84 (m, 3H), 2.05-2.19 (m, 2H), 2.46-2.58 (m, 1H), 3.70-3.78 (m, 1H), 3.99-4.16 (m, 1H), 4.45 (dd, J1=6.1 Hz, J2=2.4 Hz, 1H), 4.58 (dd, J1=13.8 Hz, J2=2.4 Hz, 1H), 5.65-5.74 (m, 1H), 6.78 (dd, J1=13.8 Hz, J2=6.1 Hz, 1H), 7.27 (dd, J1=9.0 Hz, J2=1.0 Hz, 1H), 7.51 (d, J=9.0 Hz, 1H), 8.03 (d, J=1.0 Hz, 1H)

Referential Example 47

Synthesis of 5-bromo-4-cyclopropyloxy-1-(tetrahydropyran-2-yl)-1H-indazole (Referential Compound 47)

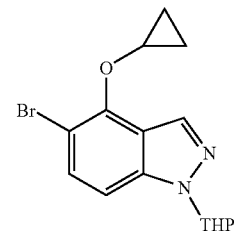

Chloroiodomethane (3.26 ml, 44.8 mmol) and 20.4 ml (22.4 mmol) of diethyl zinc were added to 1.13 g (3.50 mmol) of 5-bromo-1-(tetrahydropyran-2-yl)-4-vinyloxy-1H-indazole (referential compound 46) in an argon stream with stirring and the mixture was stirred at room temperature for 4.5 hours. After that, 3.26 ml (44.8 mmol) of chloroiodomethane and 20.4 ml (22.4 mmol) of diethyl zinc were added thereto and further the mixture was stirred at room temperature for 15 hours.

After the reaction was finished, 200 ml of a saturated aqueous solution of ammonium chloride was added to the reaction solution and the mixture was extracted with 200 ml of toluene. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=5:1 (v/v)) and the fraction containing the aimed product was concentrated in vacuo to give 0.95 g of the title compound as a pale yellow oily substance (yield: 80%).

Rf value: 0.65 (n-hexane:ethyl acetate=2:1 (v/v))
Mass spectrum (EI, m/z): 336, 338 (M$^+$)
$^1$H-NMR spectrum (CDCl$_3$, δ ppm): 0.80-0.88 (m, 2H), (m, 2H), 1.58-1.85 (m, 3H), 2.09-2.19 (m, 2H), (m, 1H), 3.69-3.78 (m, 1H), 3.96-4.06 (m, 1H), (m, 1H), 5.62-5.70 (m, 1H), 7.13 (dd, J1=8.8 Hz, J2=0.8 Hz, 1H), 7.47 (d, J=8.8 Hz, 1H), 8.32 (d, J=0.8 Hz, 1H)

Referential Example 48

Synthesis of 5-(1-aminocarbonylcyclopentyl)-2-bromopyridine (Referential Compound 48-1)

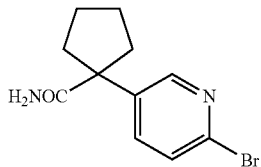

Polyphosphoric acid (80 g) was added to 12 g (48 mmol) of 2-bromo-5-(1-cyanocyclopentyl)pyridine (Referential Compound 1-6) and the mixture was heated with stirring at 100° C. for 1.5 hours.

After the reaction was finished, 200 ml of toluene and 100 ml of water were successively added to the reaction solution and then potassium carbonate was added thereto to adjust pH of the aqueous layer to 7. After that, the resulting solid was filtered off, successively washed, with toluene and, water and dried in vacuo to give 12 g of the title compound as white powder (yield: 93%).

Melting point: 211 to 212° C.
Rf value: 0.10 (n-hexane:ethyl acetate=1:1 (v/v))
Mass spectrum (CI, m/z): 269, 271 ($M^+$+1)
$^1$H-NMR spectrum (CDCl$_3$, δ ppm): 1.65-2.05 (m, 6H), 2.40-2.60 (m, 2H), 5.25 (brs, 2H), 7.46 (dd, J1=8.4 Hz, J2=0.7 Hz, 2H), 7.57 (dd, J1=8.4 Hz, J2=2.7 Hz, 2H), 8.40 (dd, J1=2.7 Hz, J2=0.7 Hz, 2H)

As hereunder, referential compound 48-2 was produced in accordance with the production process for referential compound 48-1.

5-(1-Aminocarbonyl-1-ethylpropyl)-2-bromopyridine (Referential Compound 48-2)

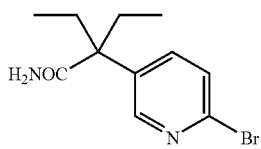

Rf value: 0.42 (n-hexane:ethyl acetate=1:1 (v/v))
Mass spectrum (CI, m/z): 271, 273 ($M^+$+1)
$^1$H-NMR spectrum (CDCl$_3$, δ ppm): 0.80 (t, J=7.4 Hz, 6H), 1.95-2.07 (m, 4H), 5.17-5.38 (m, 2H), 7.47 (dd, J1=8.4 Hz, J2=0.8 Hz, 1H), 7.51 (dd, J1=8.4 Hz, J2=2.6 Hz, 1H), 8.34 (dd, J1=2.6 Hz, J2=0.8 Hz, 1H)

Example 1

Synthesis of 1-acetyl-5-[4-(1-tert-butoxycarbonyl-amino-1-methylethyl)phenyl]-1H-indazole (Compound 1-1)

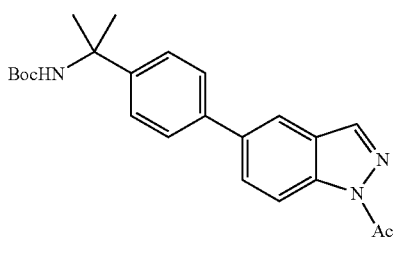

4-(1-tert-Butoxycarbonylamino-1-methylethyl)-1-(4,4,5,5-tetramethyl[1,3,2]dioxaborolanyl)benzene (Referential Compound 6-1) (1.26 g, 3.49 mmol), 792 mg (5.21 mmol) of cesium fluoride, 400 mg (0.346 mmol) of tetrakis(triphenylphosphine) palladium and 20 ml of 1,2-dimethoxyethane were added to 500 mg (1.74 mmol) of 1-acetyl-5-iodo-1H-indazole (referential compound 12-1) and the mixture was heated to reflux with stirring for 2 hours in an argon stream.

After the reaction was finished, the reaction solution was poured into 50 ml of water and the mixture was extracted with 100 ml of ethyl acetate. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=5:1 (v/v)) and the fraction containing the aimed product was concentrated in vacuo to give 385 mg of the title compound as white powder (yield: 56%).

Rf value: 0.48 (n-hexane:ethyl acetate=2:1 (v/v))
Mass spectrum (CI, m/z): 394 ($M^+$+1)
$^1$H-NMR spectrum (CDCl$_3$, δ ppm): 1.40 (brs, 9H), 1.67 (s, 6H), 2.81 (s, 3H), 4.98 (brs, 1H), 7.48-7.52 (m, 2H), 7.57-7.61 (m, 2H), 7.80 (dd, J1=8.8 Hz, J2=1.7 Hz, 1H), 7.91 (dd, J1=1.7 Hz, J2=0.8 Hz, 1H), 8.17 (d, J=0.8 Hz, 1H), 8.46-8.50 (m, 1H)

As hereunder, the compounds 1-2 to 1-31 were produced in accordance with the production process for the compound 1-1. Incidentally, in the synthesis of the compounds 1-7 to 1-11, an adduct of tris(dibenzylideneacetone) dipalladium with chloroform was used instead of tetrakis(triphenylphosphine) palladium and, in the synthesis of the compounds 1-12 to 1-31, a 2M aqueous solution of sodium carbonate was used instead of cesium fluoride.

1-tert-Butoxycarbonyl-5-[4-(1-tert-butoxycarbonyl-amino-1-methylethyl)phenyl]-3-methoxycarbonyl-1H-indazole (Compound 1-2)

Rf value: 0.30 (n-hexane:ethyl acetate=2:1
$^1$H-NMR spectrum (CDCl$_3$, δ ppm): 1.40 (brs, 9H), 1.68 (s, 6H), 1.76 (s, 9H), 4.06 (s, 3H), 4.97 (brs, 1H), 7.48-7.52 (m, 2H), 7.61-7.65 (m, 2H), 7.83 (dd, J1=8.8 Hz, J2=1.7 Hz, 1H), 8.24 (dd, J1=8.8 Hz, J2=0.7 Hz, 1H), 8.44 (dd, J1=1.7 Hz, J2=0.7 Hz, 1H)

1-Acetyl-3-tert-butoxycarbonylamino-5-[4-(1-tert-butoxycarbonylamino-1-methylethyl)phenyl]-1H-indazole (Compound 1-3)

Rf value: 0.29 (n-hexane:ethyl acetate=2:1 (v/v))

1-tert-Butoxycarbonyl-5-[4-(1-tert-butoxycarbonyl-amino-1-methylethyl)phenyl]-3-formyl-1H-indazole (Compound 1-4)

Rf value: 0.48 (n-hexane:ethyl acetate=2:1 (v/v))

1-Acetyl-5-[4-(1-tert-butoxycarbonylamino-1-methyl-ethyl)phenyl]-3-(1-methylvinyl)-1H-indazole (Compound 1-5)

Rf value: 0.43 (n-hexane:ethyl acetate=4:1 (V/V))

1-Acetyl-6-[4-(1-tert-butoxycarbonylamino-1-methyl-ethyl)phenyl]-1H-indazole (Compound 1-6)

Rf value: 0.24 (n-hexane:ethyl acetate=4:1 (v/v))
Mass spectrum (CI, m/z): 394 ($M^+$+1)
$^1$H-NMR spectrum (CDCl$_3$, δ ppm): 1.40 (brs, 1H), 1.68 (s, 6H), 2.81 (s, 3H), 4.98 (brs, 1H), 7.48-7.53 (m, 2H), 7.61 (dd, J1=8.3 Hz, J2=1.5 Hz, 1H), 7.63-7.68 (m, 2H), 7.77 (dd, J1=8.3 Hz, J2=0.7 Hz, 1H), 8.14 (d, J=0.7 Hz, 1H), 8.67-8.69 (m, 1H)

1-tert-Butoxycarbonyl-5-[4-(1-tert-butoxycarbonyl-amino-1-methylethyl)phenyl]-4-nitro-1H-indazole (Compound 1-7)

Rf value: 0.36 (n-hexane:ethyl acetate=2:1 (v/v))
Mass spectrum (FAB, m/z): 496 (M$^+$)
$^1$H-NMR spectrum (CDCl$_3$, δ ppm): 1.38 (brs, 9H), 1.67 (s, 6H), 1.75 (s, 9H), 4.95 (brs, 1H), 7.31-7.34 (m, 2H), 7.46-7.51 (m, 2H), 7.60 (d, J=8.7 Hz, 1H), 8.42 (d, J=0.7 Hz, 1H), 8.45 (dd, J1=8.7 Hz, J2=0.7 Hz, 1H)

1-tert-Butoxycarbonyl-5-[4-(4-(tert-butoxycarbonyl-aminomethyl)phenyl]-4-nitro-1H-indazole (Compound 1-8)

Rf value 0.37 (n-hexane:ethyl acetate=2:1 (v/v))
Mass spectrum (FAB, m/z): 469 (M$^+$+1)
$^1$H-NMR spectrum (CDCl$_3$, δ ppm): 1.48 (s, 9H), 1.74 (s, 9H), 4.38-4.41 (m, 2H), 4.92 (brs, 1H), 7.31-7.40 (m, 4H), 7.58 (d, J=8.8 Hz, 1H), 8.44 (d, J=0.7 Hz, 1H), 8.47 (dd, J1=8.8 Hz, J2=0.7 Hz, 1H)

1-tert-Butoxycarbonyl-5-[4-(1-tert-butoxycarbonyl-aminocyclopentyl)phenyl]-4-nitro-1H-indazole (Compound 1-9)

Rf value: 0.41 (n-hexane:ethyl acetate=2:1 (v/v))
Mass spectrum (FAB, m/z): 522 (M$^+$)
$^1$H-NMR spectrum (CDCl$_3$, δ ppm): 1.37 (brs, 9H), 1.75 (s, 9H), 1.80-1.89 (m, 4H), 2.04-2.35 (m, 4H), 4.90 (brs, 1H), 7.28-7.33 (m, 2H), 7.45-7.50 (m, 2H), 7.60 (d, J=8.5 Hz, 1H), 8.41-8.46 (m, 2H) 1-tert-Butoxycarbonyl-5-[4-(1-tert-butoxycarbonyl-amino-1-ethylpropyl)phenyl]-4-nitro-1H-indazole (Compound 1-10)

Rf value: 0.50 (n-hexane:ethyl acetate=2:1 (v/v))
Mass spectrum (FAB, m/z): 525 (M$^+$+1)
$^1$H-NMR spectrum (CDCl$_3$, δ ppm): 0.79 (t, J=7.3 Hz, 6H), 1.41 (brs, 9H), 1.75 (s, 9H), 1.87-2.12 (m, 4H), 4.81 (brs, 1H), 7.32 (d, J=8.5 Hz, 2H), 7.42 (d, J=8.5 Hz, 2H), 7.61 (d, J=8.6 Hz, 1H), 8.43 (d, J=0.8 Hz, 1H), 8.45 (dd, J1=8.6 Hz, J2=0.8 Hz, 1H)

1-tert-Butoxycarbonyl-5-[4-(1-tert-butoxycarbonyl-aminoethyl)phenyl]-4-nitro-1H-indazole (Compound 1-11)

Rf value: 0.50 (n-hexane:ethyl acetate=2:1 (v/v))
$^1$H-NMR spectrum (DMSO-d$_6$, δ ppm): 1.31-1.45 (m, 12H), 1.68 (s, 9H), 4.63-4.75 (m, 1H), 7.31-7.50 (m, 5H), 7.77 (d, J=8.6 Hz, 1H), 8.41 (dd, J1=8.6 Hz, J2=0.7 Hz, 1H), 8.57 (d, J=0.7 Hz, 1H)

4-Benzyloxy-5-[5-(1-tert-butoxycarbonylamino-1-methylethyl)pyridin-2-yl]-1-(tetrahydropyran-2-yl)-1H-indazole (Compound 1-12)

Rf value: 0.36 (n-hexane:ethyl acetate=1:1 (v/v))
Mass spectrum (CI, m/z): 543 (M$^+$+1)
$^1$H-NMR spectrum (CDCl$_3$, δ ppm): 1.38 (brs, 9H), 1.68-1.82 (m, 9H), 2.06-2.22 (m, 2H), 2.50-2.65 (m, 1H), 3.69-3.81 (m, 1H), 4.01-4.08 (m, 1H), 4.96 (brs, 1H), 5.31 (s, 2H), 5.69-5.74 (m, 1H), 7.26-7.33 (m, 5H), 7.38 (dd, J1=8.8 Hz, J2=0.9 Hz, 1H), 7.67 (dd, J1=8.4 Hz, J2=2.6 Hz, 1H), 7.85-7.91 (m, 2H), 8.09 (d, J=0.9 Hz, 1H), 8.75 (dd, J1=2.6 Hz, J2=0.9 Hz, 1H)

5-[5-(1-tert-Butoxycarbonylamino-1-methylethyl)-pyridin-2-yl]-4-nitro-2-(tetrahydropyran-2-yl)-2H-indazole (Compound 1-13)

Rf value: 0.15 (n-hexane:ethyl acetate=1:1 (v/v))
Mass spectrum (CI, m/z): 482 (M$^+$+1)
$^1$H-NMR spectrum (CDCl$_3$, δ ppm): 1.38 (brs, 9H), 1.59-1.84 (m, 9H), 2.04-2.28 (m, 3H), 3.78-3.86 (m, 1H), 4.11-4.18 (m, 1H), 4.98 (brs, 1H), 5.73-5.77 (m, 1H), 7.42 (dd, J1=8.3 Hz, J2=1.0 Hz, 1H), 7.48 (d, J=8.8 Hz, 1H), 7.79 (dd, J1=8.3 Hz, J2=2.4 Hz, 1H), 8.02 (dd, J1=8.8 Hz, J2=1.0 Hz, 1H), 8.59-8.60 (m, 1H), 8.73 (dd, J1=2.4 Hz, J2=1.0 Hz, 1H)

5-[5-(1-tert-Butoxycarbonylamino-1-methylethyl)-3-chloropyridin-2-yl]-2-(tetrahydropyran-2-yl)-2H-indazole (Compound 1-14)

Rf value: 0.27 (n-hexane:ethyl acetate=1:1 (v/v))
Mass spectrum (EI, m/z): 470 (M$^+$)
$^1$H-NMR spectrum (CDCl$_3$, δ ppm): 1.40 (brs, 9H), 1.63-1.81 (m, 9H), 2.04-2.28 (m, 3H), 3.75-3.84 (m, 1H), 4.11-4.16 (m, 1H), 5.01 (brs, 1H), 5.68-5.73 (m, 1H), 7.65 (dd, J1=9.0 Hz, J2=1.7 Hz, 1H), 7.76-7.81 (m, 2H), 8.06-8.08 (m, 1H), 8.24 (d, J=0.7 Hz, 1H), 8.63 (d, J=2.2 Hz, 1H)

5-[4-(1-tert-Butoxycarbonylamino-1-methylethyl)-phenyl]-2-(tetrahydropyran-2-yl)-4-[2-(tetrahydropyran-2-yloxy)ethyl]-2H-indazole (Compound 1-15)

Rf value: 0.36 (n-hexane:ethyl acetate=2:1 (v/v))
Mass spectrum (CI, m/z): 564 (M$^+$+1)
$^1$H-NMR spectrum (DMSO-d$_6$, δ ppm): 1.06-1.85 (m, 23H), 1.92-2.22 (m, 2H), 2.35-2.57 (m, 2H), 3.10-3.16 (m, 2H), 3.25-3.32 (m, 1H), 3.43-3.63 (m, 2H), 3.69-3.93 (m, 3H), 4.42-4.47 (m, 1H), 5.81-5.87 (m, 1H), 7.18 (brs, 1H), 7.24 (d, J=8.5 Hz, 1H), 7.30 (d, J=8.3 Hz, 2H), 7.40 (d, J=8.3 Hz, 2H), 7.61 (d, J=8.5 Hz, 1H), 8.22 (s, 1H)

5-[5-(1-tert-Butoxycarbonylamino-1-methylethyl)-pyridine-2-yl]-2-(tetrahydropyran-2-yl)-4-[(2-tetrahydropyran-2-yloxy)ethyl]-2H-indazole (Compound 1-16)

Rf value: 0.13 (n-hexane:ethyl acetate=2:1 (v/v))
Mass spectrum (CI, m/z): 565 (M$^+$+1)
$^1$H-NMR spectrum (DMSO-d$_6$, δ ppm): 1.06-1.85 (m, 23H), 1.92-2.22 (m, 2H), 2.36-2.57 (m, 2H), 3.24-3.40 (m, 3H), 3.47-3.92 (m, 5H), 4.44-4.49 (m, 1H), 5.84-5.89 (m, 1H), 7.32 (brs, 1H), 7.44 (d, J=8.8 Hz, 1H), 7.53 (d, J=8.2 Hz, 1H), 7.65 (d, J=8.8 Hz, 1H), 7.78 (dd, J1=8.2 Hz, J2=2.4 Hz, 1H), 8.26 (s, 1H), 8.63 (d, J=2.4 Hz, 1H)

5-[4-(1-tert-Butoxycarbonylamino-1-methylethyl)-phenyl]-4-formyl-2-(tetrahydropyran-2-yl)-2H-indazole (Compound 1-17)

Property: white powder
Rf value: 0.46 (n-hexane:ethyl acetate=1:1 (v/v))
Mass spectrum (EI, m/z): 463 (M$^+$)
$^1$H-NMR spectrum (CDCl$_3$, δ ppm): 1.40 (brs, 9H), 1.62-1.84 (m, 9H), 2.02-2.37 (m, 3H), 3.75-3.87 (m, 1H), 4.11-4.19 (m, 1H), 4.98 (brs, 1H), 5.70-5.77 (m, 1H), 7.35-7.44 (m, 3H), 7.48-7.54 (m, 2H), 8.02 (dd, J1=9.0 Hz, J2=0.9 Hz, 1H), 8.95 (d, J=0.9 Hz, 1H), 10.06 (s, 1H)

5-[4-(1-tert-Butoxycarbonylamino-1-methylethyl)-phenyl]-4-methylcarbonyl-2-(tetrahydropyran-2-yl)-2H-indazole (Compound 1-18)

Property: pale yellow powder
Melting point: 196 to 198° C.
Rf value: 0.46 (n-hexane:ethyl acetate=1:1 (v/v))
Mass spectrum (EI, m/z): 477 (M$^+$)
$^1$H-NMR spectrum (CDCl$_3$, δ ppm): 1.37 (brs, 9H), 1.58-1.86 (m, 9H), 1.94 (s, 3H), 2.01-2.35 (m, 3H), 3.74-3.83 (m, 1H), 4.10-4.17 (m, 1H), 4.97 (brs, 1H), 5.66-5.71 (m, 1H), 7.33-7.39 (m, 3H), 7.45-7.51 (m, 2H), 7.86 (dd, J1=8.8 Hz, J2=0.9 Hz, 1H), 8.42 (d, J=0.9 Hz, 1H)

4-Benzyloxy-5-[4-(1-tert-butoxycarbonylamino-1-methylethyl)phenyl]-2-(tetrahydropyran-2-yl)-2H-indazole (Compound 1-19)

Rf value: 0.40 (n-hexane:ethyl acetate=1:1 (v/v))
Mass spectrum (EI, m/z): 541 (M$^+$)
$^1$H-NMR spectrum (CDCl$_3$, δ ppm): 1.38 (brs, 9H), 1.60-1.80 (m, 9H), 2.00-2.10 (m, 1H), 2.17-2.24 (m, 2H), 3.74-3.83 (m, 1H), 4.11-4.15 (m, 1H), 4.85 (d, J=11.5 Hz, 1H), 4.90 (d, J=11.5 Hz, 1H), 4.94 (brs, 1H), 5.64-5.68 (m, 1H), 7.17-7.30 (m, 5H), 7.33 (d, J=8.8 Hz, 1H), 7.42-7.46 (m, 2H), 7.51 (dd, J1=8.8 Hz, J2=1.0 Hz, 1H), 7.54-7.58 (m, 2H), 8.15 (d, J=1.0 Hz, 1H)

4-Benzyloxy-5-[4-(1-tert-butoxycarbonylamino-1-methylethyl)phenyl]-1-(tetrahydropyran-2-yl)-1H-indazole (Compound 1-20)

Rf value: 0.40 (n-hexane:ethyl acetate=2:1 (v/v))
Mass spectrum (EI, m/z): 541 (M$^+$)
$^1$H-NMR spectrum (CDCl$_3$, δ ppm): 1.39 (brs, 9H), 1.60-1.81 (m, 9H), 2.04-2.17 (m, 2H), 2.51-2.63 (m, 1H), 3.73-3.80 (m, 1H), 4.03-4.14 (m, 1H), 4.86 (brs, 1H), 4.97 (s, 2H), 5.68-5.73 (m, 1H), 7.18-7.31 (m, 5H), 7.35 (dd, J1=8.5 Hz, J2=0.7 Hz, 1H), 7.39-7.46 (m, 3H), 7.51-7.55 (m, 2H), 8.07 (d, J=0.7 Hz, 1H)

5-[4-(1-tert-Butoxycarbonylamino-1-methylethyl)-phenyl]-4-methoxy-2-(tetrahydropyran-2-yl)-2H-indazole (Compound 1-21)

Rf value: 0.44 (n-hexane:ethyl acetate=1:1 (v/v))
Mass spectrum (EI, m/z): 465 (M$^+$)
$^1$H-NMR spectrum (CDCl$_3$, δ ppm): 1.38 (brs, 9H), 1.68-1.82 (m, 9H), 2.04-2.26 (m, 3H), 3.76-3.84 (m, 4H), 4.13-4.18 (m, 1H), 4.94 (brs, 1H), 5.66-5.71 (m, 1H), 7.30 (d, J=8.8 Hz, 1H), 7.42-7.55 (m, 5H), 8.30 (d, J=1.0 Hz, 1H)

4-Benzyloxy-5-[5-(1-tert-butoxycarbonylamino-1-methylethyl)pyridin-2-yl]-2-(tetrahydropyran-2-yl)-2H-indazole (Compound 1-22)

Rf value: 0.31 (n-hexane:ethyl acetate=2:1 (v/v))
Mass spectrum (CI, m/z): 543 (M$^+$+1)
$^1$H-NMR spectrum (DMSO-d$_6$, δ ppm): 1.34 (brs, 9H), 1.51-1.83 (m, 9H), 1.95-2.12 (m, 2H), 2.20-2.35 (m, 1H), 3.69-3.79 (m, 1H), 3.99-4.08 (m, 1H), 5.29 (d, J=11.2 Hz, 1H), 5.31 (d, J=11.2 Hz, 1H), 5.73-5.79 (m, 1H), 7.26-7.45 (m, 6H), 7.63 (dd, J1=8.5 Hz, J2=2.4 Hz, 1H), 7.71 (d, J=9.0 Hz, 1H), 7.82 (d, J=8.5 Hz, 1H), 8.62 (d, J=2.4 Hz, 1H), 8.82 (s, 1H)

5-[5-(1-tert-Butoxycarbonylamino-1-methylethyl)-pyridin-2-yl]-4-methoxy-2-(tetrahydropyran-2-yl)-2H-indazole (Compound 1-23)

Rf value: 0.37 (n-hexane:ethyl acetate=1:2 (v/v))
Mass spectrum (CI, m/z): 467 (M$^+$+1)
$^1$H-NMR spectrum (CDCl$_3$, δ ppm): 1.38 (brs, 9H), 1.64-1.86 (m, 9H), 2.07-2.30 (m, 3H), 3.76-3.85 (m, 1H), 3.95 (s, 3H), 4.14-4.19 (m, 1H), 4.96 (brs, 1H), 5.66-5.71 (m, 1H), 7.50 (dd, J1=9.0 Hz, J2=0.9 Hz, 1H), 7.72 (dd, J1=8.3 Hz, J2=2.4 Hz, 1H), 7.77 (d, J=9.0 Hz, 1H), 7.84 (dd, J1=8.3 Hz, J2=0.7 Hz, 1H), 8.33 (d, J=0.9 Hz, 1H), 8.76 (dd, J1=2.4 Hz, J2=0.7 Hz, 1H)

5-[5-(1-tert-Butoxycarbonylamino-1-ethylpropyl)-pyridin-2-yl]-4-methoxy-2-(tetrahydropyran-2-yl)-2H-indazole (Compound 1-24)

Rf value: 0.20 (n-hexane:ethyl acetate=2:1 (v/v))
Mass spectrum (CI, m/z): 495 (M$^+$+1)
$^1$H-NMR spectrum (CDCl$_3$, δ ppm): 0.82 (t, J=7.3 Hz, 6H), 1.41 (brs, 9H), 1.69-1.81 (m, 3H), 1.90-2.35 (m, 7H), 3.76-3.84 (m, 1H), 3.94 (s, 3H), 4.13-4.18 (m, 1H), 4.80 (brs, 1H), 5.65-5.72 (m, 1H), 7.50 (dd, J1=8.8 Hz, J2=0.7 Hz, 1H), 7.66 (dd, J1=8.4 Hz, J2=2.4 Hz, 1H), 7.81 (d, J=8.8 Hz, 1H), 7.86 (dd, J1=8.4 Hz, J2=0.7 Hz, 1H), 8.68 (d, J=0.7 Hz, 1H), 8.69 (dd, J1=2.4 Hz, J2=0.7 Hz, 1H)

5-[5-(1-tert-Butoxycarbonylamino-1-methylethyl)-pyridin-2-yl]-4-ethoxy-1-(tetrahydropyran-2-yl)-1H-indazole (Compound 1-25)

Property: pale yellow powder
Rf value: 0.13 (n-hexane:ethyl acetate=2:1 (v/v))
Mass spectrum (CI, m/z): 481 (M$^+$+1)
$^1$H-NMR spectrum (CDCl$_3$, δ ppm): 1.33 (t, J=7.0 Hz, 3H), 1.39 (brs, 9H), 1.62-1.84 (m, 9H), 2.03-2.22 (m, 2H), 2.50-2.64 (m, 1H), 3.71-3.81 (m, 1H), 4.01-4.09 (m, 1H), 4.24 (q, J=7.0 Hz, 2H), 4.98 (brs, 1H), 5.68-5.73 (m, 1H), 7.34 (dd, J1=8.8 Hz, J2=0.9 Hz, 1H), 7.72 (dd, J1=8.3 Hz, J2=2.6 Hz, 1H), 7.90 (d, J=8.8 Hz, 1H), 7.91 (dd, J1=8.3 Hz, J2=0.7 Hz, 1H), 8.16 (d, J=0.9 Hz, 1H), 8.75 (dd, J1=2.6 Hz, J2=0.7 Hz, 1H)

5-[5-(1-tert-Butoxycarbonylamino-1-ethylpropyl)-pyridin-2-yl]-4-ethoxy-1-(tetrahydropyran-2-yl)-1H-indazole (Compound 1-26)

Rf value: 0.13 (n-hexane:ethyl acetate=2:1 (v/v))
Mass spectrum (CI, m/z): 509 (M$^+$+1)
$^1$H-NMR spectrum (DMSO-d$_6$, δ ppm): 0.70 (t, J=7.1 Hz, 6H), 1.30 (t, J=6.8 Hz, 3H), 1.35 (brs, 9H), 1.50-2.12 (m, 9H), 2.35-2.55 (m, 1H), 3.71-3.80 (m, 1H), 3.80-3.95 (m, 1H), 4.35 (q, J=6.8 Hz, 2H), 5.78-5.88 (m, 1H), 7.00 (brs, 1H), 7.40-7.47 (m, 1H), 7.67 (dd, J1=8.3 Hz, J2=2.2 Hz, 1H), 7.84-7.93 (m, 2H), 8.33 (s, 1H), 8.56 (d, J=2.2 Hz, 1H)

5-[5-(1-tert-Butoxycarbonylamino-1-methylethyl)-pyridin-2-yl]-4-n-propoxy-1-(tetrahydropyran-2-yl)-1H-indazole (Compound 1-27)

Rf value: 0.34 (n-hexane:ethyl acetate=1:1 (v/v))
Mass spectrum (CI, m/z): 495 (M$^+$+1)
$^1$H-NMR spectrum (CDCl$_3$, δ ppm): 0.94 (t, J=7.4 Hz, 3H), 1.36 (brs, 9H), 1.63-1.81 (m, 11H), 2.04-2.19 (m, 2H), 2.51-

2.64 (m, 1H), 3.71-3.80 (m, 1H), 4.02-4.07 (m, 1H), 4.13 (t, J=6.5 Hz, 2H), 4.96 (brs, 1H), 5.68-5.73 (m, 1H), 7.33 (dd, J1=8.8 Hz, J2=0.7 Hz, 1H), 7.71 (dd, J1=8.3 Hz, J2=2.4 Hz, 1H), 7.87-7.90 (m, 2H), 8.16 (d, J=0.7 Hz, 1H), 8.75 (dd, J1=2.4 Hz, J2=0.9 Hz, 1H)

5-[5-(1-tert-Butoxycarbonylaminocyclopentyl)pyridin-2-yl]-4-methoxy-2-(tetrahydropyran-2-yl)-2H-indazole (Compound 1-28)

Rf value: 0.33 (n-hexane:ethyl acetate=1:2 (v/v))

Mass spectrum (CI, m/z): 493 (M$^+$+1)

$^1$H-NMR spectrum (CDCl$_3$, δ ppm): 1.37 (brs, 9H), 1.66-1.91 (m, 8H), 2.07-2.30 (m, 6H), 3.74-3.85 (m, 1H), 3.94 (s, 3H), 4.14-4.18 (m, 1H), 4.91 (brs, 1H), 5.66-5.71 (m, 1H), 7.50 (dd, J1=9.0 Hz, J2=0.7 Hz, 1H), 7.73 (dd, J1=8.3 Hz, J2=2.4 Hz, 1H), 7.78 (d, J=9.0 Hz, 1H), 7.84 (dd, J1=8.3 Hz, J2=1.0 Hz, 1H), 8.33 (d, J=0.7 Hz, 1H), 8.75 (dd, J1=2.4 Hz, J2=1.0 Hz, 1H)

5-[5-(1-tert-Butoxycarbonylamino-1-methylethyl)-pyridin-2-yl]-4-cyclopropyloxy-1-(tetrahydropyran-2-yl)-1H-indazole (Compound 1-29)

Rf value: 0.09 (n-hexane:ethyl acetate=2:1 (v/v))

Mass spectrum (CI, m/z): 493 (M$^+$+1)

$^1$H-NMR spectrum (DMSO-d$_6$, δ ppm): 0.70-0.90 (m, 4H), 1.34 (brs, 9H), 1.50-2.15 (m, 11H), 2.35-2.60 (m, 1H), 3.70-3.82 (m, 1H), 3.83-3.95 (m, 1H), 4.42-4.48 (m, 1H), 5.80-5.88 (m, 1H), 7.26-7.29 (m, 1H), 7.41 (d, J=8.1 Hz, 1H), 7.65-7.75 (m, 2H), 7.80 (d, J=8.5H, 1H), 8.55 (s, 1H), 8.60 (s, 1H)

5-[5-(1-tert-Butoxycarbonylamino-1-ethylpropyl)-pyridin-2-yl]-4-cyclopropyloxy-1-(tetrahydropyran-2-yl)-1H-indazole (Compound 1-30)

Rf value: 0.09 (n-hexane:ethyl acetate=2:1 (v/v))

Mass spectrum (CI, m/z): 521 (M$^+$+1)

$^1$H-NMR spectrum (DMSO-d$_6$, δ ppm): 0.55-0.90 (m, 10H), 1.35 (brs, 9H), 1.50-2.15 (m, 9H), 2.35-2.55 (m, 1H), 3.72-3.80 (m, 1H), 3.89-3.99 (m, 1H), 4.42-4.48 (m, 1H), 5.83-5.86 (m, 1H), 6.99 (brs, 1H), 7.42 (d, J=8.8 Hz, 1H), 7.64 (dd, J1=8.3 Hz, J2=2.4 Hz, 1H), 7.72 (d, J=8.3 Hz, 1H), 7.84 (d, J=8.8 Hz, 1H), 8.50-8.60 (m, 2H)

4-Benzyloxy-5-[4-(1-tert-butoxycarbonylamino-1-ethylpropyl)phenyl]-1-(tetrahydropyran-2-yl)-1H-indazole (Compound 1-31)

Rf value: 0.40 (n-hexane:ethyl acetate=2:1 (v/v))

Mass spectrum (CI, m/z): 570 (M$^+$+1)

$^1$H-NMR spectrum (CDCl$_3$, δ ppm): 0.73 (t, J=7.3 Hz, 3H), 0.80 (t, J=7.3 Hz, 3H), 1.41 (brs, 9H), 1.60-2.23 (m, 9H), 2.53-2.67 (m, 1H), 3.73-3.83 (m, 1H), 4.03-4.12 (m, 1H), 4.80 (brs, 1H), 4.96 (s, 2H), 5.70-5.77 (m, 1H), 7.15-7.28 (m, 5H), 7.33-7.44 (m, 4H), 7.49-7.54 (m, 2H), 8.10 (s, 1H)

Example 2

Synthesis of 1-acetyl-5-[5-(1-tert-butoxycarbonyl-amino-1-methylethyl)pyridin-2-yl]-1H-indazole (Compound 2)

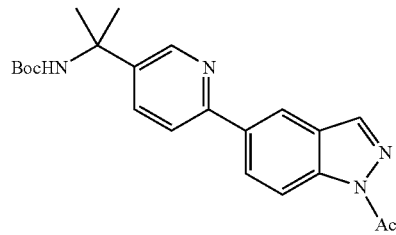

1-Acetyl-5-(4,4,5,5-tetramethyl [1,3,2] dioxa-borolanyl)-1H-indazole (referential compound 29-1) (414 mg, 1.45 mmol), 881 mg (5.80 mmol) of cesium fluoride, 406 mg (0.580 mmol) of dichlorobis(triphenylphosphine) palladium and 30 ml of 1,2-dimethoxyethane were added to 463 mg (1.45 mmol) of 2-bromo-5-(1-tert-butoxycarbonylamino-1-methylethyl)pyridine (referential compound 4-4) and the mixture was heated to reflux with stirring an in argon stream for 4 hours.

After the reaction was finished, the reaction solution was poured into 100 ml of water and the mixture was extracted with 300 ml of ethyl acetate. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=4:1 (v/v)) and the fraction containing the aimed product was concentrated in vacuo to give 155 mg of the title compound as yellow powder (yield: 27%).

Rf value: 0.24 (n-hexane:ethyl acetate=2:1 (v/v))

Mass spectrum (CI, m/z): 395 (M$^+$+1)

$^1$H-NMR spectrum (CDCl$_3$, δ ppm): 1.37 (brs, 9H), 1.69 (s, 6H), 2.81 (s, 3H), 5.00 (brs, 1H), 7.74 (dd, J1=8.3 Hz, J2=1.0 Hz, 1H), 7.80 (dd, J1=8.3 Hz, J2=2.4 Hz, 1H), 8.19 (d, J=0.7 Hz, 1H), 8.20 (dd, J1=8.8 Hz, J2=1.7 Hz, 1H), 8.37-8.38 (m, 1H), 8.51 (ddd, J1=8.8 Hz, J2=0.7 Hz, J3=0.7 Hz, 1H), 8.77 (dd, J1=2.4 Hz, J2=1.0 Hz, 1H)

Example 3

Synthesis of 5-[4-(1-tert-butoxycarbonylamino-1-methylethyl)phenyl]-1H-indazole (Compound 3-1)

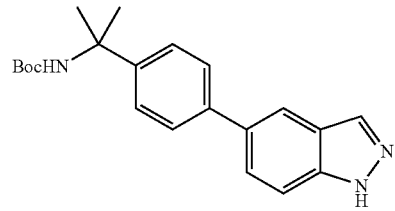

Tetrahydrofuran (5 ml), 5 ml of methanol and 0.5 ml of a 1N aqueous solution of sodium hydroxide were added to 350 mg (0.89 mmol) of 1-acetyl-5-[4-(1-tert-butoxycarbonylamino-1-methylethyl)phenyl]-1H-indazole (compound 1-1) and the mixture was stirred at room temperature for 10 minutes.

After the reaction was finished, the reaction solution was poured into 50 ml of water and the mixture was extracted with each 50 ml of chloroform for three times. The organic layer was successively washed with water and a saturated aqueous solution of sodium chloride, dried over anhydrous magnesium sulfate and concentrated in vacuo. The resulting crystals were washed with 5 ml of methanol and 20 ml of diethyl ether to give 209 mg of the title compound as white powder (yield: 67%).

Rf value: 0.32 (n-hexane:ethyl acetate=1:1 (v/v))
Mass spectrum (CI, m/z): 352 (M$^+$+1)
$^1$H-NMR spectrum (DMSO-d$_6$, δ ppm): 1.35 (brs, 9H), 1.53 (s, 6H), 7.21 (brs, 1H), 7.40 (d, J=8.5 Hz, 2H), 7.59-7.63 (m, 3H), 7.66 (dd, J1=8.8 Hz, J2=1.7 Hz, 1H), 8.00 (dd, J1=1.7 Hz, J2=1.0 Hz, 1H), 8.11 (d, J=1.0 Hz, 1H), 13.10 (brs, 1H)

As hereunder, the compounds 3-2 to 3-4 were produced in accordance with the production process for the compound 3-1.

5-[5-(1-tert-Butoxycarbonylamino-1-methylethyl)-pyridin-2-yl]-1H-indazole (Compound 3-2)

Rf value: 0.17 (n-hexane:ethyl acetate=1:1 (v/v))
Mass spectrum (CI, m/z): 353 (M$^+$+1)
$^1$H-NMR spectrum (CDCl$_3$, δ ppm): 1.39 (brs, 9H), 1.69 (s, 6H), 5.02 (brs, 1H), 7.51-7.55 (m, 1H), 7.67-7.71 (m, 1H), 7.76 (dd, J1=8.5 Hz, J2=2.4 Hz, 1H), 8.03-8.07 (m, 1H), 8.14 (d, J=1.0 Hz, 1H), 8.35-8.36 (m, 1H), 8.75 (dd, J1=2.4 Hz, J2=0.7 Hz, 1H), 10.21 (brs, 1H)

3-tert-Butoxycarbonylamino-5-[4-(1-tert-butoxycarbonylamino-1-methylethyl)phenyl]-1H-indazole (Compound 3-3)

Rf value: 0.10 (n-hexane:ethyl acetate=2:1 (v/v))
$^1$H-NMR spectrum (CDCl$_3$, δ ppm): 1.39 (brs, 9H), 1.55 (s, 9H), 1.67 (s, 6H), 4.99 (brs, 1H), 7.27-7.61 (m, 6H), 8.08-8.09 (m, 1H), 9.75 (brs, 1H)

5-[4-(1-tert-Butoxycarbonylamino-1-methylethyl)-phenyl]-3-(1-methylvinyl)-1H-indazole (Compound 3-4)

Rf value: 0.24 (n-hexane:ethyl acetate=2:1 (v/v))
Mass spectrum (CI, m/z): 392 (M$^+$+1)
$^1$H-NMR spectrum (CDCl$_3$, δ ppm): 1.39 (brs, 9H), 1.68 (s, 6H), 2.35 (dd, J1=1.5 Hz, J2=0.7 Hz, 3H), 4.97 (brs, 1H), 5.53-5.56 (m, 1H), 5.83-5.85 (m, 1H), 7.47-7.53 (m, 3H), 7.57-7.61 (m, 2H), 7.64 (dd, J1=8.5 Hz, J2=1.5 Hz, 1H), 8.12-8.13 (m, 1H)

Example 4

Synthesis of 5-[4-(1-tert-butoxycarbonylamino-1-methylethyl)phenyl]-3-methoxycarbonyl-1H-indazole (Compound 4-1)

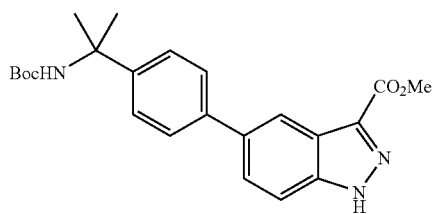

Tetrahydrofuran (2 ml), 2 ml of methanol and 0.2 ml of a 1N aqueous solution of sodium hydroxide were added to 70 mg (0.14 mmol) of 1-tert-butoxycarbonyl-5-[4-(1-tert-butoxycarbonylamino-1-methylethyl)phenyl]-3-methoxycarbonyl-1H-indazole (compound 1-2) and the mixture was stirred at room temperature for 30 minutes.

After the reaction was finished, the reaction solution was poured into 50 ml of chloroform and the mixture was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=2:1 (v/v)) and the fraction containing the aimed substance was concentrated in vacuo to give 51 mg of the title compound as white powder (yield: 91%).

Rf value: 0.24 (n-hexane:ethyl acetate=1:1 (v/v))
Mass spectrum (CI, m/z): 410 (M$^+$+1)
$^1$H-NMR spectrum (CDCl$_3$, δ ppm): 1.42 (brs, 9H), 1.68 (s, 6H), 4.07 (s, 3H), 5.05 (brs, 1H), 7.45-7.61 (m, 6H), 8.38-8.41 (m, 1H), 11.09 (brs, 1H)

As hereunder, the compounds 4-2 to 4-3 were produced in accordance with the production process for the compound 4-1.

5-[4-(1-tert-butoxycarbonylamino-1-methylethyl)-phenyl]-3-formyl-1H-indazole (Compound 4-2)

Rf value: 0.45 (n-hexane:ethyl acetate=1:1 (v/v))
Mass spectrum (CI, m/z): 380 (M$^+$+1)
$^1$H-NMR spectrum (CDCl$_3$, δ ppm): 1.44 (brs, 9H), 1.68 (s, 6H), 5.12 (brs, 1H), 7.41-7.48 (m, 6H), 8.45-8.47 (m, 1H), 10.31 (s, 1H), 11.26 (brs, 1H)

5-[4-(1-tert-butoxycarbonylamino-1-methylethyl)-phenyl]-4-(pyrrol-1-yl)-1H-indazole (Compound 4-3)

Rf value: 0.40 (n-hexane:ethyl acetate=1:1 (v/v))
Mass spectrum (CI, m/z): 417 (M$^+$+1)
$^1$H-NMR spectrum (CDCl$_3$, δ ppm): 1.38 (brs, 9H), 1.62 (s, 6H), 4.91 (brs, 1H), 6.21 (dd, J1=2.2 Hz, J2=2.2 Hz, 2H), 6.72 (dd, J1=2.2 Hz, J2=2.2 Hz, 2H), 7.04-7.09 (m, 2H), 7.29-7.33 (m, 2H), 7.46-7.53 (m, 2H), 8.06 (s, 1H), 10.23 (brs, 1H)

Example 5

Synthesis of 5-[4-(1-amino-1-methylethyl)phenyl]-1H-indazole dihydrochloride (Compound 5-1)

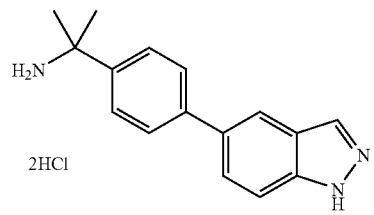

Methanol (4 ml) and 8 ml of a 4N hydrogen chloride/1,4-dioxane solution were added to 285 mg (0.63 mmol) of 5-[4-(1-tert-butoxycarbonylamino-1-methylethyl)phenyl]-1H-indazole (compound 3-1) and the mixture was stirred in argon stream at room temperature for 2.5 hours.

After the reaction was finished, the reaction solution was concentrated in vacuo. The resulting residue was dissolved in 1.5 ml of methanol, 10 ml of 1,4-dioxane was added thereto and the resulting solid was filtered off and washed with diethyl ether to give 130 mg of the title compound as white powder (yield: 63%).

Melting point: 268 to 270° C. (decomposition)
Rf value: 0.30 (chloroform:methanol: 28% aqueous ammonia=5:1:0.01 (v/v/v))
Mass spectrum (CI, m/z): 252 (M$^+$+1)
$^1$H-NMR spectrum (DMSO-d$_6$, δ ppm): 1.68 (s, 6H), 7.62-7.66 (m, 3H), 7.69 (dd, J1=8.8 Hz, J2=1.7 Hz, 1H), 7.77 (d, J=8.8 Hz, 2H), 8.06 (dd, J1=1.7 Hz, J2=1.0 Hz, 1H), 8.14 (d, J=1.0 Hz, 1H), 8.67 (brs, 3H)

As hereunder, the compounds 5-2 to 5-73 were produced in accordance with the production process for the compound 5-1. In the synthesis of the compound 5-15 however, a high performance liquid chromatography (eluting solvent: 0.03 vol % aqueous solution of trifluoroacetic acid:acetonitrile=70:30 (v/v)) was used for separation and purification. In this case, the product was converted from a hydrochloride to a trifluoroacetate.

1-Acetyl-5-[4-(1-amino-1-methylethyl)phenyl]-1H-indazole dihydrochloride (Compound 5-2)

Melting point: 247 to 250° C.
Mass spectrum (CI, m/z): 294 (M$^+$+1)
$^1$H-NMR spectrum (DMSO-d$_6$, δ ppm): 1.66 (s, 6H), 2.75 (s, 3H), 7.66 (d, J=8.6 Hz, 2H), 7.83 (d, J=8.6 Hz, 2H), (dd, J1=8.8 Hz, J2=1.7 Hz, 1H), 8.10 (brs, 3H), (dd, J1=1.7 Hz, J2=0.7 Hz, 1H), 8.38-8.41 (m, 1H), (d, J=1.0 Hz, 1H)

5-[5-(1-Amino-1-methylethyl)pyridin-2-yl]-1H-indazole trihydrochloride (Compound 5-3)

Melting point: 271 to 273° C. (decomposition)
Rf value: 0.31 (chloroform:methanol:28% aqueous ammonia=5:1:0.01 (v/v/v))
Mass spectrum (CI, m/z): 253 (M$^+$+1)
$^1$H-NMR spectrum (DMSO-d$_6$, δ ppm): 1.72 (s, 6H), 7.63-7.68 (m, 1H), 8.11-8.13 (m, 2H), 8.15 (dd, J1=8.8 Hz, J2=1.7 Hz, 1H), 8.20 (d, J=1.0 Hz, 1H), 8.54 (dd, J1=1.7 Hz, J2=0.7 Hz, 1H), 8.72 (brs, 3H), 8.85-8.86 (m, 1H) 0.5-[4-(1-Amino-1-methylethyl)phenyl]-4-nitro-1H-indazole monohydrochloride (Compound 5-4)

Melting point: 255 to 261° C. (decomposition)
Rf value: 0.33 (chloroform:methanol: 28% aqueous ammonia=5:1:0.01 (v/v/v))
IR spectrum (KBr, cm$^{-1}$): 1516, 1322
Mass spectrum (CI, m/z): 297 (M$^+$+1)
$^1$H-NMR spectrum (DMSO-d$_6$, δ ppm): 1.69 (s, 6H), 7.47-7.51 (m, 3H), 7.65-7.68 (m, 2H), 8.00 (dd, J1=8.5 Hz, J2=1.0 Hz, 1H), 8.31 (d, J=1.0 Hz, 1H), 8.66 (brs, 3H), 13.93 (brs, 1H)

4-Amino-5-[4-(1-amino-1-methylethyl)phenyl]-1H-indazole trihydrochloride (Compound 5-5)

Melting point: 228 to 235° C. (decomposition)
Rf value: 0.15 (chloroform:methanol: 28% aqueous ammonia=5:1:0.01 (v/v/v))
Mass spectrum (CI, m/z): 267 (M$^+$+1)
$^1$H-NMR spectrum (DMSO-d$_6$, δ ppm): 1.69 (s, 6H), 6.82 (dd, J1=8.4 Hz, J2=0.9 Hz, 1H), 7.03 (d, J=8.4 Hz, 1H), 7.53 (d, J=8.5 Hz, 2H), 7.62 (d, J=8.5 Hz, 2H), 8.27 (d, J=0.9 Hz, 1H), 8.60 (brs, 3H)

5-[4-(1-Amino-1-methylethyl)phenyl]-4-benzylamino-1H-indazole dihydrochloride (Compound 5-6)

Melting point: 185 to 192° C. (decomposition)
Rf value: 0.49 (chloroform:methanol: 28% aqueous ammonia=5:1:0.01 (v/v/v))
Mass spectrum (CI, m/z): 357 (M$^+$+1)
$^1$H-NMR spectrum (DMSO-d$_6$, δ ppm): 1.68 (s, 6H), 4.59 (s, 2H), 6.82 (dd, J1=8.3 Hz, J2=1.0 Hz, 1H), 6.97 (d, J=8.3 Hz, 1H), 7.16-7.31 (m, 5H), 7.50 (d, J=8.5 Hz, 2H), 7.62 (d, J=8.5 Hz, 2H), 8.08 (d, J=1.0 Hz, 1H), 8.56 (brs, 3H), 12.82 (brs, 1H)

5-[4-(1-Amino-1-methylethyl)phenyl]-4-methylamino-1H-indazole trihydrochloride (Compound 5-7)

Melting point: 202 to 206° C. (decomposition)
Rf value: 0.33 (chloroform:methanol: 28% aqueous ammonia=5:1:0.01 (v/v/v))
Mass spectrum (CI, m/z): 281 (M$^+$+1)
$^1$H-NMR spectrum (DMSO-d$_6$, δ ppm): 1.68 (s, 6H), 3.03 (s, 3H), 6.79 (d, J=8.3 Hz, 1H), 6.95 (d, J=8.3 Hz, 1H), 7.47 (d, J=8.4 Hz, 2H), 7.60 (d, J=8.4 Hz, 2H), 8.29 (s, 1H), 8.53 (brs, 3H)

5-[4-(1-Amino-1-methylethyl)phenyl]-3-methoxycarbonyl-1H-indazole dihydrochloride (Compound 5-8)

Melting point: 264 to 267° C. (decomposition)
Rf value: 0.49 (chloroform:methanol: 28% aqueous ammonia=5:1:0.01 (v/v/v))
IR spectrum (KBr, cm$^{-1}$): 1721
Mass spectrum (CI, m/z): 310 (M$^+$+1)
$^1$H-NMR spectrum (DMSO-d$_6$, δ ppm): 1.68 (s, 6H), 3.95 (s, 3H), 7.66-7.69 (m, 2H), 7.75-7.80 (m, 4H), 8.28-8.30 (m, 1H), 8.45 (brs, 3H)

5-[4-(1-Amino-1-methylethyl)phenyl]-3-carboxy-1H-indazole monohydrochloride (Compound 5-9)

Melting point: 274 to 280° C. (decomposition)
IR spectrum (KBr, cm$^1$): 1689
Mass spectrum (FAB, m/z): 296 (M$^+$+1)
$^1$H-NMR spectrum (DMSO-d$_6$, δ ppm): 1.68 (s, 6H), 7.66 (d, J=8.5 Hz, 2H), 7.76-7.80 (m, 4H), 8.30-8.31 (m, 1H), 8.51 (brs, 3H), 13.90 (brs, 1H), 3-Aminocarbonyl-5-[4-(1-amino-1-methylethyl)phenyl]-1H-indazole monohydrochloride (Compound 5-10)

Melting point: 258 to 261° C. (decomposition)
Rf value: 0.10 (chloroform:methanol: 28% aqueous ammonia=5:1:0.01 (v/v/v))
IR spectrum (KBr, cm$^{-1}$): 1664
Mass spectrum (CI, m/z): 295 (M$^+$+1)
$^1$H-NMR spectrum (DMSO-d$_6$, δ ppm): 1.68 (s, 6H), 7.38 (brs, 1H), 7.66 (d, J=8.5 Hz, 2H), 7.70 (dd, J1=8.8 Hz, J2=0.7 Hz, 1H), 7.73-7.79 (m, 4H), 8.40 (brs, 3H), 8.41-8.43 (m, 1H), 13.65 (brs, 1H)

3-Amino-5-[4-(1-amino-1-methylethyl)phenyl]-1H-indazole trihydrochloride (Compound 5-11)

Melting point: 220 to 222° C. (decomposition)
Rf value: 0.10 (chloroform:methanol: 28% aqueous ammonia=5:1:0.01 (v/v/v))
Mass spectrum (CI, m/z): 267 (M$^+$+1)
$^1$H-NMR spectrum (CD$_3$OD, δ ppm): 1.79 (s, 6H), 7.38 (brs, 3H), 7.56 (d, J=8.8 Hz, 1H), 7.63-7.66 (m, 2H), 7.78-7.81 (m, 2H), 7.99 (dd, J1=8.8 Hz, J2=1.7 Hz, 1H), 8.25-8.26 (m, 1H)

5-[4-(1-Amino-1-methylethyl)phenyl]-3-hydroxy-iminomethyl-1H-indazole monohydrochloride (Compound 5-12)

Melting point: 227 to 230° C. (decomposition)
Rf value: 0.21 (chloroform:methanol: 28% aqueous ammonia=5:1:0.01 (v/v/v))
Mass spectrum (CI, m/z): 295 ($M^+ +1$)
$^1$H-NMR spectrum (DMSO-$d_6$, δ ppm): 1.68 (s, 6H), 7.64-7.69 (m, 3H), 7.74 (d, J=8.5 Hz, 2H), 7.76 (dd, J1=8.8 Hz, J2=1.7 Hz, 1H), 8.29-8.31 (m, 1H), 8.40 (s, 1H), 8.53 (brs, 3H), 11.44 (s, 1H), 13.45 (brs, 1H)

5-[4-(1-Amino-1-methylethyl)phenyl]-3-cyano-1H-indazole dihydrochloride (Compound 5-13)

Melting point: 224 to 227° C. (decomposition)
Rf value: 0.45 (chloroform:methanol: 28% aqueous ammonia=5:1:0.01 (v/v/v))
IR spectrum (KBr, cm$^{-1}$): 2241
Mass spectrum (CI, m/z): 277 ($M^+ +1$)
$^1$H-NMR spectrum (DMSO-$d_6$±6 ppm): 1.68 (s, 6H), 7.66 (d, J=8.5 Hz, 2H), 7.84-7.92 (m, 4H), 8.14-8.15 (m, 1H), 8.61 (brs, 3H)

5-[4-(1-Amino-1-methylethyl)phenyl]-3-hydroxymethyl-1H-indazole dihydrochloride (Compound 5-14)

Melting point: 238 to 242° C. (decomposition)
Rf value: 0.17 (chloroform:methanol: 28% aqueous ammonia=5:1:0.01 (v/v/v))
Mass spectrum (CI, m/z): 282 ($M^+ +1$)
$^1$H-NMR spectrum (DMSO-$d_6$, δ ppm): 1.68 (s, 6H), 4.83 (s, 2H), 7.57 (dd, J1=8.8 Hz, J2=. 0.7 Hz, 1H), 7.64 (d, J=8.5 Hz, 2H), 7.69 (dd, J1=8.8 Hz, J2=1.7 Hz, 1H), 7.78 (d, J=8.5 Hz, 2H), 8.15 (dd, J1=1.7 Hz, J2=0.7 Hz, 1H), 8.57 (brs, 3H)

5-[4-(1-Amino-1-methylethyl)phenyl]-3-(1-methylvinyl)-1H-indazole monotrifluoroacetate (Compound 5-15)

Melting point: 221 to 225° C. (decomposition)
Rf value: 0.43 (chloroform:methanol: 28% aqueous ammonia=5:1:0.01 (v/v/v))
Mass spectrum (CI, m/z): 292 ($M^+ +1$)
$^1$H-NMR spectrum (CD$_3$OD, δ ppm): 1.79 (s, 6H), 2.31-2.33 (m, 3H), 5.43-5.45 (m, 1H), 5.80-5.83 (m, 1H), 7.58-7.63 (m, 3H), 7.70 (dd, J1=8.8 Hz, J2=1.6 Hz, 1H), 7.75-7.80 (m, 2H), 8.14 (dd, J1=1.6 Hz, J2=0.7 Hz, 1H)

5-[4-(1-Amino-1-methylethyl)phenyl]-4-dimethylamino-1H-indazole trihydrochloride (Compound 5-16)

Melting point: 219 to 224° C. (decomposition)
Rf value: 0.46 (chloroform:methanol: 28% aqueous ammonia=5:1:0.01 (v/v/v))
Mass spectrum (CI, m/z): 295 ($M^+ +1$)
$^1$H-NMR spectrum (DMSO-$d_6$, δ ppm): 1.69 (s, 6H), 2.84 (s, 6H), 7.14 (d, J=8.5 Hz, 1H), 7.21-7.25 (m, 1H), 7.49 (d, J=8.5 Hz, 2H), 7.61 (d, J=8.5 Hz, 2H), 8.34 (s, 1H), 8.64 (brs, 3H)

5-[5-(1-Amino-1-methylethyl)pyridin-2-yl]-4-nitro-1H-indazole dihydrochloride (Compound 5-17)

Rf value: 0.40 (chloroform:methanol: 28% aqueous ammonia=5:1:0.01 (v/v/v))
Mass spectrum (CI, m/z): 298 ($M^+ +1$)
$^1$H-NMR spectrum (DMSO-$d_6$, δ ppm): 1.73 (s, 6H), 7.72 (d, J=8.5 Hz, 1H), 7.85-7.88 (m, 1H), 8.02 (dd, J1=8.5 Hz, J2=1.0 Hz, 1H), 8.18 (dd, J1=8.5 Hz, J2=2.5 Hz, 1H), 8.30 (d, J=0.7 Hz, 1H), 8.75-8.85 (m, 4H)

4-(N-Acetylamino)-5-[4-(1-amino-1-methylethyl)phenyl]-1H-indazole dihydrochloride (Compound 5-18)

Melting point: 218 to 221° C.
Rf value: 0.09 (chloroform:methanol: 28% aqueous ammonia=5:1:0.01 (v/v/v))
Mass spectrum (CI, m/z): 309 ($M^+ +1$)
$^1$H-NMR spectrum (DMSO-$d_6$, δ ppm): 1.68 (s, 6H), 1.99 (s, 3H), 7.33 (d, J=8.5 Hz, 1H), 7.47-7.53 (m, 3H), 7.61 (d, J=8.3 Hz, 2H), 7.91 (s, 1H), 8.58-8.72 (m, 3H), 9.72 (brs, 1H)

5-[4-(Aminomethyl)phenyl]-4-nitro-1H-indazole dihydrochloride (Compound 5-19)

Melting point: 269 to 274° C. (decomposition)
Rf value: 0.21 (chloroform:methanol: 28% aqueous ammonia=5:1:0.01 (v/v/v))
Mass spectrum (CI, m/z): 269 ($M^+ +1$)
$^1$H-NMR spectrum (DMSO-$d_6$, δ ppm): 4.08-4.12 (m, 2H), 7.44-7.48 (m, 3H), 7.59 (d, J=8.3 Hz, 2H), 8.00 (dd, J1=8.5 Hz, J2=1.0 Hz, 1H), 8.31 (d, J=1.0 Hz, 1H), 8.46 (brs, 3H)

4-Amino-5-[4-(aminomethyl)phenyl]-1H-indazole trihydrochloride (Compound 5-20)

Rf value: 0.08 (chloroform:methanol: 28% aqueous ammonia=5:1:0.01 (v/v/v))
Mass spectrum (EI, m/z): 238 ($M^+$)
$^1$H-NMR spectrum (DMSO-$d_6$, δ ppm): 4.04-4.08 (m, 2H), 6.90-6.94 (m, 1H), 7.06 (d, J=8.3 Hz, 1H), 7.51 (d, J=8.5 Hz, 2H), 7.58 (d, J=8.5 Hz, 2H), 8.30 (d, J=1.0 Hz, 1H), 8.48 (brs, 3H)

4-Amino-5-[4-(1-aminocyclopentyl)phenyl]-1H-indazole dihydrochloride (Compound 5-21)

Melting point: 234 to 237° C.
Rf value: 0.26 (chloroform:methanol: 28% aqueous ammonia=5:1:0.01 (v/v/v))
Mass spectrum (CI, m/z): 293 ($M^+ +1$)
$^1$H-NMR spectrum (DMSO-$d_6$, δ ppm): 1.75-2.03 (m, 4H), 2.16-2.28 (m, 4H), 6.87-6.90 (m, 1H), 7.06 (d, J=8.5 Hz, 1H), 7.53 (d, J=8.5 Hz, 2H), 7.63 (d, J=8.5 Hz, 2H), 8.29 (d, J=1.0 Hz, 1H), 8.48-8.62 (m, 3H)

4-Amino-5-[4-(1-amino-1-ethylpropyl)phenyl]-1H-indazole trihydrochloride (Compound 5-22)

Melting point: 197 to 199° C. (decomposition)
Rf value: 0.35 (chloroform:methanol: 28% aqueous ammonia=5:1:0.01 (v/v/v))
Mass spectrum (CI, m/z): 295 ($M^+ +1$)
$^1$H-NMR spectrum (DMSO-$d_6$, δ ppm): 0.83 (t, J=7.3 Hz, 6H), 1.64-2.13 (m, 4H), 6.86-6.90 (m, 1H), 7.07 (d, J=8.5 Hz, 1H), 7.48-7.56 (m, 4H), 8.30 (d, J=1.0 Hz, 1H), 8.55-8.70 (m, 3H)

5-[4-(Aminomethyl)phenyl]-4-dimethylamino-1H-indazole trihydrochloride (Compound 5-23)

Melting point: 188 to 192° C. (decomposition)
Rf value: 0.30 (chloroform:methanol: 28% aqueous ammonia=5:1:0.01 (v/v/v))
Mass spectrum (CI, m/z): 267 (M$^+$+1)
$^1$H-NMR spectrum (DMSO-d$_6$, δ ppm): 2.87 (s, 6H), 4.05-4.08 (m, 2H), 7.14 (d, J=8.5 Hz, 1H), 7.20-7.30 (m, 1H), 7.48 (d, J=8.2 Hz, 2H), 7.55 (d, J=8.2 Hz, 2H), 8.33-8.55 (m, 4H)

5-[4-(1-Aminocyclopentyl)phenyl]-4-dimethylamino-1H-indazole trihydrochloride (Compound 5-24)

Melting point: 175 to 178° C. (decomposition)
Rf value: 0.44 (chloroform:methanol: 28% aqueous ammonia=~5:1:0.01 (v/v/v))
Mass spectrum (EI, m/z): 320 (M$^+$)
$^1$H-NMR spectrum (DMSO-d$_6$, δ ppm): 1.76-2.01 (m, 4H), 2.16-2.28 (m, 4H), 2.85 (s, 6H), 7.14 (d, J=8.5 Hz, 1H), 7.20-7.27 (m, 1H), 7.49 (d, J=8.4 Hz, 2H), 7.60 (d, J=8.4 Hz, 2H), 8.32-8.37 (m, 1H), 8.50 (brs, 3H)

5-[4-(1-Amino-1-ethylpropyl)phenyl]-4-dimethylamino-1H-indazole trihydrochloride (Compound 5-25)

Rf value: 0.51 (chloroform:methanol: 28% aqueous ammonia=5:1:0.01 (v/v/v))
Mass spectrum (CI, m/z): 323 (M$^+$+1)
$^1$H-NMR spectrum (DMSO-d$_6$, δ ppm): 0.81 (t, J=7.3 Hz, 6H), 1.91-2.12 (m, 4H), 2.82 (s, 6H), 7.14-7.22 (m, 2H), 7.44-7.52 (m, 4H), 8.29-8.33 (m, 1H), 8.55-8.68 (m, 3H)

5-[4-(1-Aminoethyl)phenyl]-4-dimethylamino-1H-indazole trihydrochloride (Compound 5-26)

Melting point: 180 to 182° C. (decomposition)
Rf value: 0.47 (chloroform:methanol: 28% aqueous ammonia=5:1:0.01 (v/v/v))
Mass spectrum (EI, m/z): 280 (M$^+$)
$^1$H-NMR spectrum (DMSO-d$_6$, δ ppm): 1.55 (d, J=6.8 Hz, 3H), 2.79 (s, 6H), 4.39-4.52 (m, 1H), 7.12 (d, J=8.4 Hz, 1H), 7.17 (d, J=8.4 Hz, 1H), 7.44-7.55 (m, 4H), 8.28 (s, 1H), 8.31 (brs, 3H)

5-[5-(1-Amino-1-methylethyl)-3-chloropyridin-2-yl]-1H-indazole trihydrochloride (Compound 5-27)

Melting point: 179 to 182° C.
Rf value: 0.47 (chloroform:methanol: 28% aqueous ammonia=5:1:0.01 (v/v/v))
Mass spectrum (CI, m/z): 287 (M$^+$+1)
$^1$H-NMR spectrum (DMSO-d$_6$, δ ppm): 1.73 (s, 6H), 7.62-7.70 (m, 2H), 8.13-8.14 (m, 1H), 8.18 (d, J=0.7 Hz, 1H), 8.28 (d, J=2.2 Hz, 1H), 8.84 (d, J=2.2 Hz, 1H), 8.85-8.98 (m, 3H)

5-[5-(1-Amino-1-methylethyl)pyridin-2-yl]-4-ethyl-1H-indazole trihydrochloride (Compound 5-28)

Melting point: 247 to 255° C. (decomposition)
Rf value: 0.44 (chloroform:methanol: 28% aqueous ammonia 5:1:0.01 (v/v/v))
Mass spectrum (CI, m/z): 281 (M$^+$+1)
$^1$H-NMR spectrum (DMSO-d$_6$, δ ppm): 1.19 (t, J=7.6 Hz, 3H), 1.78 (s, 6H), 2.97 (q, J=7.6 Hz, 2H), 7.39 (d, J=8.5 Hz, 1H), 7.52 (dd, J1=8.5 Hz, J2=0.9 Hz, 1H), 7.88 (d, J=8.3 Hz, 1H), 8.31 (d, J=0.9 Hz, 1H), 8.43-8.47 (m, 1H), 9.00-9.21 (m, 4H)

5-[5-(1-Amino-1-methylethyl)pyridin-2-yl]-4-cyclopropyl-1H-indazole trihydrochloride (Compound 5-29)

Melting point: 209 to 213° C. (decomposition)
Rf value: 0.47 (chloroform:methanol: 28% aqueous ammonia=5:1:0.01 (v/v/v))
Mass spectrum (CI, m/z): 293 (M$^+$+1)
$^1$H-NMR spectrum (DMSO-d$_6$, δ ppm): 0.47-0.53 (m, 2H), 0.86-0.93 (m, 2H), 1.78 (s, 6H), 2.41-2.50 (m, 1H), 7.47 (d, J=8.5 Hz, 1H), 7.52-7.56 (m, 1H), 8.02 (d, J=8.3 Hz, 1H), 8.25 (d, J=1.0 Hz, 1H), 8.43-8.46 (m, 1H), 8.99-9.10 (m, 4H)

5-[5-(1-Amino-1-methylethyl)pyridin-2-yl]-4-vinyl-1H-indazole trihydrochloride (Compound 5-30)

Melting point: 162 to 166° C. (decomposition)
Rf value: 0.35 (chloroform:methanol: 28% aqueous ammonia=5:1:0.01 (v/v/v))
Mass spectrum (CI, m/z): 279 (M$^+$+1)
$^1$H-NMR spectrum (DMSO-d$_6$, δ ppm): 1.75 (s, 6H), 5.59 (dd, J1=11.5 Hz, J2=1.2 Hz, 1H), 5.98 (dd, J1=17.8 Hz, J21.2 Hz, 1H), 6.92 (dd, J1=17.8 Hz, J2=11.5 Hz, 1H), 7.51 (d, J=8.8 Hz, 1H), 7.62 (dd, J1=8.8 Hz, J2=0.9 Hz, 1H), 7.73 (d, J=8.5 Hz, 1H), 8.26-8.29 (m, 1H), 8.40 (d, J=0.9 Hz, 1H), 8.91-8.98 (m, 4H)

5-[4-(1-Amino-1-methylethyl)phenyl]-4-diethylamino-1H-indazole trihydrochloride (Compound 5-31)

Melting point: 182 to 184° C. (decomposition)
Rf value: 0.51 (chloroform:methanol: 28% aqueous ammonia=5:1:0.01 (v/v/v))
Mass spectrum (CI, m/z): 323 (M$^+$+1)
$^1$H-NMR spectrum (DMSO-d$_6$, δ ppm): 0.78-1.04 (m, 6H), 1.68 (s, 6H), 3.00-3.17 (m, 4H), 7.17 (d, J=8.5 Hz, 1H), 7.24-7.33 (m, 1H), 7.39-7.74 (m, 4H), 8.21 (s, 1H), 8.50 (brs, 3H)

5-[4-(1-Amino-1-methylethyl)phenyl]-4-(2-hydroxyethyl)-1H-indazole dihydrochloride (Compound 5-32)

Melting point: 202 to 203° C. (decomposition)
Rf value: 0.11 (chloroform:methanol: 28% aqueous ammonia=5:1:0.01 (v/v/v))
Mass spectrum (CI, m/z): 296 (M$^+$+1)
$^1$H-NMR spectrum (DMSO-d$_6$, δ ppm): 1.70 (s, 6H), 3.02 (t, J=7.4 Hz, 2H), 3.61 (t, J=7.4 Hz, 2H), 7.15 (d, J=8.5 Hz, 1H), 7.41-7.47 (m, 3H), 7.65 (d, J=8.4 Hz, 2H), 8.18 (d, J=1.0 Hz, 1H), 8.68 (brs, 3H)

5-[5-(1-Amino-1-methylethyl)pyridin-2-yl]-4-(2-hydroxyethyl)-1H-indazole trihydrochloride (Compound 5-33)

Rf value: 0.44 (chloroform:methanol: 28% aqueous ammonia 5:1:0.01 (v/v/v))
Mass spectrum (CI, m/z): 297 (M$^+$+1)
$^1$H-NMR spectrum (DMSO-d$_6$, δ ppm): 1.74 (s, 6H), 3.16 (t, J=7.1 Hz, 2H), 3.73 (t, J=7.1 Hz, 2H), 7.39 (d, J=8.5 Hz, 1H), 7.49 (dd, J1=8.5 Hz, J2=1.0 Hz, 1H), 7.76 (d, J=8.3 Hz, 1H), 8.12 (dd, J1=8.3 Hz, J2=2.4 Hz, 1H), 8.23 (d, J=1.0 Hz, 1H), 8.59-8.82 (m, 3H), 8.86 (d, J=2.4 Hz, 1H)

5-[4-(1-Amino-1-methylethyl)phenyl]-4-(1-hydroxyethyl)-1H-indazole dihydrochloride (Compound 5-34)

Property: white powder
Rf value: 0.25 (chloroform:methanol: 28% aqueous ammonia=10:1:0.1 (v/v/v))
Mass spectrum (CI, m/z): 296 ($M^+$+1)
$^1$H-NMR spectrum (DMSO-$d_6$, δ ppm): 1.43 (d, J=6.5 Hz, 3H), 1.70 (s, 6H), 4.95 (q, J=6.5 Hz, 1H), 7.10 (d, J=8.5 Hz, 1H), 7.40 (d, J=8.4 Hz, 2H), 7.45 (dd, J1=8.5 Hz, J2=1.0 Hz, 1H), 7.65 (d, J=8.4 Hz, 2H), 8.35 (d, J=1.0 Hz, 1H), 8.65-8.81 (m, 3H)

5-[4-(1-Amino-1-methylethyl)phenyl]-4-hydroxymethyl-1H-indazole dihydrochloride (Compound 5-35)

Property: white powder
Rf value: 0.18 (chloroform:methanol: 28% aqueous ammonia=10:1:0.1 (v/v/v))
Mass spectrum (CI, m/z): 282 ($M^+$+1)
$^1$H-NMR spectrum (DMSO-$d_6$, δ ppm): 1.70 (s, 6H), 4.68 (s, 2H), 7.25 (d, J=8.5 Hz, 1H), 7.49-7.55 (m, 3H), 7.64 (d, J=8.5 Hz, 2H), 8.28 (d, J=1.0 Hz, 1H), 8.59-8.77 (m, 3H)

5-[4-(1-Amino-1-methylethyl)phenyl]-4-cyano-1H-indazole monohydrochloride (Compound 5-36)

Property: white powder
Melting point: 276 to 272° C.
Rf value: 0.38 (chloroform:methanol: 28% aqueous ammonia=10:1:0.1 (v/v/v))
Mass spectrum (CI, m/z): 277 ($M^+$+1)
$^1$H-NMR spectrum (DMSO-$d_6$, δ ppm): 1.71 (s, 6H), 7.61 (d, J=8.8 Hz, 1H), 7.69-7.81 (m, 4H), 8.02 (d, J=8.8 Hz, 1H), 8.31 (s, 1H), 8.68-8.85 (m, 3H), 13.85 (brs, 1H)

6-[4-(1-Amino-1-methylethyl)phenyl]-1H-indazole dihydrochloride (Compound 5-37)

Melting point: 265 to 269° C.
Rf value: 0.44 (chloroform:methanol: 28% aqueous ammonia=5:1:0.01 (v/v/v))
Mass spectrum (CI, m/z): 252 ($M^+$+1)
$^1$H-NMR spectrum (DMSO-$d_6$, δ ppm): 1.69 (s, 6H), 7.44 (dd, J1=8.4 Hz, J2=1.5 Hz, 1H), 7.66-7.70 (m, 2H), 7.76-7.82 (m, 3H), 7.85 (dd, J1=8.4 Hz, J2=0.7 Hz, 1H), 8.11 (d, J=1.0 Hz, 1H), 8.73 (brs, 3H)

1-Acetyl-6-[4-(1-amino-1-methylethyl)phenyl]-1H-indazole dihydrochloride (Compound 5-38)

Melting point: 225 to 230° C.
Rf value: 0.64 (chloroform:methanol: 28% aqueous ammonia=5:1:0.01 (v/v/v))
Mass spectrum (CI, m/z): 294 ($M^+$+1)
$^1$H-NMR spectrum (DMSO-$d_6$, δ ppm): 1.69 (s, 6H), 2.75 (s, 3H), 7.69-7.73 (m, 2H), 7.76 (dd, J1=8.3 Hz, J2=1.7 Hz, 1H), 7.78-7.83 (m, 2H), 8.01 (dd, J=8.3 Hz, J2=0.7 Hz, 1H), 8.52 (d, J=0.7 Hz, 1H), 8.55-8.56 (m, 1H), 8.60 (brs, 3H)

5-[4-(1-Amino-1-methylethyl)phenyl]-4-(pyrrol-1-yl)-1H-indazole dihydrochloride (Compound 5-39)

Melting point: 244 to 247° C. (decomposition)
Rf value: 0.44 (chloroform:methanol: 28% aqueous ammonia=5:1:0.01 (v/v/v))
Mass spectrum (CI, m/z): 317 ($M^+$+1)
$^1$H-NMR spectrum (DMSO-$d_6$, δ ppm): 1.61 (s, 6H), 6.18 (dd, J1=2.2 Hz, J2=2.0 Hz, 2H), 6.80 (dd, J1=2.2 Hz, J2=2.0 Hz, 2H), 7.16-7.22 (m, 2H), 7.44-7.49 (m, 3H), 7.67 (dd, J1=8.5 Hz, J2=1.0 Hz, 1H), 7.86-7.87 (m, 1H), 8.46 (brs, 3H), 13.47 (brs, 1H)

5-[4-(1-Amino-1-methylethyl)phenyl]-4-isopropoxy-1H-indazole dihydrochloride (Compound 5-40)

Melting point: 242 to 246° C. (decomposition)
Rf value: 0.39 (chloroform:methanol: 28% aqueous ammonia=5:1:0.01 (v/v/v))
Mass spectrum (CI, m/z): 310 ($M^+$+1)
$^1$H-NMR spectrum (DMSO-$d_6$, δ ppm): 1.13 (d, J=6.1 Hz, 6H), 1.68 (s, 6H), 4.52 (septet, J=6.1 Hz, 1H), 7.29 (dd, J1=8.5 Hz, J2=0.7 Hz, 1H), 7.33 (d, J=8.5 Hz, 1H), 7.55-7.70 (m, 4H), 8.18 (d, J=0.7 Hz, 1H), 8.65 (brs, 3H)

5-[4-(1-Amino-1-methylethyl)phenyl]-4-(piperidin-1-yl)-1H-indazole trihydrochloride (Compound 5-41)

Melting point: 205 to 208° C. (decomposition)
Rf value: 0.46 (chloroform:methanol: 28% aqueous ammonia=5:1:0.01 (v/v/v))
Mass spectrum (CI, m/z): 335 ($M^+$+1)
$^1$H-NMR spectrum (DMSO-$d_6$, δ ppm): 1.35-1.55 (m, 6H), 1.68 (s, 6H), 3.00-3.12 (m, 4H), 7.14 (d, J=8.5 Hz, 1H), 7.19 (dd, J1=8.5 Hz, J2=0.7 Hz, 1H), 7.53-7.62 (m, 4H), 8.23 (d, J=0.7 Hz, 1H), 8.61 (brs, 3H)

5-[4-(1-Amino-1-methylethyl)phenyl]-4-(pyrrolidin-1-yl)-1H-indazole trihydrochloride (Compound 5-42)

Melting point: 218 to 224° C. (decomposition)
Rf value: 0.44 (chloroform:methanol: 28% aqueous ammonia=5:1:0.01 (v/v/v))
Mass spectrum (EI, m/z): 320 ($M^+$)
$^1$H-NMR spectrum (DMSO-$d_6$, δ ppm): 1.67 (s, 6H), 1.71-1.80 (m, 4H), 3.18-3.34 (m, 4H), 6.91 (d, J=8.2 Hz, 1H), 7.01 (d, J=8.2 Hz, 1H), 7.41 (d, J=8.4 Hz, 2H), 7.54 (d, J=8.4 Hz, 2H), 8.30 (s, 1H), 8.57 (brs, 3H)

5-[4-(1-Amino-1-methylethyl)phenyl]-4-(morpholin-4-yl)-1H-indazole trihydrochloride (Compound 5-43)

Melting point: 268 to 272° C. (decomposition)
Rf value: 0.39 (chloroform:methanol: 28% aqueous ammonia=5:1:0.01 (v/v/v))
Mass spectrum (CI, m/z): 337 ($M^+$+1)
$^1$H-NMR spectrum (DMSO-$d_6$, δ ppm): 1.68 (s, 6H), 3.05-3.11 (m, 4H), 3.50-3.68 (m, 4H), 7.17 (d, J=8.5 Hz, 1H), 7.25 (dd, J1=8.5 Hz, J2=0.8 Hz, 1H), 7.55-7.64 (m, 4H), 8.28 (d, J=0.8 Hz, 1H), 8.55-8.67 (m, 3H)

5-[4-(1-Amino-1-methylethyl)phenyl]-4-methoxy-1H-indazole dihydrochloride (Compound 5-44)

Melting point: 258 to 261° C. (decomposition)
Rf value: 0.34 (chloroform:methanol: 28% aqueous ammonia=5:1:0.01 (v/v/v))
Mass spectrum (CI, m/z): 282 (M$^+$+1)
$^1$H-NMR spectrum (DMSO-d$_6$, δ ppm): 1.68 (s, 6H), 4.07 (s, 3H), 7.24 (dd, J1=8.5 Hz, J2=0.7 Hz, 1H), 7.29 (d, J=8.5 Hz, 1H), 7.53-7.62 (m, 4H), 8.37 (d, J=0.7 Hz, 1H), 8.61-8.73 (m, 3H)

5-[5-(1-Amino-1-methylethyl)pyridin-2-yl]-4-methoxy-1H-indazole trihydrochloride (Compound 5-45)

Melting point: 195 to 201° C. (decomposition)
Rf value: 0.32 (chloroform:methanol: 28% aqueous ammonia=5:1:0.01 (v/v/v))
Mass spectrum (CI, m/z): 283 (M$^+$+1)
$^1$H-NMR spectrum (DMSO-d$_6$, δ ppm): 1.76 (s, 6H), 4.26 (s, 3H), 7.31 (dd, J1=8.6 Hz, J2=1.0 Hz, 1H), 7.68 (d, J=8.6 Hz, 1H), 8.14 (d, J=8.3 Hz, 1H), 8.39-8.47 (m, 1H), 8.52-8.53 (m, 1H), 8.95 (d, J=2.2 Hz, 1H), 8.97-9.13 (m, 3H)

5-[5-(1-Aminocyclopentyl)pyridin-2-yl]-4-methoxy-1H-indazole trihydrochloride (Compound 5-46)

Melting point: 195 to 203° C. (decomposition)
Rf value: 0.41 (chloroform:methanol: 28% aqueous ammonia=5:1:0.01 (v/v/v))
Mass spectrum (CI, m/z): 309 (M$^+$+1)
$^1$H-NMR spectrum (DMSO-d$_6$, δ ppm): 1.70-2.05 (m, 4H), 2.20-2.37 (m, 4H), 4.26 (s, 3H), 7.31 (dd, J1=8.6 Hz, J2=1.0 Hz, 1H), 7.69 (d, J=8.6 Hz, 1H), 8.12 (d, J=8.3 Hz, 1H), 8.34-8.40 (m, 1H), 8.52-8.53 (m, 1H), 8.79-8.95 (m, 4H)

5-[5-(1-Amino-1-methylethyl)pyridin-2-yl]-4-ethoxy-1H-indazole trihydrochloride (Compound 5-47)

Property: yellow powder
Melting point: 198 to 201° C.
Rf value: 0.39 (chloroform:methanol: 28% aqueous ammonia=10:1:0.1 (v/v/v))
Mass spectrum (CI, m/z): 297 (M$^+$+1)
$^1$H-NMR spectrum (DMSO-d$_6$, δ ppm): 1.36 (t, J=6.9 Hz, 3H), 1.77 (s, 6H), 4.58 (q, J=6.9 Hz, 2H), 7.32 (dd, J1=8.5 Hz, J2=1.0 Hz, 1H), 7.69 (d, J=8.5 Hz, 1H), 8.21 (d, J=8.8 Hz, 1H), 8.44-8.51 (m, 2H), 897 (d, J=2.4 Hz, 1H), 9.00-9.18 (m, 3H)

5-[4-(1-Amino-1-methylethyl)phenyl]-4-hydroxy-1H-indazole dihydrochloride (Compound 5-48)

Melting point: 194 to 198° C. (decomposition)
Rf value: 0.12 (chloroform:methanol: 28% aqueous ammonia=5:1:0.01 (v/v/v))
Mass spectrum (CI, m/z): 268 (M$^+$+1)
$^1$H-NMR spectrum (DMSO-d$_6$, δ ppm): 1.68 (s, 6H), 7.05 (dd, J1=8.5 Hz, J2=0.9 Hz, 1H), 7.27 (d, J=8.5 Hz, 1H), 7.57 (d, J=8.5 Hz, 2H), 7.63 (d, J=8.5 Hz, 2H), 8.32 (d, J=0.9 Hz, 1H), 8.59 (brs, 3H), 10.06 (brs, 1H)

5-[4-(1-Amino-1-methylethyl)phenyl]-4-ethoxy-1H-indazole dihydrochloride (Compound 5-49)

Melting point: 248 to 256° C. (decomposition)
Rf value: 0.34 (chloroform:methanol: 28% aqueous ammonia=5:1:0.01 (v/v/v))
Mass spectrum (CI, m/z): 296 (M$^+$+1)
$^1$H-NMR spectrum (DMSO-d$_6$, δ ppm): 1.25 (t, J=7.0 Hz, 3H), 1.68 (s, 6H), 4.32 (q, J=7.0 Hz, 2H), 7.26 (dd, J1=8.5 Hz, J2=1.0 Hz, 1H), 7.31 (d, J=8.5 Hz, 1H), 7.52-7.70 (m, 4H), 8.28 (d, J=1.0 Hz, 1H), 8.62 (brs, 3H)

5-[5-(1-Amino-1-methylethyl)pyridin-2-yl]-4-isopropoxy-1H-indazole trihydrochloride (Compound 5-50)

Melting point: 211 to 213° C. (decomposition)
Rf value: 0.39 (chloroform:methanol: 28% aqueous ammonia=5:1:0.01 (v/v/v))
Mass spectrum (CI, m/z): 311 (M$^+$+1)
$^1$H-NMR spectrum (DMSO-d$_6$, δ ppm): 1.22 (d, J=6.1 Hz, 6H), 1.74 (s, 6H), 4.77-4.86 (m, 1H), 7.34 (dd, J1=8.7 Hz, J2=1.0 Hz, 1H), 7.75 (d, J=8.7 Hz, 1H), 8.15 (d, J=8.5 Hz, 1H), 8.23-8.35 (m, 2H), 8.87 (brs, 3H), 8.93 (d, J=2.2 Hz, 1H)

5-[5-(1-Amino-1-ethylpropyl)pyridin-2-yl]-4-methoxy-1H-indazole trihydrochloride (Compound 5-51)

Melting point: 204 to 206° C. (decomposition)
Rf value: 0.41 (chloroform:methanol: 28% aqueous ammonia=5:1:0.01 (v/v/v))
Mass spectrum (CI, m/z): 311 (M$^+$+1)
$^1$H-NMR spectrum (DMSO-d$_6$, δ ppm): 0.85 (t, J=7.3 Hz, 6H), 1.95-2.25 (m, 4H), 4.29 (s, 3H), 7.32 (d, J=8.8 Hz, 1H), 7.70 (d, J=8.8 Hz, 1H), 8.22 (d, J=8.3 Hz, 1H), 8.35-8.47 (m, 1H), 8.57 (s, 1H), 8.87-8.94 (m, 1H), 9.00-9.24 (m, 3H)

5-[4-(1-Amino-1-methylethyl)phenyl]-4-n-propoxy-1H-indazole dihydrochloride (Compound 5-52)

Melting point: 237 to 243° C. (decomposition)
Rf value: 0.41 (chloroform:methanol: 28% aqueous ammonia=5:1:0.01 (v/v/v))
Mass spectrum (CI, m/z): 310 (M$^+$+1)
$^1$H-NMR spectrum (DMSO-d$_6$, δ ppm): 0.89 (t, J=7.4 Hz, 3H), 1.58-1.69 (m, 8H), 4.22 (t, J=6.5 Hz, 2H), 7.26 (dd, J1=8.5 Hz, J2=1.0 Hz, 1H), 7.31 (d, J=8.5 Hz, 1H), 7.55-7.64 (m, 4H), 8.28 (d, J=1.0 Hz, 1H), 8.65 (brs, 3H)

5-[4-(1-Amino-1-methylethyl)phenyl]-4-difluoromethoxy-1H-indazole dihydrochloride (Compound 5-53)

Melting point: 227 to 230° C. (decomposition)
Rf value: 0.32 (chloroform:methanol: 28% aqueous ammonia=5:1:0.01 (v/v/v))
Mass spectrum (CI, m/z): 318 (M$^+$+1)
$^1$H-NMR spectrum (DMSO-d$_6$, δ ppm): 1.69 (s, 6H), 7.20 (t, $^2J_{F-H}$=73.6 Hz, 1H), 7.42 (d, J=8.5 Hz, 1H), 7.54-7.70 (m, 5H), 8.14 (d, 0.7 Hz, 1H), 8.63 (brs, 3H)

5-[4-(1-Amino-1-methylethyl)phenyl]-4-(2,2,2-trifluoroethoxy)-1H-indazole dihydrochloride (Compound 5-54)

Rf value: 0.35 (chloroform:methanol: 28% aqueous ammonia=5:1:0.01 (v/v/v))

Mass spectrum (CI, m/z): 350 (M$^+$+1)

$^1$H-NMR spectrum (DMSO-d$_6$, δ ppm): 1.73 (s, 6H), 4.91 (q, $^3J_{F-H}$=9.0 Hz, 2H), 7.35 (d, J=8.5 Hz, 1H), 7.39 (dd, J1=8.5 Hz, J2=0.7 Hz, 1H), 7.55-65 (m, 4H), 8.33 (d, J=0.7 Hz, 1H), 8.60 (brs, 3H)

5-[4-(1-Amino-1-methylethyl)phenyl]-4-n-butoxy-1H-indazole dihydrochloride (Compound 5-55)

Melting point: 227 to 229° C. (decomposition)

Rf value: 0.36 (chloroform:methanol: 28% aqueous ammonia=5:1:0.01 (v/v/v))

Mass spectrum (EI, m/z): 323 (M$^+$)

$^1$H-NMR spectrum (DMSO-d$_6$, δ ppm): 0.83 (t, J=7.3 Hz, 3H), 1.27-1.39 (m, 2H), 1.55-1.65 (m, 2H), 1.67 (s, 6H), 4.24 (t, J=6.5 Hz, 2H), 7.24-7.32 (m, 2H), 7.52-7.65 (m, 4H), 8.28 (s, 1H), 8.42-8.55 (m, 3H)

5-[4-(1-Amino-1-methylethyl)phenyl]-4-(2-fluoroethoxy)-1H-indazole dihydrochloride (Compound 5-56)

Rf value: 0.31 (chloroform:methanol: 28% aqueous ammonia=5:1:0.01 (v/v/v))

Mass spectrum (CI, m/z): 314 (M$^+$+1)

$^1$H-NMR spectrum (DMSO-d$_6$, δ ppm): 1.68 (s, 6H), 4.46-4.77 (m, 4H), 7.29 (dd, J1=8.5 Hz, J2=0.7 Hz, 1H), 7.33 (d, J=8.5 Hz, 1H), 7.56-7.66 (m, 4H), 8.30 (d, J=0.7 Hz, 1H), 8.50 (brs, 3H)

4-Allyloxy-5-[4-(1-amino-1-methylethyl)phenyl]-1H-indazole dihydrochloride (Compound 5-57)

Melting point: 205 to 207° C. (decomposition)

Rf value: 0.33 (chloroform:methanol: 28% aqueous ammonia=5:1:0.01 (v/v/v))

Mass spectrum (CI, m/z): 308 (M$^+$+1)

$^1$H-NMR spectrum (DMSO-d$_6$, δ ppm): 1.68 (s, 6H), 4.83 (ddd, J1=5.1 Hz, J2=1.6 Hz, J3=1.5 Hz, 2H), 5.15 (ddd, J1=10.5 Hz, J2=3.4 Hz, J3=1.6 Hz, 1H), 5.30 (ddd, J1=17.1 Hz, J2=3.4 Hz, J3=1.5 Hz, 1H), 5.92-6.05 (m, 1H), 7.24-7.34 (m, 2H), 7.55-7.66 (m, 4H), 8.29 (s, 1H), 8.63 (brs, 3H)

5-[5-(1-Amino-1-methylethyl)pyridin-2-yl]-4-n-propoxy-1H-indazole trihydrochloride (Compound 5-58)

Melting point: 194 to 198° C. (decomposition)

Rf value: 0.38 (chloroform:methanol: 28% aqueous ammonia=5:1:0.01 (v/v/v))

Mass spectrum (CI, m/z): 311 (M$^+$+1)

$^1$H-NMR spectrum (DMSO-d$_6$, δ ppm): 0.93 (t, J=7.3 Hz, 3H), 1.68-1.80 (m, 8H), 4.46 (t, J=6.5 Hz, 2H), 7.33 (dd, J1=8.7 Hz, J2=1.0 Hz, 1H), 7.71 (d, J=8.7 Hz, 1H), 8.17 (d, J=8.5 Hz, 1H), 8.40-8.44 (m, 2H), 8.95-9.08 (m, 4H)

5-[5-(1-Amino-1-methylethyl)pyridin-2-yl]-4-difluoromethoxy-1H-indazole trihydrochloride (Compound 5-59)

Melting point: 170 to 173° C.

Rf value: 0.37 (chloroform:methanol: 28% aqueous ammonia=5:1:0.01 (v/v/v))

Mass spectrum (CI, m/z): 319 (M$^+$+1)

$^1$H-NMR spectrum (DMSO-d$_6$, δ ppm): 1.73 (s, 6H), 7.31 (t, $^2J_{F-H}$=73.7 Hz, 1H), 7.60 (dd, J1=8.8 Hz, J2=0.7 Hz, 1H), 7.78 (d, J=8.8 Hz, 1H), 7.88 (dd, J1=8.3 Hz, J2=0.7 Hz, 1H), 8.10 (dd, J1=8.3 Hz, J2=2.4 Hz, 1H), 8.18 (d, J=0.7 Hz, 1H), 8.69 (brs, 3H), 8.90 (dd, J1=2.4 Hz, J2=0.7 Hz, 1H)

5-[5-(1-Amino-1-ethylpropyl)pyridin-2-yl]-4-ethoxy-1H-indazole trihydrochloride (Compound 5-60)

Melting point: 200 to 202° C. (decomposition)

Rf value: 0.49 (chloroform:methanol: 28% aqueous ammonia=5:1:0.01 (v/v/v))

Mass spectrum (CI, m/z): 325 (M$^+$+1)

$^1$H-NMR spectrum (DMSO-d$_6$, δ ppm): 0.85 (t, J=7.3 Hz, 6H), 1.34 (t, J=7.0 Hz, 3H), 1.95-2.30 (m, 4H), 4.58 (q, J=7.0 Hz, 2H), 7.33 (dd, J=8.8 Hz, J=0.9 Hz, 1H), 7.71 (d, J=8.5 Hz, 1H), 8.26 (d, J=8.8 Hz, 1H), 8.40-8.55 (m, 2H), 8.92 (d, J=2.2 Hz, 1H), 9.00-9.25 (m, 3H)

5-[4-(1-Amino-1-methylethyl)phenyl]-4-(pyridin-4-yl)-1H-indazole trihydrochloride (Compound 5-61)

Melting point: 266 to 269° C. (decomposition)

Rf value: 0.31 (chloroform:methanol: 28% aqueous ammonia=5:1:0.01 (v/v/v))

Mass spectrum (CI, m/z): 329 (M$^+$+1)

$^1$H-NMR spectrum (DMSO-d$_6$, δ ppm): 1.62 (s, 6H), 7.26 (d, J=8.3 Hz, 2H), 7.46-7.52 (m, 3H), 7.70-7.73 (m, 2H), 7.80 (dd, J1=8.8 Hz, J2-=1.0 Hz, 1H), 7.95 (d, J=1.0 Hz, 1H), 8.59-8.70 (m, 3H), 8.77 (dd, J1=5.1 Hz, J2=1.4 Hz, 2H)

5-[4-(1-Amino-1-methylethyl)phenyl]-4-(pyridin-3-yl)-1H-indazole trihydrochloride (Compound 5-62)

Rf value: 0.32 (chloroform:methanol: 28% aqueous ammonia=5:1:0.01 (v/v/v))

Mass spectrum (CI, m/z): 329 (M$^+$+1)

$^1$H-NMR spectrum (DMSO-d$_6$, δ ppm): 1.59 (s, 6H), 7.24 (d, J=8.5 Hz, 2H), 7.42-7.47 (m, 3H), 7.54 (dd, J1=7.8 Hz, J2=5.0 Hz, 1H), 7.71 (dd, J1=8.8 Hz, J2=1.0 Hz, 1H), 7.85 (d, J=1.0 Hz, 1H), 7.90-7.94 (m, 1H), 8.44-8.50 (m, 4H), 8.58 (dd, J1=5.0 Hz, J2=1.6 Hz, 1H)

5-[4-(1-Amino-1-methylethyl)phenyl]-4-(pyridin-2-yl)-1H-indazole trihydrochloride (Compound 5-63)

Melting point: 210 to 214° C. (decomposition)

Rf value: 0.28 (chloroform:methanol: 28% aqueous ammonia=5:1:0.01 (v/v/v))

Mass spectrum (CI, m/z): 329 (M$^+$+1)

$^1$H-NMR spectrum (DMSO-d$_6$, δ ppm): 1.59 (s, 6H), 7.15-7.24 (m, 3H), 7.36-7.63 (m, 4H), 7.69-7.75 (m, 2H), 7.87 (s, 1H), 8.40-8.50 (m, 3H), 8.67-8.70 (m, 1H)

5-[4-(1-Amino-1-methylethyl)phenyl]-4-(pyrazol-4-yl)-1H-indazole trihydrochloride (Compound 5-64)

Melting point: 259 to 267° C. (decomposition)
Rf value: 0.15 (chloroform:methanol: 28% aqueous ammonia=5:1:0.01 (v/v/v))
Mass spectrum (CI, m/z): 318 (M$^+$+1)
$^1$H-NMR spectrum (DMSO-d$_6$, δ ppm): 1.66 (s, 6H), 7.26-7.31 (m, 3H), 7.47-7.53 (m, 5H), 8.05 (d, J=1.2 Hz, 1H), 8.62 (brs, 3H)

5-[5-(1-Amino-1-methylethyl)pyridin-2-yl]-4-(pyrazol-4-yl)-1H-indazole tetrahydrochloride (Compound 5-65)

Rf value: 0.17 (chloroform:methanol: 28% aqueous ammonia=5:1:0.01 (v/v/v))
Mass spectrum (CI, m/z): 319 (M$^+$+1)
$^1$H-NMR spectrum (DMSO-d$_6$, δ ppm): 1.71 (s, 6H), 7.35 (d, J=8.1 Hz, 1H), 7.48-7.59 (m, 4H), 7.97-8.00 (m, 1H), 8.10 (d, J=1.0 Hz, 1H), 8.71-8.80 (m, 3H), 8.88 (d, J=2.4 Hz, 1H)

5-[4-(1-Amino-1-methylethyl)phenyl]-4-(oxazol-5-yl)-1H-indazole dihydrochloride (Compound 5-66)

Property: pale yellow powder
Melting point: 212 to 214° C. (decomposition)
Rf value: 0.27 (chloroform:methanol: 28% aqueous ammonia=10:1:0.1 (v/v/v))
Mass spectrum (CI, m/z): 319 (M$^+$+1)
$^1$H-NMR spectrum (DMSO-d$_6$, δ ppm): 1.69 (s, 6H), 6.60 (s, 1H), 7.33 (d, J=8.7 Hz, 1H), 7.36 (d, J=8.3 Hz, 2H), 7.62 (d, J=8.3 Hz, 2H), 7.68 (dd, J1=8.7 Hz, J2=1.0 Hz, 1H), 8.32 (d, J=1.0 Hz, 1H), 8.41 (s, 1H), 8.61-8.78 (m, 3H)

5-[4-(1-Amino-1-methylethyl)phenyl]-4-(pyrazol-3-yl)-1H-indazole trihydrochloride (Compound 5-67)

Property: yellow powder
Rf value: 0.15 (chloroform:methanol: 28% aqueous ammonia=10:1:0.1 (v/v/v))
Mass spectrum (CI, m/z): 318 (M$^+$+1)
$^1$H-NMR spectrum (DMSO-d$_6$, δ ppm): 1.66 (s, 6H), 5.90 (d, J=2.2 Hz, —H), 7.28 (d, J=8.4 Hz, 2H), 7.34 (d, J=8.5 Hz, 1H), 7.53 (d, J=8.4 Hz, 2H), 7.62 (dd, J1=8.5 Hz, J2=1.0 Hz, 1H), 7.69 (d, J=2.2 Hz, 1H), 8.11 (d, J=0.1.0 Hz, 1H), 8.66-8.82 (m, 3H)

5-[4-(1-Amino-1-methylethyl)phenyl]-4-(isoxazol-5-yl)-1H-indazole dihydrochloride (Compound 5-68)

Property: pale yellow powder
Melting point: 256 to 258° C. (decomposition)
Rf value: 0.41 (chloroform:methanol: 28% aqueous ammonia=10:1:0.1 (v/v/v))
Mass spectrum (CI, m/z): 319 (M$^+$+1)
$^1$H-NMR spectrum (DMSO-d$_6$, δ ppm): 1.68 (s, 6H), 6.24 (d, J=2.0 Hz, 1H), 7.31-7.37 (m, 2H), 7.42 (d, J=8.5 Hz, 1H), 7.56-7.62 (m, 2H), 7.79 (dd, J1=8.5 Hz, J2=1.0 Hz, 1H), 8.21 (d, J=1.0 Hz, 1H), 8.59 (d, J=2.0 Hz, 1H), 8.63-8.80 (m, 3H)

5-[5-(1-Amino-1-methylethyl)pyridin-2-yl]-4-hydroxy-1H-indazole trihydrochloride (Compound 5-69)

Melting point: 255 to 260° C. (decomposition)
Rf value: 0.40 (chloroform:methanol: 28% aqueous ammonia=5:1:0.01 (v/v/v))
Mass spectrum (CI, m/z): 269 (M$^+$+1)
$^1$H-NMR spectrum (DMSO-d$_6$, δ ppm): 1.74 (s, 6H), 7.08 (dd, J1=8.8 Hz, J2=0.9 Hz, 1H), 7.95 (d, J=8.8 Hz, 1H), 8.21 (d, J=0.9 Hz, 1H), 8.26 (d, J=8.8 Hz, 1H), 8.33 (dd, J1=8.8 Hz, J2=2.3 Hz, 1H), 8.82 (d, J=2.3 Hz, 1H), 8.89-9.01 (m, 3H)

5-[5-(1-Amino-1-methylethyl)pyridin-2-yl]-4-cyclopropyloxy-1H-indazole trihydrochloride (Compound 5-70)

Melting point: 203 to 205° C. (decomposition)
Rf value: 0.52 (chloroform:methanol: 28% aqueous ammonia=5:1:0.01 (v/v/v))
Mass spectrum (CI, m/z): 309 (M$^+$+1)
$^1$H-NMR spectrum (DMSO-d$_6$, δ ppm): 0.88-0.92 (m, 4H), 1.76 (s, 6H), 4.53-4.56 (m, 1H), 7.31 (dd, J1=8.5 Hz, J2=0.9 Hz, 1H), 7.65 (d, J=8.5 Hz, 1H), 8.10 (d, J=8.5 Hz, 1H), 8.47-8.51 (m, 1H), 8.65 (d, J=0.9 Hz, 1H), 8.96 (d, J=2.2 Hz, 1H), 9.00-9.12 (m, 3H)

5-[5-(1-Amino-1-ethylpropyl)pyridin-2-yl]-4-cyclopropyloxy-1H-indazole trihydrochloride (Compound 5-71)

Melting point: 207 to 209° C. (decomposition)
Rf value: 0.58 (chloroform:methanol: 28% aqueous ammonia=5:1:0.01 (v/v/v).)
Mass spectrum (CI, m/z): 337 (M$^+$+1)
$^1$H-NMR spectrum (DMSO-d$_6$, δ ppm): 0.85-0.91 (m, 10H), 1.85-2.31 (m, 4H), 4.50-4.59 (m, 1H), 7.32 (d, J=9.0 Hz, 1H), 7.68 (d, J=9.0 Hz, 1H), 8.55 (d, J=8.5 Hz, 1H), 8.30-42 (m, 1H), 8.65 (s, 1H), 8.80-8.95 (m, 1H), 8.91-9.20 (m, 3H)

5-[4-(1-Amino-1-ethylpropyl)phenyl]-4-difluoromethoxy-1H-indazole dihydrochloride (Compound 5-72)

Melting point: 234 to 237° C.
Rf value: 0.54 (chloroform:methanol: 28% aqueous ammonia=5:1:0.01 (v/v/v))
Mass spectrum (CI, m/z): 346 (M$^+$+1)
$^1$H-NMR spectrum (DMSO-d$_6$, δ ppm): 0.80 (dd, J1=7.3 Hz, J2=7.3 Hz, 6H), 1.97 (dq, J1=15.1 Hz, J2=7.3 Hz, 2H), 2.10 (dq, J1=15.1 Hz, J2=7.3 Hz, 2H), 7.14 (t, $^2J_{F-H}$=73.6 Hz, 1H), 7.45 (d, J=8.5 Hz, 1H), 7.50-7.62 (m, 5H), 8.13 (d, J=0.7 Hz, 1H), 8.59-8.76 (m, 3H)

5-[5-(1-Amino-1-methylethyl)pyridin-2-yl]-4-cyclopropylmethyloxy-1H-indazole trihydrochloride (Compound 5-73)

Melting point: 270 to 272° C. (decomposition)
Rf value: 0.68 (chloroform:methanol: 28% aqueous ammonia=5:1:0.01 (v/v/v))
Mass spectrum (CI, m/z): 323 (M$^+$+1)
$^1$H-NMR spectrum (DMSO-d$_6$, δ ppm): 0.25-0.34 (m, 2H), 0.45-0.53 (m, 2H), 1.11-1.26 (m, 1H), 1.78 (s, 6H), 4.35 (d, J=7.1 Hz, 2H), 7.35 (dd, J1=8.5 Hz, J2=1.0 Hz, 1H), 7.69

(d, J=8.5 Hz, 1H), 8.32 (d, J=8.5 Hz, 1H), 8.45 (d, J=1.0 Hz, 1H), 8.55-8.65 (m, 1H), 9.01 (d, J=2.2 Hz, 1H), 9.08-9.30 (m, 3H)

Example 6

Synthesis of 4-amino-1-tert-butoxycarbonyl-5-[4-(1-tert-butoxycarbonylamino-1-methylethyl)phenyl]-1H-indazole (Compound 6-1)

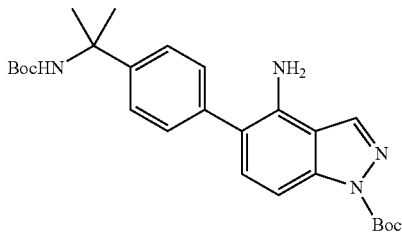

1,4-Dioxane (10 ml) and 20 ml of ethanol were added to 336 mg (0.68 mmol) of 1-tert-butoxycarbonyl-5-[4-(1-tert-butoxycarbonylamino-1-methylethyl)phenyl]-4-nitro-1H-indazole (Compound 1-7), then a suspension of 672 mg of 5% palladium-carbon (wet) in 10 ml of ethanol was added thereto and the mixture was stirred in a hydrogen atmosphere at room temperature for 1 hour.

After the reaction was finished, the reaction solution was filtered through Celite and the filtrate was concentrated in vacuo. The resulting residue was subjected to a silica gel column chromatography (eluting solvent: n-hexane:ethyl acetate=2:1 (v/v)) and the fraction containing the aimed product was concentrated in vacuo to give 225 mg of the title compound as white powder (yield: 81%).

Rf value: 0.45 (n-hexane:ethyl acetate=1:1 (v/v))

Mass spectrum (FAB, m/z): 466 (M$^+$+1)

$^1$H-NMR spectrum (CDCl$_3$, δ ppm): 1.40 (brs, 9H), 1.68 (s, 6H), 1.73 (s, 9H), 4.98 (brs, 1H), 7.30 (d, J=8.5 Hz, 1H), 7.40-7.43 (m, 2H), 7.48-7.51 (m, 2H), 7.56 (d, J=8.5 Hz, 1H), 8.14 (s, 1H)

As hereunder, the compounds 6-2 to 6-5 were produced in accordance with the production process for the compound 6-1.

4-Amino-1-tert-butoxycarbonyl-5-[4-(tert-butoxycarbonylaminomethyl)phenyl]-1H-indazole (Compound 6-2)

Rf value: 0.32 (n-hexane:ethyl acetate=1:1 (v/v))

Mass spectrum (FAB, m/z): 438 (M$^+$)

$^1$H-NMR spectrum (CDCl$_3$, δ ppm): 1.49 (s, 9H), 1.73 (s, 9H), 4.25-4.40 (m, 4H), 4.92 (brs, 1H), 7.28 (d, J=8.5 Hz, 1H), 7.37-7.45 (m, 4H), 7.57 (dd, J1=8.5 Hz, J2=0.7 Hz, 1H), 8.14 (d, J=0.7 Hz, 1H)

4-Amino-1-tert-butoxycarbonyl-5-[4-(1-tert-butoxycarbonylaminocyclopentyl)phenyl]-1H-indazole (Compound 6-3)

Rf value: 0.40 (n-hexane:ethyl acetate=1:1 (v/v))

Mass spectrum (FAB, m/z): 492 (M$^+$)

$^1$H-NMR spectrum (CDCl$_3$, δ ppm): 1.39 (brs, 9H), 1.73 (s, 9H), 1.79-1.94+(m, 4H), 2.06-2.27 (m, 4H), 4.31 (brs, 2H), 4.91 (brs, 1H), 7.30 (d, J=8.5 Hz, 1H), 7.38-7.42 (m, 2H), 7.47-7.51 (m, 2H), 7.55-7.57 (m, 1H), 8.14 (d, J=0.7 Hz, 1H)

4-Amino-1-tert-butoxycarbonyl-5-[4-(1-tert-butoxycarbonylamino-1-ethylpropyl)phenyl]-1H-indazole (Compound 6-4)

Rf value: 0.22 (n-hexane:ethyl acetate=2:1 (v/v))

Mass spectrum (EI, m/z): 494 (M$^+$)

$^1$H-NMR spectrum (CDCl$_3$, δ ppm): 0.80 (t, J=7.3 Hz, 6H), 1.42 (brs, 9H), 1.73 (s, 9H), 1.90-2.14 (m, 4H), 4.29 (brs, 2H), 4.81 (brs, 1H), 7.31 (d, J=8.5 Hz, 1H), 7.38-7.45 (m, 4H), 7.55-7.58 (m, 1H), 8.14 (d, J=0.7 Hz, 1H)

4-Amino-1-tert-butoxycarbonyl-5-[4-(1-tert-butoxycarbonylaminoethyl)phenyl]-1H-indazole (Compound 6-5)

Rf value: 0.31 (n-hexane:ethyl acetate=2:1 (v/v))

Mass spectrum (FAB, m/z): 452 (M$^+$)

$^1$H-NMR spectrum (DMSO-d$_6$, δ ppm): 1.30-1.47 (m, 12H), 1.64 (s, 9H), 4.61-4.75 (m, 1H), 5.77 (brs, 2H), 7.19 (d, J=8.4 Hz, 1H), 7.25-7.30 (m, 1H), 7.33-7.47 (m, 5H), 8.59 (d, J=0.7 Hz, 1H)

Example 7

Synthesis of 4-benzylamino-1-tert-butoxycarbonyl-5-[4-(1-tert-butoxycarbonylamino-1-methylethyl)phenyl]-1H-indazole (Compound 7)

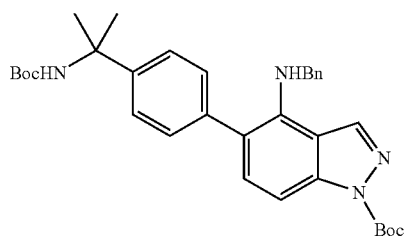

A solution of 11 mg (0.10 mmol) of benzaldehyde in 1 ml of 1,2-dichloroethane and a solution of 7.0 mg (0.12 mmol) of acetic acid in 1 ml of 1,2-dichloroethane were added to 47 mg (0.10 mmol) of 4-amino-1-tert-butoxycarbonyl-5-[4-(1-tert-butoxycarbonylamino-1-methylethyl)phenyl]-1H-indazole (Compound 6-1) and then 28 mg (0.13 mmol) of sodium triacetoxyborohydride was added thereto. The mixture was stirred in an argon stream at room temperature for 1.5 hours, then 42 mg (0.20 mmol) of sodium triacetoxyborohydride was added thereto and the mixture was stirred at room temperature for 17.5 hours.

After that, a solution of 11 mg (0.10 mmol) of benzaldehyde in 1 ml of 1,2-dichloroethane, a solution of 7.0 mg (0.12 mmol) of acetic acid in 1 ml of 1,2-dichloroethane and 42 mg (0.20 mmol) of sodium triacetoxyborohydride were added thereto and the mixture was stirred at room temperature for 24 hours.

After the reaction was finished, the reaction solution was poured into 20 ml of water and the mixture was neutralized with an aqueous solution of sodium hydroxide and extracted with each 30 ml of ethyl acetate twice. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane ethyl acetate=6:1 (v/v)) and the fraction containing the aimed substance was concentrated in vacuo to give 28 mg of the title compound as white powder (yield: 49%).

Rf value: 0.29 (n-hexane:ethyl acetate=2:1 (v/v))

$^1$H-NMR spectrum (CDCl$_3$, δ ppm): 1.40 (brs, 9H), 1.66 (s, 6H), 1.70 (s, 9H), 4.69 (s, 2H), 4.80-5.03 (m, 2H), 7.27-7.32 (m, 6H), 7.35-7.38 (m, 2H), 7.45-7.49 (m, 2H), 7.58 (d, J=8.0 Hz, 1H), 8.08 (s, 1H)

Example 8

Synthesis of 5-[4-(1-tert-butoxycarbonylamino-1-methylethyl)phenyl]-4-methylamino-1H-indazole (Compound 8)

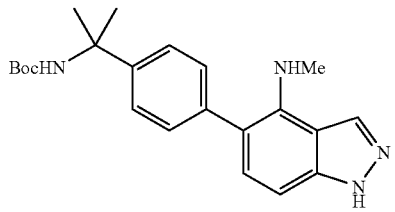

Ethyl orthoformate (2 ml) was added to 47 mg (0.10 mmol) of 4-amino-1-tert-butoxycarbonyl-5-[4-(1-tert-butoxycarbonylamino-1-methylethyl)phenyl]-1H-indazole (Compound 6-1) and the mixture was stirred in an argon stream at 100° C. for 1 hour.

After that, the mixture was concentrated in vacuo, 3 ml of ethanol was added to the resulting residue, then 40 mg (1.1 mmol) of sodium borohydride was added thereto and the mixture was stirred in an argon stream at room temperature for 17.5 hours. After that, 200 mg (5.3 mmol) of sodium borohydride was added thereto and the mixture was heated to reflux for 7 hours with stirring.

After the reaction was finished, the reaction solution was poured into 50 ml of water and the mixture was extracted with 50 ml of chloroform. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=2:1 (v/v)) and the fraction containing the aimed substance was concentrated in vacuo to give 4.2 mg of the title compound as white powder (yield: 11%).

Rf value: 0.38 (n-hexane:ethyl acetate=1:1 (v/v))

Mass spectrum (CI, m/z): 381 (M$^+$+1)

$^1$H-NMR spectrum (CDCl$_3$, δ ppm): 1.40 (brs, 9H), 1.68 (s, 6H), 3.24 (s, 3H), 4.99 (brs, 1H), 6.82 (dd, J1=8.3 Hz, J2=0.8 Hz, 1H), 7.11 (d, J=8.3 Hz, 1H), 7.34-7.38 (m, 2H), 7.45-7.48 (m, 2H), 8.29 (d, J=0.8 Hz, 1H)

Example 9

Synthesis of 5-[4-(1-tert-butoxycarbonylamino-1-methylethyl)phenyl]-3-carboxy-1H-indazole (Compound 9)

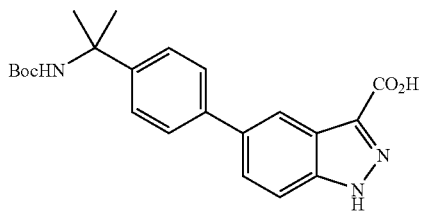

Tetrahydrofuran (10 ml), 4 ml of methanol and 20 ml of a 1N aqueous solution of sodium hydroxide were added to 120 mg (0.29 mmol) of 5-[4-(1-tert-butoxycarbonylamino-1-methylethyl)phenyl]-3-methoxycarbonyl-1H-indazole (Compound 4-1) and the mixture was stirred at 75° C. for 7 hours.

After the reaction was finished, the reaction solution was poured into 50 ml of a 10 weight % aqueous solution of citric acid and the mixture was extracted with 200 ml of chloroform. The organic layer was successively washed with water and a saturated aqueous solution of sodium chloride, dried over anhydrous magnesium sulfate and concentrated in vacuo. The resulting crude crystals were washed with diethyl ether to give 21 mg of the title compound as white powder (yield: 18%).

Mass spectrum (CI, m/z): 396 (M$^+$+1)

$^1$H-NMR spectrum (DMSO-d$_6$, δ ppm): 1.35 (brs, 9H), 1.54 (s, 6H), 7.22 (brs, 1H), 7.44 (d, J=8.4 Hz, 2H), 7.61 (d, J=8.4 Hz, 2H), 7.70-7.80 (m, 2H), 8.27 (s, 1H), 12.96 (brs, 1H), 13.82 (brs, 1H)

Example 10

Synthesis of 3-aminocarbonyl-5-[4-(1-tert-butoxycarbonylamino-1-methylethyl)phenyl]-1H-indazole (Compound 10)

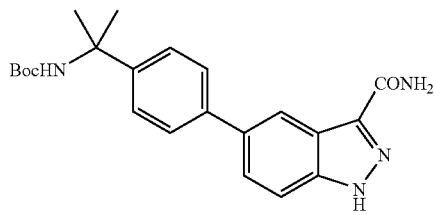

1,1'-Carbonyldiimidazole (11 mg, 0.068 mmol) and 2 ml of tetrahydrofuran were added to 21 mg (0.053 mmol) of 5-[4-(1-tert-butoxycarbonylamino-1-methylethyl)phenyl]-3-carboxy-1H-indazole (compound 9) and the mixture was stirred in an argon stream at 45° C. for 30 minutes. After cooling it to room temperature, 2 ml of 28% aqueous ammonia was added thereto and the mixture was stirred at room temperature for 30 minutes.

After the reaction was finished, the reaction solution was poured into 20 ml of a saturated aqueous solution of ammonium chloride and the mixture was extracted with 30 ml of ethyl acetate. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=1:1 (v/v)) and the fraction containing the aimed substance was concentrated in vacuo to give 14 mg of the title compound as white powder (yield: 67%).

Rf value: 0.15 (n-hexane:ethyl acetate=1:1 (v/v))

$^1$H-NMR spectrum (DMSO-$d_6$, δ ppm): 1.36 (brs, 9H), 1.53 (s, 6H), 7.21 (brs, 1H), 7.36 (brs, 1H), 7.43 (d, J=8.3 Hz, 2H), 7.59-7.74 (m, 5H), 8.37-8.38 (m, 1H), 13.55 (brs, 1H)

Example 11

Synthesis of 5-[4-(1-tert-butoxycarbonylamino-1-methylethyl)phenyl]-3-hydroxyiminomethyl-1H-indazole (Compound 11-1)

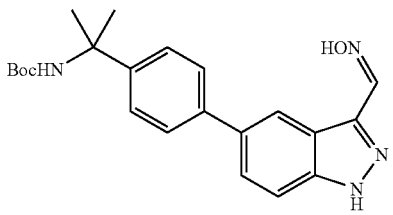

A solution of 194 mg (1.50 mmol) of N,N-diisopropylethylamine in 1 ml of ethanol was added to a solution of 114 mg (0.300 mmol) of 5-[4-(1-tert-butoxycarbonylamino-1-methylethyl)phenyl]-3-formyl-1H-indazole (Compound 4-2) in 25 ml of ethanol in an argon stream with stirring. After that, 83.0 mg (1.29 mmol) of hydroxylamine monohydrochloride was added thereto and the mixture was stirred at room temperature for 7 hours.

After the reaction was finished, the reaction solution was concentrated in vacuo, 50 ml of saturated aqueous solution of ammonium chloride was added thereto and the mixture was extracted with 100 ml of ethyl acetate. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=2:1 (v/v)) and the fraction containing the aimed substance was concentrated in vacuo to give 105 mg of the title compound as white powder (yield: 89%).

Rf value: 0.40 (n-hexane:ethyl acetate=1:1 (V/V))

Mass spectrum (CI, m/z): 395 (M$^+$+1)

$^1$H-NMR spectrum (DMSO-$d_6$, δ ppm): 1.35 (brs, 9H), 1.53 (s, 6H), 7.19 (brs, 1H), 7.43 (d, J=8.5 Hz, 2H), 7.57 (d, J=8.5 Hz, 2H), 7.64 (dd, J1=8.8 Hz, J2=0.7 Hz, 1H), 7.72 (dd, J1=8.8 Hz, J2=1.7 Hz, 1H), 8.26-8.27 (m, 1H), 8.39 (s, 1H), 11.42 (s, 1H), 13.38 (brs, 1H)

As hereunder, the compound 11-2 was produced in accordance with the production process for the compound 11-1.

5-[4-(1-tert-Butoxycarbonylamino-1-methylethyl)-phenyl]-4-hydroxyiminomethyl-2-(tetrahydropyran-2-yl)-2H-indazole (Compound 11-2)

Rf value: 0.36 (n-hexane:ethyl acetate=1:1 (v/v))

Mass spectrum (CI, m/z): 479 (M$^+$+1)

$^1$H-NMR spectrum (CDCl$_3$, δ ppm): 1.39 (brs, 9H), 1.63-1.85 (m, 9H), 2.02-2.13 (m, 1H), 2.18-2.31 (m, 2H), 3.76-3.85 (m, 1H), 4.11-4.19 (m, 1H), 4.96 (brs, 1H), 5.68-5.73 (m, 1H), 7.25 (d, J=8.8 Hz, 1H), 7.29-7.35 (m, 2H), 7.43-7.50 (m, 2H), 7.79 (dd, J1=8.8 Hz, J2=0.9 Hz, 1H), 8.30 (s, 1H), 8.71 (d, J=0.9 Hz, 1H)

Example 12

Synthesis of 5-[4-(1-tert-butoxycarbonylamino-1-methylethyl)phenyl]-3-cyano-1H-indazole (Compound 12-1)

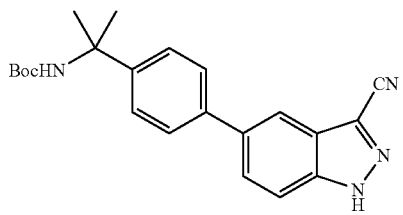

A solution of 220 mg (1.7 mmol) of N,N-diisopropylethylamine in 0.5 ml of tetrahydrofuran and a solution of 240 mg (1.1 mmol) of trifluoroacetic anhydride in 0.5 ml of tetrahydrofuran were added to a solution of 45 mg (0.11 mmol) of 5-[4-(1-tert-butoxycarbonylamino-1-methylethyl)phenyl]-3-hydroxyiminomethyl-1H-indazole (Compound 11-1) in 5 ml of tetrahydrofuran at 0° C. in an argon stream with stirring. The mixture was stirred at 0° C. for 2 hours, a solution of 100 mg (0.77 mmol) of N,N-diisopropylethylamine in 0.5 ml of tetrahydrofuran and a solution of 100 mg (0.48 mmol) of trifluoroacetic anhydride in 0.5 ml of tetrahydrofuran were added thereto and the mixture was stirred at 0° C. for 1 hour. After that, 5 ml of 28% aqueous ammonia was added thereto, a cooling bath was removed to warm up the mixture gradually to room temperature.

After the reaction was finished, the reaction solution was poured into 50 ml of a saturated aqueous solution of ammonium chloride and the mixture was extracted with 50 ml of ethyl acetate. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=2:1 (v/v)) and the fraction containing the aimed substance was concentrated in vacuo to give 25 mg of the title compound as white powder (yield: 58%).

Rf value: 0.43 (n-hexane:ethyl acetate=1:1 (v/v))

Mass spectrum (CI, m/z): 377 (M$^+$+1)

$^1$H-NMR spectrum (DMSO-$d_6$, δ ppm): 1.35 (brs, 9H), 1.54 (s, 6H), 7.21 (brs, 1H), 7.44 (d, J=8.4 Hz, 2H), 7.71 (d, J=8.4 Hz, 2H), 7.81-7.88 (m, 2H), 8.06-8.07 (m, 1H)

As hereunder, the compound 12-2 was produced in accordance with the production process for the compound 12-1.

5-[4-(1-tert-Butoxycarbonylamino-1-methylethyl)-phenyl]-4-cyano-2-(tetrahydropyran-2-yl)-2H-indazole (Compound 12-2)

Rf value: 0.55 (n-hexane:ethyl acetate=1:1 (v/v))

Mass spectrum (EI, m/z): 460 (M$^+$+1)

$^1$H-NMR spectrum (CDCl$_3$, δ ppm): 1.39 (brs, 9H), 1.63-1.88 (m, 9H), 2.01-2.32 (m, 3H), 3.78-3.87 (m, 1H), 4.12-4.23 (m, 1H), 4.97 (brs, 1H), 5.72-5.77 (m, 1H), 7.45 (d, J=9.0 Hz, 1H), 7.50-7.64 (m, 4H), 7.98 (dd, J1=9.0 Hz, J2=0.9 Hz, 1H), 8.41 (d, J=0.9 Hz, 1H)

Example 13

Synthesis of 5-[4-(1-tert-butoxycarbonylamino-1-methylethyl)phenyl]-3-hydroxymethyl-1H-indazole (Compound 13-1)

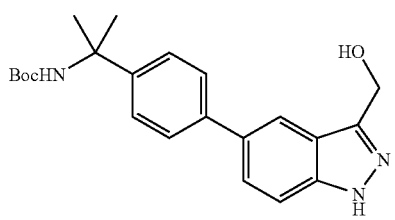

Sodium borohydride (2.0 mg, 0.053 mmol) was added to a solution of 11 mg (0.029 mmol) of 5-[4-(1-tert-butoxycarbonylamino-1-methylethyl)phenyl]-3-formyl-1H-indazole (Compound 4-2) in 3 ml of ethanol in an argon stream with stirring and the mixture was stirred at room temperature for 30 minutes.

After the reaction was finished, the reaction solution was concentrated in vacuo. Ethyl acetate (50 ml) was added to the residue, the mixture was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=1:1 (v/v)) and the fraction containing the aimed substance was concentrated in vacuo to give 10 mg of the title compound as white powder (yield: 91%).

Rf value: 0.32 (n-hexane:ethyl acetate=1:2 (v/v))
Mass spectrum (CI, m/z): 382 ($M^+$+1)
$^1$H-NMR spectrum (DMSO-$d_6$, δ ppm): 1.35 (brs, 9H), 1.53 (s, 6H), 4.82 (d, J=5.6 Hz, 2H), 5.24 (t, J=5.6 Hz, 1H), 7.19 (brs, 1H), 7.41 (d, J=8.5 Hz, 2H), 7.53-7.67 (m, 4H), 8.09-8.10 (m, 1H), 12.80 (brs, 1H)

As hereunder, the compounds 13-2 to 13-3 were produced in accordance with the production process for the compound 13-1.

5-[4-(1-tert-Butoxycarbonylamino-1-methylethyl)-phenyl]-4-hydroxymethyl-2-(tetrahydropyran-2-yl)-2H-indazole (Compound 13-2)

Rf value: 0.74 (ethyl acetate)
Mass spectrum (EI, m/z): 465 ($M^+$)
$^1$H-NMR spectrum (CDCl$_3$, δ ppm): 1.39 (brs, 9H), 1.58-1.86 (m, 10H), 1.99-2.13 (m, 1H), 2.18-2.30 (m, 2H), 3.75-3.86 (m, 1H), 4.12-4.20 (m, 1H), 4.89 (d, J=5.4 Hz, 2H), 4.96 (brs, 1H), 5.68-5.73 (m, 1H), 7.25 (d, J=8.8 Hz, 1H), 7.31-7.37 (m, 2H), 7.42-7.48 (m, 2H), 7.69 (dd, J1=8.8 Hz, J2=0.7 Hz, 1H), 8.45 (d, J=0.7 Hz, 1H)

5-[4-(1-tert-Butoxycarbonylamino-1-methylethyl)-phenyl]-4-(1-hydroxyethyl)-2-(tetrahydropyran-2-yl)-2H-indazole (Compound 13-3)

Property: white powder
Rf value: 0.29 (n-hexane:ethyl acetate=1:1 (v/v))
Mass spectrum (EI, m/z): 479 ($M^+$)
$^1$H-NMR spectrum (CDCl$_3$, δ ppm): 1.39 (brs, 9H), 1.59 (d, J=5.1 Hz, 3H), 1.60-1.83 (m, 9H), 2.03-2.13 (m, 1H), 2.18-2.33 (m, 2H), 3.73-3.82 (m, 1H), 4.13-4.19 (m, 1H), 4.96 (brs, 1H), 5.19 (q, J=5.1 Hz, 1H), 5.65-5.72 (m, 1H), 7.12 (d, J=9.0 Hz, 1H), 7.21-7.28 (m, 2H), 7.40-7.46 (m, 2H), 7.60-7.65 (m, 1H), 8.56 (d, J=0.7 Hz, 1H)

Example 14

Synthesis of 1-tert-butoxycarbonyl-5-[4-(1-tert-butoxycarbonylamino-1-methylethyl)phenyl]-4-dimethylamino-1H-indazole (Compound 14-1)

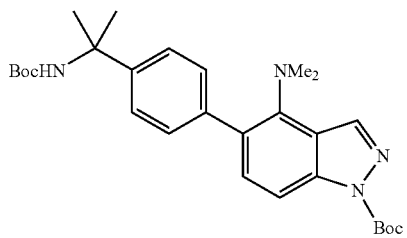

A 38% aqueous solution of formaldehyde (4.00 ml, 50.6 mmol) and a suspension of 940 mg of 5% palladium-carbon (wet) in 10 ml of ethyl acetate were added to a solution of 470 mg (1.01 mmol) of 4-amino-1-tert-butoxycarbonyl-5-[4-(1-tert-butoxycarbonylamino-1-methylethyl)phenyl]-1H-indazole (Compound 6-1) in 60 ml of methanol and the mixture was stirred in a hydrogen atmosphere at room temperature for 4 hours.

After the reaction was finished, the reaction solution was filtered and the filtrate was concentrated in vacuo. Ethyl acetate (200 ml) was added to the resulting residue, the mixture was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=4:1 (v/v)) and the fraction containing the aimed substance was concentrated in vacuo to give 408 mg of the title compound as white powder (yield: 82%).

Rf value: 0.44 (n-hexane:ethyl acetate=2:1 (v/v))
Mass spectrum (CI, m/z): 495 ($M^+$+1)
$^1$H-NMR spectrum (CDCl$_3$, δ ppm): 1.38 (brs, 9H), 1.68 (s, 6H), 1.73 (s, 9H), 2.81 (s, 6H), 4.94 (brs, 1H), 7.34-7.38 (m, 3H), 7.41-7.45 (m, 2H), 7.75-7.78 (m, 1H), 8.35 (d, J=0.7 Hz, 1H)

As hereunder, the compounds 14-2 to 14-6 were produced in accordance with the production process for the compound 14-1.

1-tert-Butoxycarbonyl-5-[4-(1-tert-butoxycarbonylaminomethyl)phenyl]-4-dimethylamino-1H-indazole (Compound 14-2)

Rf value: 0.55 (n-hexane:ethyl acetate=1:1 (v/v)
Mass spectrum (EI, m/z): 466 ($M^+$)
$^1$H-NMR spectrum (CDCl$_3$, δ ppm): 1.48 (s, 9H), 1.73 (s, 9H), 2.82 (s, 6H), 4.36-4.38 (m, 2H), 4.88 (brs, 1H), 7.30-7.35 (m, 3H), 7.37-7.41 (m, 2H), 7.75-7.79 (m, 1H), 8.36 (d, J=1.0 Hz, 1H)

1-tert-Butoxycarbonyl-5-[4-(1-tert-butoxycarbonyl-aminocyclopentyl)phenyl]-4-dimethylamino-1H-indazole (Compound 14-3)

Rf value: 0.37 (n-hexane:ethyl acetate=2:1 (v/v))
Mass spectrum (EI, m/z): 520 (M$^+$)
$^1$H-NMR spectrum (CDCl$_3$, δ ppm): 1.35 (brs, 9H), 1.72 (s, 9H), 1.77-1.89 (m, 4H), 2.04-2.33 (m, 4H), 2.80 (s, 6H), 4.88 (brs, 1H), 7.33-7.37 (m, 3H), 7.41-7.45 (m, 2H), 7.74-7.77 (m, 1H), 8.35 (d, J=0.7 Hz, 1H)

1-tert-Butoxycarbonyl-5-[4-(1-tert-butoxycarbonyl-amino-1-ethylpropyl)phenyl]-4-dimethylamino-1H-indazole (Compound 14-4)

Rf value: 0.48 (n-hexane:ethyl acetate=2:1 (v/v))
Mass spectrum (EI, m/z): 522 (M$^+$)
$^1$H-NMR spectrum (CDCl$_3$, δ ppm): 0.78 (t, J=7.3 Hz, 6H), 1.41 (brs, 9H), 1.73 (s, 9H), 1.90-2.16 (m, 4H), 2.80 (s, 6H), 4.80 (brs, 1H), 7.35-7.38 (m, 5H), 7.74-7.78 (m, 1H), 8.35 (d, J=0.7 Hz, 1H)

1-tert-Butoxycarbonyl-5-[4-(1-tert-butoxycarbonyl-aminoethyl)phenyl]-4-dimethylamino-1H-indazole (Compound 14-5)

Rf value: 0.42 (n-hexane:ethyl acetate=2:1 (v/v))
Mass spectrum (FAB, m/z): 480 (M$^+$)
$^1$H-NMR spectrum (DMSO-d$_6$, δ ppm): 1.30-1.44 (m, 12H), 1.65 (s, 9H), 2.76 (s, 6H), 4.61-4.72 (m, 1H), 7.31-7.41 (m, 6H), 7.68 (d, J=8.5 Hz, 1H), 8.56 (s, 1H)

1-tert-Butoxycarbonyl-5-[4-(1-tert-butoxycarbonyl-amino-1-methylethyl)phenyl]-4-diethylamino-1H-indazole (Compound 14-6)

Rf value: 0.55 (n-hexane:ethyl acetate=2:1 (v/v))
Mass spectrum (CI, m/z): 523 (M$^+$+1)
$^1$H-NMR spectrum (CDCl$_3$, δ ppm): 0.95 (t, J=7.1 Hz, 6H), 1.38 (brs, 9H), 1.68 (s, 6H), 1.73 (s, 9H), 3.10 (q, J=7.1 Hz, 4H), 4.93 (brs, 1H), 7.38 (d, J=8.9 Hz, 1H), 7.40-7.44 (m, 4H), 7.86 (d, J=8.9 Hz, 1H), 8.28 (s, 1H)

Example 15

Synthesis of 4-(N-acetylamino)-1-tert-butoxycarbonyl-5-[4-(1-tert-butoxycarbonylamino-1-methylethyl)phenyl]-1H-indazole (Compound 15)

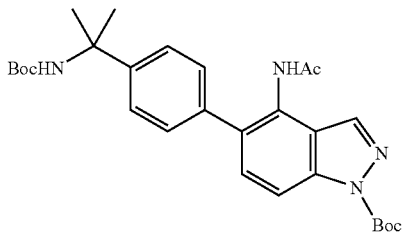

Acetic acid (5 ml) and acetic anhydride (2.5 ml) were added to 238 mg (0.510 mmol) of 4-amino-1-tert-butoxycarbonyl-5-[4-(1-tert-butoxycarbonylamino-1-methylethyl)phenyl]-1H-indazole (Compound 6-1) and the mixture was stirred at room temperature for 30 minutes.

After the reaction was finished, the reaction solution was poured into 100 ml of water and the mixture was extracted with 100 ml of ethyl acetate. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=1:1 (v/v)) and the fraction containing the aimed substance was concentrated in vacuo to give 254 mg of the title compound as white powder (yield: 98%).

Rf value: 0.15 (n-hexane:ethyl acetate=1:2 (v/v))
Mass spectrum (FAB, m/z): 509 (M$^+$+1)
$^1$H-NMR spectrum (CDCl$_3$, δ ppm): 1.40 (brs, 9H), 1.68 (s, 6H), 1.73 (s, 9H), 2.14 (s, 3H), 5.02 (brs, 1H), 7.18 (brs, 1H), 7.31-7.36 (m, 2H), 7.45-7.53 (m, 3H), 8.08-8.12 (m, 1H), 8.21 (d, J=1.0 Hz, 1H)

Example 16

Synthesis of 5-[5-(1-tert-butoxycarbonylamino-1-methylethyl)-pyridin-2-yl]-4-hydroxy-1-(tetrahydropyran-2-yl)-1H-indazole (Compound 16-1)

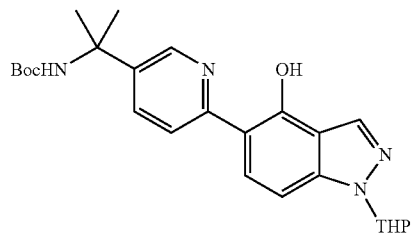

Tetrahydrofuran (50 ml) and 100 ml of ethanol were added to 7.55 g (13.9 mmol) of 4-benzyloxy-5-[5-(1-tert-butoxycarbonylamino-1-methylethyl)pyridin-2-yl]-1-(tetrahydropyran-2-yl)-1H-indazole (compound 1-12), then suspension of 3.32 g of 5% palladium-carbon (wet) in 50 ml of ethanol was added thereto and the mixture was stirred in a hydrogen atmosphere at room temperature for 30 minutes.

After the reaction was finished, the reaction solution was filtered through Celite and the filtrate was concentrated in vacuo. The resulting residue was dissolved in 20 ml of tetrahydrofuran, 200 ml of n-hexane was added thereto and the resulting solid was filtered off to give 5.70 g of the title compound as pale yellow powder (yield: 91%).

Rf value: 0.45 (n-hexane:ethyl acetate=1:1 (v/v))
Mass spectrum (CI, m/z): 453 (M$^+$+1)
$^1$H-NMR spectrum (CDCl$_3$, δ ppm): 1.37 (brs, 9H), 1.60-1.85 (m, 9H), 2.05-2.20 (m, 2H), 2.51-2.63 (m, 1H), 3.70-3.79 (m, 1H), 4.01-4.08 (m, 1H), 4.97 (brs, 1H), 5.65-5.70 (m, 1H), 7.06 (dd, J1=8.8 Hz, J2=0.7 Hz, 1H), 7.75-7.86 (m, 3H), 8.24 (d, J=0.7 Hz, 1H), 8.52 (dd, J1=2.2 Hz, J2=1.0 Hz, 1H), 15.84 (brs, 1H)

As hereunder, the compounds 16-2 to 16-4 were produced in accordance with the production process for the compound 16-1.

5-[5-(1-tert-Butoxycarbonylamino-1-methylethyl)-pyridin-2-yl]-4-hydroxy-2-(tetrahydrofuran-2-yl)-2H-indazole (Compound 16-2)

Rf value: 0.32 (n-hexane:ethyl acetate=1:1 (v/v))
Mass spectrum (EI, m/z): 452 (M$^+$)
$^1$H-NMR spectrum (DMSO-d$_6$, δ ppm): 1.34 (brs, 9H), 1.51-1.90 (m, 9H), 1.92-2.08 (m, 2H), 2.20-2.30 (m, 1H), 3.66-3.77 (m, 1H), 3.93-4.10 (m, 1H), 5.67-5.73 (m, 1H), 7.11 (d, J=9.3 Hz, 1H), 7.35 (brs, 1H), 7.83 (d, J=9.3 Hz, 1H), 7.90 (dd, J1=8.8 Hz, J2=2.2 Hz, 1H), 8.06 (d, J=8.8 Hz, 1H), 8.52 (d, J=2.2 Hz, 1H), 8.59 (s, 1H), 16.07 (brs, 1H)

5-[4-(1-tert-Butoxycarbonylamino-1-methylethyl)-phenyl]-4-hydroxy-1-(tetrahydropyran-2-yl)-1H-indazole (Compound 16-3)

Rf value: 0.24 (n-hexane:ethyl acetate=1:1 (v/v))
Mass spectrum (CI, m/z): 452 (M$^+$+1)
$^1$H-NMR spectrum (DMSO-d$_6$, δ ppm): 1.35 (brs, 9H), 1.48-1.58 (m, 8H), 1.73-1.79 (m, 1H), 1.90-2.06 (m, 2H), 2.34-2.49 (m, 1H), 3.68-3.77 (m, 1H), 3.87-3.92 (m, 1H), 5.73-5.78 (m, 1H), 7.12-7.21 (m, 2H), 7.29-7.36 (m, 3H), 7.49 (d, J=8.5 Hz, 2H), 8.30 (s, 1H), 10.07 (brs, 1H)

5-[4-(1-tert-Butoxycarbonylamino-1-ethylpropyl)-phenyl]-4-hydroxy-1-(tetrahydropyran-2-yl)-1H-indazole (Compound 16-4)

Rf value: 0.20 (n-hexane:ethyl acetate=4:1 (v/v))
Mass spectrum (CI, m/z): 480 (M$^+$+1)
$^1$H-NMR spectrum (DMSO-d$_6$, δ ppm): 0.61 (t, J=7.3 Hz, 3H), 0.68 (t, J=7.3 Hz, 3H), 1.36 (brs, 9H), 1.52-2.10 (m, 9H), 2.25-2.68 (m, 1H), 3.67-3.78 (m, 1H), 3.85-3.93 (m, 1H), 5.73-5.79 (m, 1H), 6.79 (brs, 1H), 7.18 (d, J=8.8 Hz, 1H), 7.30 (d, J=8.3 Hz, 2H), 7.33 (d, J=8.8 Hz, 1H), 7.51 (d, J=8.3 Hz, 2H), 8.29 (s, 1H), 9.11 (brs, 1H)

Example 17

Synthesis of 5-[5-(1-tert-butoxycarbonylamino-1-methylethyl)pyridin-2-yl]-1-(tetrahydropyran-2-yl)-4-trifluoromethanesulfonyloxy-1H-indazole (Compound 17-1)

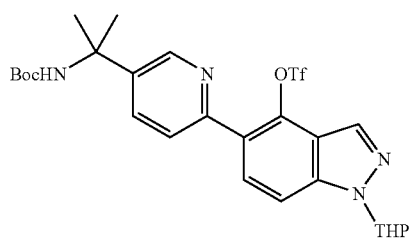

A solution of 1.61 ml (9.57 mmol) of trifluoromethanesulfonic anhydride in 15 ml of methylene chloride was dropped in a solution of 2.26 g (4.99 mmol) of 5-[5-(1-tert-butoxycarbonylamino-1-methylethyl)pyridin-2-yl]-4-hydroxy-1-(tetrahydropyran-2-yl)-1H-indazole (compound 16-1) and 4.35 ml (23.9 mmol) of N,N-diisoproylethylamine in 50 ml of methylene chloride at 0° C. during 30 minutes and the mixture was stirred for 20 minutes.

After the reaction was finished, the reaction solution was poured into 40 ml of a saturated aqueous solution of sodium hydrogen carbonate and the mixture was extracted with 100 ml of chloroform. The organic layer was washed with a saturated aqueous solution of sodium chloride, dried over anhydrous magnesium sulfate and concentrated in vacuo. The resulting residue was subjected to a silica gel column chromatography (eluting solvent: n-hexane:ethyl acetate=4:1 to 2:1 (v/v)) and the fraction containing the aimed substance was concentrated in vacuo to give 2.80 g of the title compound as slightly yellow foamy substance (yield: 96%).

Rf value: 0.41 (n-hexane:ethyl acetate=1:1 (v/v))
Mass spectrum (CI, m/z): 585 (M$^+$+1)
$^1$H-NMR spectrum (CDCl$_3$, δ ppm): 1.38 (brs, 9H), 1.60-1.84 (m, 9H), 2.09-2.21 (m, 2H), 2.50-2.61 (m, 1H), 3.72-3.81 (m, 1H), 3.99-4.05 (m, 1H), 5.01 (brs, 1H), 5.76-5.80 (m, 1H), 7.59 (d, J=8.5 Hz, 1H), 7.71 (dd, J1=8.7 Hz, J2=0.9 Hz, 1H), 7.77-7.82 (m, 2H), 8.16 (s, 1H), 8.80 (dd, J1=2.6 Hz, J2=0.9 Hz, 1H)

As hereunder, the compounds 17-2 to 17-3 were produced in accordance with the production process for the compound 17-1.

5-[4-(1-tert-Butoxycarbonylamino-1-methylethyl)-phenyl]-2-(tetrahydropyran-2-yl)-4-trifluoromethanesulfonyloxy-2H-indazole (Compound 17-2)

Rf value: 0.32 (n-hexane:ethyl acetate=2:1 (v/v))
Mass spectrum (EI, m/z): 583 (M$^+$)
$^1$H-NMR spectrum (DMSO-d$_6$, δ ppm): 1.34 (brs, 9H), 1.53 (s, 6H), 1.60-1.80 (m, 3H), 1.95-2.02 (m, 1H), 2.06-2.12 (m, 1H), 2.17-2.28 (m, 1H), 3.71-3.80 (m, 1H), 4.00-4.05 (m, 1H), 5.87-5.92 (m, 1H), 7.23 (brs, 1H), 7.42-7.48 (m, 5H), 7.86 (dd, J1=8.9 Hz, J2=0.9 Hz, 1H), 8.58-8.59 (m, 1H)

5-[5-(1-tert-Butoxycarbonylamino-1-methylethyl)-pyridin-2-yl]-2-(tetrahydropyran-2-yl)-4-trifluoromethanesulfonyloxy-2H-indazole (Compound 17-3)

Rf value: 0.56 (n-hexane:ethyl acetate=1:2 (v/v))
Mass spectrum (CI, m/z): 585 (M$^+$+1)
$^1$H-NMR spectrum (DMSO-d$_6$, ppm): 1.09 (brs, 9H), 1.44-1.80 (m, 9H), 1.89-2.36 (m, 3H), 3.67-3.78 (m, 1H), 3.95-4.10 (m, 1H), 5.88-5.93 (m, 1H), 7.34 (brs, 1H), 7.65-7.72 (m, 2H), 7.81-7.91 (m, 2H), 8.63 (s, 1H), 8.68 (d, J=2.0 Hz, 1H)

Example 18

Synthesis of 5-[5-(1-tert-butoxycarbonylamino-1-methylethyl)pyridin-2-yl]-4-cyclopropyl-1-(tetrahydropyran-2-yl)-1H-indazole (Compound 18-1)

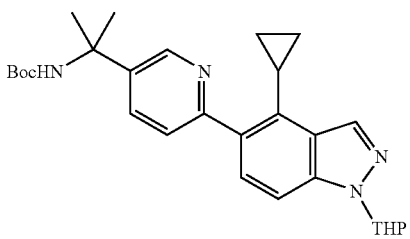

Cyclopropylboronic acid (206 mg, 2.40 mmol), 556 mg (2.40 nmol) of silver (I) oxide, 365 mg (2.40 mmol) of cesium fluoride, 185 mg (0.160 mmol) of tetrakis(triphenylphosphine)palladium and 20 ml of 1,2-dimethoxyethane were added to 468 mg (0.801 mmol) of 5-[5-(1-tert-butoxycarbonylamino-1-methylethyl)pyridin-2-yl]-1-(tetrahydropyran-2-yl)-4-trifluoromethanesulfonyloxy-1H-indazole (Compound 17-1) and the mixture was heated to reflux in an argon stream with stirring for 30 minutes.

After the reaction was finished, the reaction solution was poured into 100 ml of water and the mixture was extracted with 100 ml of ethyl acetate. The organic layer was washed with a saturated aqueous solution of sodium chloride, dried over anhydrous magnesium sulfate and concentrated in vacuo. The resulting residue was subjected to a silica gel column chromatography (eluting solvent: n-hexane:ethyl acetate=3:1 (v/v)) and the fraction containing the aimed substance was concentrated in vacuo to give 260 mg of the title compound as slightly orange powder (yield: 68%).

Rf value: 0.33 (n-hexane ethyl acetate=1:1 (v/v))

Mass spectrum (CI, m/z): 477 ($M^+$+1)

$^1$H-NMR spectrum (CDCl$_3$, δ ppm): 0.55-0.61 (m, 2H), (m, 2H), 1.37 (brs, 9H), 1.60-1.86 (m, 9H), (m, 2H), 2.30-2.36 (m, 1H), 2.54-2.65 (m, 1H), (m, 1H), 4.02-4.06 (m, 1H), 4.99 (brs, 1H), 5.70-5.75 (m, 1H), 7.46-7.57 (m, 3H), 7.74 (dd, J1=8.3 Hz, J2=2.6 Hz, 1H), 8.20 (s, 1H), 8.76 (dd, J1=2.6 Hz, J2=0.7 Hz, 1H)

As hereunder, the compound 18-2 was produced in accordance with the production process for the compound 18-1.

5-[5-(1-tert-Butoxycarbonylamino-1-methylethyl)-pyridin-2-yl]-1-(tetrahydropyran-2-yl)-4-vinyl-1H-indazole (Compound 18-2)

Rf value: 0.37 (n-hexane:ethyl acetate=1:1 (v/v))

Mass spectrum (CI, m/z): 463 ($M^+$+1)

$^1$H-NMR spectrum (CDCl$_3$, δ ppm): 1.38 (brs, 9H), 1.68-1.82 (m, 9H), 2.08-2.19 (m, 2H), 2.54-2.67 (m, 1H), 3.73-3.81 (m, 1H), 4.02-4.06 (m, 1H), 4.99 (brs, 1H), 5.56 (dd, J1=11.2 Hz, J2=1.5 Hz, 1H), 5.74-5.78 (m, 1H), 5.90 (dd, J1=17.8 Hz, J2=1.5 Hz, 1H), 6.96 (dd, J1=17.8 Hz, J2=11.2 Hz, 1H), 7.43 (dd, J1=8.3 Hz, J2=0.9 Hz, 1H), 7.57 (d, J=9.0 Hz, 1H), 7.62 (d, J=9.0 Hz, 1H), 7.73 (dd, J1=8.3 Hz, J2=2.4 Hz, 1H), 8.29 (s, 1H), 8.77 (dd, J1=2.4 Hz, J2=0.9 Hz, 1H)

Example 19

Synthesis of 5-[5-(1-tert-butoxycarbonylamino-1-methylethyl)-pyridin-2-yl]-4-ethyl-1-(tetrahydropyran-2-yl)-1H-indazole (Compound 19)

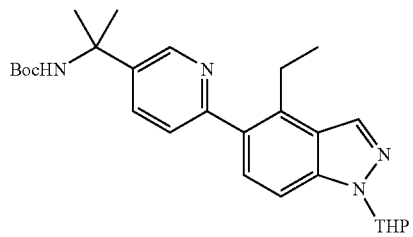

A suspension of 80 mg of 5% palladium-carbon (wet) in 5 ml of ethanol was added to a solution of 155 mg (0.335 mmol) of 5-[5-(1-tert-butoxycarbonylamino-1-methylethyl)pyridin-2-yl]-1-(tetrahydropyran-2-yl)-4-vinyl-1H-indazole (compound 18-2) in 10 ml of ethanol and the mixture was stirred in a hydrogen atmosphere at room temperature for 1 hour.

After the reaction was finished, the reaction solution was filtered and the filtrate was concentrated in vacuo. The resulting residue was subjected to a silica gel column chromatography (eluting solvent: toluene ethyl acetate=6:1 (v/v)) and the fraction containing the aimed substance was concentrated in vacuo to give 120 mg of the title compound as white powder (yield: 77%).

Rf value: 0.38 (toluene:ethyl acetate=2:1 (v/v))

Mass spectrum (CI, m/z): 465 ($M^+$+1)

$^1$H-NMR spectrum (CDCl$_3$, δ ppm): 1.25 (t, J=7.6 Hz, 3H), 1.38 (brs, 9H), 1.66-1.82 (m, 9H), 2.07-2.20 (m, 2H), 2.54-2.66 (m, 1H), 3.02 (q, J=7.6 Hz, 2H), 3.72-3.80 (m, 1H), 4.02-4.07 (m, 1H), 4.98 (brs, 1H), 5.71-5.76 (m, 1H), 7.36 (dd, J1=8.2 Hz, J2=0.9 Hz, 1H), 7.44 (d, J=8.9 Hz, 1H), 7.48 (d, J=8.9 Hz, 1H), 7.75 (dd, J1=8.2 Hz, J2=2.6 Hz, 1H), 8.12 (s, 1H), 8.75 (dd, J1=2.6 Hz, J2=0.9 Hz, 1H)

Example 20

Synthesis of 1-tert-butoxycarbonyl-5-[4-(1-tert-butoxycarbonylamino-1-methylethyl)phenyl]-4-(pyrrol-1-yl)-1H-indazole (Compound 20)

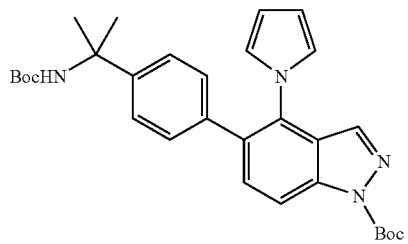

Methanol (2.0 ml), 2.0 ml of acetic acid and 0.50 ml of 2,5-dimethoxytetrahydrofuran were added to 20 mg (0.043 mmol) of 4-amino-1-tert-butoxycarbonyl-5-[4-(1-tert-butoxycarbonylamino-1-methylethyl)phenyl]-1H-indazole (compound 6-1) and the mixture was stirred at 60° C. for 30 minutes.

After the reaction was finished, the reaction solution was poured into 20 ml of water, and the mixture was neutralized with a saturated aqueous solution of sodium hydrogen carbonate and extracted with 50 ml of ethyl acetate. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=10:1 to 2:1 (v/v)) and the fraction containing the aimed substance was concentrated in vacuo to give 23 mg of the title compound as yellow oily substance (yield: quantitative).

Rf value: 0.49 (n-hexane:ethyl acetate=2:1 (v/v))

Mass spectrum (CI, m/z): 517 ($M^+$+1)

$^1$H-NMR spectrum (CDCl$_3$, ppm): 1.37 (brs, 9H), 1.62 (s, 6H), 1.75 (s, 9H), 4.90 (brs, 1H), 6.23 (dd, J1=2.2 Hz, J2=2.0 Hz, 2H), 6.67 (dd, J1=2.2 Hz, J2=2.0 Hz, 2H), 7.03-7.08 (m, 2H), 7.30-7.34 (m, 2H), 7.64 (d, J=8.5 Hz, 1H), 8.12 (d, J=0.7 Hz, 1H), 8.19 (dd, J1=8.5 Hz, J2=0.7 Hz, 1H)

Example 21

Synthesis of 5-[4-(1-tert-butoxycarbonylamino-1-methylethyl)phenyl]-4-hydroxy-1H-indazole (Compound 21)

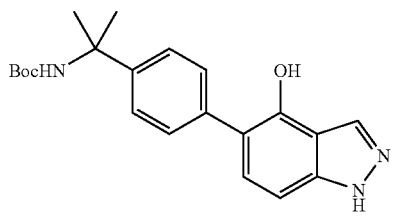

1,4-Dioxane (15 ml) and 30 ml of ethanol were added to 2.17 g (4.01 mmol) of 4-benzyloxy-5-[4-(1-tert-butoxy-carbonylamino-1-methylethyl)phenyl]-2-(tetrahydropyran-2-yl)-2H-indazole (compound 1-19), then a suspension of 1.00 g of 5% palladium-carbon (wet) in 10 ml of ethanol was added thereto and the mixture was stirred in a hydrogen atmosphere at room temperature for 8 hours.

After that, the reaction solution was filtered through Celite and the filtrate was concentrated in vacuo. Tetrahydrofuran (30 ml) and 30 ml of ethanol were added to the resulting residue, then a suspension of 1.10 g of 5% palladium-carbon (wet) in 10 ml of ethanol was added thereto and the mixture was stirred in a hydrogen atmosphere at room temperature for 16 hours.

After the reaction was finished, the reaction solution was filtered through Celite and the filtrate was concentrated in vacuo. The resulting residue was dissolved in tetrahydrofuran, n-hexane was added thereto and the resulting solid was filtered off and washed with n-hexane to give 1.14 g of the title compound as white powder (yield: 78%).

Rf value: 0.25 (n-hexane:ethyl acetate=1:1 (v/v))

Mass spectrum (CI, m/z): 368 (M$^+$+1)

$^1$H-NMR spectrum (DMSO-d$_6$, δ ppm): 1.35 (brs, 9H), 1.53 (s, 6H), 7.02 (dd, J1=8.4 Hz, J2=0.8 Hz, 1H), 7.14 (brs, 1H), 7.25 (d, J=8.4 Hz, 1H), 7.34 (d, J=8.4 Hz, 2H), 7.48 (d, J=8.4 Hz, 2H), 8.26-8.27 (m, 1H), 9.88 (brs, 1H), 12.91 (brs, 1H)

Example 22

Synthesis of 5-[4-(1-tert-butoxycarbonylamino-1-methylethyl)phenyl]-4-isopropoxy-1H-indazole (Compound 22-1)

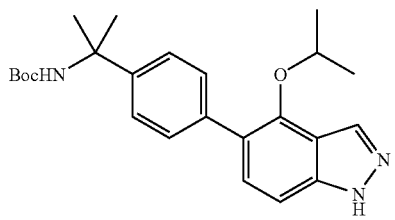

Potassium carbonate (289 mg, 2.09 mmol) and 5 ml of N,N-dimethylformamide Were added to 256 mg (0.697 mmol) of 5-[4-(1-tert-butoxycarbonylamino-1-methylethyl)phenyl]-4-hydroxy-1H-indazole (compound 21). After that, a solution of 118 mg (0.694 mmol) of isopropyl iodide in 1 ml of N,N-dimethylformamide was added thereto with stirring in an argon stream and the mixture was stirred at room temperature for 18 hours.

After the reaction was finished, the reaction solution was poured into 50 ml of water and the mixture was extracted with 50 ml of ethyl acetate. The organic layer was washed with a saturated aqueous solution of sodium chloride, dried over anhydrous magnesium sulfate and concentrated in vacuo. The resulting residue was subjected to a silica gel column chromatography (eluting solvent: n-hexane:ethyl acetate=4:1 (v/v)) and the fraction containing the aimed product was concentrated in vacuo. The resulting crude crystals was dissolved in tetrahydrofuran, n-hexane was added thereto and the resulting solid was filtered off and washed with n-hexane to give 173 mg of the title compound as slightly orange powder (yield: 61%).

Rf value: 0.41 (n-hexane:ethyl acetate=1:1 (v/v))

Mass spectrum (CI, m/z): 410 (M$^+$+1)

$^1$H-NMR spectrum (DMSO-d$_6$, δ ppm): 1.08 (d, J=6.1 Hz, 6H), 1.34 (brs, 9H), 1.53 (s, 6H), 4.34-4.44 (m, 1H), 7.15 (brs, 1H), 7.27 (dd, J1=8.5 Hz, J2=0.7 Hz, 1H), 7.31 (d, J=8.5 Hz, 1H), 7.37 (d, J=8.5 Hz, 2H), 7.47 (d, J=8.5 Hz, 2H), 8.12-8.14 (m, 1H), 13.10 (brs, 1H)

As hereunder, the compounds 22-2 to 22-9 were produced in accordance with the production process for the compound 22-1.

5-[4-(1-tert-Butoxycarbonylamino-1-methylethyl)-phenyl]-4-ethoxy-1H-indazole (Compound 22-2)

Rf value: 0.37 (n-hexane:ethyl acetate=1:1 (v/v))

Mass spectrum (EI, m/z): 395 (M$^+$)

$^1$H-NMR spectrum (DMSO-d$_6$, δ ppm): 1.23 (t, J=7.0 Hz, 3H), 1.35 (brs, 9H), 1.53 (s, 6H), 4.25 (q, J=7.0 Hz, 2H), 7.16 (brs, 1H), 7.24 (dd, J1=8.5 Hz, J2=0.7 Hz, 1H), 7.30 (d, J=8.5 Hz, 1H), 7.36 (d, J=8.5 Hz, 2H), 7.45 (d, J=8.5 Hz, 2H), 8.24 (d, J=0.7 Hz, 1H), 13.12 (brs, 1H)

5-[4-(1-tert-butoxycarbonylamino-1-methylethyl)-phenyl]-4-n-propoxy-1H-indazole (Compound 22-3)

Rf value: 0.37 (n-hexane:ethyl acetate=1:1 (V/V))

Mass spectrum (EI, m/z): 409 (M$^+$)

$^1$H-NMR spectrum (DMSO-d$_6$, δ ppm): 0.87 (t, J=7.4 Hz, 3H), 1.35 (brs, 9H), 1.53-1.68 (m, 8H), 4.15 (t, J=6.3 Hz, 2H), 7.16 (brs, 1H), 7.24 (dd, J1=8.5 Hz, J2=0.7 Hz, 1H), 7.30 (d, J=8.5 Hz, 1H), 7.35 (d, J=8.5 Hz, 2H), 7.44 (d, J=8.5 Hz, 0.2H), 8.23 (d, J=0.7 Hz, 1H), 13.12 (brs, 1H)

4-n-Butoxy-5-[4-(1-tert-butoxycarbonylamino-1-methylethyl)phenyl]-1H-indazole (Compound 22-4)

Rf value: 0.50 (n-hexane:ethyl acetate=1:1 (V/V))

Mass spectrum (EI, m/z): 423 (M$^+$)

$^1$H-NMR spectrum (DMSO-d$_6$, δ ppm): 0.81 (t, J=7.3 Hz, 3H), 1.00-1.45 (m, 11H), 1.53 (s, 6H), 1.55-1.65 (m, 2H), 4.17 (t, J=6.3 Hz, 2H), 7.15 (brs, 1H), 7.22-7.31 (m, 2H), 7.35 (d, J=8.4 Hz, 2H), 7.43 (d, J=8.4 Hz, 2H), 8.22 (s, 1H), 13.10 (brs, 1H)

5-[4-(1-tert-Butoxycarbonylamino-1-methylethyl)-
phenyl]-4-(2,2,2-trifluoroethoxy)-1H-indazole
(Compound 22-5)

Rf value: 0.43 (n-hexane:ethyl acetate=2:1 (v/v))

Mass spectrum (EI, m/z): 533 (M$^+$)

$^1$H-NMR spectrum (DMSO-d$_6$, δ ppm): 1.34 (brs, 9H), 1.46-1.87 (m, 9H), 1.93-2.13 (m, 2H), 2.30-2.50 (m, 1H), 3.67-3.80 (m, 1H), 3.84-3.95 (m, 1H), 4.76 (q, $^3J_{F-H}$=8.8 Hz, 2H), 5.82-5.90 (m, 1H), 7.18 (brs, 1H), 7.36-7.49 (m, 5H), 7.57 (d, J=8.5 Hz, 1H), 8.29 (s, 1H)

5-[4-(1-tert-Butoxycarbonylamino-1-methylethyl)-
phenyl]-4-(2-fluoroethoxy)-1H-indazole (Compound
22-6)

Rf value: 0.34 (n-hexane:ethyl acetate=2:1 (v/v))

Mass spectrum (EI, m/z): 497 (M$^+$)

$^1$H-NMR spectrum (DMSO-d$_6$, δ ppm): 1.35 (brs, 9H), 1.48-1.85 (m, 9H), 1.93-2.12 (m, 2H), 2.34-2.58 (m, 1H), (m, 1H), 3.87-3.94 (m, 1H), 4.35-4.75 (m, 4H), (m, 1H), 7.17 (brs, 1H), 7.35-7.42 (m, 3H), (m, 3H), 8.29 (s, 1H)

4-Allyloxy-5-[4-(1-tert-butoxycarbonylamino-1-
methylethyl)phenyl]-1H-indazole (Compound 22-7)

Rf value: 0.51 (n-hexane:ethyl acetate=2:1 (v/v))

Mass spectrum (EI, m/z): 407 (M$^+$)

5-[5-(1-tert-Butoxycarbonylamino-1-methylethyl)-
pyridin-2-yl]-4-isopropoxy-2-(tetrahydropyran-2-yl)-
2H-indazole (Compound 22-8)

Rf value: 0.27 (n-hexane:ethyl acetate=1:1 (v/v))

Mass spectrum (CI, m/z): 495 (M$^+$+1)

$^1$H-NMR spectrum (DMSO-d$_6$): 1.13 (d, J=6.0 Hz, 3H), 1.15 (d, J=6.0 Hz, 3H), 1.34 (bra, 9H), 1.50-1.80 (m, 9H), 1.90-2.16 (m, 2H), 2.20-2.36 (m, 1H), 3.67-3.78 (m, 1H), 3.98-4.05 (m, 1H), 4.50-4.62 (m, 1H), 5.71-5.77 (m, 1H), 7.29 (brs, 1H), 7.38 (dd, J1=8.8 Hz, J2=0.9 Hz, 1H), 7.74-7.76 (m, 2H), 7.93 (d, J=8.3 Hz, 1H), 8.62 (d, J=2.0 Hz, 1H), 8.65 (d, J=0.9 Hz, 1H)

5-[5-(1-tert-Butoxycarbonylamino-1-methylethyl)-
pyridin-2-yl]-4-cyclopropylmethyloxy-1-(tetrahydro-
pyran-2-yl)-1H-indazole (Compound 22-9)

Rf value: 0.57 (n-hexane:ethyl acetate=1:1 (v/v))

Mass spectrum (CI, m/z): 507 (M$^+$+1)

$^1$H-NMR spectrum (DMSO-d$_6$): 0.20-0.28 (m, 2H), 0.42-0.51 (m, 2H), 1.12-1.40 (m, 10H), 1.56-1.63 (m, 8H), 1.69-1.84 (m, 1H), 1.91-2.11 (m, 2H), 2.31-2.47 (m, 1H), 3.70-3.81 (m, 1H), 3.86-3.97 (m, 1H), 4.10 (d, J=7.1 Hz, 2H), 5.81-5.86 (m, 1H), 7.30 (brs, 1H), 7.45 (dd, J1=8.5 Hz, J2=0.7 Hz, 1H), 7.73 (dd, J1=8.5 Hz, J2=2.7 Hz, 1H), 7.87 (d, J=8.5 Hz, 1H), 7.96 (dd, J1=8.5 Hz, J2=0.7 Hz, 1H), 8.30-8.31 (m, 1H), 8.58-8.64 (m, 1H)

Example 23

Synthesis of 5-[4-(1-tert-butoxycarbonylamino-1-
methylethyl)phenyl]-4-hydroxy-2-(tetrahydropyran-
2-yl)-2H-indazole (Compound 23)

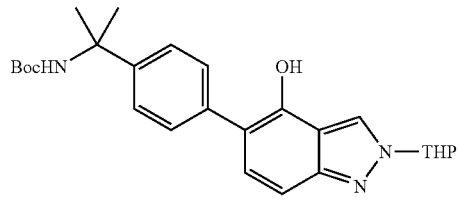

Pyridine (0.81 ml, 10.0 mol) and a suspension of 1.18 g of 5% palladium-carbon (wet) in 10 ml of ethanol were added to a solution of 2.71 g (5.00 mmol) of 4-benzyloxy-5-[4-(1-tert-butoxycarbonylamino-1-methylethyl)phenyl]-2-(tetrahydropyran-2-yl)-2H-indazole (compound 1-19) in 15 ml of tetrahydrofuran and 15 ml of ethanol and the mixture was stirred in a hydrogen atmosphere at room temperature for 5 hours. After that, a suspension of 600 mg of 5% palladium-carbon (wet) in 5 ml of ethanol was added thereto and the mixture was stirred in a hydrogen atmosphere at room temperature for 2 hours.

After the reaction was finished, the reaction solution was filtered through Celite, 100 ml of 10 weight % aqueous solution of citric acid was added to the filtrate and the mixture was extracted with 300 ml of ethyl acetate. The organic layer was successively washed with water and a saturated aqueous solution of sodium chloride, dried over anhydrous magnesium sulfate and concentrated in vacuo to give 2.16 g of the title compound as slightly pink powder (yield: 96%).

Rf value: 0.30 (n-hexane:ethyl acetate=1:1 (v/v))

Mass spectrum (EI, m/z): 451 (M$^+$)

$^1$H-NMR spectrum (DMSO-d$_6$, δ ppm): 1.36 (brs, 9H), 1.53 (s, 6H), 1.57-1.80 (m, 3H), 1.90-1.99 (m, 1H), 2.07-2.15 (m, 2H), 3.71-3.80 (m, 1H), 3.91-4.05 (m, 1H), 5.71-5.76 (m, 1H), 7.11-7.16 (m, 2H), 7.22 (d, J=9.0 Hz, 1H), 7.34 (d, J=8.5 Hz, 2H), 7.50 (d, J=8.5 Hz, 2H), 8.58 (d, J=0.7 Hz, 1H), 9.71 (s, 1H)

Example 24

Synthesis of 5-[4-(1-tert-butoxycarbonylamino-1-
methylethyl)phenyl]-4-(pyridin-4-yl)-2-(tetrahydro-
pyran-2-yl)-2H-indazole (Compound 24-1)

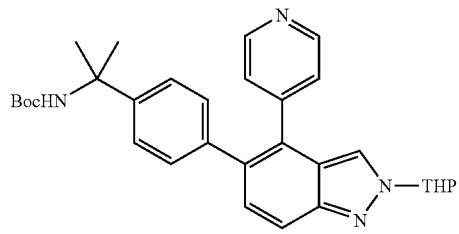

4-(4,4,5,5-Tetramethyl[1,3,2]dioxaborolanyl)pyridine (211 mg, 1.03 mmol), 119 mg (0.103 mmol) of tetrakis(triphenylphosphine)palladium, 5 ml of 1,2-dimethoxyethane and 2 ml of 2M aqueous solution of sodium carbonate were added to 300 mg (0.514 mmol) of 5-[4-(1-tert-butoxycarbonylamino-1-methylethyl)phenyl]-2-(tetrahydropyran-2-yl)-4-trifluoromethanesulfonyloxy-2H-indazole (compound 17-2) and the mixture was heated to reflux with stirring in an argon stream for 1 hours.

After the reaction was finished, the reaction solution was poured into 50 ml of water and the mixture was extracted with 100 ml of ethyl acetate. The organic layer was washed with a saturated aqueous solution of sodium chloride, dried over anhydrous magnesium sulfate and concentrated in vacuo. The resulting residue was subjected to a silica gel column chromatography (eluting solvent: n-hexane:ethyl acetate=2:1 to 1:1 to 1:2 (v/v)) and the fraction containing the aimed product was concentrated in vacuo to give 236 mg of the title compound as slightly orange powder (yield: 90%).

Rf value: 0.34 (n-hexane:ethyl acetate=1:2 (v/v))
Mass spectrum (CI, m/z): 513 ($M^+$+1)
$^1$H-NMR spectrum (CDCl$_3$, δ ppm): 1.35 (brs, 9H), 1.58-1.85 (m, 9H), 2.04-2.27 (m, 3H), 3.74-3.82 (m, 1H), 4.11-4.15 (m, 1H), 4.87 (brs, 1H), 5.64-5.69 (m, 1H), 7.09-7.13 (m, 2H), 7.20 (dd, J1=4.4 Hz, J2=1.7 Hz, 2H), 7.23-7.28 (m, 2H), 7.42 (d, J=9.0 Hz, 1H), 7.80 (dd, J1=9.0 Hz, J2=1.0 Hz, 1H), 8.00-8.01 (m, 1H), 8.51 (dd, J1=4.4 Hz, J2=1.7 Hz, 2H)

As hereunder, the compounds 24-2 to 24-3 were produced in accordance with the production process for the compound 24-1.

5-[4-(1-tert-Butoxycarbonylamino-1-methylethyl)-phenyl]-4-(pyridin-3-yl)-2-(tetrahydropyran-2-yl)-2H-indazole (Compound 24-2)

Rf value: 0.19 (n-hexane:ethyl acetate=1:1 (v/v))
Mass spectrum (CI, m/z): 513 ($M^+$+1)

5-[4-(1-tert-Butoxycarbonylamino-1-methylethyl)-phenyl]-4-(pyridin-2-yl)-2-(tetrahydropyran-2-yl)-2H-indazole (Compound 24-3)

Rf value: 0.29 (n-hexane:ethyl acetate=1:1 (v/v))
Mass spectrum (CI, m/z): 513 ($M^+$+1)

Example 25

Synthesis of 1-tert-butoxycarbonyl-5-[4-(1-tert-butoxycarbonylamino-1-methylethyl)phenyl]-4-(piperidin-1-yl)-1H-indazole (Compound 25-1)

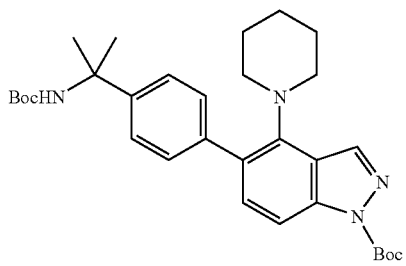

A suspension of 320 mg of 5% palladium-carbon (wet) in 3 ml of ethanol and 6.87 ml of a 50% aqueous solution of glutaraldehyde were added to a solution of 160 mg (0.343 mmol) of 4-amino-1-tert-butoxycarbonyl-5-[4-(1-tert-butoxycarbonylamino-1-methylethyl)phenyl]-1H-indazole (Compound 6-1) in 30 ml of ethanol and the mixture was stirred in a hydrogen atmosphere at room temperature for 5 hours. After that, 3.44 ml of a 50% aqueous solution of glutaraldehyde was added thereto and the mixture was stirred in a hydrogen atmosphere at room temperature for 2 hours.

After the reaction was finished, the reaction solution was filtered through Celite and the filtrate was concentrated in vacuo. Water was added to the resulting residue and the resulting precipitate was filtered off and washed with water. The resulting powder was subjected to a silica gel column chromatography (eluting solvent: n-hexane:ethyl acetate=6:1 (v/v)) and the fraction containing the aimed product was concentrated in vacuo to give 163 mg of the title compound as a white foamy substance (yield: 89%).

Rf value: 0.38 (n-hexane:ethyl acetate=2:1 (v/v))
Mass spectrum (CI, m/z): 535 ($M^+$+1)
$^1$H-NMR spectrum (CDCl$_3$, δ ppm): 1.27-1.54 (m, 15H), 1.68 (s, 6H), 1.73 (s, 9H), 3.05-3.10 (m, 4H), 4.97 (brs, 1H), 7.35 (d, J=8.5 Hz, 1H), 7.40-7.45 (m, 4H), 7.79 (d, J=8.5 Hz, 1H), 8.34 (s, 1H)

As hereunder, the compounds 25-2 to 25-3 were produced in accordance with the production process for the compound 25-1. Incidentally, succinaldehyde used for the synthesis of the compound 25-2 was synthesized by referring to A. R. Katritzky, et al., *J. Org. Chem.*, 65, 3685 (2000). Similarly, oxy-bis-acetaldehyde used for the synthesis of the compound 25-3 was synthesized by referring to J-C. Florent, et al., *J. Med. Chem.*, 36, 1364 (1993).

1-tert-Butoxycarbonyl-5-[4-(1-tert-butoxycarbonylamino-1-methylethyl)phenyl]-4-(pyrrolidin-1-yl)-1H-indazole (Compound 25-2)

Rf value: 0.46 (n-hexane:ethyl acetate=2:1 (v/v))
Mass spectrum (CI, m/z): 521 ($M^+$+1)
$^1$H-NMR spectrum (CDCl$_3$, δ ppm): 1.37 (brs, 9H), 1.67 (s, 6H), 1.72 (s, 9H), 1.77-1.82 (m, 4H), 3.23-3.28 (m, 4H), 4.94 (brs, 1H), 7.25-7.40 (m, 5H), 7.58-7.62 (m, 1H), 8.41 (d, J=0.7 Hz, 1H)

1-tert-Butoxycarbonyl-5-[4-(1-tert-butoxycarbonylamino-1-methylethyl)phenyl]-4-(morpholin-4-yl)-1H-indazole (Compound 25-3)

Rf value: 0.53 (n-hexane:ethyl acetate=1:1 (v/v))
$^1$H-NMR spectrum (CDCl$_3$, δ ppm): 1.39 (s, 9H), 1.67 (s, 6H) 1.73 (s, 9H), 3.12-3.16 (m, 4H), 3.56-3.63 (m, 4H), 4.97 (brs, 1H), 7.39 (d, J=8.8 Hz, 1H), 7.42-7.48 (m, 4H), 7.89 (dd, J1=8.8 Hz, J2=0.7 Hz, 1H), 8.36 (d, J=0.7 Hz, 1H)

Example 26

Synthesis of 5-[4-(1-tert-butoxycarbonylamino-1-methylethyl)phenyl]-4-difluoromethoxy-1-(tetrahydropyran-2-yl)-1H-indazole (Compound 26-1)

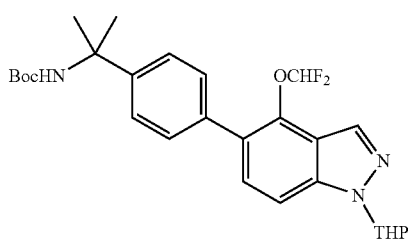

Cesium carbonate (1.47 g, 4.51 mmol) and 458 mg (3.00 mmol) of sodium chlorodifluoroacetate were added to a solution of 680 mg (1.50 mmol) of 5-[4-(1-tert-butoxycarbonylamino-1-methylethyl)phenyl]-4-hydroxy-1-(tetrahydropyran-2-yl)-1H-indazole (Compound 16-3) in 10 ml of N,N-dimethylformamide. The mixture was stirred in an argon stream at 100° C. for 45 minutes.

After the reaction was finished, the reaction solution was poured into 50 ml of water and the mixture was extracted with 50 ml of toluene. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane:ethyl acetate=4:1 (v/v)) and the fraction containing the aimed product was concentrated in vacuo to give 343 mg of the title compound as white powder (yield: 46%).

Rf value: 0.46 (n-hexane:ethyl acetate=2:1 (v/v))
Mass spectrum (EI, m/z): 501 (M$^+$)
$^1$H-NMR spectrum (DMSO-d$_6$, δ ppm): 1.35 (brs, 9H), 1.48-1.85 (m, 9H), 1.95-2.12 (m, 2H), 2.34-2.57 (m, 1H), 3.72-3.82 (m, 1H), 3.86-3.94 (m, 1H), 5.89-5.95 (m, 1H), 7.10 (t, $^2J_{F-H}$ 74.0 Hz, 1H), 7.18 (brs, 1H), 7.37-7.48 (m, 4H), 7.49 (d, J=8.8 Hz, 1H), 7.75 (d, J=8.8 Hz, 1H), 8.15 (s, 1H)

As hereunder, the compounds 26-2 to 26-3 were produced in accordance with the production process for the compound 26-1.

5-[5-(1-tert-Butoxycarbonylamino-1-methylethyl)-pyridin-2-yl]-4-difluoromethoxy-1-(tetrahydropyran-2-yl)-1H-indazole (Compound 26-2)

Rf value: 0.29 (n-hexane:ethyl acetate=2:1 (v/v))
Mass spectrum (CI, m/z): 503 (M$^+$+1)
$^1$H-NMR spectrum (DMSO-d$_6$, δ ppm): 1.34 (brs, 9H), 1.50-1.86 (m, 9H), 1.96-2.12 (m, 2H), 2.34-2.53 (m, 1H), 3.72-3.83 (m, 1H), 3.86-3.95 (m, 1H), 5.89-5.96 (m, 1H), 7.26 (t, $^2J_{F-H}$=74.0 Hz, 1H), 7.33 (brs, 1H), 7.72 (dd, J1=8.5 Hz, J20.7 Hz, 1H), 7.76-7.88 (m, 3H), 8.18 (s, 1H), 8.66 (dd, J1=2.4 Hz, J2=0.7 Hz, 1H)

5-[4-(1-tert-Butoxycarbonylamino-1-ethylpropyl)-phenyl]-4-difluoromethoxy-1-(tetrahydropyran-2-yl)-1H-indazole (Compound 26-3)

Rf value: 0.40 (n-hexane:ethyl acetate=4:1 (v/v))
Mass spectrum (EI, m/z): 529 (M$^+$)
$^1$H-NMR spectrum (DMSO-d$_6$, δ ppm): 0.68 (t, J=7.3 Hz, 6H), 1.35 (brs, 9H), 1.55-1.65 (m, 2H), 1.70-1.90 (m, 3H), 1.92-2.12 (m, 4H), 2.34-2.57 (m, 1H), 3.71-3.83 (m, 1H), 3.85-3.95 (m, 1H), 5.87-5.97 (m, 1H), 6.81 (brs, 1H), 7.04 (t, $^2J_{F-H}$=73.6 Hz, 1H), 7.36 (d, J=8.5 Hz, 2H), 7.44 (d, J=8.5 Hz, 2H), 7.51 (d, J=8.7 Hz, 1H), 7.76 (d, J=8.7 Hz, 1H), 8.15 (s, 1H)

Example 27

Synthesis of 5-[4-(1-tert-butoxycarbonylamino-1-methylethyl)phenyl]-4-(pyrazol-4-yl)-2-(tetrahydropyran-2-yl)-2H-indazole (Compound 27-1)

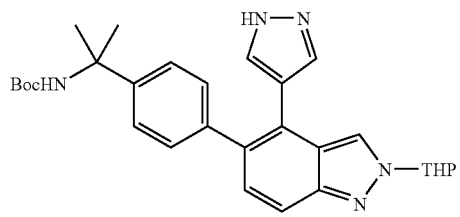

1-tert-Butoxycarbonyl-4-(4,4,5,5-tetramethyl[1,3,2]dioxaborolanyl)pyrazole (312 mg, 1.06 mmol), 123 mg (0.106 mmol) of tetrakistriphenylphosphine palladium, 5 ml of 1,2-dimethoxyethane and 2 ml of 2M aqueous solution of sodium carbonate were added to 310 mg (0.531 mmol) of 5-[4-(1-tert-butoxycarbonylamino-1-methylethyl)phenyl]-2-(tetrahydropyran-2-yl)-4-trifluoromethanesulfonyloxy-2H-indazole (compound 17-2) and the mixture was heated to reflux in an argon stream for 30 minutes with stirring. After the mixture was cooled down to room temperature, 5 ml of methanol and 1 ml of 1N sodium hydroxide solution were added thereto and the mixture was stirred at room temperature for 30 minutes.

After the reaction was finished, the reaction solution was poured into a saturated aqueous solution of ammonium chloride and the mixture was extracted with ethyl acetate. The organic layer was successively washed with water and a saturated aqueous solution of sodium chloride, dried over anhydrous magnesium sulfate and concentrated in vacuo. The resulting residue was subjected to a silica gel column chromatography (eluting solvent: n-hexane ethyl acetate=1:1 (v/v)) and the fraction containing the aimed product was concentrated in vacuo to give 215 mg of the title compound as slightly yellow powder (yield: 81%).

Rf value: 0.20 (n-hexane:ethyl acetate=1:2 (v/v))
Mass spectrum (CI, m/z): 502 (M$^+$+1)
$^1$H-NMR spectrum (CDCl$_3$, δ ppm): 1.38 (brs, 9H), 1.64-1.83 (m, 9H), 2.04-2.25 (m, 3H), 3.74-3.83 (m, 1H), 4.11-4.16 (m, 1H), 4.95 (brs, 1H), 5.66-5.71 (m, 1H), 7.17-7.22 (m, 2H), 7.30-7.35 (m, 3H), 7.40-7.42 (m, 2H), 7.69 (dd, J1=8.9 Hz, J2=1.1 Hz, 1H), 8.20-8.21 (m, 1H)

As hereunder, the compound 27-2 was produced in accordance with the production process for the compound 27-1.

5-[5-(1-tert-Butoxycarbonylamino-1-methylethyl)-pyridin-2-yl]-4-(pyrazol-4-yl)-2-(tetrahydropyran-2-yl)-2H-indazole (Compound 27-2)

Rf value: 0.22 (ethyl acetate)
Mass spectrum (CI, m/z): 503 (M$^+$+1)
$^1$H-NMR spectrum (CDCl$_3$, δ ppm): 1.37 (brs, 9H), 1.65-1.80 (m, 9H), 2.04-2.25 (m, 3H), 3.75-3.83 (m, 1H), 4.11-4.16 (m, 1H), 4.98 (brs, 1H), 5.66-5.71 (m, 1H), 7.08 (d, J=8.3 Hz, 1H), 7.46-7.57 (m, 4H), 7.73 (dd, J1=9.0 Hz, J21.0 Hz, 1H), 8.18-8.20 (m, 1H), 8.72 (d, J=1.7 Hz, 1H)

Example 28

Synthesis of 5-[4-(1-tert-butoxycarbonylamino-1-methylethyl)phenyl]-4-(oxazol-5-yl)-2-(tetrahydropyran-2-yl)-2H-indazole (Compound 28)

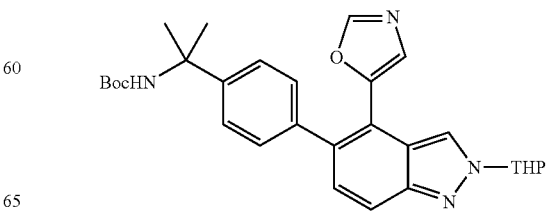

(p-toluenesulfonyl)methyl isocyanide (200 mg, 1.02 mmol) and 150 mg (1.09 mmol) of potassium carbonate were added in an argon stream to a solution of 398 mg (0.858 mmol) of 5-[4-(1-tert-butoxycarbonylamino-1-methylethyl)]phenyl]-4-formyl-2-(tetrahydropyran-2-yl)-2H-indazole (compound 1-17) in 5 ml of methanol and the mixture was heated to reflux with stirring for 1.5 hours.

After the reaction was finished, the reaction solution was concentrated in vacuo. The resulting residue was subjected to a silica gel column chromatography (eluting solvent: n-hexane:ethyl acetate=2:1 to 1:1 (v/v)) and the fraction containing the aimed product was concentrated in vacuo to give 139 mg of the title compound as pale yellow powder (yield: 32%).

Rf value: 0.29 (n-hexane:ethyl acetate=1:1 (v/v))

Mass spectrum (EI, m/z): 502 (M$^+$)

$^1$H-NMR spectrum (CDCl$_3$, δ ppm): 1.39 (brs, 9H), 1.62-1.85 (m, 9H), 2.02-2.14 (m, 1H), 2.20-2.31 (m, 2H), 3.77-3.88 (m, 1H), 4.13-4.21 (m, 1H), 4.95 (brs, 1H), 5.71-5.76 (m, 1H), 6.34 (s, 1H), 7.23-7.32 (m, 3H), 7.42-7.49 (m, 2H), 7.75 (dd, J1=8.8 Hz, J2=1.0 Hz, 1H), 7.90 (s, 1H), 8.56 (d, J=1.0 Hz, 1H)

Example 29

Synthesis of 5-[4-(1-tert-butoxycarbonylamino-1-methylethyl)phenyl]-4-(3-dimethylaminoacryloyl)-2-(tetrahydropyran-2-yl)-2H-indazole (Compound 29)

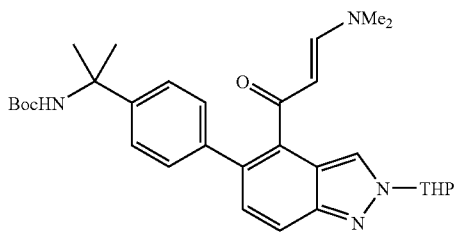

N,N-Dimethylformamide dimethylacetal (2.0 ml, 15 mmol) was added to a solution of 500 mg (1.05 mmol) of 5-[4-(1-tert-butoxycarbonylamino-1-methylethyl)]phenyl]-4-methylcarbonyl-2-(tetrahydropyran-2-yl)-2H-indazole (Compound 1-18) in 6 ml of N,N-dimethylformamide in an argon stream and the mixture was stirred at 70° C. for 1.5 hours and then at 100° C. for 4 hours.

After the reaction was finished, the reaction solution was concentrated in vacuo, the resulting residue was subjected to a silica gel column chromatography (eluting solvent: ethyl acetate) and the fraction containing the aimed substance was concentrated in vacuo. The resulting residue was recrystallized from chloroform/ethyl acetate/n-hexane and filtered off to give 450 mg of the title compound as yellow powder (yield: 81%).

Melting point: 191 to 194° C.

Rf value: 0.22 (ethyl acetate)

Mass spectrum (CI, m/z): 533 (M$^+$+1)

$^1$H-NMR spectrum (CDCl$_3$, δ ppm): 1.39 (brs, 9H), 1.59-1.82 (m, 9H), 1.97-2.11 (m, 1H), 2.14-2.30 (m, 2H), 2.45 (brs, 3H), 2.90 (brs, 3H), 3.73-3.83 (m, 1H), 4.08-4.19 (m, 1H), 4.71-4.80 (m, 1H), 4.94 (brs, 1H), 5.64-5.69 (m, 1H), 7.34 (d, J=8.8 Hz, 1H), 7.35-7.45 (m, 5H), 7.77 (dd, J1=8.8 Hz, J2=1.0 Hz, 1H), 8.38-8.42 (m, 1H)

Example 30

Synthesis of 5-[4-(1-tert-butoxycarbonylamino-1-methylethyl)phenyl]-4-(pyrazol-3-yl)-2-(tetrahydropyran-2-yl)-2H-indazole (Compound 30)

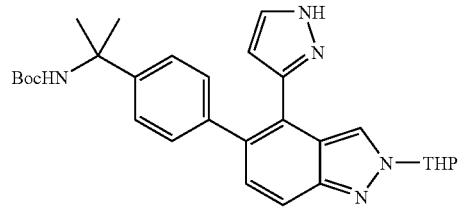

Hydrazine monohydrate (0.40 ml, 8.3 mmol) was added to a solution of 450 mg (0.85 mmol) of 5-[4-(1-tert-butoxycarbonylamino-1-methylethyl)phenyl]-4-(3-dimethylaminoacryloyl)-2-(tetrahydropyran-2-yl)-2H-indazole (Compound 29) in 4 ml of tetrahydrofuran in an argon stream and the mixture was stirred at 70° C. for 1 hour.

After the reaction was finished, water was added to the reaction solution and the mixture was extracted with ethyl acetate. The organic layer was washed with a saturated aqueous solution of sodium chloride, dried over anhydrous magnesium sulfate and concentrated in vacuo. The resulting residue was subjected to a silica gel column chromatography (eluting solvent: n-hexane:ethyl acetate=1:1 to 1:2 (v/v)) and the fraction containing the aimed substance was concentrated in vacuo to give 430 mg of the title compound as yellow powder (yield: quantitative).

Melting point: 99 to 105° C.

Rf value: 0.55 (ethyl acetate)

Mass spectrum (CI, m/z): 502 (M$^+$+1)

$^1$H-NMR spectrum (CDCl$_3$, δ ppm): 1.37 (brs, 9H), 1.60-1.85 (m, 9H), 1.99-2.15 (m, 1H), 2.21-2.32 (m, 2H), 3.73-3.82 (m, 1H), 4.09-4.17 (m, 1H), 4.93 (brs, 1H), 5.65-5.71 (m, 1H), 6.07-6.12 (m, 1H), 7.20-7.38 (m, 5H), 7.46 (d, J=2.2 Hz, 1H), 7.75 (dd, J1=8.8 Hz, J21.0 Hz, 1H), 8.39-8.43 (m, 1H)

Example 31

Synthesis of 5-[4-(1-tert-butoxycarbonylamino-1-methylethyl)phenyl]-4-(isoxazol-5-yl)-1H-indazole (Compound 31)

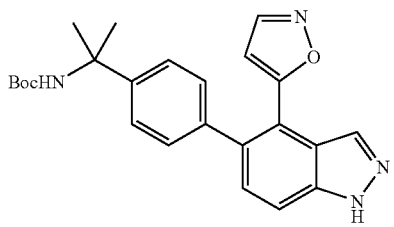

Hydroxylamine hydrochloride (150 mg, 2.2 mmol) and 150 mg (1.1 mmol) of potassium carbonate were added, in an argon stream, to a solution of 400 mg (0.75 mmol) of 5-[4-(1-tert-butoxycarbonylamino-1-methylethyl)phenyl]-4-(3-dimethylaminoacryloyl)-2-(tetrahydropyran-2-yl)-2H-indazole (compound 29) in 5 ml of ethanol and the mixture was heated to reflux for 3 hours with stirring.

After the reaction was finished, the reaction solution was concentrated in vacuo, water was added thereto and the mixture was extracted with ethyl acetate. The organic layer was washed with a saturated aqueous solution of sodium chloride, dried over anhydrous magnesium sulfate and concentrated in vacuo. The resulting residue was subjected to a silica gel column chromatography (eluting solvent: n-hexane:ethyl acetate=1:1 (v/v)) and the fraction containing the aimed substance was concentrated in vacuo to give 300 mg of the title compound as a pale yellow foaming substance (yield: 95%).

Rf value: 0.33 (n-hexane:ethyl acetate=1:1 (v/v))

Mass spectrum (CI, m/z): 419 ($M^++1$)

$^1$H-NMR spectrum (CDCl$_3$, δ ppm): 1.39 (brs, 9H), 1.68 (s, 6H), 5.02 (brs, 1H), 5.48-5.60 (m, 1H), 7.21-7.28 (m, 2H), 7.40 (d, J=8.5 Hz, 1H), 7.41-7.48 (m, 2H), 7.55-7.62 (m, 1H), 8.09 (d, J=2.0 Hz, 1H), 8.57 (s, 1H), 10.41 (brs, 1H)

Examples of Pharmaceutical Preparations

General examples of pharmaceutical preparations for the compounds of the present invention are as follows.

1) Tablets

| Formulation 1 (amounts in 100 mg) | |
| --- | --- |
| Compound of the present invention | 1 mg |
| Lactose | 66.4 mg |
| Corn starch | 20 mg |
| Carxboxymethyl cellulose calcium | 6 mg |
| Hydroxypropyl cellulose | 4 mg |
| Magnesium stearate | 0.6 mg |

The tablet having the above formulation is coated with 2 mg of a coating agent (common coating agent such as hydroxypropyl methylcellulose, macrogol and silicone resin) to prepare an aimed coated tablet. Other tablets are also prepared in the same manner. Further, desired tablets are able to be prepared when types and amounts of the compound of the present invention and of the additives are appropriately changed.

2) Capsules

| Formuation 2 (amounts in 150 mg) | |
| --- | --- |
| Compound of the present invention | 5 mg |
| Lactose | 145 mg |

Desired capsule preparations are able to be prepared when mixing ratio of the compound of the present invention to lactose are appropriately changed.

3) Eye Drops

| Formuation 3 (amounts in 100 ml) | |
| --- | --- |
| Compound of the present invention | 100 mg |
| Sodium chloride | 900 mg |
| Polysorbate 80 | 200 mg |
| Sodium hydroxide | q.s. |
| Hydrochloric acid | q.s. |
| Sterilized purified water | q.s. |

Desired eye drops are able to be prepared when types and amounts of the compound and the additives are appropriately changed.

[Pharmacological Tests]

A. Test for Evaluation of Inhibiting Activity to Rho Kinase

In order to test the usefulness of the compounds of the present invention as a Rho kinase inhibitor, inhibiting activities of the compounds of the present invention to Rho kinase were evaluated and investigated in accordance with the methods of Kaibuchi, et al. mentioned in *J. Biol. Chem.*, 274, 32418, 1999 and also with the methods mentioned in the instruction manual for use attached to commercially available activated ROCK II [Upstate Biotechnology, Catalog No. 14-338, (5 unite/50 μl)]. With regard to the test compounds, the compounds 5-1 to 5-73 (except the compounds 5-2, 5-9, 5-18, 5-37 and 5-38) were used.

(Preparation of the Reagents)

1) Preparation of Buffer

A buffer was prepared so as to make tris(hydroxymethyl) aminomethane (Tris) (pH 7.5), 50 mM, ethyleneglycol bis(O-aminoethyl ether)-N,N,N',N'-tetraacetic acid (EGTA), 2 mM, ethylenediaminetetraacetic acid (EDTA), 1 mM, magnesium chloride (MgCl$_2$) 5 mM, β-glycerol phosphate, 5 mM, and dithiothreitol (DTT), 2 mM, by mixing them.

2) Preparation of 300 μM ATP [γ-$^{32}$P]ATP solution

A mixed liquid of a 10 mM ATP solution with a commercially available [γ-$^{32}$P]ATP solution [NEN, Code No. NEG-002A] was diluted with the buffer to prepare a 300 μM ATP [γ-$^{32}$P] ATP solution.

3) Preparation of an activated ROCK II Solution.

A commercially available activated ROCK II [Upstate Biotechnology, Catalog No. 14-338, (5 Units/50 μl)] was diluted to a concentration of 1/100 with the buffer to prepare an activated ROCK II solution.

4) Preparation of a 1 mM Substrate Solution

A S6 Kinase Substrate Peptide [Upstate Biotechnology, Catalog No. 12-124,] (2 mg) was dissolved in distilled water to prepare a 1 mM substrate solution.

5) Preparation of a Test Compound Solution

A test compound was dissolved in 10% aqueous dimethyl sulfoxide solution.

(Method for Evaluation)

1) The test compound solution is placed in a microtube.

2) The 300 μM ATP [γ-$^{32}$P]ATP solution is added to the microtube followed by cooling to 4° C.

3) After that, a permanently activated ROCK II solution, 1 mM substrate solution and buffer are added to each microtube in that order, and the whole is mixed and cooled again at 4° C.

4) The microtube is placed in an incubator (30° C.) and the mixture is subjected to reaction for 15 minutes.

5) After cooling to 4° C., a 250 mM phosphoric acid solution (5 μl) is added to each microtube to stop the reaction.

6) The reaction solution (30 μl) is taken out from each microtube and spotted on a filter paper (Whatman P81) so that the reaction product (phosphorylated substrate) is adsorbed to the filter paper.

7) The filter paper is transferred to a beaker in which a 75 mM phosphoric acid solution is placed and shaken for 5 minutes so that unreacted [γ-$^{32}$P]ATP is washed out. The washing operation as such is carried out four times.

8) After that, the filter paper is dipped in ethanol to dehydrate and energy amount (radioactivity) of the reaction product adsorbed to the filter paper is measured with a liquid scintillation counter.

(Calculation of $Ic_{50}$)

The $IC_{50}$ value was calculated by an XL-fit (IDBS)

(Calculation of Ki Value)

The Ki value is calculated by the following formula. S is an ATP concentration contained in the reaction solution while Km is a Michaelis-Menten constant.

$Ki=IC_{50}/(1+S/Km)$ (Results and Considerations)

Result when the compounds 5-1 to 5-73 (except the compounds 5-2, 5-9, 5-18, 5-37 and 5-38) were used as test compounds is shown in Table 1.

TABLE 1

| Test Compounds | Ki Value (nM) |
|---|---|
| Compound 5-1 | 19 |
| Compound 5-3 | 20 |
| Compound 5-4 | 28 |
| Compound 5-5 | 44 |
| Compound 5-6 | 260 |
| Compound 5-7 | 15 |
| Compound 5-8 | 97 |
| Compound 5-10 | 134 |
| Compound 5-11 | 144 |
| Compound 5-12 | 7.5 |
| Compound 5-13 | 103 |
| Compound 5-14 | 142 |
| Compound 5-15 | 56 |
| Compound 5-16 | 16 |
| Compound 5-17 | 199 |
| Compound 5-19 | 55 |
| Compound 5-20 | 61 |
| Compound 5-21 | 26 |
| Compound 5-22 | 38 |
| Compound 5-23 | 29 |
| Compound 5-24 | 14 |
| Compound 5-25 | 23 |
| Compound 5-26 | 27 |
| Compound 5-27 | 86 |
| Compound 5-28 | 15 |
| Compound 5-29 | 2.7 |
| Compound 5-30 | 17 |
| Compound 5-31 | 614 |
| Compound 5-32 | 47 |
| Compound 5-33 | 234 |
| Compound 5-34 | 294 |
| Compound 5-35 | 139 |
| Compound 5-36 | 35 |
| Compound 5-39 | 12 |
| Compound 5-40 | 33 |
| Compound 5-41 | 14 |
| Compound 5-42 | 14 |
| Compound 5-43 | 211 |
| Compound 5-44 | 13 |
| Compound 5-45 | 27 |
| Compound 5-46 | 27 |
| Compound 5-47 | 45 |
| Compound 5-48 | 29 |
| Compound 5-49 | 17 |
| Compound 5-50 | 84 |
| Compound 5-51 | 38 |
| Compound 5-52 | 14 |
| Compound 5-53 | 3.6 |
| Compound 5-54 | 31 |
| Compound 5-55 | 13 |
| Compound 5-56 | 26 |
| Compound 5-57 | 23 |
| Compound 5-58 | 39 |
| Compound 5-59 | 6.9 |
| Compound 5-60 | 35 |
| Compound 5-61 | 45 |
| Compound 5-62 | 126 |

TABLE 1-continued

| Test Compounds | Ki Value (nM) |
|---|---|
| Compound 5-63 | 241 |
| Compound 5-64 | 4.4 |
| Compound 5-65 | 56 |
| Compound 5-66 | 2.6 |
| Compound 5-67 | 11 |
| Compound 5-68 | 6.4 |
| Compound 5-69 | 55 |
| Compound 5-70 | 28 |
| Compound 5-71 | 34 |
| Compound 5-72 | 13 |
| Compound 5-73 | 146 |

AS is apparent from Table 1, all of the compounds of the present invention exhibited an excellent Rho kinase inhibiting action. From the above-mentioned results, it was found that the compound of the present invention is very useful as a therapeutic agent for diseases in which Rho kinase is involved.

B. Test for Measuring the Intraocular Pressure-reducing Action

In order to check the usefulness of the compounds of the present invention as therapeutic agents for glaucoma, their intraocular pressure-reducing action when the compounds of the present, invention were topically administered to cynomolgus monkeys (*Macaca fascicularis*) (sex: male; one group comprising 2 to 6 monkeys) was evaluated. With regard to the test compounds, there were used the compound 5-3 (hereinafter, referred to as a test compound 1), the compound 5-4 (hereinafter, referred to as a test compound 2), the compound 5-42 (hereinafter, referred to as a test compound 3) and the compound 5-44 (hereinafter, referred to as a test compound 4).

(Preparation of a Test Compound Solution)

The test compounds 1, 2, 3 and 4 were dissolved in a 2.6% glycerol solution, respectively, and sodium hydroxide was added thereto to adjust the pH (pH 3.5 to 7.0) to prepare a test compound solution of a 1% concentration (of the test compound 1, 2), a 0.3% concentration (of the test compound 3) and a 0.1% concentration (of the test compound 4).

(Test Methods for Ocular Hypotension)

1) One drop of a 0.4% eyedrop of oxybuprocaine hydrochloride was instilled into each of both eyes of a cynomolgus monkey (*Macaca fascicularis*) to induce local anesthesia.

2) Intraocular pressure was measured immediately before administration of a test compound solution and defined as the initial intraocular pressure.

3) A test compound solution was instilled into one of the eyes of the experimental animal (while another eye was not treated).

4) After 2, 4 and 6 hours after instillation of the test compound solution, one drop of a 0.4% eyedrop of oxybuprocaine hydrochloride was instilled into each of both eyes to induce local anesthesia and then intraocular pressure was measured. The measuring intraocular pressure for each time was carried out three times and a mean value thereof was calculated.

As a control, only a vehicle (2.6% glycerol solution) instead of a test compound solution was topically administered and the same test procedure as in the methods of the above 1) to 4) was conducted.

(Results and Considerations)

Figure 2:
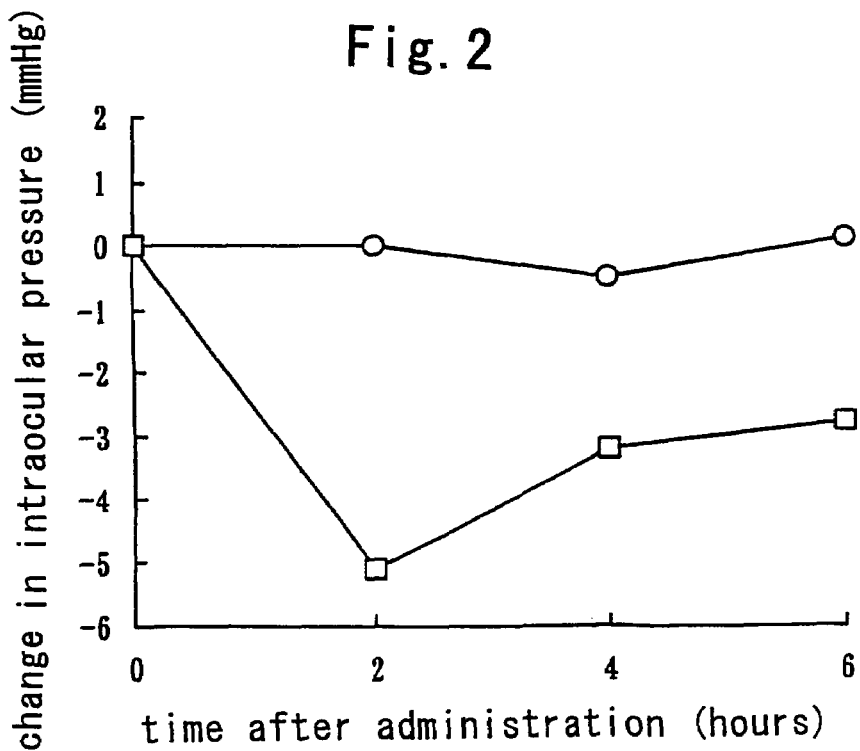
FIG. 2 is a graph which shows the changes in intraocular pressure in each administration group with lapse of time. The intraocular pressure is shown by the pressure change from the initial intraocular pressure. □ shows the group to which the test compound 2 was administered and ○ shows a control group.

FIGS. 1, 2, 3 and 4 show the results when the test compounds 1, 2, 3 and 4 were used, respectively. In Figs., the change in intraocular pressure shows the change from the initial intraocular pressure.

As apparent from FIGS. 1, 2, 3 and 4, all of the compounds of the present invention exhibited an excellent ocular hypotensive action. From the above-mentioned results, it was found that the compound of the present invention is particularly useful as a therapeutic agent for glaucoma.

INDUSTRIAL APPLICABILITY

The present invention is to provide a novel indazole derivative or a salt thereof exhibiting a Rho kinase inhibiting action and being useful as a therapeutic agent for diseases in which Rho kinase is involved such as ocular diseases including glaucoma.

What is claimed is:

1. A method for treating glaucoma comprising administering to a patient in need thereof a pharmaceutically effective amount of a compound represented by the following formula [I] or a pharmaceutically acceptable salt thereof:

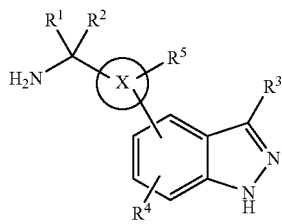

wherein the ring X is a benzene ring or a pyridine ring;
$R^1$ and $R^2$ are the same or different and are a hydrogen atom or an alkyl group; or
$R^1$ and $R^2$ are bonded together to form an unsubstituted cycloalkane ring;
$R^3$ is a hydrogen atom, a substituted alkyl group, an unsubstituted alkenyl group, a carboxyl group or an ester or an amide thereof, an amino group or a cyano group, wherein the substituted alkyl group is an alkyl group substituted with one or more groups selected from the group consisting of a hydroxyl group and a hydroxyimino group;
$R^4$ is a hydrogen atom, a hydroxyl group, a substituted or unsubstituted alkoxy group, an unsubstituted alkenyloxy group, an unsubstituted cycloalkyloxy group, a substituted or unsubstituted alkyl group, an unsubstituted alkenyl group, an unsubstituted cycloalkyl group, an amino group, a substituted or unsubstituted alkylamino group, a nitro group, a cyano group or a monocyclic heterocycle group, wherein the substituted alkoxy group is an alkoxy group substituted with one or more groups selected from the group consisting of a halogen atom and a cycloalkyl group, the substituted alkyl group is an alkyl group substituted with one or more hydroxyl groups and the substituted alkylamino group is an alkylamino group substituted with one or more aryl groups; and
$R^5$ is a halogen atom or a hydrogen atom.

2. The method according to claim 1, wherein the ring X is a benzene ring or a pyridine ring;
$R^1$ and $R^2$ are the same or different and are a hydrogen atom, a methyl group or an ethyl group; or $R^1$ and $R^2$ are bonded together to form a cyclopentane ring;
$R^3$ is a hydrogen atom, a hydroxymethyl group, a hydroxyiminomethyl group, a 1-methylvinyl group, a carboxyl group, a methoxycarbonyl group, an aminocarbonyl group, an amino group or a cyano group;
$R^4$ is a hydrogen atom, a hydroxyl group, a methoxy group, an ethoxy group, a n-propyloxy group, a n-butyloxy group, an isopropyloxy group, a difluoromethoxy group, a 2-fluoroethoxy group, a 2,2,2-trifluoroethoxy group, an allyloxy group, a cyclopropyloxy group, a cyclopropylmethyloxy group, an ethyl group, a vinyl group, a hydroxymethyl group, a 1-hydroxyethyl group, a 2-hydroxyethyl group, a cyclopropyl group, an amino group, a methylamino group, a dimethylamino group, a diethylamino group, a benzylamino group, a nitro group, a cyano group, a pyrrolidine ring, a pyrrole ring, a pyrazole ring, an oxazole ring, an isoxazole ring, a piperidine ring, a pyridine ring or a morpholine ring; and
$R^5$ is a chlorine atom or a hydrogen atom,
or a pharmaceutically acceptable salt thereof.

3. The method according to claim 1, wherein the ring X is a benzene ring or a pyridine ring;
$R^1$ and $R^2$ are the same or different and are a hydrogen atom, a methyl group or an ethyl group; or $R^1$ and $R^2$ are bonded together to form a cyclopentane ring;
$R^3$ is a hydrogen atom;
$R^4$ is a hydroxyl group, a methoxy group, an ethoxy group, a n-propyloxy group, a n-butyloxy group, an isopropyloxy group, a difluoromethoxy group, a 2-fluoroethoxy group, a 2,2,2-trifluoroethoxy group, an allyloxy group, a cyclopropyloxy group, a cyclopropylmethyloxy group, an ethyl group, a vinyl group, a hydroxymethyl group, a 1-hydroxyethyl group, a 2-hydroxyethyl group, a cyclopropyl group, an amino group, a methylamino group, a dimethylamino group, a diethylamino group, a benzylamino group, nitro group, a cyano group, a pyrrolidine ring, a pyrrole ring, a pyrazole ring, an oxazole ring, an isoxazole ring, a piperidine ring, a pyridine ring or a morpholine ring; and
$R^5$ is a chlorine atom or a hydrogen atom,
or a pharmaceutically acceptable salt thereof.

4. The method according to claim 1, wherein the ring X is connected at the 5-position of the indazole ring, or a pharmaceutically acceptable salt thereof.

5. The method according to claim 1, wherein when the ring X is a benzene ring, the ring X is connected to the 5-position of the indazole ring and the

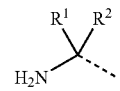

group is connected to the 4-position of the benzene ring; or when the ring X is a pyridine ring, the ring X is connected to the 5-position of the indazole ring and the

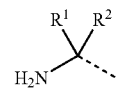

group is connected to the 5-position of the pyridine ring,
or a pharmaceutically acceptable salt thereof.

6. The method according to claim 2, wherein the ring X is connected at the 5-position of the indazole ring, or a pharmaceutically acceptable salt thereof.

7. The method according to claim 2, wherein when the ring X is a benzene ring, the ring X is connected to the 3-position of the indazole ring and the

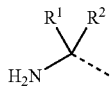

group is connected to the 4-position of the benzene ring; or when the ring X is a pyridine ring, the ring X is connected to the 5-position of the indazole ring and the

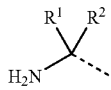

group is connected to the 5-position of the pyridine ring, or a pharmaceutically acceptable salt thereof.

8. The method according to claim 3, wherein the ring X is connected at the 5-position of the indazole ring, or a pharmaceutically acceptable salt thereof.

9. The method according to claim 3, wherein when the ring X is a benzene ring, the ring X is connected to the 5-position of the indazole ring and the

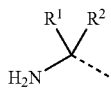

group is connected to the 4-position of the benzene ring; or when the ring X is a pyridine ring, the ring X is connected to the 5-position of the indazole ring and the

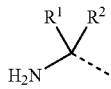

group is connected to the 5-position of the pyridine ring, or a pharmaceutically acceptable salt thereof.

10. The method according to claim 1, wherein the glaucoma is primary open angle glaucoma, normal tension glaucoma, hypersecretion glaucoma, ocular hypertension, acute angle-closure glaucoma, chronic angle-closure glaucoma, combined mechanism glaucoma, steroid glaucoma, amyloid glaucoma, neovascular glaucoma, malignant glaucoma, capsular glaucoma or plateau iris syndrome.

11. The method according to claim 1, wherein the compound is selected from the group consisting of
5-[4-(1-amino-1-methylethyl)phenyl]-1H-indazole,
1-acetyl-5-[4-(1-amino-1-methylethyl)phenyl]-1H-indazole,
5-[5-(1-amino-1-methylethyl)pyridin-2-yl]-1H-indazole,
5-[4-(1-amino-1-methylethyl)phenyl]-4-nitro-1H-indazole,
4-amino-5-[4-(1-amino-1-methylethyl)phenyl]-1H-indazole,
5-[4-(1-amino-1-methylethyl)phenyl]-4-benzylamino-1H-indazole,
5-[4-(1-amino-1-methylethyl)phenyl]-4-methylamino-1H-indazole,
5-[4-(1-amino-1-methylethyl)phenyl]-3-methoxycarbonyl-1H-indazole,
5-[4-(1-amino-1-methylethyl)phenyl]-3-carboxy-1H-indazole,
3-aminocarbonyl-5-[4-(1-amino-1-methylethyl)phenyl]-1H-indazole,
3-amino-5-[4-(1-amino-1-methylethyl)phenyl]-1H-indazole,
5-[4-(1-amino-1-methylethyl)phenyl]-3-hydroxyiminomethyl-1H-indazole,
5-[4-(1-amino-1-methylethyl)phenyl]-3-cyano-1H-indazole,
5-[4-(1-amino-1-methylethyl)phenyl]-3-hydroxymethyl-1H-indazole,
5-[4-(1-amino-1-methylethyl)phenyl]-3-(1-methylvinyl)-1H-indazole,
5-[4-(1-amino-1-methylethyl)phenyl]-4-dimethylamino-1H-indazole,
[5-(1-amino-1-methylethyl)pyridin-2-yl]-4-nitro-1H-indazole,
4-(N-acetylamino)-5-[4-(1-amino-1-methylethyl)-phenyl]-1H-indazole,
5-[4-(aminomethyl)-phenyl]-4-nitro-1H-indazole,
4-amino-5-[4-(aminomethyl)phenyl]-1H-indazole,
4-amino-5-[4-(1-aminocyclopentyl)phenyl]-1H-indazole,
4-amino-5-[4-(1-amino-1-ethylpropyl)phenyl]-1H-indazole,
5-[4-(aminomethyl)phenyl]-4-dimethylamino-1H-indazole,
5-[4-(1-aminocyclopentyl)phenyl]-4-dimethylamino-1H-indazole,
5-[4-(1-amino-1-ethylpropyl)phenyl]-4-dimethyl-amino-1H-indazole,
5-[4-(1-aminoethyl)phenyl]-4-dimethylamino-1H-indazole,
5-[5-(1-amino-1-methylethyl)-3-chloropyridin-2-yl]-1H-indazole,
5-[5-(1-amino-1-methylethyl)pyridin-2-yl]-4-ethyl-1H-indazole,
5-H-(1-amino-1 methylethyl)pyridin-2-yl]-4-cyclopropyl-1H-indazole,
5-[5-(1-amino-1-methylethyl)pyridin-2-yl]-4-vinyl-1H-indazole,
5-[4-(1-amino-1-methylethyl)phenyl]-4-diethylamino-1H-indazole,
5-[4-(1-amino-1-methylethyl)phenyl]-4-(2-hydroxyethyl)-1H-indazole,
5-[5-(1-amino-1-methylethyl)pyridin-2-yl]-4-(2-hydroxyethyl)-1H-inazole,
5-[4-(1-amino-1-methylethyl)phenyl]-4-(1-hydroxyethyl)-1H-indazole,
5-[4-(1-amino-1-methylethyl)phenyl]-4-hydroxymethyl-1H-indazole,
5-[4-(1-amino-1-methylethyl)phenyl]-4-cyano-1H-indazole,
[4-(1-amino-1-methylethyl)phenyl]-1H-indazole,
1-acetyl-6-[4-(1-amino-1-methylethyl)phenyl]-1H-indazole,
5-[4-(1-amino-1-methylethyl)phenyl]-4-(pyrrol-1-yl)-1H-indazole,
5-[4-(1-amino-1-methylethyl)phenyl]-4-isopropoxy-1H-indazole,
5-[4-(1-amino-1-methylethyl)phenyl]-4-(piperidin-1-yl)-1H-indazole,
5-[4-(1-amino-1-methylethyl)phenyl]-4-(pyrrolidin-1-yl)-1H-indazole, 5-[4-(1-amino-1-methylethyl)phenyl]-4-(morpholin-4-yl)-1H-indazole,
5-[4-(1-amino-1-methylethyl)phenyl]-4-methoxy-1H-indazole,
5-[5-(1-amino-1-methylethyl)pyrridin-2-yl]-4-methoxy-1H-indazole,
5-[5-(1-aminocyclopentyl)pyridin-2-yl]-4-methoxy-1H-indazole,
5-[5-(1-amino-1-methylethyl)pyridin-2-yl]-4-ethoxy-1H-indazole,
5-[4-(1-amino-1-methylethyl)phenyl]-4-hydroxy-1H-indazole,
5-[4-(1-amino-1-methylethyl)phenyl]-4-ethoxy-1H-indazole,
5-[5-(1-amino-1-methylethyl)pyridin-2-yl]-4-isopropoxy-1H-indazole,
5-[5-(1-amino-1-ethylpropyl)pyridin-2-yl]-4-methoxy-1H-indazole,
5-[4-(1-amino-1-methylethyl)phenyl]-4-n-propoxy-1H-indazole,
5-[4-(1-amino-1-methylethyl)phenyl]-4-difluoromethoxy-1H-indazole,
5-[4-(1-amino-1-methylethyl)phenyl]-4-(2,2,2-trifluoroethoxy)-1H-indazole,
5-[4-(1-amino-1-methylethyl)phenyl]-4-n-butoxy-1H-indazole,
5-[4-(1-amino-1-methylethyl)phenyl]-4-(2-fluoroethoxy)-1H-indozole,
4-allyloxy-5-[4-(1-amino-1-methylethyl)phenyl]-1H-indazole,
5-[5-(1-amino-1-methylethyl)pyridin-2-yl]-4-n-propoxy-1H-indazole,
5-[5-(1-amino-1-methylethyl)pyridin-2-yl]-4-difluoromethoxy-1H-indezole,
5-[5-(1-amino-1-ethylpropyl)pyridin-2-yl]-4-ethoxy-1H-indazole,
5-[4-(1-amino-1-methylethyl)phenyl]-4-(pyridin-4-yl)-1H-indazole,
5-[4-(1-amino-1-methylethyl)phenyl]-4-(pyridin-3-yl)-1H-indazole,
5-[4-(1-amino-1-methylethyl)phenyl]-4-(pyridin-2-yl)-1H-indazole,
5-[4-(1-amino-1-methylethyl)phenyl]-4-(pyrazol-4-yl)-1H-indazole,
5-[5-(1-amino-1-methylethyl)pyridin-2-yl]-4-(pyrazol-4-yl)-1H-indazole,
5-[4-(1-amino-1-methylethyl)phenyl]-4-(oxazol-5-yl)-1H-indazole,
5-[4-(1-amino-1-methylethyl)phenyl]-4-(pyrazol-3-yl)-1H-indazole,
5-[4-(1-amino-1-methylethyl)phenyl]-4-(isoxazol-5-yl)-1H-indazole,
5-[5-(1-amino-]-methethyl)pyridin-2-yl]-4-hydroxyl-1H-indazole,
5-[5-(1-amino-1-methylethyl)pyridin-2-yl]-4-cyclopropyloxy-1H-indazole,
5-[5-(1-amino-1-ethylpropyl)pyridin-2-yl]-4-cyclopropyloxy-1H-indazole,
5-[4-(1-amino-1-ethylpropyl)phenyl]-4-difluoromethoxy-1H-indazole and
5-[5-(1-amino-1-methylethyl)pyridin-2-yl]-4-cyclopropylmethyloxy-1H-indazole,
or a pharmaceutically acceptable salt thereof.

12. The method according to claim 11, wherein the glaucoma is primary open angle glaucoma, normal tension glaucoma, hypersecretion glaucoma, ocular hypertension, acute angle-closure glaucoma, chronic angle-closure glaucoma, combined mechanism glaucoma, steroid glaucoma, amyloid glaucoma, neovascular glaucoma, malignant glaucoma, capsular glaucoma or plateau iris syndrome.

* * * * *